US011638660B2

(12) United States Patent
Balkenbush et al.

(10) Patent No.: US 11,638,660 B2
(45) Date of Patent: May 2, 2023

(54) OPHTHALMIC MICROSURGICAL TOOLS, SYSTEMS, AND METHODS OF USE

(71) Applicant: Carl Zeiss Meditec Cataract Technology Inc., Reno, NV (US)

(72) Inventors: Casey Balkenbush, Reno, NV (US); Peter Bentley, Reno, NV (US); Luke W. Clauson, Reno, NV (US); Matthew Newell, Reno, NV (US); Michael Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 989 days.

(21) Appl. No.: 16/431,560

(22) Filed: Jun. 4, 2019

(65) Prior Publication Data

US 2019/0365567 A1 Dec. 5, 2019

Related U.S. Application Data

(60) Provisional application No. 62/846,280, filed on May 10, 2019, provisional application No. 62/789,348, (Continued)

(51) Int. Cl.
*A61F 9/007* (2006.01)
*A61F 9/008* (2006.01)
*A61M 1/00* (2006.01)

(52) U.S. Cl.
CPC .......... *A61F 9/00745* (2013.01); *A61F 9/008* (2013.01); *A61M 1/75* (2021.05);
(Continued)

(58) Field of Classification Search
CPC .. A61F 9/00745; A61F 9/008; A61F 9/00754; A61F 2009/00887;
(Continued)

(56) References Cited

U.S. PATENT DOCUMENTS 1,833,687 A 11/1931 Neivert
2,947,470 A 8/1960 Ruben et al.
(Continued)

FOREIGN PATENT DOCUMENTS

CN 1242824 A 1/2000
CN 1494443 A 5/2004
(Continued)

OTHER PUBLICATIONS

Vibration, First recorded in 1645-1655, Dictionary.com (Year: 1645). 5 pages.

*Primary Examiner* — Gary Jackson
*Assistant Examiner* — Sebastian X Lukjan
(74) *Attorney, Agent, or Firm* — Mintz Levin Cohn Ferris Glovsky and Popeo, P.C.

(57) ABSTRACT

A system for extracting lens material from an eye including an instrument having a first aspiration pump driven by a drive mechanism having a motor, and an elongate member sized and configured to extend through an anterior chamber to a capsular bag of the eye. The elongate member configured to be oscillated by the drive mechanism includes an inner lumen fluidly coupled to the first aspiration pump and defining at least a portion of an aspiration waste line, and an open distal end having a distal cutting tip. The system can further include a fluid system remote from the surgical instrument including a second aspiration pump and a fluid line configured to deliver background aspiration from the second aspiration pump to the inner lumen of the elongate member to aspirate the lens material from the eye towards the inner lumen. Related devices, systems, and methods are also provided.

43 Claims, 73 Drawing Sheets

Related U.S. Application Data filed on Jan. 7, 2019, provisional application No. 62/692,443, filed on Jun. 29, 2018, provisional application No. 62/680,723, filed on Jun. 5, 2018.

(52) U.S. Cl.
CPC ........... *A61M 1/77* (2021.05); *A61F 9/00754* (2013.01); *A61F 2009/00887* (2013.01); *A61M 1/74* (2021.05); *A61M 1/741* (2021.05); *A61M 1/81* (2021.05); *A61M 2210/0612* (2013.01)

(58) Field of Classification Search
CPC ......... A61F 2250/0093; A61M 1/0058; A61M 2210/0612; A61M 1/75; A61M 1/74; A61M 1/741; A61M 1/81; A61M 3/022; A61M 2209/08; A61M 2205/3334; A61M 2205/3344; A61M 2005/3561; A61M 2205/50; A61M 1/77; F04B 5/02; F04B 9/042; F04B 23/02; F04B 23/1253; F04B 49/065; F04B 49/12
See application file for complete search history.

(56) References Cited

U.S. PATENT DOCUMENTS

| | | |
|---|---|---|
| 3,183,849 A | 5/1965 | Raymond |
| 3,589,363 A | 6/1971 | Banko et al. |
| 3,957,052 A | 5/1976 | Topham |
| 3,990,452 A | 11/1976 | Murry et al. |
| 4,368,734 A | 1/1983 | Banko |
| 4,493,706 A | 1/1985 | Borsanyi et al. |
| 4,508,532 A | 4/1985 | Drews et al. |
| 4,643,187 A | 2/1987 | Okada |
| 4,705,500 A | 11/1987 | Reimels et al. |
| 4,732,150 A | 3/1988 | Keener Jr. |
| 4,764,165 A | 8/1988 | Reimels et al. |
| 4,854,825 A | 8/1989 | Bez et al. |
| 4,869,716 A | 9/1989 | Smirmaul |
| 4,891,044 A | 1/1990 | Mitchell |
| 4,908,015 A | 3/1990 | Anis |
| 4,921,477 A | 5/1990 | Davis |
| 5,146,921 A | 9/1992 | Terwilliger et al. |
| 5,222,959 A | 6/1993 | Anis |
| 5,275,607 A | 1/1994 | Lo et al. |
| 5,279,547 A | 1/1994 | Costin |
| 5,337,780 A | 8/1994 | Kee et al. |
| 5,350,390 A | 9/1994 | Sher |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,755,561 A | 5/1998 | Couillard et al. |
| 5,788,667 A | 8/1998 | Stoller et al. |
| 5,788,679 A | 8/1998 | Gravlee, Jr. |
| 5,807,401 A | 9/1998 | Grieshaber et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,004,284 A | 12/1999 | Sussman et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,132,436 A | 10/2000 | Portney |
| 6,165,190 A | 12/2000 | Nguyen |
| 6,183,433 B1 | 2/2001 | Bays |
| 6,186,148 B1 * | 2/2001 | Okada .................... A61F 2/161 128/898 |
| 6,241,700 B1 | 6/2001 | Leukanech |
| 6,254,587 B1 | 7/2001 | Christ et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,398,754 B1 | 6/2002 | Sutton et al. |
| 6,428,508 B1 | 8/2002 | Ross |
| 6,485,499 B1 | 11/2002 | Oberkamp et al. |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,549,972 B2 | 6/2009 | Luloh et al. |
| 7,588,553 B2 | 9/2009 | Dewey |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,876,025 B2 | 1/2011 | Ma et al. |
| 7,955,060 B2 | 6/2011 | Gottschalk |
| 7,967,775 B2 | 6/2011 | Hong |
| 8,070,711 B2 | 12/2011 | Bassinger et al. |
| 8,080,029 B2 | 12/2011 | Charles |
| 8,142,388 B2 | 3/2012 | Gomez |
| 8,187,293 B2 | 5/2012 | Kirchhevel |
| 8,216,246 B2 | 7/2012 | Luloh et al. |
| 8,246,644 B2 | 8/2012 | Rockley et al. |
| 8,287,484 B2 | 10/2012 | Rockley |
| 8,298,253 B2 | 10/2012 | Charles |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |
| 8,801,653 B2 | 8/2014 | Maaskamp et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,486,360 B2 | 11/2016 | Chon |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,750,639 B2 | 9/2017 | Barnes et al. |

(56) References Cited

U.S. PATENT DOCUMENTS

| | | |
|---|---|---|
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |
| 9,889,247 B2 | 2/2018 | Akahoshi |
| 9,913,752 B2 | 3/2018 | Hauger |
| 10,231,870 B2 | 3/2019 | Clauson et al. |
| 10,251,782 B2 | 4/2019 | Farley |
| 10,278,861 B2 | 5/2019 | Bourne |
| 10,294,934 B2 | 5/2019 | Bourne et al. |
| 10,603,213 B2 | 3/2020 | Clauson et al. |
| 11,278,450 B2 | 3/2022 | Clauson et al. |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |
| 2004/0099247 A1 | 5/2004 | Nelson |
| 2004/0153093 A1 | 8/2004 | Donovan |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0060926 A1 | 3/2007 | Escaf |
| 2007/0260173 A1 | 11/2007 | Boukhny et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1* | 7/2009 | Hibner ............... A61B 10/0275 600/568 |
| 2010/0030134 A1 | 2/2010 | Fitzgerald et al. |
| 2010/0191178 A1 | 7/2010 | Ross et al. |
| 2010/0286651 A1* | 11/2010 | Sorensen ............ A61M 1/0058 604/151 |
| 2010/0292631 A1 | 11/2010 | Holden |
| 2010/0312170 A1 | 12/2010 | Maaskamp et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0290854 A1 | 12/2011 | Timm et al. |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0078181 A1 | 3/2012 | Smith et al. |
| 2012/0089080 A1 | 4/2012 | Ross et al. |
| 2012/0157908 A1 | 6/2012 | Underwood et al. |
| 2012/0158030 A1 | 6/2012 | Underwood et al. |
| 2012/0165734 A1 | 6/2012 | Auld et al. |
| 2012/0184892 A1 | 7/2012 | Bigler et al. |
| 2012/0259320 A1 | 10/2012 | Loesel et al. |
| 2013/0043023 A1 | 2/2013 | Hallundbaek |
| 2013/0060210 A1 | 3/2013 | Ross et al. |
| 2013/0231605 A1 | 9/2013 | Walter |
| 2013/0282020 A1 | 10/2013 | Hunter |
| 2014/0005681 A1 | 1/2014 | Gee et al. |
| 2014/0012186 A1 | 1/2014 | Thyzel |
| 2014/0052113 A1 | 2/2014 | Kuehnert et al. |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1* | 6/2014 | Wilson ............... A61M 1/774 604/28 |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0309649 A1 | 10/2014 | Alvarez et al. |
| 2014/0358155 A1 | 12/2014 | DeBoer et al. |
| 2014/0360494 A1 | 12/2014 | Herskovic |
| 2014/0364885 A1* | 12/2014 | Wells ............... A61F 9/00763 606/170 |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0125328 A1 | 5/2015 | Bourne et al. |
| 2015/0141801 A1 | 5/2015 | Jean et al. |
| 2015/0144514 A1 | 5/2015 | Brennan et al. |
| 2015/0148615 A1* | 5/2015 | Brennan ............. A61G 13/121 128/853 |
| 2015/0196426 A1 | 7/2015 | Kuebler et al. |
| 2015/0202081 A1 | 7/2015 | Eichler |
| 2015/0216722 A1 | 8/2015 | Choate |
| 2015/0216728 A1 | 8/2015 | Keller |
| 2015/0257927 A1 | 9/2015 | Olson |
| 2015/0297407 A1 | 10/2015 | Saimovici |
| 2015/0306286 A1 | 10/2015 | Ross et al. |
| 2015/0328047 A1 | 11/2015 | Falck, Jr. |
| 2015/0359672 A1 | 12/2015 | Van Valen et al. |
| 2016/0022489 A1 | 1/2016 | Hartstra |
| 2016/0058614 A1 | 3/2016 | Ross et al. |
| 2016/0067091 A1 | 3/2016 | Wells et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0135991 A1 | 5/2016 | Farley et al. |
| 2016/0143780 A1 | 5/2016 | Gunn |
| 2016/0166432 A1 | 6/2016 | Kahook et al. |
| 2016/0175578 A1 | 6/2016 | Roholt |
| 2016/0220807 A1 | 8/2016 | Bono |
| 2017/0007451 A1 | 1/2017 | Depenbusch |
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0151091 A1 | 6/2017 | Bourne et al. |
| 2017/0151378 A1 | 6/2017 | Raney et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0049921 A1 | 2/2018 | Sorensen et al. |
| 2018/0058438 A1 | 3/2018 | Ochoa |
| 2018/0064578 A1 | 3/2018 | Clauson et al. |
| 2018/0318132 A1 | 11/2018 | Clauson et al. |
| 2018/0318133 A1 | 11/2018 | Clauson et al. |
| 2019/0015252 A1 | 1/2019 | Lake et al. |
| 2019/0041665 A1 | 2/2019 | Widman et al. |
| 2019/0099292 A1 | 4/2019 | Strayer et al. |
| 2019/0133825 A1 | 5/2019 | Clauson et al. |
| 2019/0151149 A1 | 5/2019 | Clauson et al. |
| 2019/0183679 A1 | 6/2019 | Sawicz |
| 2019/0183681 A1 | 6/2019 | Schaller et al. |
| 2019/0184071 A1 | 6/2019 | Steen |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0321223 A1 | 10/2019 | Chamness et al. |
| 2019/0388272 A1 | 12/2019 | Clauson et al. |

(56) References Cited

U.S. PATENT DOCUMENTS

| | | |
|---|---|---|
| 2020/0016001 A1 | 1/2020 | McDonell et al. |
| 2020/0022841 A1 | 1/2020 | Chamness et al. |
| 2020/0060875 A1 | 2/2020 | Clauson et al. |
| 2020/0289319 A1 | 9/2020 | Carter et al. |
| 2020/0360185 A1 | 11/2020 | Carter et al. |
| 2020/0383833 A1 | 12/2020 | Schaller |

FOREIGN PATENT DOCUMENTS

| | | | |
|---|---|---|---|
| CN | 103671079 A | 3/2014 | |
| CN | 108024854 A | 5/2018 | |
| DE | 10 2007 031722 A1 | 1/2009 | |
| DE | 10 2007 040290 B4 | 7/2019 | |
| EP | 1832259 B1 | 6/2009 | |
| EP | 1556099 B1 | 7/2013 | |
| EP | 2 168 540 B1 | 4/2015 | |
| EP | 2 094 173 B1 | 3/2016 | |
| EP | 1735030 B1 | 8/2016 | |
| EP | 2 892 438 B1 | 10/2018 | |
| GB | 1304324 A | 1/1973 | |
| GB | 2018601 A | 10/1979 | |
| JP | H0779826 B2 | 8/1995 | |
| JP | 2018035761 A | 3/2018 | |
| JP | 6654763 B2 | 2/2020 | |
| WO | WO-2006119557 A1 * | 11/2006 | .......... A61M 1/0025 |
| WO | WO-2013/039742 A2 | 3/2013 | |
| WO | WO-2014/039093 A1 | 3/2014 | |
| WO | WO-2015/161149 A | 10/2015 | |
| WO | WO-2018/081295 A1 | 5/2018 | |
| WO | WO-2018/217579 A1 | 11/2018 | |

* cited by examiner

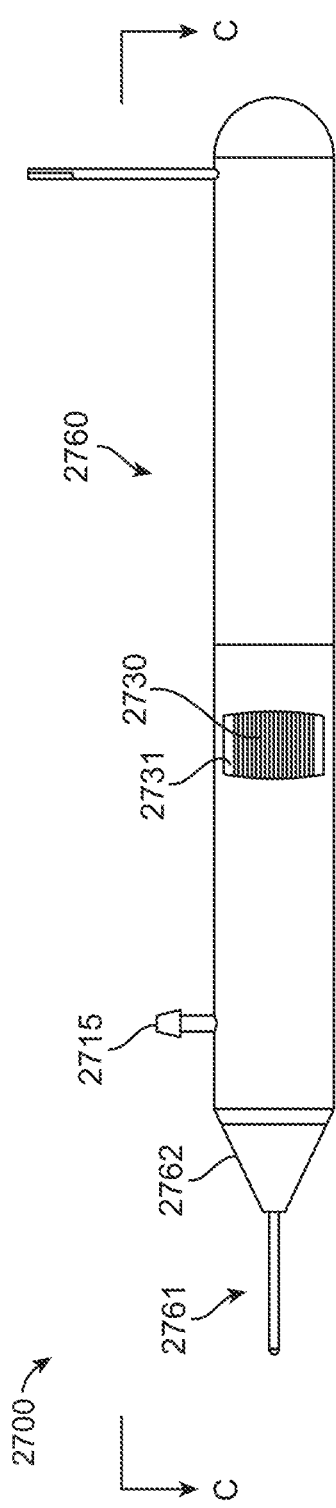
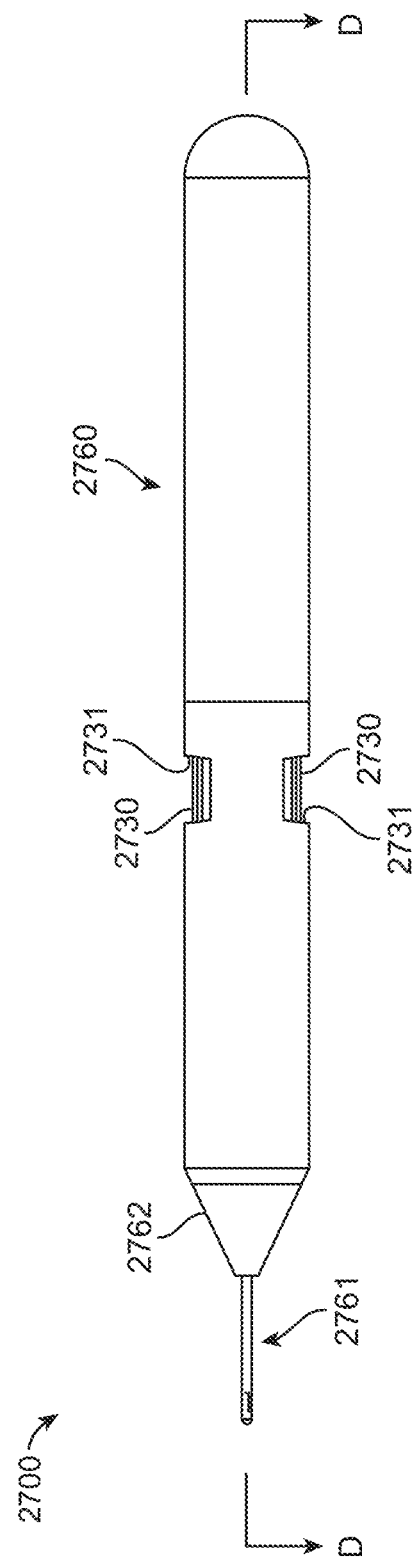

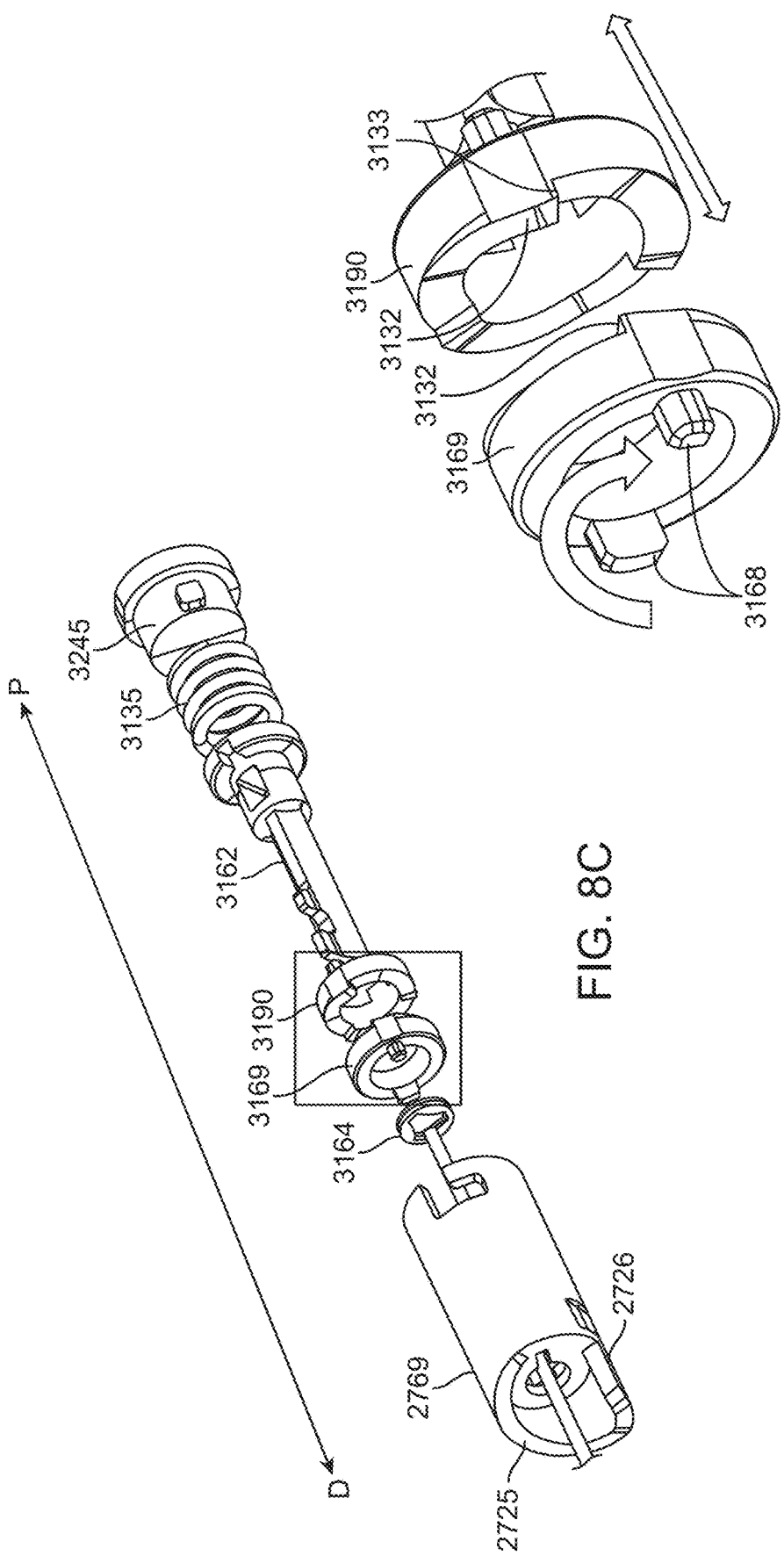

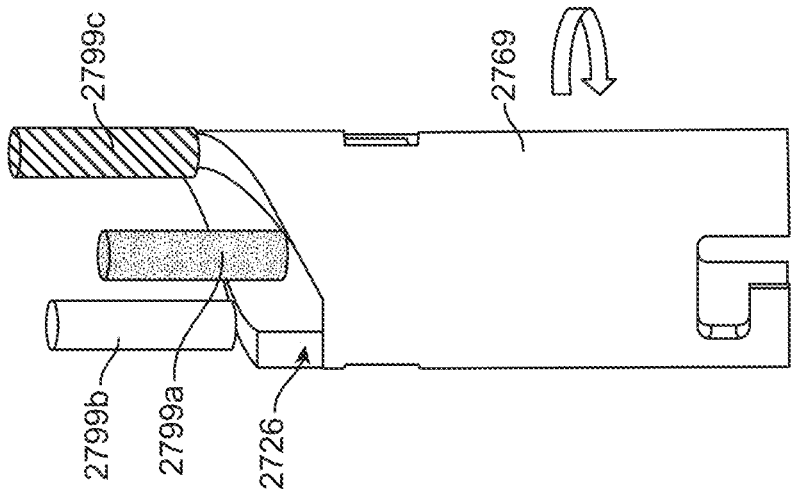
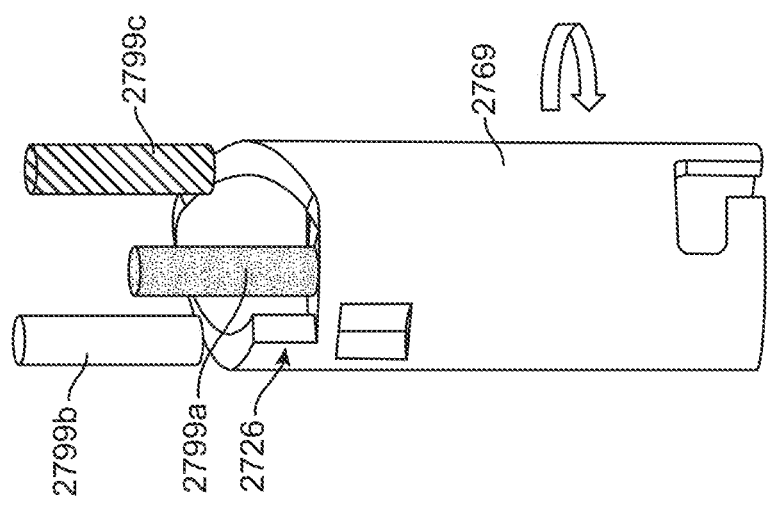
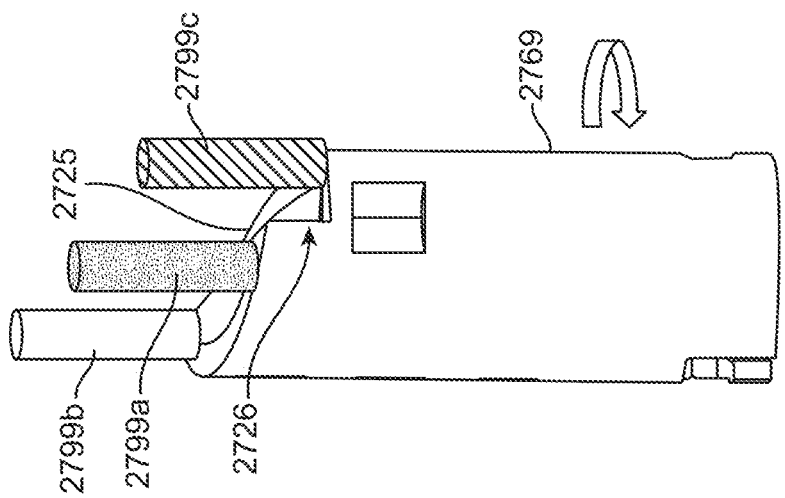

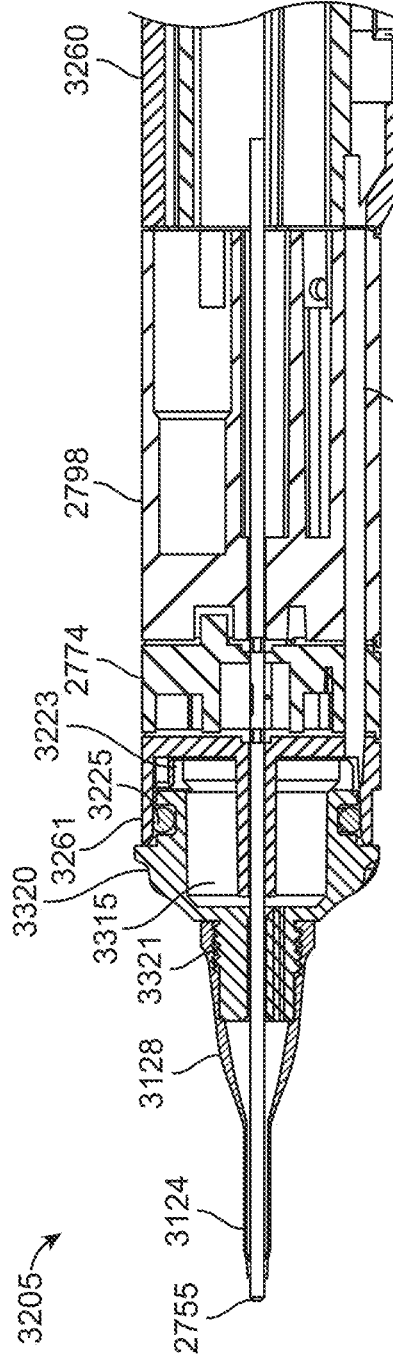
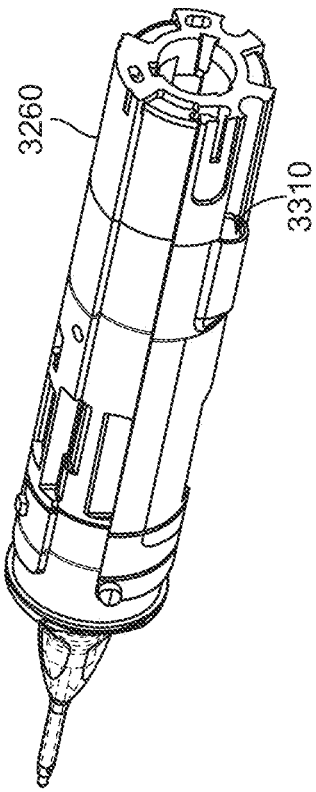
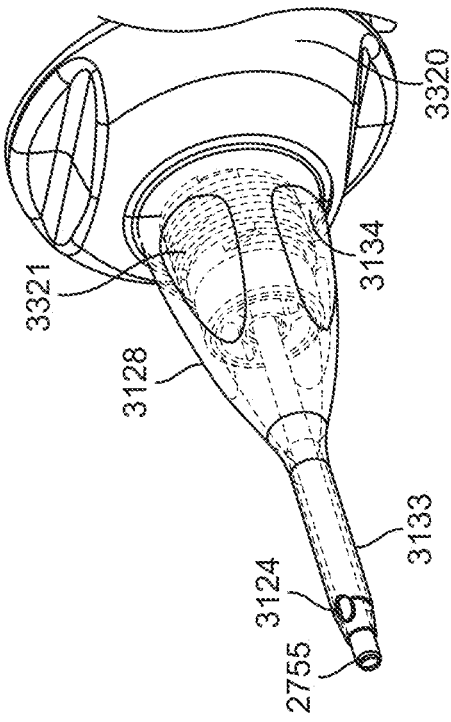
FIG. 9A
FIG. 9C
FIG. 9B

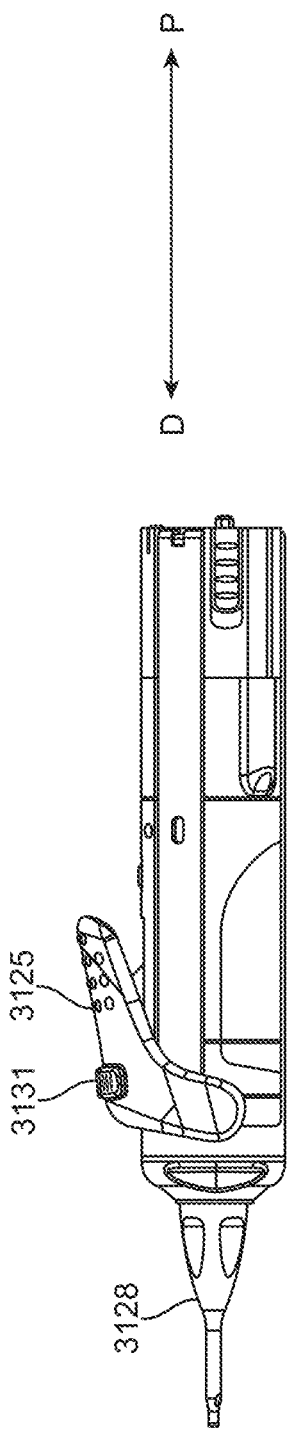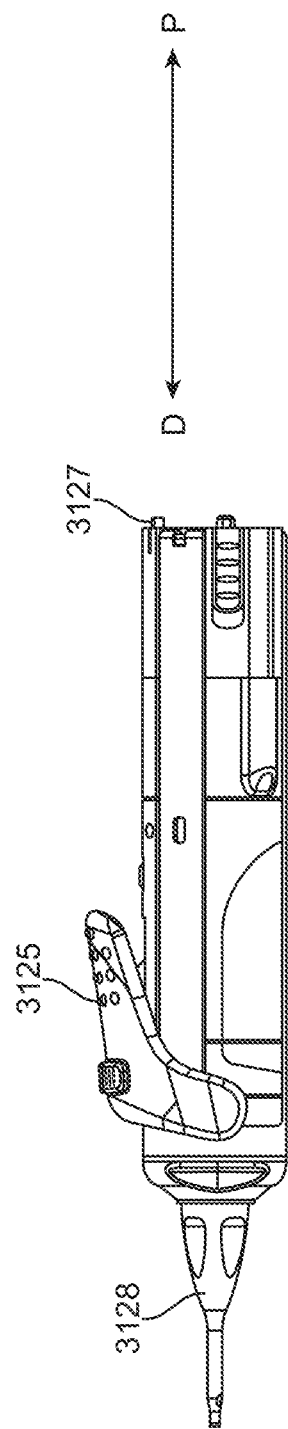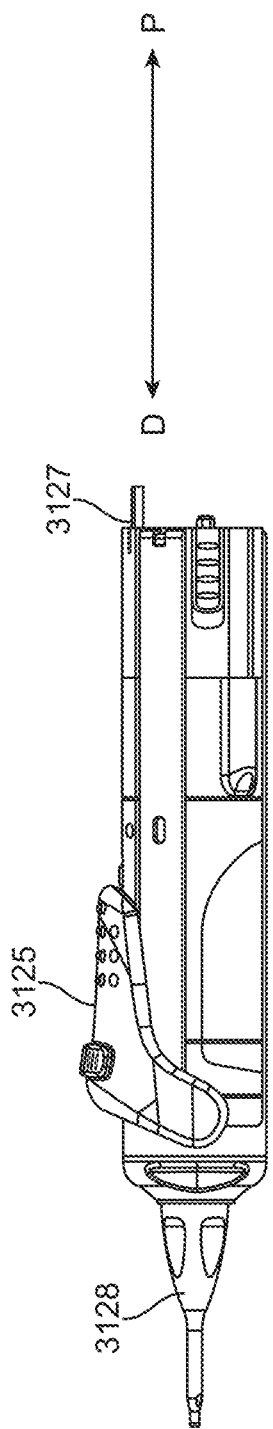

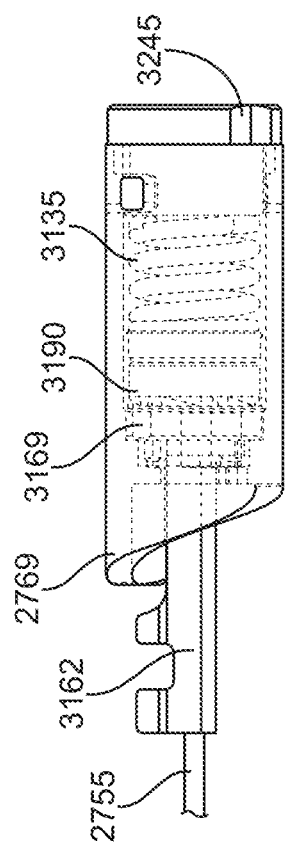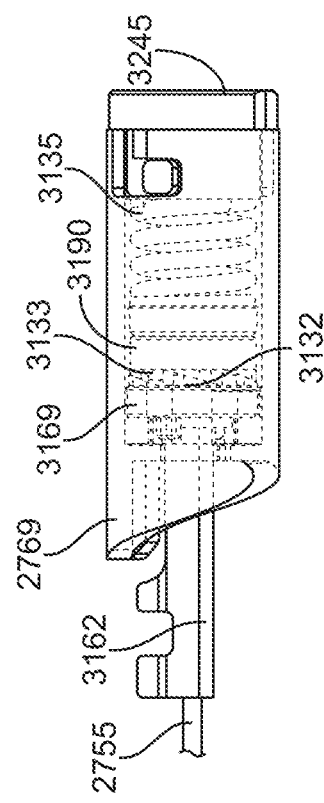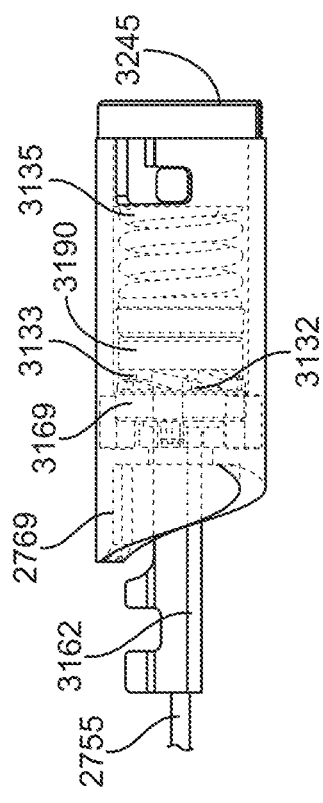

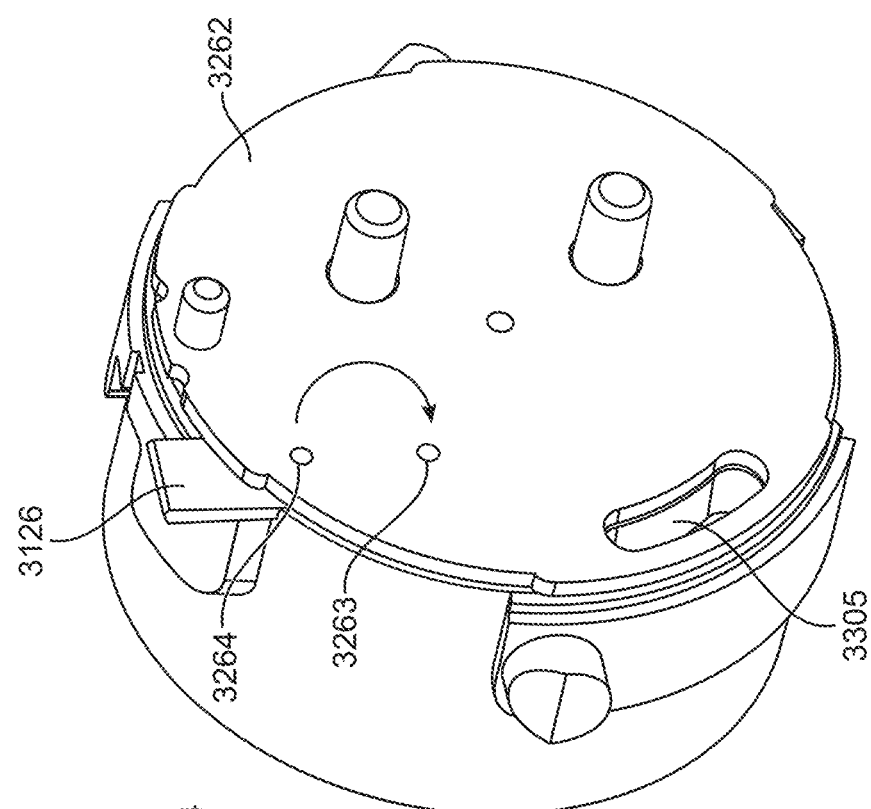
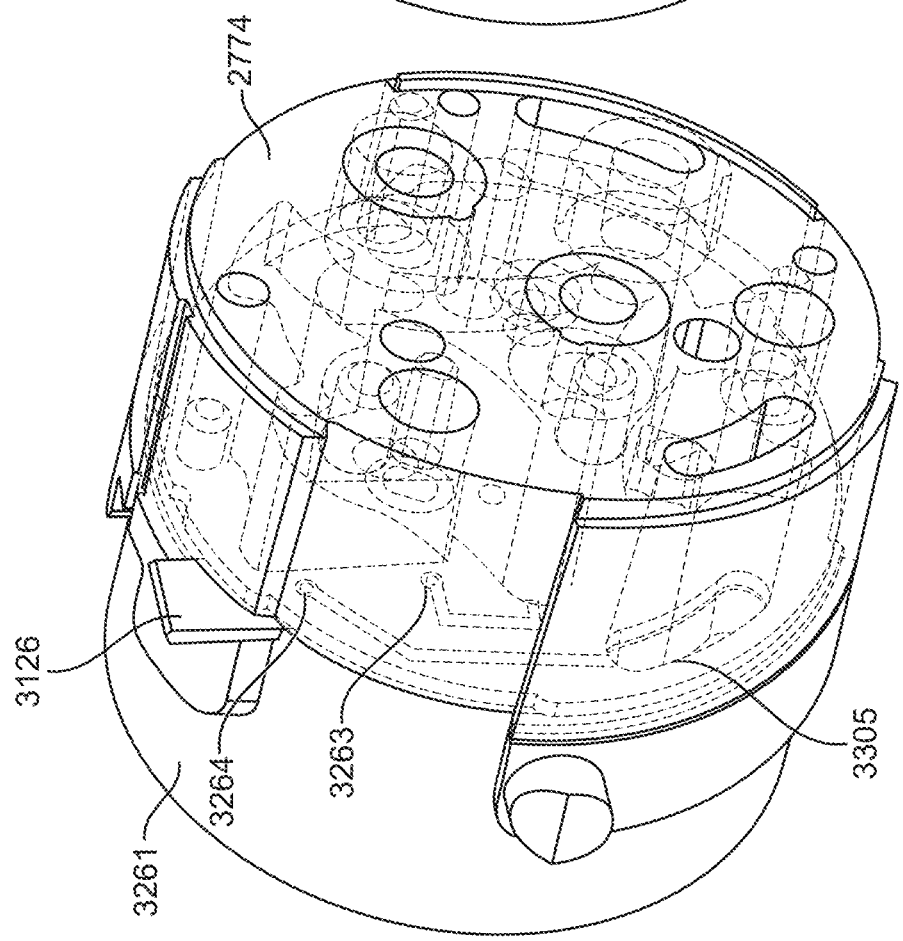
FIG. 16F
FIG. 16E

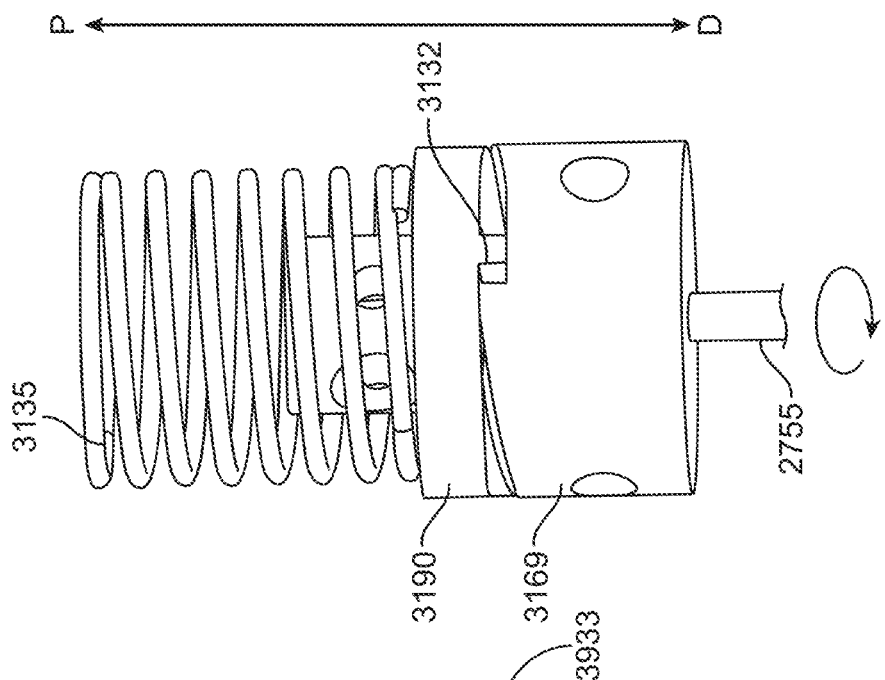
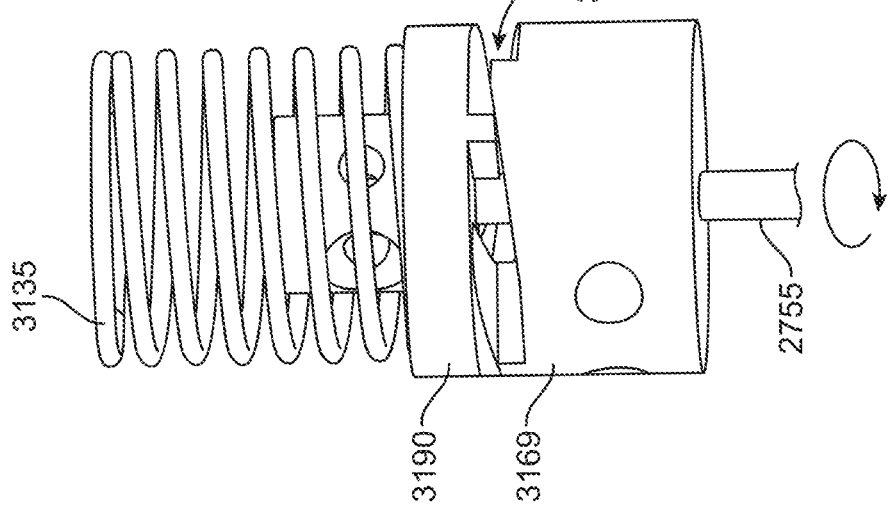
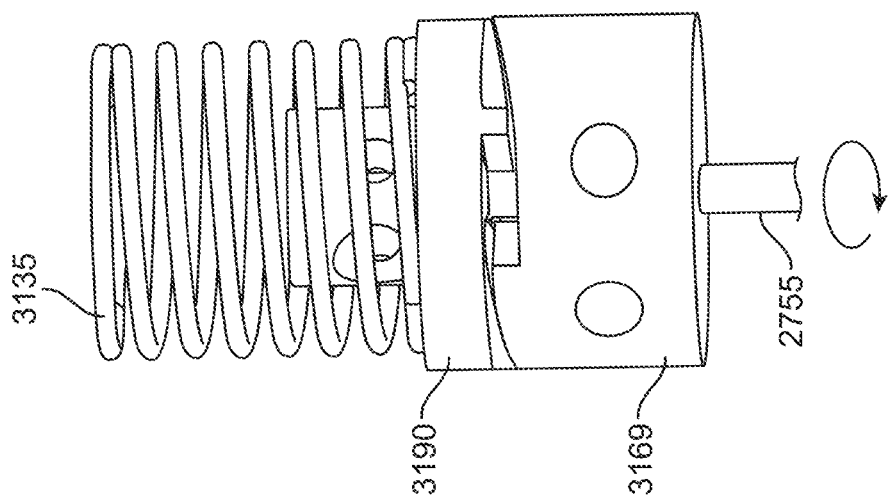

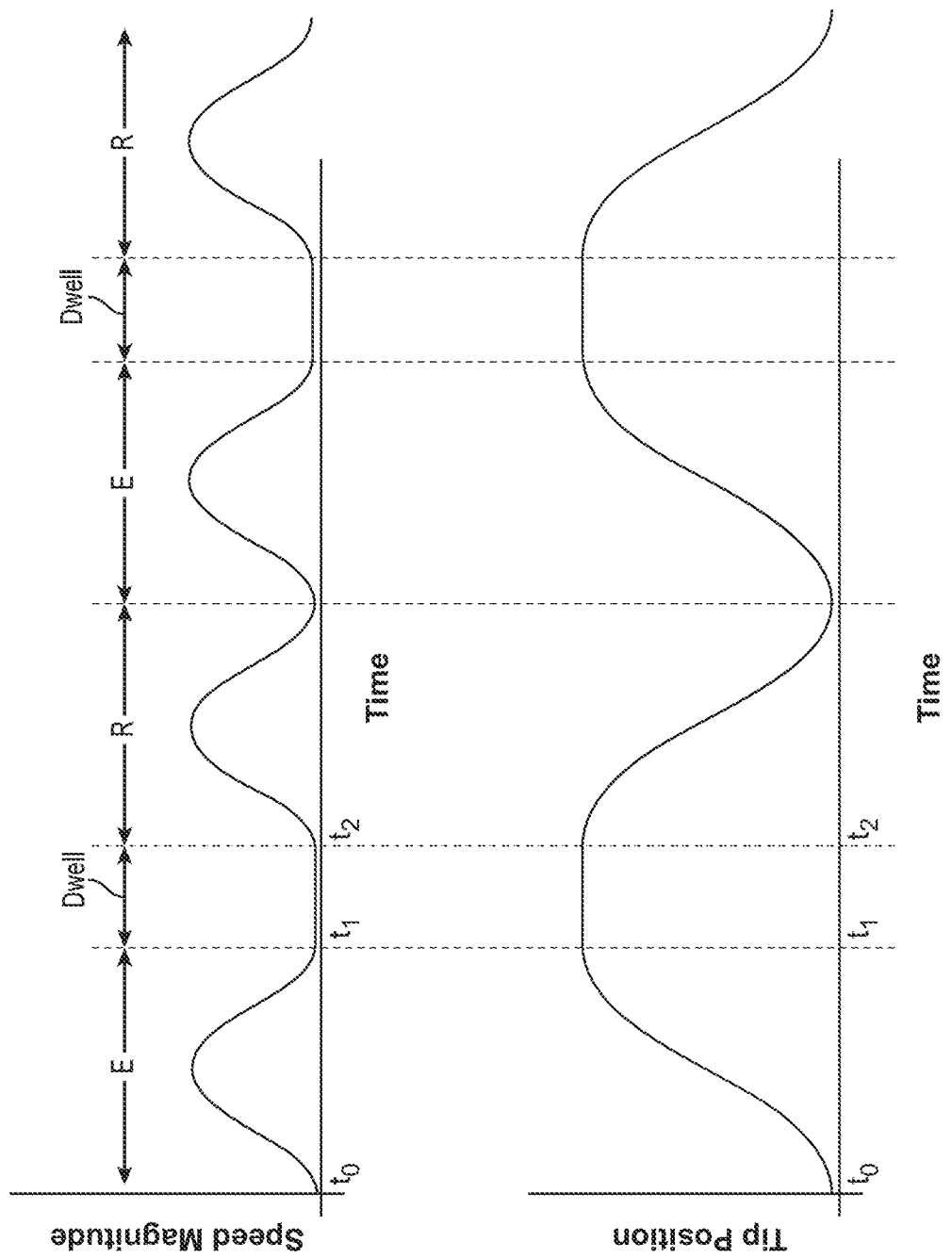

OPHTHALMIC MICROSURGICAL TOOLS, SYSTEMS, AND METHODS OF USE

CROSS-REFERENCE TO RELATED APPLICATIONS

The present application claims the benefit of priority under 35 U.S.C. § 119(e) to U.S. Provisional Patent Application Serial Nos. 62/680,723, filed Jun. 5, 2018; 62/692,443, filed Jun. 29, 2018; 62/789,348, filed Jan. 7, 2019; and 62/846,280, filed May 10, 2019. The disclosures of the provisional applications are hereby incorporated by reference in their entireties.

FIELD

The present technology relates generally to ophthalmic microsurgical tools and systems, in particular, ophthalmic microsurgical tools and systems having integrated pumping and fluid management systems.

BACKGROUND

Certain types of conventional ophthalmic surgery require breaking up lenticular tissue and intraocular objects, such as the intraocular lens or vitreous so that they can be extracted from the eye. For example, extraction of lenses for cataract surgery is one of the most common surgical procedures with more than 3 million cases performed annually in the United States alone. During cataract surgery a commonly-used method for lens extraction is phacoemulsification, which uses ultrasonic energy to emulsify the lens and aspiration to remove the lens emulsate from the eye. Other methods of lens fragmentation and extraction may include the use of instruments such as hooks, knives, or lasers to fragment the lens into pieces small enough to be extracted through an incision in the cornea in an ab interno approach. Intraocular, ab interno fragmentation of the lenticular tissue is important in cataract surgery in order to allow removal of cataracts from ocular incisions that are typically not exceeding 2.8-3.0 mm.

Typical phacoemulsification systems include a console in operative communication with a phacoemulsification hand piece. The console typically includes a cabinet, including a power supply, a pump, electronic and associated hardware. The console provides the control of the electronics of the hand piece, aspiration, and irrigation. The hand piece includes a resonating bar directly attached to a set of piezoelectric crystals on a first end and a needle-like cutting tube on the second end. The crystals supply ultrasonic vibration needed to drive the resonating bar and attached cutting tube during phacoemulsification.

During typical phacoemulsification procedures, the phaco tip extends past the distal end of the irrigation sleeve and is inserted into the anterior segment of the eye through a small incision in the cornea. The phaco tip of the cutting tube is brought into contact with the lens of the eye so that the oscillating phaco tip emulsifies the lens. The emulsate is then aspirated through the lumen of the phaco tip, along with any irrigation fluid provided to the eye during the procedure through the irrigation sleeve and directed toward a waste container. During cutting, irrigation fluid is delivered to the eye (i.e. passively or actively) through the irrigation sleeve positioned over the cutting tube. The irrigation fluid is intended to maintain the pressure balance within the eye and prevent collapse of the anterior chamber during the removal of the emulsified lens.

A challenge associated with conventional phaco devices and other devices using a remote vacuum source is that the suction lines are quite long and flexible contributing to the fluidic system compliance. Lastly, the system often contains compressible gas or other material that further adds to the compliance of the system. Long, compliant suction lines containing compressible material affects the responsive times at the tip when suction is turned on and off. Yet another problem with some systems, such as venturi-based systems, is that the waste fluid disposal enclosure is also exposed to vacuum pressure and, as such, the container and gas or other compressible material therein, also responds to changes in pressure and further contributing to the delay in initiation and termination of suction at the tip and contributing to the low responsiveness of some systems.

Conventional methods and devices for delivery of irrigation to an eye, for example during cataract surgery, may also use a substantial amount of circulated irrigation balanced saline solution (BSS). For example, bottles and bags of BSS may be in the range of 250 cc to 500 cc. Corneal endothelial cells can be damaged in multiple ways including the amount of ultrasonic energy delivered to the eye as well the amount of irrigation fluid that circulates through the anterior chamber. Additionally, when larger amounts of irrigation fluid are used, flow rates through the eye are higher and therefore additional turbulence of the irrigating fluid may exist and further cause corneal endothelial cell damage.

SUMMARY

In some implementations, disclosed is a system for extracting lens material from an eye. The system includes a surgical instrument having a drive mechanism having a motor, a first aspiration pump driven by the drive mechanism, and an elongate member sized and configured to extend through an anterior chamber of the eye and to a capsular bag of the eye. The elongate member includes an inner lumen fluidly coupled to the first aspiration pump and defining at least a portion of an aspiration waste line, and an open distal end having a distal cutting tip. The elongate member is configured to be oscillated by the drive mechanism. The system further includes a fluid system remote from the surgical instrument including a second aspiration pump, and a fluid line fluidly coupled to the second aspiration pump. The fluid line is configured to deliver background aspiration from the second aspiration pump to the inner lumen of the elongate member to aspirate the lens material from the eye towards the inner lumen.

The first aspiration pump can be configured to create discontinuous, pulsatile aspiration through the inner lumen to aspirate the lens material from the eye into the inner lumen. The first aspiration pump can be a piston pump. The background aspiration delivered by the second aspiration pump can be continuous, background aspiration through the inner lumen. The second aspiration pump can be a peristaltic pump or a roller pump. A flow rate of the background aspiration created by the second aspiration pump can be less than a flow rate of aspiration created by the first aspiration pump. The flow rate of the second aspiration pump can be about 10 mL/minute and the flow rate of the first aspiration pump can be about 30 mL/minute.

The surgical instrument can further include an irrigation line coupleable to a source of irrigation fluid. The source of irrigation fluid can be part of the surgical instrument. The source of irrigation fluid can be part of the fluid system. A total volume of irrigation fluid provided to the surgical instrument during use can be less than about 250 mL down to about 10 mL. The fluid system can further include an irrigation line fluidly coupling a source of irrigation fluid of the fluid system to the irrigation line of the surgical instrument. The irrigation line of the fluid system can include a valve configured to control irrigation fluid flow through the irrigation line of the fluid system.

The instrument can further include an input on a housing of the surgical instrument. The input can be a multi-way trigger configured to activate different functions of the surgical instrument depending on degree of trigger depression. A first degree of trigger depression can open the valve of the irrigation line of the fluid system placing the surgical instrument into an irrigation-only mode. A second degree of trigger depression can activate the second aspiration pump placing the surgical instrument in an irrigation-continuous aspiration mode. A third degree of trigger depression can activate the first aspiration pump and oscillation of the elongate member placing the surgical instrument in an irrigation-pulsed aspiration-cutting mode. Trigger depression beyond the third degree of trigger depression can increase at least one of oscillation frequency and aspiration flow rate. The third degree of trigger depression can additionally deactivate the second aspiration pump. The input can incorporate a sensing mechanism selected from the group consisting of capacitive sensor, optical sensor, magnetic sensor, electromagnetic sensor, and Hall-Effect sensor. The first aspiration pump and the second aspiration pump can be configured to concurrently apply aspiration through the inner lumen.

The surgical instrument can further include a hand-held portion having a proximal, reusable portion releasably coupleable to a distal, disposable portion. The hand-held portion can include a rotatable coupler configured for releasably operatively coupling rotation of the motor to the distal, disposable portion. The proximal, reusable portion can remain outside of the eye. The first aspiration pump can include a plurality of pistons, each of the plurality of pistons being housed within a respective cylinder, each of the cylinders fluidly coupled to the inner lumen of the elongate member. The drive mechanism can further include a rotational cam assembly capable of being rotated by the motor via a rotatable coupler, Rotation of the rotational cam assembly can cause the plurality of pistons to generate pulses of discontinuous negative pressure within the inner lumen.

The aspiration created by the first aspiration pump can be selectively modifiable by a user. The surgical instrument can further include a piston hard stop configured to limit proximal travel of the plurality of pistons within their respective cylinders. The piston hard stop can be configured to toggle between a high vacuum position and a low vacuum position. When in the high vacuum position, the piston hard stop can be retracted proximally relative to the cylinders allowing for maximum proximal travel of each piston within its respective cylinder. When in the low vacuum position, the piston hard stop can be advanced distally relative to the cylinders limiting proximal travel of the each piston within its respective cylinder to less than a maximum proximal travel. The piston hard stop can be configured to toggle between a continuous aspiration position and a pulsatile aspiration position. When in the continuous aspiration position, the piston hard stop can be advanced distally relative to the cylinders limiting proximal travel of each piston within its respective cylinder and relative to the rotational cam assembly of the drive mechanism. When in the pulsatile aspiration position, the piston hard stop can be retracted proximally relative to the cylinders allowing full proximal travel of each piston within its respective cylinder and relative to the rotational cam assembly of the drive mechanism.

The surgical instrument can further include an anti-surge valve located within the aspiration waste line of the surgical instrument. The anti-surge valve can be configured to limit flow through the aspiration waste line when a flow rate of aspiration is above a threshold value and configured to allow flow through the aspiration waste line when the flow rate of aspiration is below the threshold value. The threshold value can be 40 ml/minute. The anti-surge valve can be a diaphragm valve, an umbrella valve, or a mushroom valve. The anti-surge valve can further include a filter.

In an interrelated aspect, disclosed is a device for extracting lens material from an eye. The device includes a drive mechanism having a motor, an aspiration pump driven by the drive mechanism that is selectively modifiable by a user, and an elongate member configured to be oscillated by the drive mechanism. The elongate member is sized and configured to extend through an anterior chamber of the eye and to a capsular bag of the eye. The elongate member includes an inner lumen fluidly coupled to the aspiration pump and defining at least a portion of an aspiration waste line, and an open distal end having a distal cutting tip.

The aspiration created by the aspiration pump and delivered through the inner lumen to aspirate the lens material from the eye into the inner lumen can be selectively modifiable between continuous, background aspiration and discontinuous, pulsatile aspiration. The aspiration pump can be a piston pump having a plurality of pistons. Each of the plurality of pistons can be housed within a respective cylinder. Each of the cylinders can be fluidly coupled to the inner lumen of the elongate member. The drive mechanism can further include a rotational cam assembly capable of being rotated by the motor via a rotatable coupler. Rotation of the rotational cam assembly can cause the plurality of pistons to generate pulses of discontinuous negative pressure within the inner lumen. The device can further include a piston hard stop configured to limit proximal travel of the plurality of pistons within their respective cylinders. The piston hard stop can be configured to toggle between a high vacuum position and a low vacuum position. When in the high vacuum position, the piston hard stop can be retracted proximally relative to the cylinders allowing for maximum proximal travel of each piston within its respective cylinder. When in the low vacuum position, the piston hard stop can be advanced distally relative to the cylinders limiting proximal travel of each piston within its respective cylinder to less than maximum proximal travel. The piston hard stop can be configured to toggle between a continuous aspiration position and a pulsatile aspiration position. When in the continuous aspiration position, the piston hard stop can be advanced distally relative to the cylinders limiting proximal travel of each piston within its respective cylinder and relative to the rotational cam assembly of the drive mechanism. When in the pulsatile aspiration position, the piston hard stop can be retracted proximally relative to the cylinders allowing full proximal travel of each piston within its respective cylinder and relative to the rotational cam assembly of the drive mechanism.

The device can include a proximal, reusable portion releasably coupleable to a distal, disposable portion. The proximal, reusable portion can be configured to remain outside of the eye. The piston pump can be located within the distal, disposable portion and the rotational cam assembly can be located within the proximal, reusable portion or the distal, disposable portion.

In some variations, one or more of the following can optionally be included in any feasible combination in the above methods, apparatus, devices, and systems. More details of the methods, apparatus, devices, and systems are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIGS. 4A-4B show side views of an implementation of a microsurgical tool for cutting and aspirating material from an eye configured to be used with a microsurgical control system.

FIGS. 8A-8D illustrate cam mechanisms of the microsurgical instrument of FIGS. 7A-7H.

FIGS. 8F-8H schematically illustrates piston movements on another cam surface.

FIGS. 9A-9C show various views of an implementation of a microsurgical instrument.

FIGS. 13A-13C illustrate various stages of actuation of a microsurgical tool having an elongate member.

FIGS. 15A-15C illustrate partial views of the tool of FIGS. 13A-13C in the various stages of actuation.

FIGS. 16E-16F illustrate the venting mechanism of FIGS. 16C-16D from a proximal end perspective through the vacuum manifold in transparency.

FIGS. 17B-17D are side views of the oscillating mechanism of FIG. 17A in various stages of rotation.

FIG. 18G shows a non-sinusoidal movement of the distal tip of an elongate member (bottom panel) relative to its extension speed profile (top panel).

and a vacuum profile for aspiration through the elongate member (hatched line) with the piston pump.

Figure 20A:
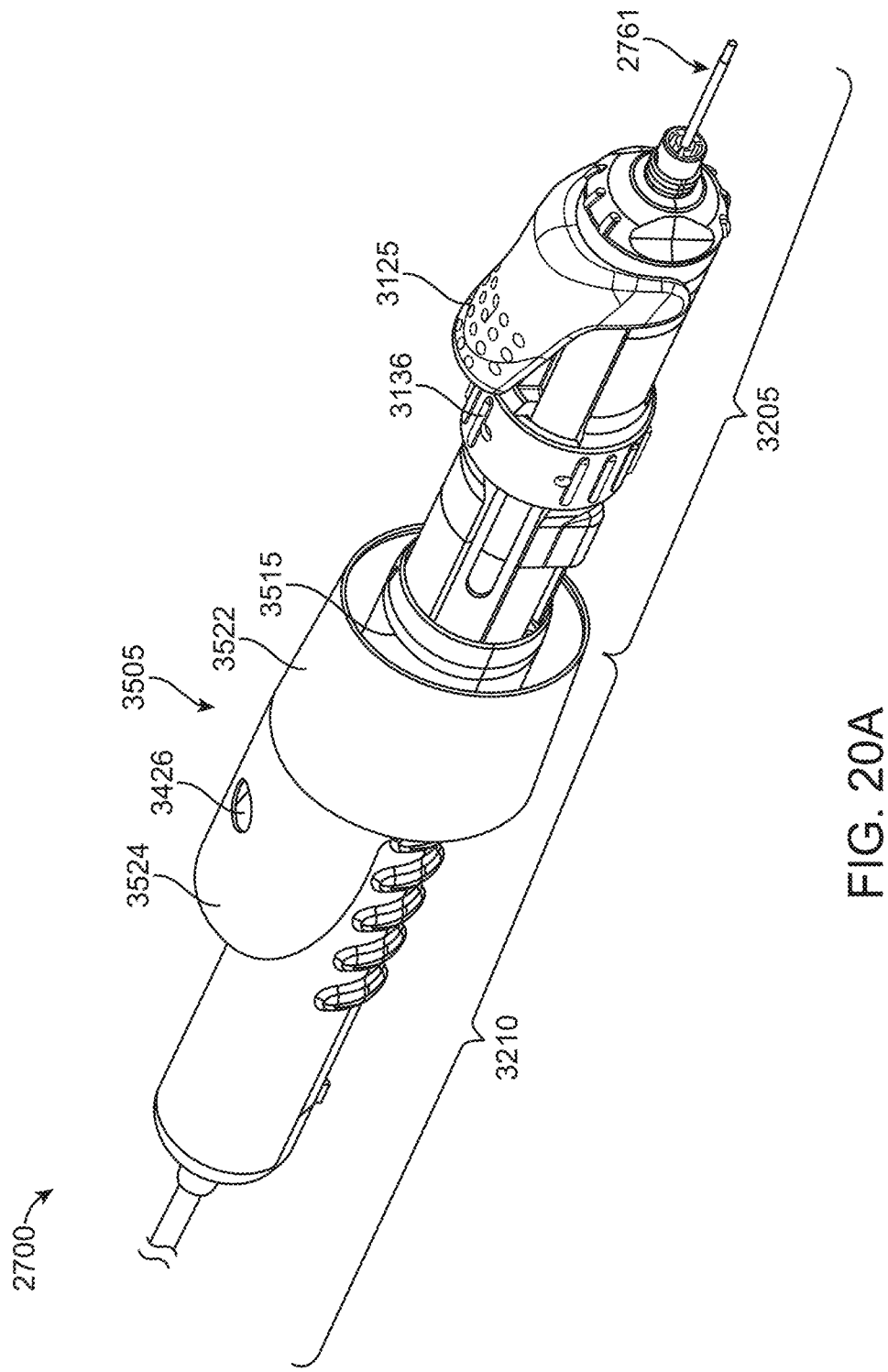

FIG. 20A shows a sterility sheath in a furled configuration positioned on a housing of an instrument.

Figure 20B:
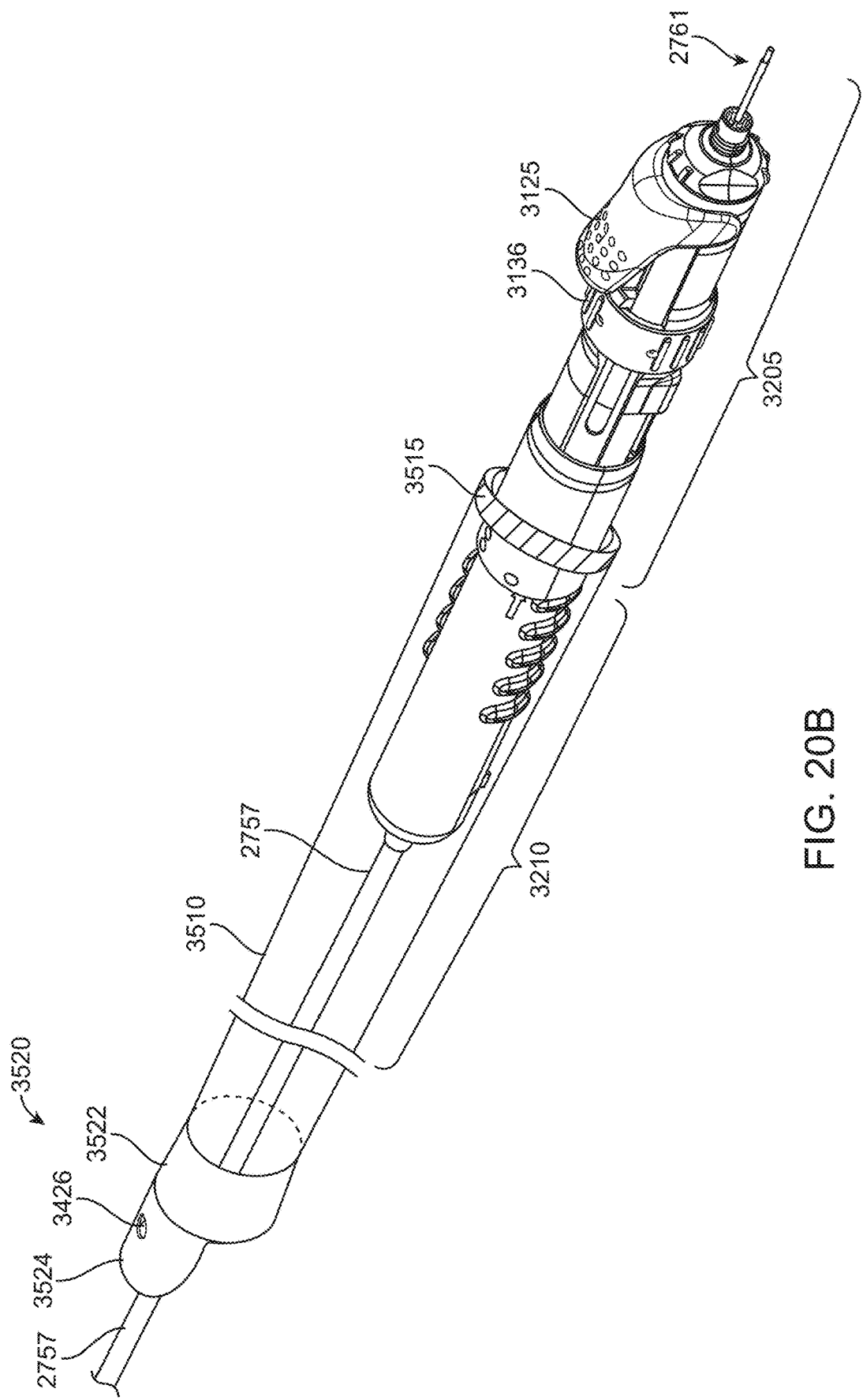

FIG. 20B shows the sterility sheath of FIG. 20A in an unfurled configuration after deployment over the housing of the instrument.

Figure 21:
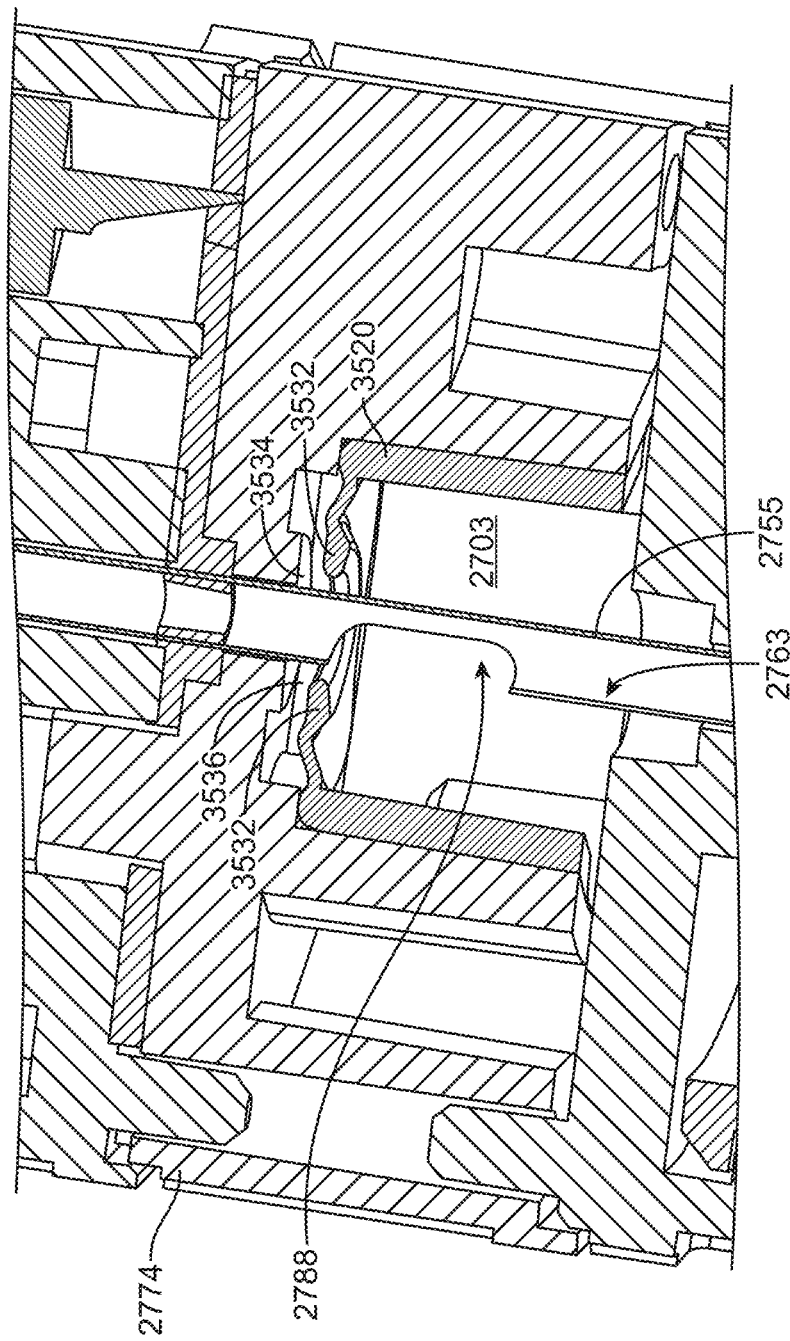

FIG. 21 shows a valve within the vacuum manifold of the instrument configured to prevent post-occlusion surge.

FIGS. 22A-22D show an implementation of a filter for a valve configured to prevent post-occlusion surge.

Figure 23:
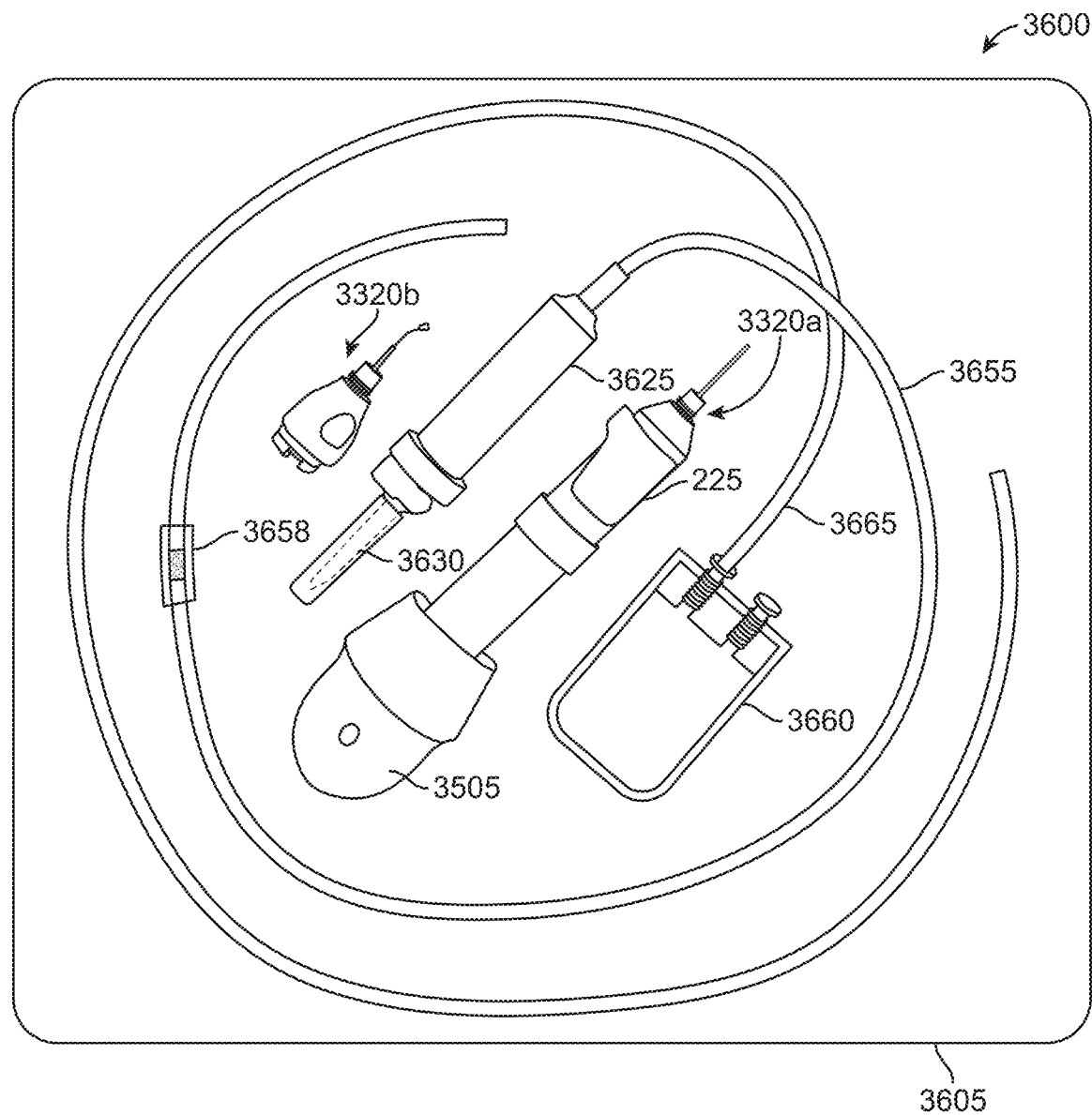

FIG. 23 shows an implementation of a kit containing an instrument in a sterile package.

It should be appreciated that the drawings are for example only and are not meant to be to scale. It is to be understood that devices described herein may include features not necessarily depicted in each figure.

DETAILED DESCRIPTION

Described herein are systems, devices, and methods for ophthalmic microsurgical tools useful for intraocular fragmentation and removal of the lens, vitreous, and other tissues during intraocular surgery. The various systems, devices, and methods are configured to perform one or more functions useful in ophthalmic procedures including, but not limited to, cutting, fragmentation, emulsification, aspiration, and/or irrigation of material present at a target location during a procedure in the eye. "Material" as used herein can include fluids (from the eye or provided to the eye), tissues, or fragments of tissues such as lenticular tissue, vitreous, cells, and any other fluid or tissue or other material that may be present during a procedure in the eye (e.g. cataract procedure, vitrectomy procedures, and the like). The systems, devices, and methods described herein are configured to apply vacuum and deliver fluids to maintain a pressure balance within the eye. The systems, devices, and methods described herein that apply vacuum and/or deliver fluids may also be configured to cut, fragment, emulsify, or otherwise make smaller material in and near the surgical site. The systems, devices, and methods described herein that allow for vacuum to be applied can provide that vacuum using pulsed vacuum with or without interspersed pulsed positive pressure to provide momentary retrograde flow.

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, bag polishing systems, and other tools useful in performing cataract surgeries or vitrectomy surgery, and the like.

Microsurgical System

Figure 1A:
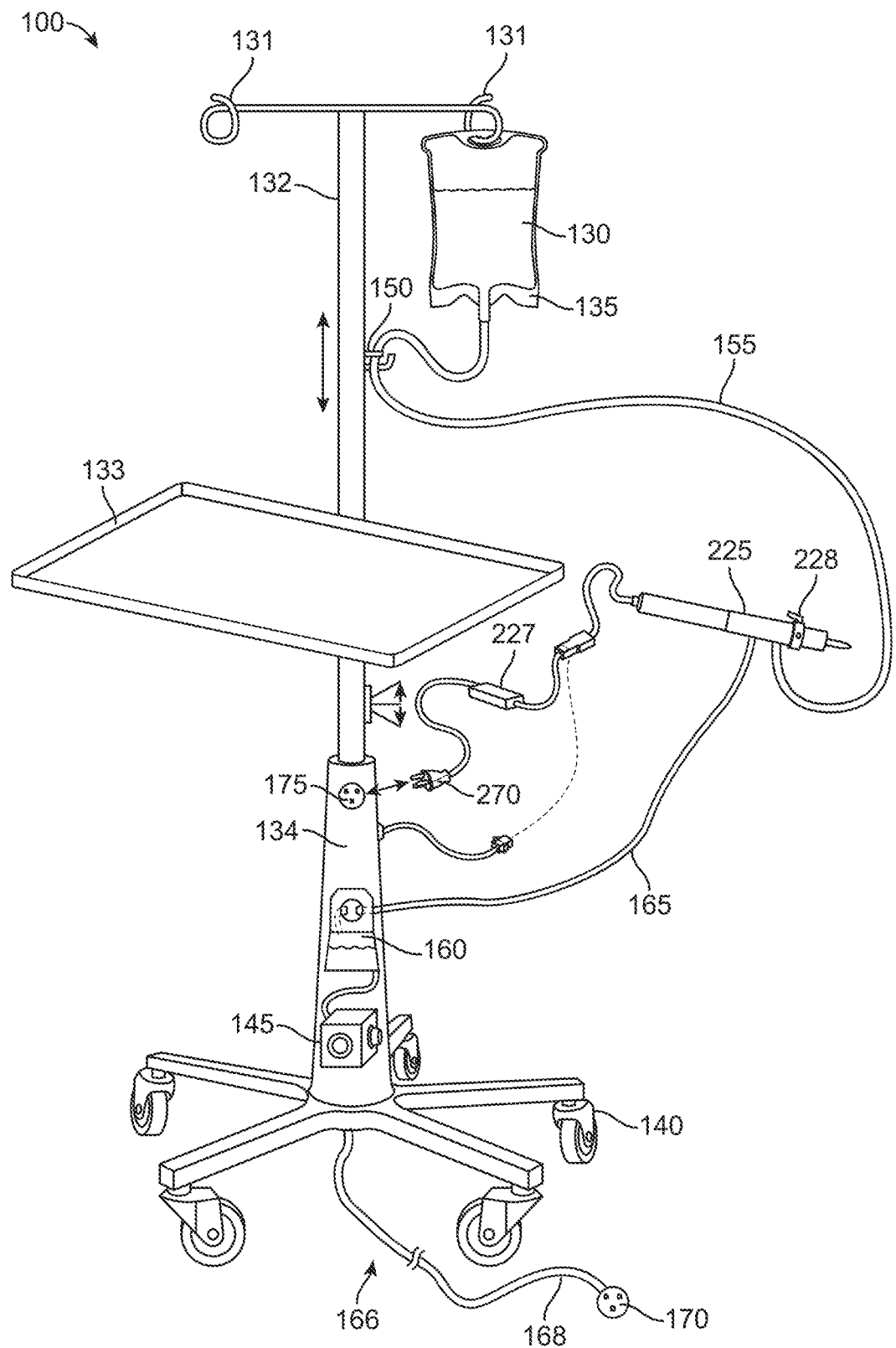
FIG. 1A is a perspective view of a microsurgical control system according to an implementation for use with ophthalmic microsurgical tools.
Figure 1B:
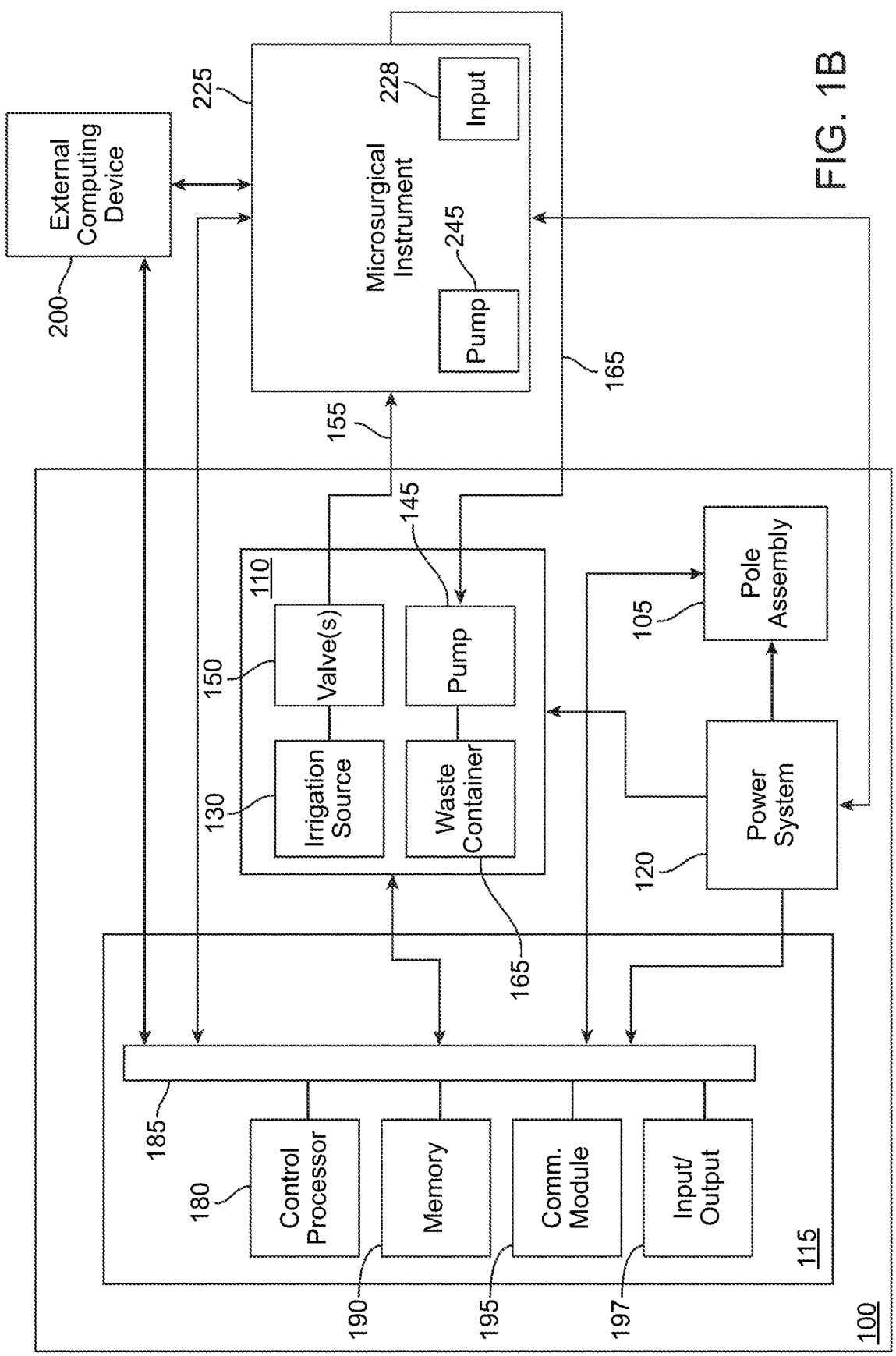
FIG. 1B is a block diagram of the microsurgical control system of FIG. 1A.

FIGS. 1A and 1B illustrate a microsurgical system 100 according to an implementation. The microsurgical system 100 can be used with one or more ophthalmic microsurgical instruments 225 (sometimes referred to herein as a "device" or "tool" or "peripheral device" or "hand piece" or "hand held unit") for use by a surgeon in performing various ophthalmic surgical procedures. Any of the microsurgical instruments and devices described herein can be operatively coupled with the system 100. The microsurgical system 100 can include a fluid system 110 that is coupled to a pole assembly 105. The pole assembly 105 and the fluid system 110 can each be controlled by a computing unit 115 powered by power system 120. The fluid system 110 can include an irrigation fluid source 130 in a container 135, an irrigation line 155 leading to the microsurgical instrument 225, a waste line 165 leading from the microsurgical instrument 225 towards a waste container 160, and at least one aspiration pump 145. The system 100 can provide irrigation to the microsurgical instrument 225 by coupling the irrigation line 155 of the fluid system 110 to an irrigation inlet of the instrument 225. The system 100 can also supply aspiration pressure for the microsurgical instrument 225 by coupling the waste line 165 of the fluid system 110 to a waste outlet of the instrument 225. The relative amounts of fluids entering and exiting the surgical field of the eye are preferably balanced such that the anterior chamber of the eye does not collapse. It is also preferred that the total irrigation volumes provided to the microsurgical instrument 225 be kept under a certain volume, for example, less than about 250 mL, less than about 200 mL, less than about 150 mL, less than about 100 mL, less than about 50 mL, down to about 10 mL. Each of the components of the microsurgical system 100 and the microsurgical instrument 225 will be described in more detail below.

As best shown in FIG. 1B, one or more components of the system 100 can be controlled by the computing unit 115. The computing unit 115 can include a control processor 180, a memory 190, a communication module 195, and one or more input/outputs 197. Components of the computing unit 115 such as the control processor 180, memory 190, communication module 195, one or more input/outputs 197, storage devices, etc. can be interconnected via a system bus 185. The control processor 180 can be in operative communication with one or more of the pole assembly 105, the fluid system 110, and the microsurgical instrument 225 coupled to the system 100. The control processor 180 can also be in operative communication with one or more external computing devices 200. The external computing device 200 can vary including, but not limited to, desktop computer, laptop computer, tablet computer, smartphone, or other device capable of communicating and receiving user input. The memory 190 is configured for receiving and storing user input data. The memory 190 can be any type of memory capable of storing data and communication that data to one or more other components of the system 100, such as the control processor 180. The memory 190 may be one or more of a Flash memory, SRAM, ROM, DRAM, RAM, EPROM, dynamic storage, and the like. The memory 190 can be configured to store one or more user-defined profiles relating to the intended use of the instrument 225. The memory 190 can be configured to store user information, history of use, measurements made, and the like.

The communication module 195 of the computing unit 115 can be in operative communication with one or more components of the system 100, such as the control processor 180, as well as with one or more peripheral devices such as the one or more external computing devices 200 and the microsurgical instrument 225. The connection between the communication module 195 of the computing unit 115 and the external computing device 200 or microsurgical instrument 225 can include a wired communication port such as a RS22 connection, USB, Fire wire connections, proprietary connections, or any other suitable type of hard-wired connection configured to receive and/or send information to the external computing device 200 and/or microsurgical instrument 225. The communication module 195 can also include a wireless communication port such that information can be fed between the computing unit 115 and the external computing device 200 and/or microsurgical instrument 225 via a wireless link, for example, to display information in real-time on the external computing device 200 about operation of the system 100, and/or control programming of the microsurgical instrument 225. It should be appreciated that the external computing device 200 can communicate directly to the microsurgical instrument 225, for example, if the instrument 225 is being operated independently of the system 100. Any of a variety of adjustments to and programming of the system 100 can be performed using the external computing device 200. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols.

The control processor 180 can be capable of processing instructions for execution within the system 100. Such executed instructions can implement one or more of the processes described herein related to the use of the system or peripheral devices in operative communication with the system 100. The control processor 180 can be a single-threaded processor or a multi-threaded processor. The control processor 180 can be capable of processing instructions stored in the memory 190 and/or on a storage device to provide an output of information to the user about operation of the system 100. The control processor 180 can include software capable of being programmed to adjust or provide limits on the one or more aspects of the system 100 as well as a microsurgical instrument 225 coupled to the system 100. The software run by the control processor 180 can provide certain aspects of the system 100 or a microsurgical instrument connected to the system 100 without any user input during use. In an implementation, the adjustments or programming can be via the control processor 180 that is controlled by software, either within the system 100 or on the external computer device 200. A user can program the controller 180 remotely via the external computing device 200 in communication with the system 100 via a wireless connection such as Bluetooth. One or more aspects of the system 100, which will be described in detail below, can be programmed including the height of irrigation source 130, height of waste container 160, the speed of pump 145, etc. The instrument 225 can also include a computing unit including a control processor, memory, and/or communication module in operative communication with one or more components of the instrument (e.g. drive mechanism, vacuum source, or other components of the instrument). One or more aspects of the microsurgical instrument 225, which will also be described in detail below, can be programmed including, speed of pulsatile suction, speed of oscillating mechanical tip, limits of maximum speeds, disable/enable various modes (i.e. pulsed mode or burst mode), adjust parameters of modes (i.e. on time vs. off time during pulse mode), and various other controllable parameters of the instrument 225 as described elsewhere herein. A user can also program the microsurgical instrument 225 using the external computing device 200 in communication with the instrument 225 directly rather than through the system 100 as described in more detail below.

The instrument 225 and/or the system 100 can also be programmed to provide limits on a particular action upon actuation of the input. For example, the drive mechanism of the instrument 225 can be programmed to have a minimum and/or maximum speed upon actuation of the input or, in the case of fluid infusion and aspiration, the instrument 225 can be programmed to have a minimum and/or maximum fluid pressure upon actuation of an input. Thus, the instruments 225 described herein can be programmed using inputs adjustable by a user as well as by pre-programmed instructions that impact the one or more aspects of the instrument 225 upon actuation of the inputs.

As mentioned, the computing unit 115 of the system 100 (or of the instrument 225) can be controlled, adjusted, and/or programmed remotely such as via an external computing device 200. The computing unit 115 of the system 100 can also be controlled, adjusted, and/or programmed directly via one or more inputs 197 on the system 100 as well as one or more inputs 228 on the instrument 225. Thus, the devices described herein can be used such that one or more aspects are manually controlled and/or adjusted according to manual inputs by the user or programmed to control the one or more aspects. The controller can include software capable of being programmed to adjust or provide limits on the one or more aspects of the device. Thus, the software run by the controller can provide certain aspects of the device without any user input during use. In an implementation, the adjustments or programming can be via a controller that is controlled by software, either within the device or on an external computer device 200 in operative communication with the device directly or via the system 100. A user can program the controller remotely via an external computing device in communication with the device via a wireless connection such as Bluetooth.

The inputs 197 of the system 100 can include one or more triggers, buttons, sliders, dials, keypads, switches, touch-screens, foot pedals, or other input that can be retracted, pressed, squeezed, slid, tapped, or otherwise actuated to activate, modify, or otherwise cause a response of the system 100. In some implementations, the one or more inputs 197 includes a microphone 198 configured to receive voice commands to control, adjust, and/or program one or more components of the system 100 as well as peripheral devices in operative communication with the system 100. The inputs 197 of the system can be separate from and in addition to one or more inputs 228 on the microsurgical instrument 225, which will be discussed in more detail below.

Again with respect to FIGS. 1A and 1B, one or more of the pole assembly 105, the fluid system 110, the computing unit 115, as well as a microsurgical instrument 225 or other peripheral device connected to the system 100, can be powered by the power system 120. For example, the power system 120 can provide power to the pole assembly 105 to adjust the height of the irrigation source 130 by telescopically adjusting the pole 132 relative to the base 134 such as with a motor or other powered mechanism. The power system 120 can provide power to the aspiration pump 145 of the fluid system 110 as well as the one or more valves 150 configured to control fluid flow towards the irrigation line 155. The power system 120 can also provide power to any peripheral devices, such as the microsurgical instrument 225, in operative communication with the system 100. The power system 120 can include a power outlet 166 having a cord 168 and a plug 170. The plug 170 is configured to insert within a wall socket to provide electrical power to the power system 120. The power system 120 can additionally include one or more sockets 175 configured to receive a plug of one or more peripheral devices such as the plug 270 of the microsurgical instrument power source 227. The power source 227 of the microsurgical instrument 225 can be plugged into one of the sockets 175 of the power system 120 of the system 100. The pole assembly 105 can also incorporate the power source 227 of the instrument such that the instrument need not include its own power source 227 and can plug directly into the pole assembly 105.

The pole assembly 105 can include one or more features typical of an intravenous (IV) pole. The pole assembly 105 can include a telescoping pole 132 configured to be movable relative to a base 134 such that the height of one or more hangers 131 can be adjusted. The hangers 131 are configured to suspend the irrigation fluid source 130 contained within one or more irrigation containers 135 of the fluid system 110 at a height calculated to create the proper fluid pressure in the irrigation line 155 between the irrigation source 130 and the microsurgical instrument 225. The irrigation source 130 can be suspended above the level of the patient by the hangers 131 of the pole assembly 105 and the irrigation line 155 can be coupled to a lower end region of the irrigation source 130.

The pole assembly 105 can incorporate one or more buttons, levers, foot pedals, or other actuators configured to adjust the height of the one or more hangers 131 thereby altering the irrigation fluid pressure and, correspondingly, alter the flow rate of the fluid in the inlet line. The height of the one or more hangers 131 can be adjusted manually and/or via a powered adjustment. For example, the pole assembly 105 can include a motorized system configured to move the telescoping pole 132 relative to the base 134. The pole assembly 105 can be in operative communication with the computing unit 115 such that the powered adjustment can be automatic depending on the fluid needs during a procedure, which will be described in more detail below. The base 134 of the pole assembly 105 can have a plurality of rotating casters 140 to ensure full mobility of the pole assembly 105. The casters 140 can be locked as is known in the art to prevent inadvertent movements during use. The pole assembly 105 can include one or more other user features such as an adjustable surgical tray or shelves or other storage site as well as one or more clamps, pinch valves, tubing loops, clips, etc. In some implementations, the pole assembly 105 can include an integrated surgical instrument tray 133, for example, a tray 133 clamped to the pole 132 (see FIG. 1A).

Still with respect to FIGS. 1A and 1B, and as mentioned above, the fluid system 110 can include an irrigation fluid source 130, irrigation line 155, waste line 165, waste container 160, and at least one aspiration pump 145. The aspiration pump 145 can be fluidly coupled to a fluid line configured to deliver background aspiration from the pump 145 to the inner lumen of the elongate member to aspirate the lens material from the eye towards the inner lumen. The fluid system 110 may optionally include an irrigation fluid pump configured to deliver irrigation fluid from the irrigation fluid source 130. Irrigation fluid may exit the irrigation fluid source 130 and travel toward the microsurgical instrument 225 through the irrigation fluid line 155. An optional irrigation fluid reservoir near the treatment site may be incorporated as well. For example, an irrigation fluid reservoir may be located within the distal end of the microsurgical instrument 225 to meet demand for fluid instantaneously, which will be described in more detail below.

The irrigation fluid source 130, instrument 225 and/or the irrigation line 155 may optionally include one or more valves 150 and/or sensors configured to provide additional control of fluid flow through the irrigation line 155 fluidly coupled to the instrument 225 either directly or through an irrigation port. The one or more valves 150 can be pinch valves or pinch clamps configured to tightly pinch the irrigation line 155 thereby preventing fluid flow towards the microsurgical instrument 225 or allowing full fluid flow from the irrigation source 130 towards the microsurgical instrument 225 upon opening the valve 150.

The valve 150 can be opened/closed manually as is known in the art. The valve 150 can alternatively or additionally be actuated upon input by the computing unit 115, for example, upon actuation of the microsurgical instrument 225 as will be described in more detail below. Other valve and clamp types are considered herein. The instrument 225 and/or the waste line 165 (which may be referred to herein as the aspiration line) may optionally include one or more valves and/or sensors configured to provide additional control of fluid flow from the instrument 225. The one or more valves 150 can be integrated within a region of the telescoping pole 132 near wherein the irrigation source 130 hangs such that the valves 150 can control flow through the irrigation line 155.

The irrigation source 130 can be positioned above the level of the eye providing a positive pressure gradient to cause fluid flow out of the irrigation source 130 towards the microsurgical instrument 225, for example, upon opening the valve 150. Opening valve 150 primes the line 155 with irrigation fluid removing any "dead volume" or "surge volume" such that the microsurgical instrument 225 is ready to deliver irrigation fluid, for example, out an irrigation sleeve (see, e.g., irrigation sleeve 3128 shown in FIG. 9B). As discussed below, the irrigation fluid will generally not flow out the openings in the sleeve of the instrument 225 until the valves in the aspiration system open. The hydrostatic pressure from an elevated irrigation source 130 is generally less than the cracking pressure of the one or more valves in the vacuum system of the hand-held portion, which remain in a closed position when the motor is turned off and open upon reaching a certain pressure difference. Irrigation can be passively fed towards the eye and the opening/closing of waste line can dictate whether and when the irrigation fluid flows out the openings and into the eye.

The fluid head pressure varies depending on the height of the irrigation source 130 relative to the eye. As the height of the irrigation source 130 increases relative to the treatment site, the greater fluid pressure through the irrigation line 155. As the height of the irrigation source 130 decreases relative to the treatment site, the lower fluid pressure through the irrigation line 155. Aspiration pressure drawing fluid away from the treatment site (e.g., via the aspiration pump 145 of the system) can be affected by the relative height of the waste container 160. The waste container 160 can be set at atmospheric pressure or lower. The lower the waste container 160 is relative to the treatment site, the greater the pressure differential and greater potential siphoning pressure. For example, the waste container 160 can be positioned below the level of the patient causing flow of fluid and materials from the eye towards the waste container 160. Lowering the waste container 160 further below the level of the patient causes a greater pressure differential.

The relative heights of both the irrigation source 130 and the waste container 160 can be adjustable, manually and/or automatically. The user can control the heights manually such as with an adjustment element on the pole assembly 105 or using an external computing device 200 that is in communication with the system 100. The heights can also be controlled automatically via the computing unit 115 of the system 100. The computing unit 115 of the system 100 can automatically adjust the height of the irrigation source 130 relative to the treatment site to provide a greater pressure differential, for example, when more fluid is needed at the treatment site. In this way, the system 100 can maintain a proper balance of fluid delivery and fluid withdrawal at the treatment site such as the anterior chamber. For example, during use of the system 100 the fluid level in the irrigation source 130 can decrease as more fluid is delivered to through the instrument 225. The system 100 can sense the change in fluid level and automatically raise the irrigation source 130 (i.e. raise the IV pole height) to maintain the fluid head of the irrigation source 130.

The system 100 and/or the microsurgical instrument 225 can sense relative amounts of fluid moving in and out of the eye by any of a variety of methods. In some implementations, the pole assembly 105 can include one or more sensors configured to assess how much fluid is being delivered to the eye and how much fluid is being removed. For example, the irrigation source 130 can be positioned relative to a sensor configured to assess fluid volume and/or weight at the source 130. In another implementation, one or more sensors can measure fluid flow from the irrigation source 130, for example using non-contact fluid flow sensors. Similarly, the waste container 160 can be positioned relative to a sensor configured to assess fluid volume, fluid weight, and/or fluid flow into the waste container 160. In other implementations, the one or more sensors can be positioned relative to the microsurgical instrument 225 such as at the inlet and outlet lines to assess overall fluid balance within the eye. The sensors, at least on the irrigation side, can be non-contact liquid level or fluid flow sensors including, but not limited to ultrasonic, radar, laser, Doppler, and other types of sensing technologies for fluids configured to measure the volumetric flow rate in the irrigation and/or waste lines. The information from the sensors can be used by the system to automatically adjust the fluid balance, for example, by increasing the height of the irrigation source 130 relative to the instrument 225 and thus, increasing the fluid head to offset the decrease in liquid in the container.

In some implementations, an ultrasonic sensor, or any other type of non-contact fluid sensor, is place onto the irrigation line 155 or waste line 165. The one or more sensors may be placed anywhere along the length of the tubing. In some embodiments, the sensors are placed close to where the lines 155, 165 enter and exit the hand held instrument 225. The sensors can detect the flow rate through the tubing at the location where they are placed similar to other blood or fluid measurement sensors. In some implementations, the sensors are placed within the hand held device 225 and are incorporated into the fluid pathways described herein. For example, certain components of the instrument 225 may be manufactured from optically transparent components that allows the non-contact sensors to detect the flow rates through the device. In other embodiments, a spring flow meter may be used. The spring flow meter may be located in a disposable part of the instrument 225 and may include a plunger that extends as flow rate increases within the device. In such an embodiment, the plunger may interact with features on the reusable part of the instrument such that the position of the plunger may be sensed and inputted into the electronic control. For example, a potentiometer may be used to sense the position of the plunger and thereby determine the flow rate through either the irrigation or aspiration flow lines 155, 165 or both.

The instruments 225 described herein are configured to deliver irrigation fluid to the work site from the irrigation fluid source 130 contained within the irrigation container 135 fluidly coupled to the hand piece 225 through the irrigation line 155. Conventional irrigation containers 135 for ophthalmic surgery can be between 250 mL to about 500 mL each resulting in a relatively large volume of irrigation fluid available for delivery to the eye. The volume of irrigation fluid needed and thus, the size of the irrigation fluid source 130 and container 135 used during a procedure using the instruments 225 described herein can be drastically reduced compared to conventional systems. As will be described in more detail below, the instrument 225 can include an integrated aspiration pump 245 positioned near the distal cutting tip. For example, the aspiration pump 245 can be a piston pump within the hand piece configured to create a pulsatile vacuum profile. The strength of the pulsatile vacuum to aspirate fluid may be much stronger than vacuum applied in conventional systems not incorporating pulsed vacuum. The very strong and very short pulses are sufficient to remove the lenticular tissue and thus, require only relatively small amounts of fluid. The ratio of lenticular tissue to fluid being aspirated from the anterior chamber may be higher in the hand-held devices described herein than in other currently used devices and methods. Also, the fluid volumes delivered using the instruments 225 described herein can be significantly reduced compared to known systems because irrigation is delivered only upon activation of the device. The total volume of irrigation fluid needed for a procedure using the instruments 225 described herein is significantly less (e.g. as low as about 10 mL) compared to conventional systems.

The aspiration can be activated with finer control than currently used devices and methods. For example, the instruments 225 can use a finger control, which will be described in more detail below. Finger control on the instrument 225 allows the surgeon to easily activate the system for short periods of time in a manner more convenient and easier than would a foot pedal used in most conventional phacoemulsification systems. Further, since a vacuum source 245 can be located within the hand piece 225 there may be a significantly faster response time for the surgeon to activate device on and off than in other devices where the vacuum source is located only in a remote console that is several feet away and connected by long, compressible tubing. The instruments 225 described herein have a relatively low amount of surge volume, and therefore cycling the device on and off has minimal downside. These features can allow the instruments 225 to be activated for only brief periods when the surgeon is ready to remove lenticular tissue. This contributes to overall less irrigation fluid being removed and thus less irrigation fluid needed to be delivered.

The volume of a human lens is about 0.10 mL-0.15 mL. The total irrigation fluid volume needed for a procedure using the instruments 225 described herein is generally less than 250 mL, such as about 10 mL, 25 mL, 50 mL, 75 mL, 100 mL, 125 mL, 150 mL, 200 mL. Thus, the size of the irrigation container 135 holding the irrigation source 130 can be limited to volumes that are less than 250 mL as well. Generally, for the devices described herein, the ratio of irrigation fluid volume needed for a procedure to lens fluid volume is kept very low, between about 50:1, 75:1, 100:1, 150:1, 200:1, up to about 2000:1. As an example, using 10 mL of BSS is a ratio of about 100:1. In contrast, using 250 mL of BSS is a ratio of about 2500:1 of irrigation fluid to lenticular tissue.

The instruments 225 described herein have low volume needs and thus, the irrigation fluid source 130 can be held in a small container 135 that need not be suspended by the pole assembly 105. The irrigation container 135 can be sized small enough that it can be placed near the surgical site or positioned on a portion of the user's wrist or arm (e.g. via a band or other article) that does not rely on gravity in order to deliver irrigation fluid. The irrigation container 135 can be a collapsible bag or syringe that can provide the irrigation flow without the need for gravity or for being suspended from an IV pole. Because the irrigation fluid source 130 need not be suspended and is significantly reduced in overall form factor and volume, the fluid source 130 can be placed near the surgeon performing the procedure and/or may be hand-held. For example, the irrigation fluid source 130 (and the waste container 160 as described in more detail below) can be sized to fit onto a wrist strap or an arm band. In this configuration no tethers are incorporated allowing for the instrument 225 to remain light and more easily manipulated. The fluid source 130 and its container 135 can be sterile such that it can be positioned near the surgical site. In turn, the irrigation line 155 fluidly coupled and extending from the irrigation container 135 can be shortened and the risk of air introduction to the tubing reduced. It should be appreciated that the smaller volume irrigation container 135 need not be a syringe. The irrigation container 135 can be a flexible, collapsible bag or syringe. The container 135 can have a volume less than 250 ml, for example, between about 25 mL-100 mL. The flexible bag or syringe can be placed under pressure by the drive element 2015 such as a spring or gas pressure, such as an air-filled bag.

Figure 2:
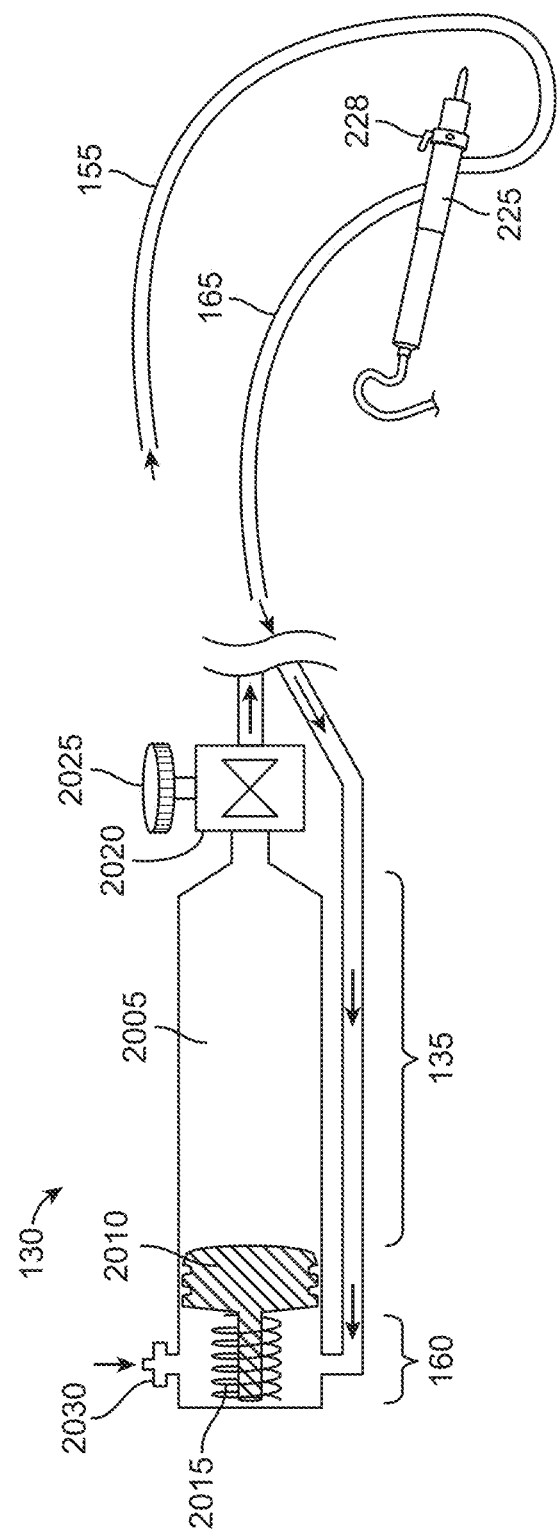
FIG. 2 is a schematic view of a microsurgical system according to another implementation.

The source of irrigation fluid can be part of a fluid system as described above or can be part of or coupled to the surgical instrument. FIG. 2 shows an irrigation fluid source 130 held within a syringe-type container configured to direct fluid toward the instrument using a plunger or other feature such that it need not be suspended or pressurized with gravity. The irrigation fluid container and the instrument 225 can have small form factors. The connection between the container and the instrument 225 can be with a short irrigation line length that can be positioned on a user's wrist or arm or patient's sterile drape during use of the instrument 225. The irrigation fluid (such as balanced saline solution BSS) can be contained within a cylindrical barrel 2005 arranged relative to a plunger 2010 configured to urge irrigation fluid from the barrel 2005. The barrel 2005 can be pre-filled with the irrigation fluid or filled at the time of use. The plunger 2010 can be driven by a drive element 2015 configured to apply a pressure on the plunger 2010 to deliver irrigation fluid from the barrel 2005. The drive element 2015 can be an active mechanism typical of syringe pumps or can be a passive system such as a spring configured to push against the plunger 2010 in a direction configured to urge irrigation fluid from the barrel 2005. The drive element 2015 can be a constant force spring that provides constant force against the plunger 2010 (or bag) regardless of the position of the plunger 2010 or the fill level of the container. Constant force spring can include, but generally needs no pressure regulator. In some implementations, an adjustment mechanism can be included that adjusts the force applied by the constant force spring. For example, the adjustment mechanism can adjust the friction against a part of the plunger 2010 to change the force needed to slide the plunger 2010 relative to the inner surface of the barrel 2005. The drive force provided by the drive element 2015 can be adjustable such that the flow rate and flow pressure of the irrigation fluid can be adjusted. The irrigation fluid can exit the barrel 2005 and travel through a pressure regulator 2020. The pressure regulator 2020 can be adjusted, for example, by turning a pressure control knob 2025. A user can adjust the delivered irrigation pressure to the eye, for example between 0 and 100 inH2O by adjusting the pressure control knob 2025. The pressure control knob 2025 may also include a dial or other indicator that displays the set pressure to the user. It should be appreciated that the knob 2025 can be another type of adjustment mechanism as is known in the art and is provided as an example only.

In some implementations, the irrigation container 135 and the waste container 160 can both have a small form factor and can be coupled together. This arrangement can provide for both the irrigation line 155 and the waste line 165 being attached and/or routed together. In some implementations, a waste line 165 can run along the length of the irrigation line 155 from the irrigation container 135 to the instrument 225. For example, as shown in FIG. 2, the waste line 165 can be routed to a back area of the barrel 2005 of the irrigation fluid source 130, for example, near where the spring 2015 is located. Thus, the barrel 2005 can be divided into a distal, irrigation container 135 located distal to the plunger 2010 and a proximal, waste container 160 located proximal to the plunger 2010. As the plunger 2010 moves distally within the barrel 2005, irrigation fluid from the barrel 2005 is evacuated from the distal end of the barrel 2005 into the irrigation line 155 towards the instrument 225. The volume of the irrigation container 135, i.e. the volume of the barrel 2005 distal to the plunger 2010, decreases during delivery of the irrigation fluid and the volume of the waste container 160, i.e. the volume of the barrel 2005 proximal to the plunger 2010, increases during delivery of the irrigation fluid. The aspirated waste fluid can enter the waste container 160 cavity proximal to the barrel 2005 and can be stored there for disposal once the surgical case is complete.

The waste container 160 of the syringe barrel 2005 can include a one-way valve 2030 that allows air to enter the waste container 160. If there is leaking from the eye, the irrigation fluid may not correspond 1:1 with the waste fluid. Meaning, the plunger 2010 may move distally within the barrel 2005, but an equal amount of waste fluid may not enter the waste container portion 160 of the barrel 2005. The one-way valve 2030 can allow for air to enter the waste container 160 so that creation of a significant negative pressure within the waste container 160 is avoided that could otherwise reduce the force on the plunger 2010.

In some implementations, the waste container 160 can be separate from the irrigation container 135. The waste container 160 can be flexible container like a bag as described elsewhere herein. The flexible bags of one or both of the waste container 160 and the irrigation container 135 can be squeezed to impart pressure such as by a compressed air bladder or spring pushing against the side of the bag.

Again with respect to FIGS. 1A-1B, the aspiration pump 145 of the fluid system 110 may draw fluid and other materials from the eye through the waste line 165 directing material toward the waste container 160. The pump 145 can be integrated within a region of the base 134 of the pole assembly 105. The aspiration pump 145 can be activated manually such as by an input on the system 100 and/or upon actuation of the microsurgical instrument 225, which will be described in more detail below. Aspiration can be achieved with a variety of different pump types, including volumetric flow or positive displacement pumps (e.g. peristaltic pump, roller pump, piston pump, scroll pump, and the like) or vacuum-based pumps (e.g., venturi or pneumatic, diaphragm, or rotary-vane pumps). In an implementation, the aspiration pump 145 is a low pressure, peristaltic pump integrated within the base 134 of the pole assembly 105 and configured to provide fluid movement within the waste line 165 towards the waste container 160. The aspiration pump 145 can be configured to directly accept the waste line 165 to direct fluid into the waste container 160. For example, the aspiration pump 145 can include rotating pump head having rollers around its perimeter. As the pump head rotates, the rollers press against the waste line 165 causing fluid to flow within the line 165 a certain direction (i.e. towards the waste container 160). The fluid system 110 can also be configured such that the aspiration pump 145 accepts a pump cartridge having an integrated waste container 160.

The aspiration pump 145 of the system 100 can be used additionally or alternatively with the aspiration pump 245 within or coupled to the microsurgical instrument 225. The aspiration pumps, whether it is the aspiration pump 145 of the fluid system 110 (i.e. remote from the instrument 225) or the aspiration pump 245 on the instrument 225 itself, or both, can be configured to apply continuous, semi-continuous, and/or discontinuous pulsatile aspiration as will be discussed in more detail below.

In an implementation, the aspiration pump 145 of the fluid system 110 is a low pressure, peristaltic pump and the aspiration pump 245 of the instrument 225 is a piston pump or other pump configured to provide pulsatile or semi-continuous aspiration. The different flow rates and flow types can also be applied by the first aspiration pump 145 within the fluid system 110 and the second aspiration pump 245 within the instrument 225. For example, the aspiration pump 145 in the system 100 can be configured to apply a continuous low-level flow rate configured to support the aspiration provided by the aspiration pump 245 within the microsurgical instrument 225. As such, during a first portion of use, aspiration through the instrument 225 may be provided by the remote aspiration pump 145 within the fluid system 110 and during a second portion of use, aspiration through the instrument 225 may be provided by the integrated aspiration pump 245 within the hand piece.

The flow rate of the background aspiration created by the first aspiration pump 145 can be less than a flow rate of aspiration created by the second aspiration pump 245. For example, the flow rate of the first aspiration pump 145 can be about 10 mL/minute and the flow rate of the second aspiration pump 245 can be about 30 mL/minute. These flow rates are provided for example only and are not intended to be limiting.

The microsurgical instrument 225 can have more than a single aspiration pump 245 where each aspiration source may be programmed to apply (simultaneously, if desired) different flow rates. For example, the microsurgical instrument 225 can include a first pump 245 internal to the hand-piece configured to apply a continuous low-level flow rate and a second pump 245 internal to the hand-piece configured to apply a pulsatile, higher-level flow rate. The different flow rates and flow types can also be applied by a single pump 245 (of the instrument 225) that may be selectively activated to achieve the different aspiration types. The user selectively modifiable aspiration created by the aspiration pump 245 of the microsurgical instrument will be described in detail below.

The aspiration pump 145 of the system 100 can draw negative pressure directly through valves within the microsurgical instrument 225 and provide a low to variable higher flow causing fluid and other materials from the eye to be drawn towards the waste container 160 via the waste line 165. The aspiration pump 245 within the hand-piece of the instrument 225 can be used for certain parts of a procedure, for example, during cutting with the instrument 225. The aspiration pump 145 of the system 100 can be used during other parts of the procedure, for example, cleanup of small particles remaining in the eye after the work performed using the microsurgical instrument 225 is complete.

As mentioned above, the microsurgical instrument 225 can include one or more user inputs 228 separate from and in addition to the one or more inputs 197 of the system 100. The instrument 225 can be actuated using the one or more user inputs 228 on the instrument itself, as well as inputs remote from the device (e.g. on the system 100 or an external computing device 200 in operative communication with the system 100), or both. In some implementations, the one or more user inputs can be on an external computing device 200 in operative communication with the system 100 that, in turn, can control the microsurgical instrument devices also in operative communication with the system 100. The one or more inputs 228 on the instrument 225 include any of a variety of actuator, trigger, button, slider, dial, keypad, switch, touchscreen, foot pedal, footswitch, or other input that can be retracted, pressed, squeezed, slid, tapped, or otherwise actuated to activate, modify, or otherwise cause the oscillation, aspiration, and/or infusion of fluid through the elongate member. In some implementations, the microsurgical instrument 225 can be an all-in-one, fully hand-held without any foot pedal or other tethering connection linked to the instrument. The instrument 225 can be capable of multiple functions (i.e. irrigation, aspiration, and cutting functions) all while maintaining full portability, flexibility, and freedom of movement. The functions of the instrument 225 can be initiated using the input 228 on the device capable of being actuated with a single finger or thumb. Because the instrument 225 requires no foot pedal, a user can stand more comfortably and naturally (e.g. on two feet or shifting their weight from foot to foot however they please) to perform a procedure.

Control of the drive mechanism of the instrument 225 can be completed through the use of a motion controller, electronic speed controller, or the like. The actuator or input for the motion controller of the can be an on/off sort of input to initiate cutting and/or vacuum. Alternatively, the input for the motion controller can be a multi-way input that causes, for example, the motor to spin faster depending on degree of actuation of the input (e.g. pressing further down on a button, dialing up a dial, tapping a displayed key on a touchpad, or sliding a further distance in a direction relative to the housing). The controller can be programmed (e.g. remotely or on the device itself) to have a minimum and/or maximum speed upon actuation of the input, as will be described in more detail below.

The instrument 225 can include separate inputs to activate each function of the instrument 225 and/or the system 100 in operative communication with the instrument 225 (i.e. cutting, infusion, aspiration, including continuous aspiration, pulsed vacuum, and/or pulsed vacuum with regurgitation between pulses, etc.). Alternatively, the input 228 can be a multi-way button or trigger to activate more than a single function, for example, depending on the degree of trigger depression. For example, the instrument 225 can be configured for fluid delivery, fluid aspiration, and cutting. The one or more inputs 228 can be urged by a user into a position that causes the drive mechanism to ramp up one or more of the actions, for example, increase the frequency of oscillation of the elongate member the more the trigger is actuated by increasing the spinning of a motor). The hand-piece of the microsurgical instrument 225 can incorporate one or more sensors configured to send a signal (e.g. via Bluetooth or a non-wireless method) identifying actuation/position of a multi-way input (e.g. the input 3125 shown in FIGS. 13A-13C) of the instrument 225 thereby activating and/or modifying the level of irrigation and aspiration.

The one or more inputs can activate irrigation-only function, continuous aspiration-only function, irrigation-plus-continuous aspiration function, or irrigation-plus-pulsed aspiration-plus-cutting function, etc. Generally, cutting without aspiration is not desired, however, a cutting-only function is considered herein as well. As an example and not to be limiting, a user can activate a first button or place the button in a first position or first degree of trigger depression to turn on the irrigation-only function or continuous aspiration-only function. For example, the first degree of trigger depression can open a valve of the irrigation line of the fluid system placing the surgical instrument into the irrigation-only mode. After the first button is activated, the user can then activate a second button or place the button in a second position or second degree of trigger depression to turn on the irrigation-plus-continuous aspiration function. For example, the second degree of trigger depression can activate the aspiration pump 145 placing the surgical instrument into the irrigation-continuous aspiration mode. The user can then activate a third button or place the button in a third position or third degree of trigger depression to turn on the irrigation-plus-pulsed vacuum-plus-cutting function. For example, a third degree of trigger depression can activate the aspiration pump 245 and oscillation of the elongate member placing the surgical instrument in the irrigation-pulsed aspiration-cutting mode. Trigger depression beyond the third degree can increase at least one of oscillation frequency and aspiration flow rate. The third degree of trigger depression can additionally deactivate the aspiration pump 145 although it should be appreciated that both aspiration pumps 145, 245 can apply aspiration through the inner lumen. The user can then commence cutting while vacuum continues. In some implementations, the second button activation is only possible after the first button activation occurs. In another implementation described in more detail below, the input can be a multi-way actuator that has a first position configured to turn on both vacuum and oscillate the elongate member (i.e. vacuum-plus-cutting function) and a second position configured to pause oscillation of the elongate member while the vacuum through the elongate member continues. The multi-way actuator will be described in more detail below.

Figure 1C:
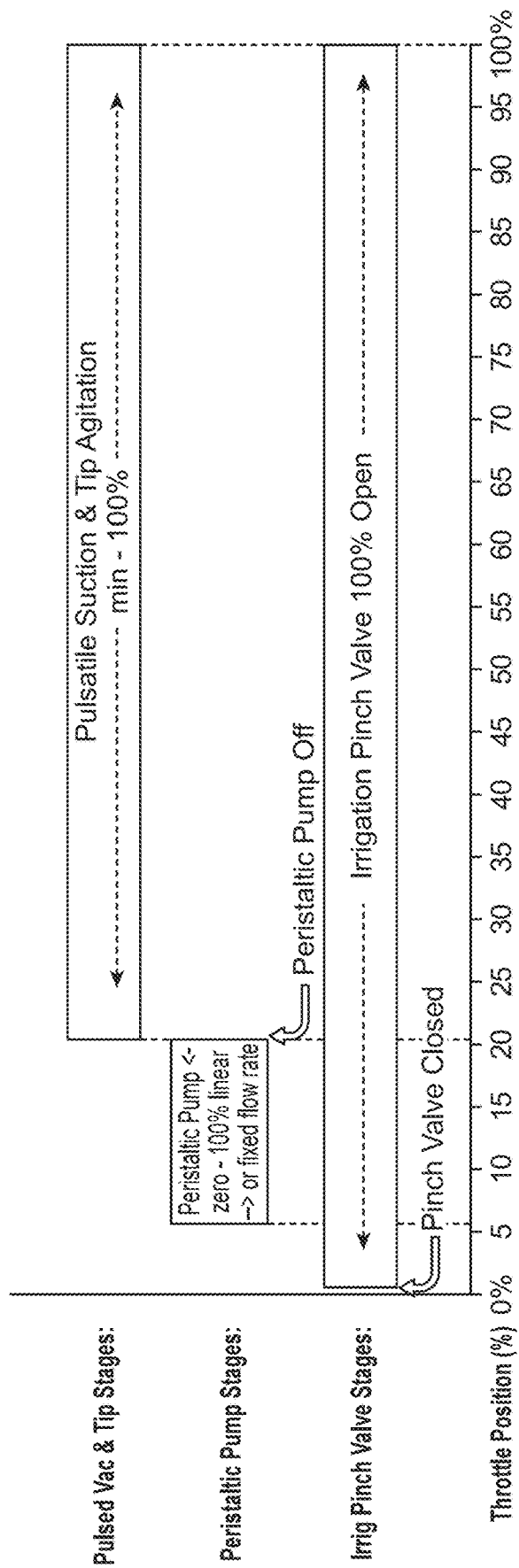
FIG. 1C illustrates stages of operation of the system relative to throttle position of a multi-way input on the instrument according to an implementation.

FIG. 1C illustrates the stages of operation of the system relative to throttle position of a multi-way input 228. For example, the input 228 of the instrument 225 can be actuated to move a first amount (x-axis labeled "throttle position" as a percentage of total travel capable of the input). One or more sensors can assess the travel of the input is greater than 0%, but less than a certain amount of total travel the input is capable of traveling, for example between about 0% to about 5%. A signal can be sent to the computing unit 115 of the system 100 causing the computing unit 115 to communicate with the fluid system 110 to open valve 150. When the valve 150 opens, irrigation fluid from the irrigation source 130 can flow through irrigation line 155 towards the microsurgical instrument 225. This places the system 100 in an initial irrigation-only phase in which the line 155 is primed with irrigation fluid and the microsurgical instrument 225 is able to deliver irrigation fluid to the treatment site. The input 228 of the instrument 225 can be actuated to move a second amount. The one or more sensors can assess the travel of the input is greater than 5%, but less than a second amount of total travel, for example between about 6% up to about 20%. A signal from the one or more sensors can be sent to the computing unit 115 of the system 100 causing the computing unit 115 to communicate with the fluid system 110 to activate background flow via the aspiration pump 145 of the fluid system 110. The aspiration pump 145 of the fluid system 110 can provide a low level continuous negative pressure to begin drawing fluid from the microsurgical instrument 225 through the waste line 165. The valve 150 can remain open such that irrigation fluid from the irrigation source 130 continues to be delivered toward the eye, preferably such that the fluid volume entering the eye is substantially equal to the fluid volume exiting the eye. This places the microsurgical instrument 225 in an irrigation-plus-continuous aspiration phase. The background I/A-only flow can have a low flow rate such as about 2 mL/minute up to about 20 mL/minute at the 20% finger trigger position. The input of the instrument 225 can be actuated to move a third amount. The one or more sensors can assess the travel of the input is greater than 20% up to about 100%. The pulsatile vacuum within the hand-piece of the microsurgical instrument 225 can be activated by the aspiration pump 245 as can an additional function, such as an oscillating cutting function of the instrument 225. A signal from the one or more sensors can be sent to the computing unit 115 of the system 100 causing the computing unit 115 to communicate with the fluid system 110 to deactivate the aspiration pump 145 of the fluid system 110. The valve 150 can remain open such that irrigation supply continues. This places the microsurgical instrument 225 in an irrigation-plus-pulsed aspiration phase or an irrigation-plus-pulsed aspiration-plus-cutting phase as described elsewhere herein. The mechanical oscillation of the cutting phase can initiate once trigger position reaches a threshold (i.e. 20% travel) and further increase to higher frequencies as the trigger is further depressed. Once a procedure completes, the user can then adjust the input 228 of the microsurgical instrument 225 back down to 0% at which point the pulsed vacuum via the aspiration pump 245 ceases and the continuous vacuum via aspiration pump 145 from the fluid system 110 are both deactivated. The valve 150 can close a period of time after deactivating the pumps (e.g. about 2 s) thereby suspending irrigation toward the microsurgical instrument 225.

The aspiration pump 145 of the fluid system 110 need not be shut down during the pulsed vacuum phase using the aspiration pump 245 of the hand piece 225 as shown in FIG. 1C. The system 100 may be configured to apply a continuous aspiration via the aspiration pump 145 concurrent with applying a pulsatile aspiration via the aspiration pump 245 within the instrument 225. For example, a small amount of steady suction can be applied via the pump 145 helping to attract tissue towards the tip of the microsurgical instrument 225. Generally, the continuous aspiration via the aspiration pump 145 is at a low-level flow rate (e.g. 10 cc/min) whereas the pulsatile aspiration via the aspiration pump 245 within the instrument 225 is at a higher flow rate (e.g. 30 cc/min).

The aspiration pump 245 of the instrument 225 can be a positive displacement pump configured to pull fluid and material from the eye into the instrument and then push that fluid and material into the waste container 160. The peristaltic aspiration pump 145 of the fluid system 110 can provide a continuous background flow in addition to the flow provided by the pump 245. Thus, there is flow from the eye that occurs due to vacuum applied at two sources. The aspiration pump 245 of the instrument 225 can deliver a greater flow rate than the flow rate of the aspiration pump 145 of the system generating a difference in flow rate between the two. The system 100 can incorporate a waste system configured to capture this difference in flow rate.

Figure 3B:
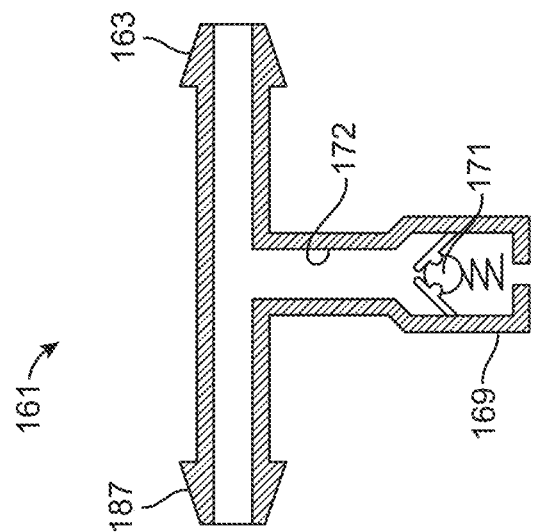
FIG. 3B illustrates a fitting for coupling a primary and secondary waste container to the fluid system.
Figure 3A:
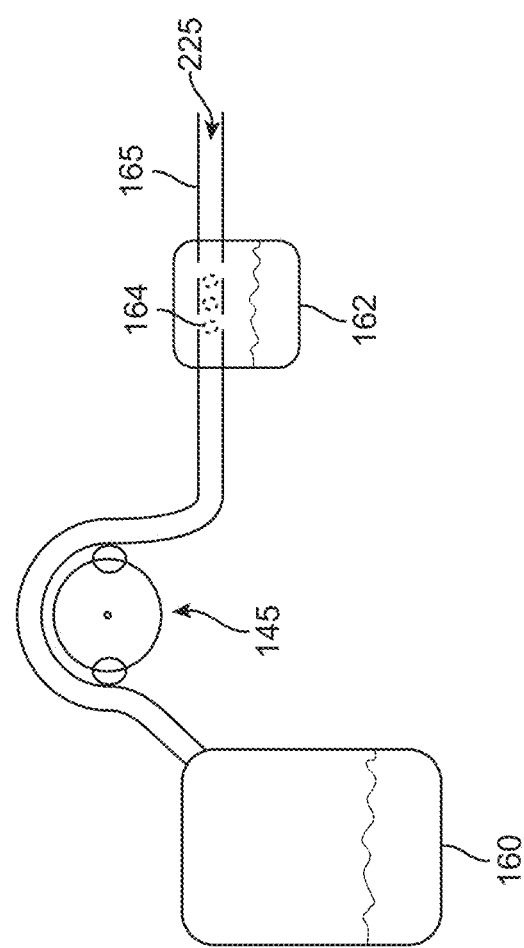
FIG. 3A illustrates an optional secondary waste container for use with a control system.

FIG. 3A shows the system 100 having two waste containers—a primary waste container 160 and a secondary waste container 162. The secondary waste container 162 can receive a fluid volume equal to a difference between the higher-level flow rate of the aspiration pump 245 of the instrument 225 and the low-level flow rate of the aspiration pump 145 of the fluid system 110 thereby maintaining balance within a closed-loop system. The secondary waste container 162 can be positioned upstream to both the primary waste container 160 and the aspiration pump 145 of the fluid system 110. The secondary waste container 162 can be in fluid communication with the waste line 165 via a plurality of holes 164 such that the secondary waste container 162 can accommodate flow in excess of the continuous flow via the aspiration pump 145 (i.e. flow due to pulsatile vacuum by the aspiration pump 245). The pulsatile, discontinuous outflow can be accommodated while maintaining continuous suction downstream of the waste container. The secondary waste container 162 creates, in essence, a fluid volume buffer or accumulator. Any fluid into the system that exceeds the fluid out of the system can be contained within the secondary waste container 162. When inflow rate is less than outflow rate from the system, the volume of fluid contained within the secondary waste container 162 can be drawn down until the container 162 is empty at which time fluid will be drawn straight through the line 165 and the container 162 plays no role in the balance. The waste line 165 and the secondary waste container 162 can be sealed upstream and downstream of the container 162. For example, a portion of the waste line 165 on the upstream side can be sealed with an inlet to the secondary waste container 162 and a portion of the waste line 165 on the downstream side can be sealed with an outlet from the secondary waste container 162 such that the tube and the container 162 are sealed to one another where the tube enters and exits the container 162.

FIG. 3B shows a fitting 161 for use with a system 100 having two waste containers. The primary waste container 160 and the secondary waste container 162 can be coupled to the waste line 165 from the instrument 225 by the fitting 161 such as a t- or y-connector. The fitting 161 can include a first barb 163 configured to connect with the part of the waste line 165a leading from the instrument 225, a second barb 167 configured to connect with the part of the waste line 165b leading to the aspiration pump 145, and a third barb 169 configured to connect to the secondary waste container 162. The third barb 169 can incorporate a check valve 171 within its lumen 172. The secondary waste container 162 captures any flow in excess of the peristaltic flow rate provided by aspiration pump 145 of the fluid system. Waste in excess of the peristaltic pump flow rate opens the check valve 171 allowing for fluid from the waste line tubing 165a to enter into the secondary waste container 162.

Figure 3C:
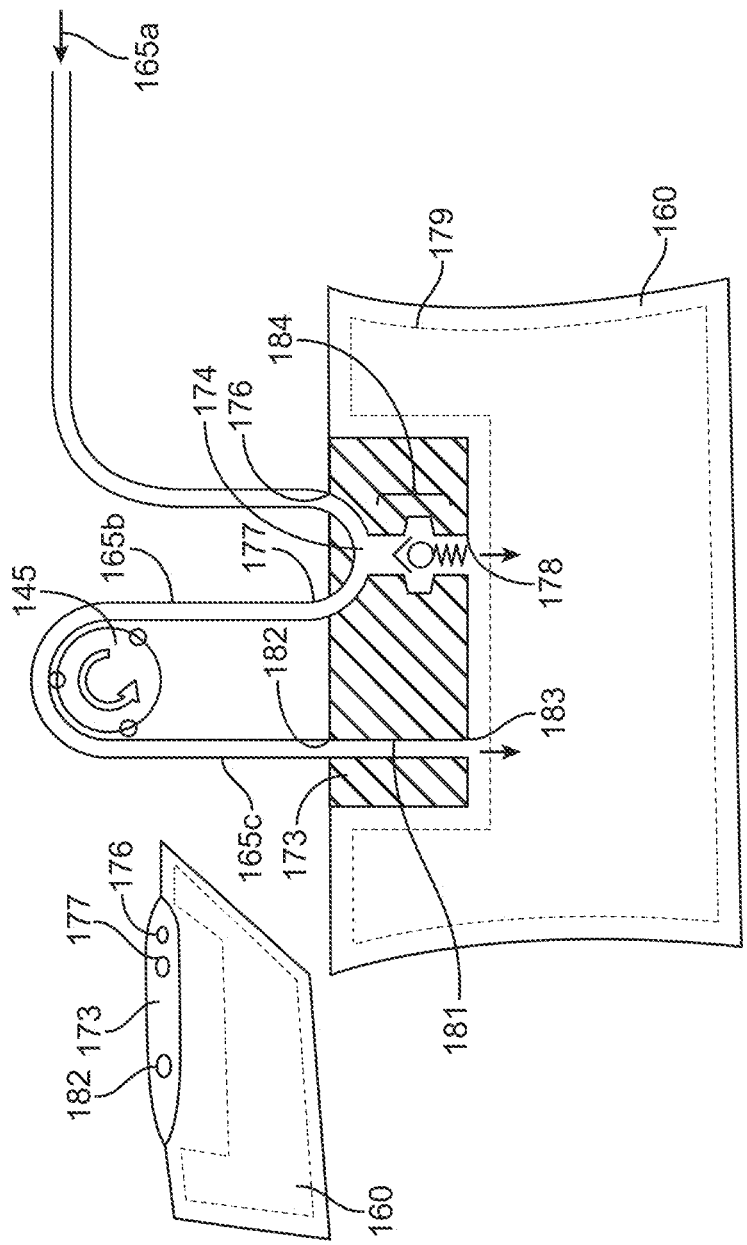
FIG. 3C illustrates an implementation of a waste container for use with the fluid system.

FIG. 3C shows another implementation of the system 100 having a single waste container configured to capture the difference in flow rate between the two aspiration pumps. In this implementation, the waste container 160 can be a bag or pouch having a sealed perimeter and a tapered header block 173. The header block 173 can be injection-molded and define a plurality of passages. A first passage 174 through the header block 173 can have a first inlet 176 on an external surface of the header block 173, a first outlet 177 on an external surface of the header block 173, and an opening 178 to the interior 179 of the waste container 160. A second passage 181 through the header block 173 can have an inlet 182 on the external surface of the header block 173 and an opening 183 to the interior 179 of the waste container 160. The first passage 174 can have a t- or y-shape whereas the second passage 181 can be generally straight lumen. The first inlet 176 of the first passage 174 is configured to fluidly couple with the part of the waste line 165a leading from the instrument 225 and towards the waste container 160, for example, via a barb or other tubing coupling feature. The first outlet 177 of the first passage 174 is configured to fluidly couple with the part of the waste line 165b leading from the waste container 160 to the aspiration pump 145. The inlet 182 of the second passage 181 is configured to fluidly couple with the part of the waste line 165c leading from the aspiration pump 145 and back to the header block 173. The couplings between the inlets and outlets of the header block 173 can couple with waste line tubing via a barb or other coupling feature. Fluid from the instrument 225 flows through the waste line 165a into first inlet 176 of the first passage 174 and out the first outlet 177 of the first passage 174 into waste line 165b. The fluid is pumped via the aspiration pump 145 into waste line 165c towards the inlet 182 of the second passage 181 through the opening 183 and into the interior 179 of the waste container 160. A check valve 184 can be positioned within the opening 178 of the first passageway 174 leading to the interior 179 of the waste container 160. Waste in excess of the peristaltic pump 145 flow rate opens the check valve 184 such that fluid passing through the first passage 174 can be directed into the interior of the waste container 160 through the opening 178.

Figure 3D:
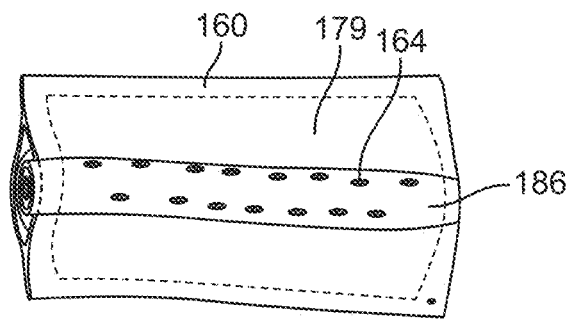
FIGS. 3D-3E illustrates another implementation of a waste container for use with the fluid system.
Figure 3E:
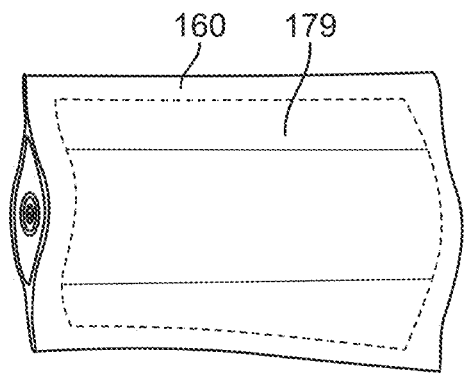
Figure 3F:
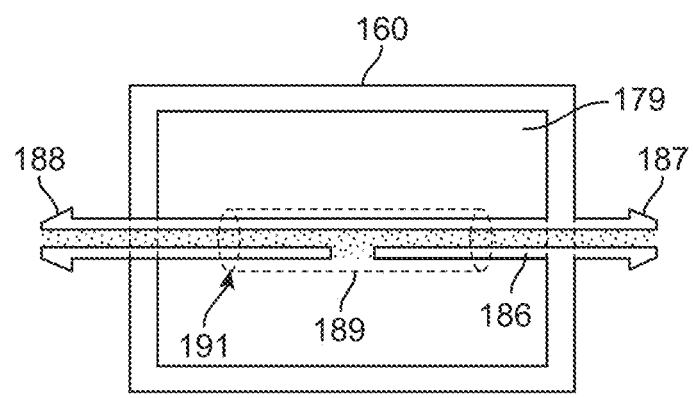
FIG. 3F illustrates another implementation of a waste container for use with the fluid system.

FIGS. 3D-3E show an implementation of a waste container 160 having a tube 186 extending through the waste container 160 such that the interior 179 of the waste container 160 surrounds and seals with at least a portion of the tube 186. The tube 186 can be a rigid tube and the waste container 160 can be a flexible bag or pouch configured to enlarge upon filling. The tube 186 can connect on an upstream end 187 via a barbed fitting (not shown) with the waste line 165 from the instrument 225 and on a downstream end 188 with the waste line 165 leading to the peristaltic pump 145. The tube 186 can include the plurality of holes 164 extending through its side wall that are configured to allow fluid from the waste line 165 to enter the interior 179 of the container 160 through the holes 164. The tube 186 need not incorporate a plurality of holes 164 through its side wall. FIG. 3F shows the tube 186 can include a single side opening 189 regulated by a check valve (not shown) or another feature. In an implementation, the feature regulating the side opening 189 is a compliant sleeve 191 surrounding the tube 186 and covering the opening 189. The sleeve 191 can be very close-fitting such that it can function as a one-way valve for fluid to exit the lumen 192 of the tube 186 and enter the interior 179 of the waste container 160.

The waste line management systems described above can maintain a balance of fluid through the system 100 and the instrument 225 to manage the flow being generated by two different sources.

The balance within the closed-loop system can be maintained by automatic adjustment of the aspiration pump 145 of the fluid system 110 based on sensing of fluid removal via the instrument 225. For example, as described elsewhere herein the system 100 can continuously communicate with instrument 225 during use (e.g. via sensors, Bluetooth, etc.) such that the system 100 tracks the rate of fluid removal. In some implementations, the flow rate can be empirically determined such that sensing is performed only on one of the inlet or outlet lines. For example, a correlation between how irrigation responds to a given amount of suction, rate, and acceleration, can allow for the estimation of the irrigation without directly measuring the flow rate on the irrigation side. Alternatively, the irrigation flow rate can be monitored and the aspiration flow rate estimated based on the irrigation flow rate and the suction amounts via the aspiration pump 145 of the system and pulsed vacuum applied by the aspiration pump 245 of the instrument. Alternatively, fluid volume flow may be assessed electronically via relative current draw from the motor. The fluid volume removed can be quantified (e.g. by programmable software) based on motor current or the amount of work the motor does. Regardless how the fluid through the system is determined, the system 100 can adjust in real-time, the speed of the aspiration pump 145 to match the flow rate of removal at the instrument 225.

Whether or not the aspiration pump 145 remains on during pulsatile vacuum can be adjusted by the user, either by pre-programming or in real-time during use of the system.

As described elsewhere herein, the inputs can activate one or more components of the system such that the pumping and cutting features can gradually ramp up with further actuation of the input, such as like a gas pedal. Generally, the greater the input is actuated, the greater the aspiration vacuum applied. The irrigation delivery can be passive and deliver fluid on demand. As fluid exits the eye, it can be replaced by a substantially equivalent volume at a substantially equivalent rate. Imbalance between fluid volume exiting the eye and fluid volume entering the eye can cause decompression of the anterior chamber, which is referred to colloquially as "chamber bounce" or "surge" or "trampolining". The irrigation source can be held above the eye such that hydrostatic pressure maintains the positive pressure to the anterior chamber. The fluid path is substantially sealed such that when fluid is aspirated, the irrigation fluid immediately replaces it.

In some implementations, control of the system 100 and/or instrument 225 can occur due to sensing within the microinstrument 225. For example, the input can be mechanical such that travel of the input modifies one or more functions of the system 100 and/or the microsurgical instrument 225 such as initiating the irrigation by causing the valve 150 to open, activating continuous aspiration via aspiration pump 145 or pulsatile aspiration within the handle, and/or changing the oscillation speed of the elongate shaft. Any of a variety of configurations are considered herein, including axial coupling and/or rotational coupling. For example, actuation of the input can result in actuation of a potentiometer by an element configured to translate axially or rotate around the longitudinal axis of the device. Non-contact coupling between the throttle and the motor is also considered herein. The throttle can incorporate any number of different sensing mechanisms, including capacitive sensors, optical sensors, magnetic or electromagnetic sensors, Hall-Effect sensors, or other sensor that confirms mechanical movement into a signal that is interpreted electronically. In some implementations, the sensor can be a touch sensor on an upper surface of the handle or push button. The signal can be interpreted by the electronics and provide input such that the electronics control the device according to the input.

In another implementation, control of the system 100 can occur via sensing within the power system 120. As mentioned above, the microsurgical instrument 225 can include a power source 227 having a plug 270 configured to couple with the socket 175 on the system 100. The power source 227 of the microsurgical instrument 225 can be a low volt power supply 227 having a plug 270 configured to couple with a low volt socket 175 on the system 100. The sockets 175 on the system 100 can each include a sensor configured to sense when the instrument 225 draws power through the sockets 175 to activate the valve 150 to cause fluid flow and/or activate the aspiration pump 145 of the fluid system 110 for continuous aspiration. Alternatively, the instrument 225 may draw power through the sockets 175 when pulsatile vacuum and/or cutting is initiated. This draw of power can be sensed at the socket 175 of the power system 120, which when communicated to the computing unit 115 can power down the aspiration pump 145 of the fluid system 110 and suspend the continuous aspiration. In some implementations, power can be drawn by the instrument 225 through socket 175 when the instrument 225 is plugged into the socket 175. The amount of current drawn can be high enough to be sensed, but remain below the minimum current required to turn a motor in the instrument 225. Thus, the motor remains turned off even though it may be drawing the small amount of current. In another implementation, the socket 175 can include a simple circuit configured to bleed a small amount of current that is directed to a resistor bank or another component like an LED. The low power can be drawn during the first or second stage before the pulsed vacuum is applied and then ramped up to a higher power during the third stage when pulsed vacuum begins using the aspiration pump 245 of the instrument. Thus, the power can be sensed as current going to the instrument 225 and be interpreted to determine speed of the aspiration pump 145 of the fluid system 110.

As described throughout, the irrigation fluid volumes used to complete a surgical procedure using the microsurgical systems described herein can be significantly reduced compared to conventional systems. Conventional systems perform surgical procedures using continuous aspiration and continuous irrigation and thus, require large irrigation volumes to complete a surgical procedure (e.g. greater than 250 mL up to about 1000 mL for a cataract procedure). In contrast, the irrigation fluid volumes used to complete a surgical procedure with the systems described herein can be less than 250 mL, for example, between about 25 mL to about 100 mL, or as little as 10 mL. The significant reduction in irrigation fluid can be due to one or more features of the systems described herein. For example, the systems described herein are capable of applying stronger, shorter pulses of vacuum to remove lenticular tissue in a more efficient manner. The systems described herein can deliver the irrigation fluid to the eye only upon activation of the pulsed vacuum. Intermittent irrigation fluid delivery and pulsed vacuum can each reduce the need for total irrigation fluid volume for a particular procedure. Conventional phacoemulsification systems require continuous irrigation fluid delivery to the eye. The phacoemulsification tip moves at an ultrasonic frequency that generates heat, which is damaging to cells. Delivering continuous irrigation can keep the eye cool and avoid heat-related cell damage. As will be described in more detail below, the devices described herein may operate below ultrasonic frequency and thus, avoid generating the heat-associated harmful effects in the eye. Because the devices avoid generating heat, irrigation fluid can be intermittently delivered, for example, only upon initiation of vacuum pulses. The smaller "dead volume" or "surge volume" typical of the systems described herein can also aid in the reduction in overall irrigation fluid delivery to the eye. The lower surge volume allows for the microsurgical device to be cycled on and off with minimal downside. There is less irrigation fluid being removed such that less irrigation fluid needs to be delivered. The reduction in irrigation fluid delivery to the eye during a procedure can reduce cost and the potential harm caused inside the eye.

Microsurgical Instruments

The microsurgical instruments 225 described herein can be coupled to the microsurgical system 100 that, in turn, provides irrigation and aspiration support as well as power to the instrument 225. However, the low level aspiration via the pump 145 of the fluid system 110 is optional. The microsurgical instruments 225 described herein can be used independently of the microsurgical system 100. The microsurgical instruments 225 described herein can be all-in-one devices in which the only linkage to the system 100 may be for power. Thus, the all-in-one devices may not have any foot pedal or other linkage for control. The power can be provided by the power system 120 of the system 100 as described above or the power can be a wall socket as is known in the art. The microsurgical instruments 225 can rely solely on the vacuum source within the hand piece and an integrated power source, such as an internal battery.

Any of a number of microsurgical instruments 225 are considered herein for use with the microsurgical system 100 described above, including vitrectomy cutters, phacoemulsification or phacofragmentation hand-pieces, electric micro-scissors, fiber optic illumination instruments, coagulation hand-pieces, and other microsurgical instrument. In some implementations, the instrument 225 is one or more of those described in U.S. Patent publication No. 2018/0318132, filed May 3, 2018, which is incorporated by reference herein in its entirety. The operating parameters can differ according to, for example, the particular procedure being performed, the different stages of the procedure, the surgeon's personal preferences, whether the procedure is being performed in the anterior or posterior portion of the patient's eye, and so on.

FIGS. 4A-4P, FIGS. 5A-5H, FIGS. 6A-6D, FIGS. 7A-7H, FIGS. 8A-8H, FIGS. 9A-9C, FIGS. 10A-10C, FIGS. 11A-11B, FIGS. 13A-13C, FIGS. 14A-14C, FIGS. 15A-15C, FIGS. 16A-16H, and FIGS. 17A-17G illustrate implementations of microsurgical instruments configured for surgeries (such as cataract surgeries) that are performed in a minimally-invasive, ab interno approach through clear corneal incisions. Where features are described with respect to one implementation of the instrument, it should be appreciated that the same feature may be present on another implementation of the instrument even though the feature may not be explicitly described with respect to that implementation.

Cataracts are typically classified based on severity on a scale of 1 to 5. The microsurgical instruments described herein require less energy, time, and fluid to remove the tissues from the eye compared to, for example, conventional phacoemulsification hand pieces, particularly for use for cataracts in a range of 1 to 3. The microsurgical instruments described herein can be useful for harder cataracts above 3 to about 4 on the hardness scale as well. The microsurgical instruments described herein can be all-in-one and configured to create small lens fragments in situ and aspirated with little to no phacoemulsification. The microsurgical instruments can be used with the system 100 described with respect to FIGS. 1A-1B. The microsurgical instruments described herein can also be used separate from the system 100. The microsurgical instruments described herein can be used with the irrigation container 135 described with respect to FIG. 2.

Figure 4C:
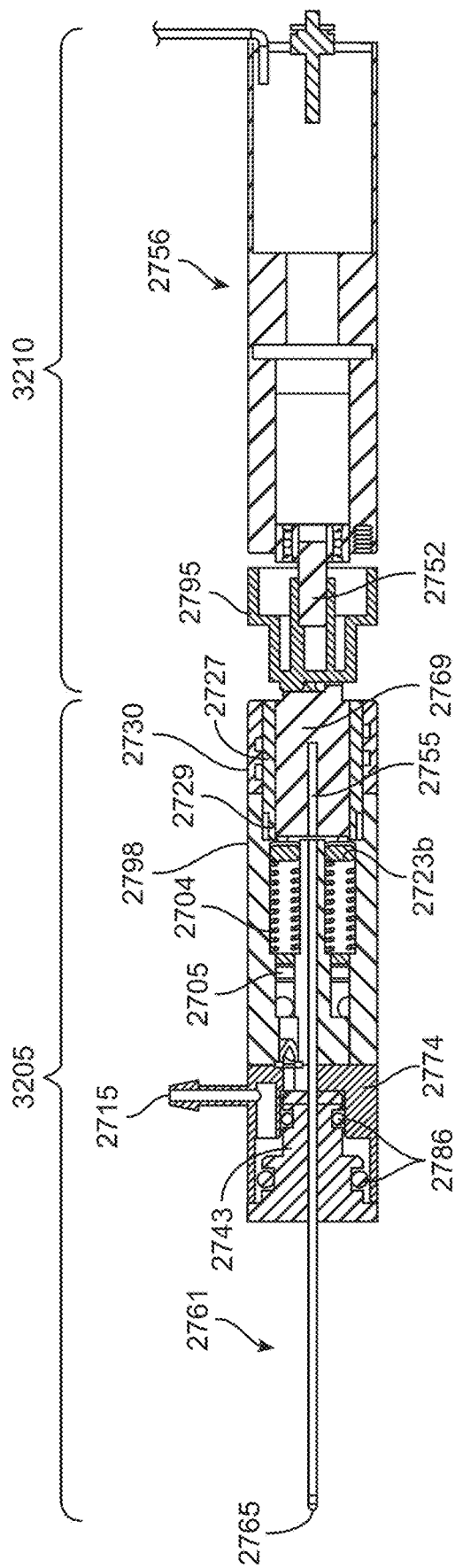
FIGS. 4C-4D show cross-sectional view of the device of FIGS. 4A-4B taken along line C-C and D-D, respectively.
Figure 4D:
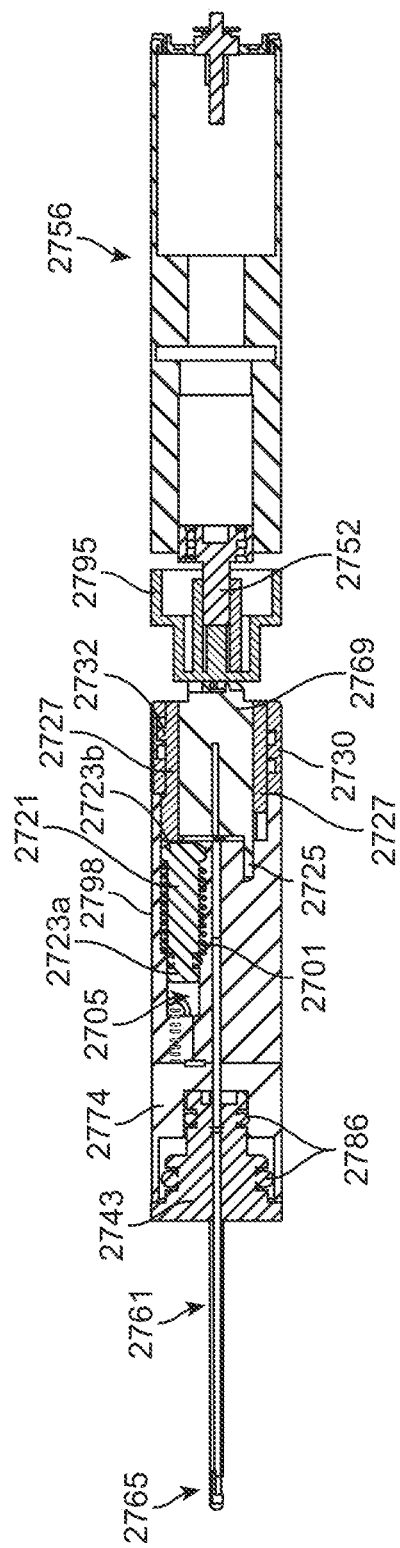
Figure 4E:
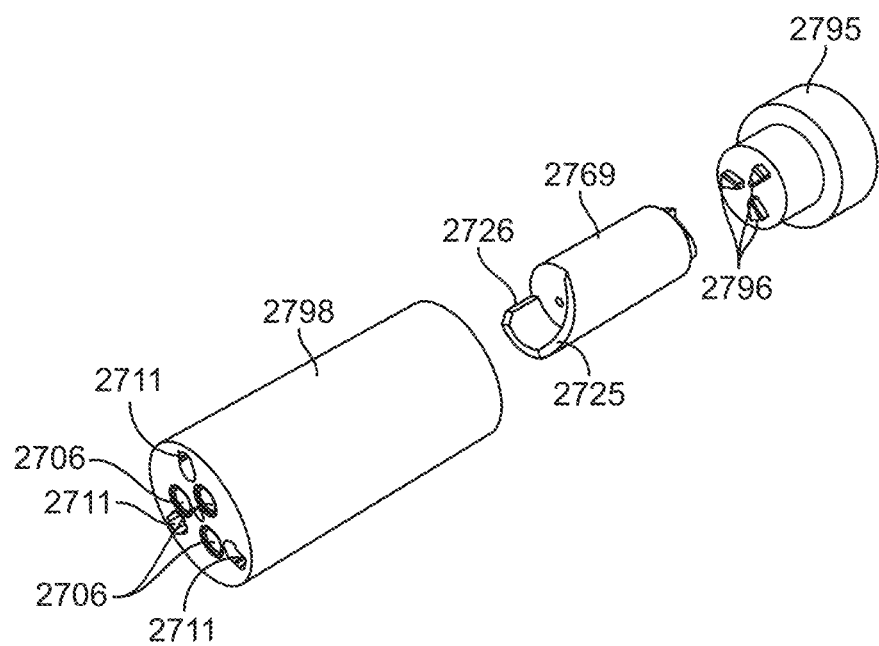
FIGS. 4E-4G show various view of a rotating cam of the device of FIGS. 4A-4B.
Figure 4F:
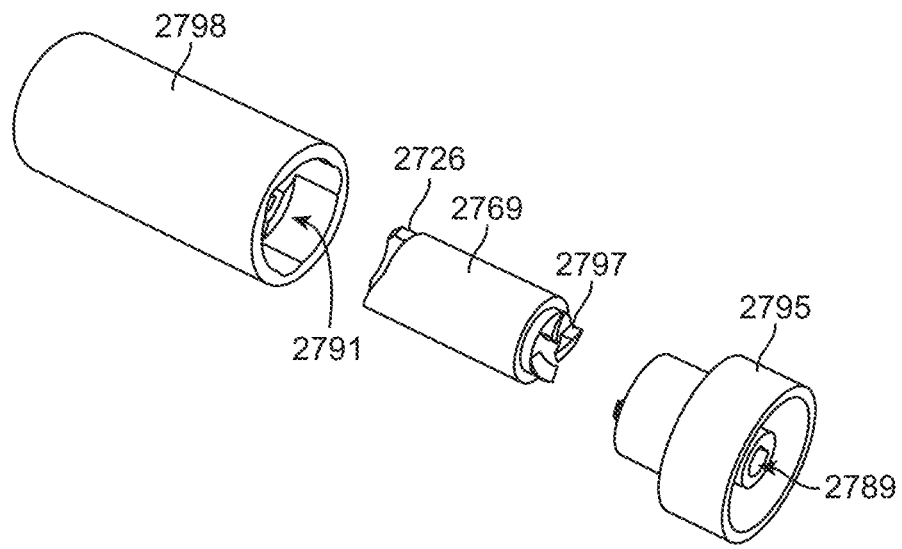
Figure 4G:
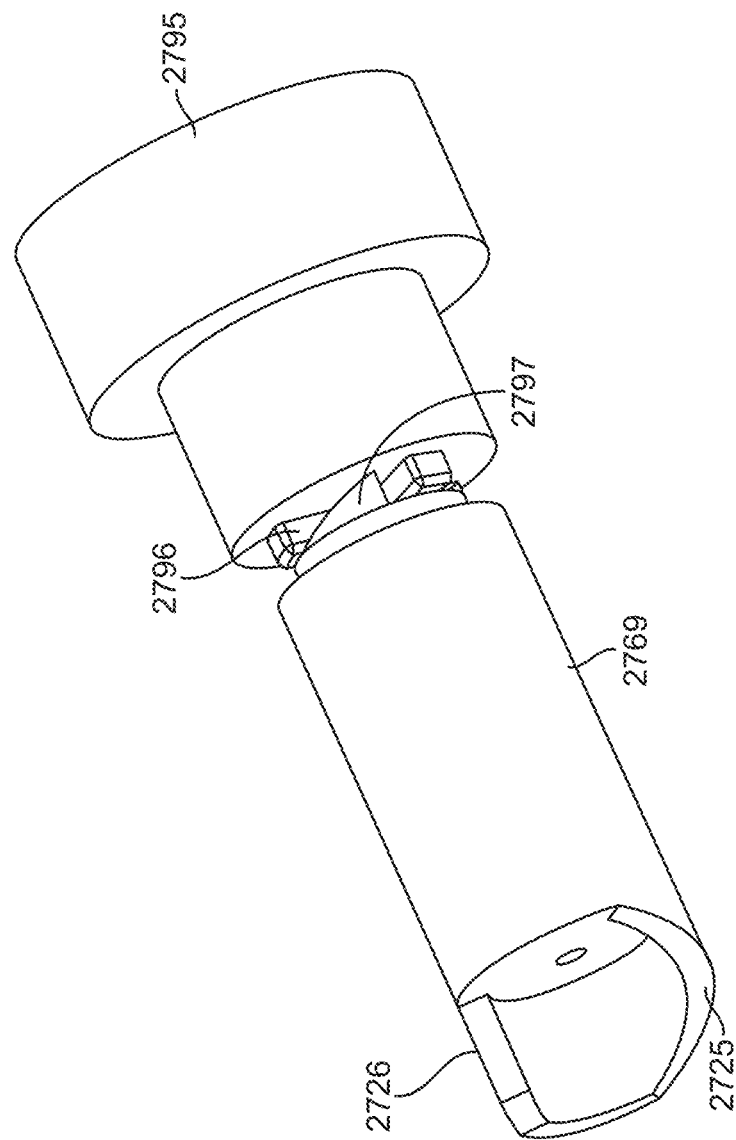
Figure 4H:
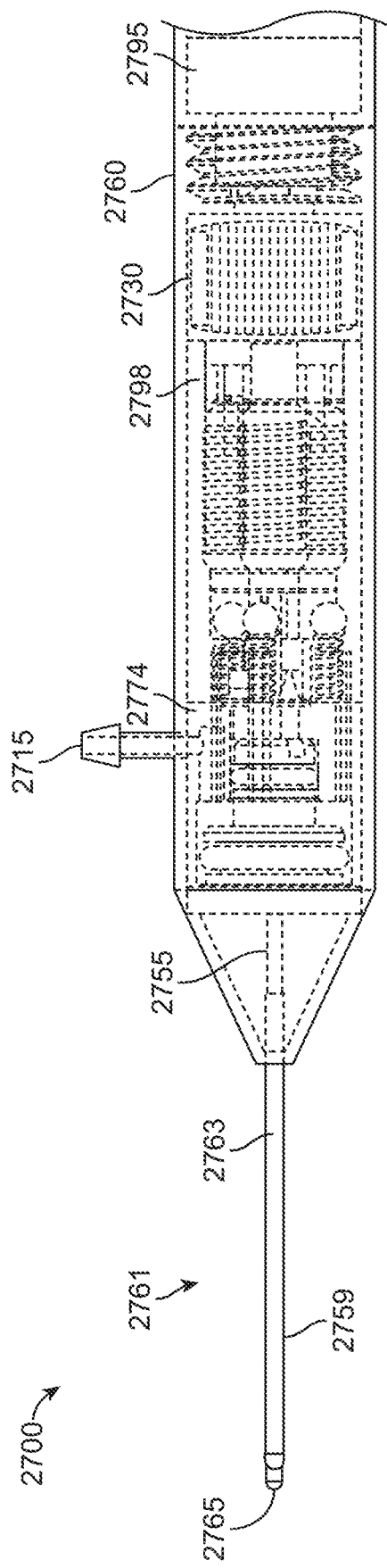
FIGS. 4H-4O are additional views of various components of the device of FIGS. 4A-4B.
Figure 4I:
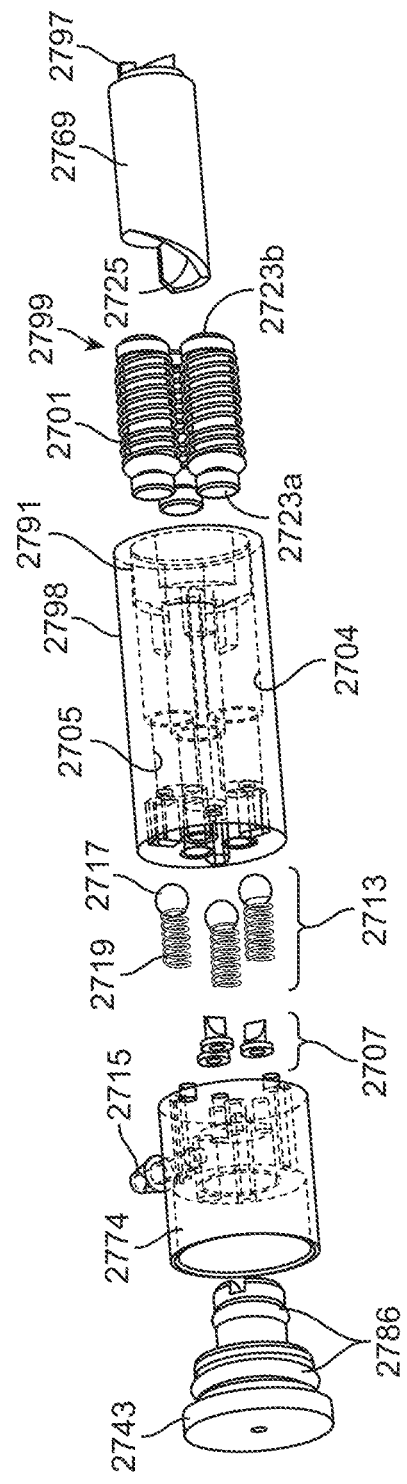
Figure 4J:
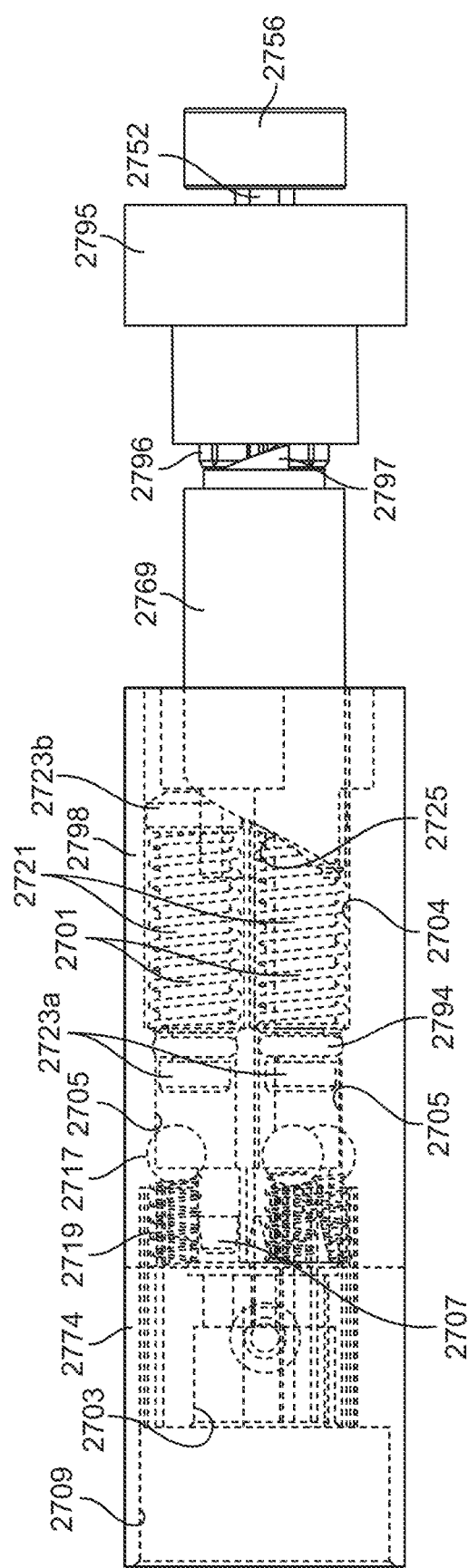
Figure 4K:
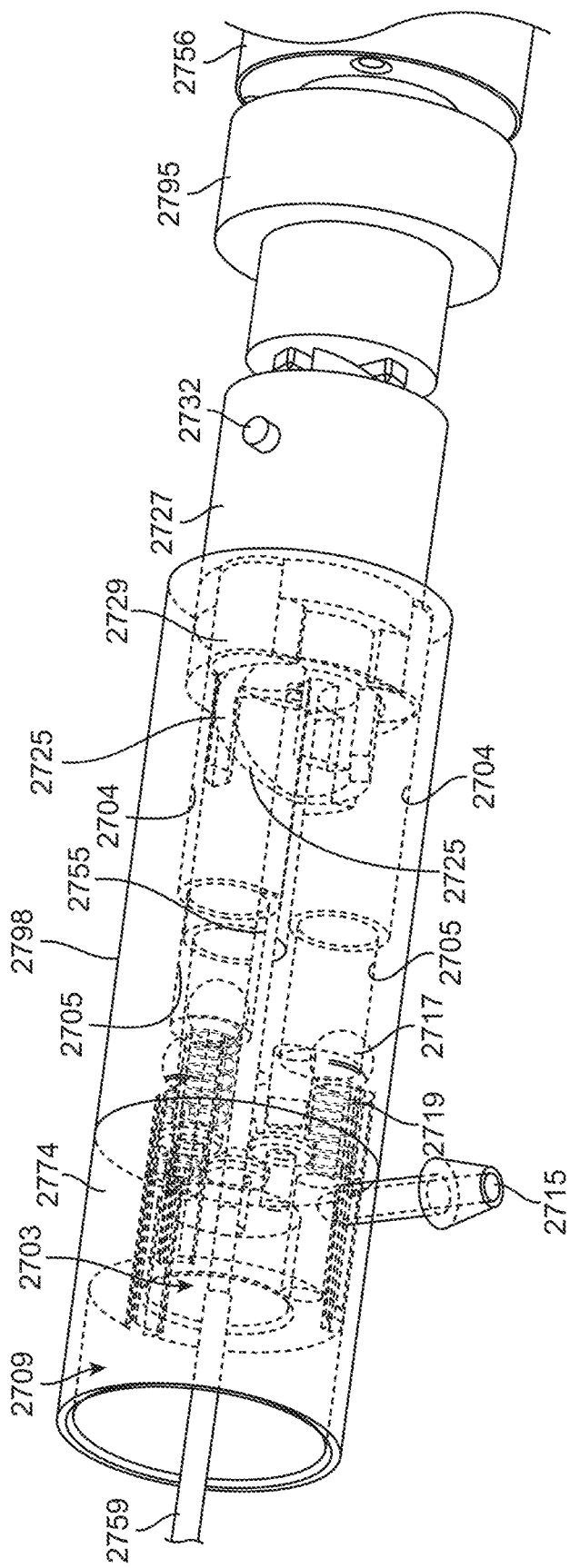
Figure 4L:
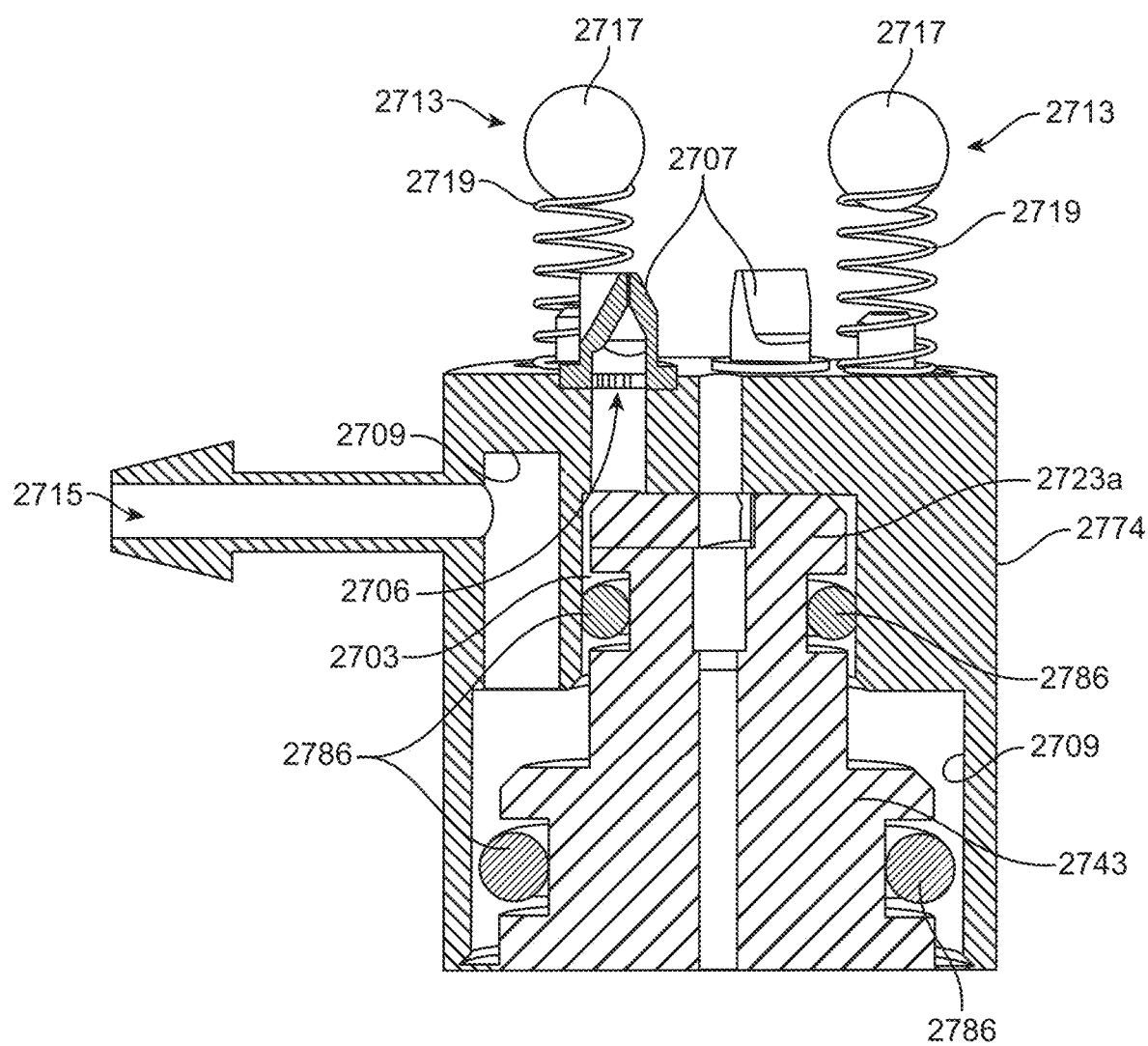
Figure 4M:
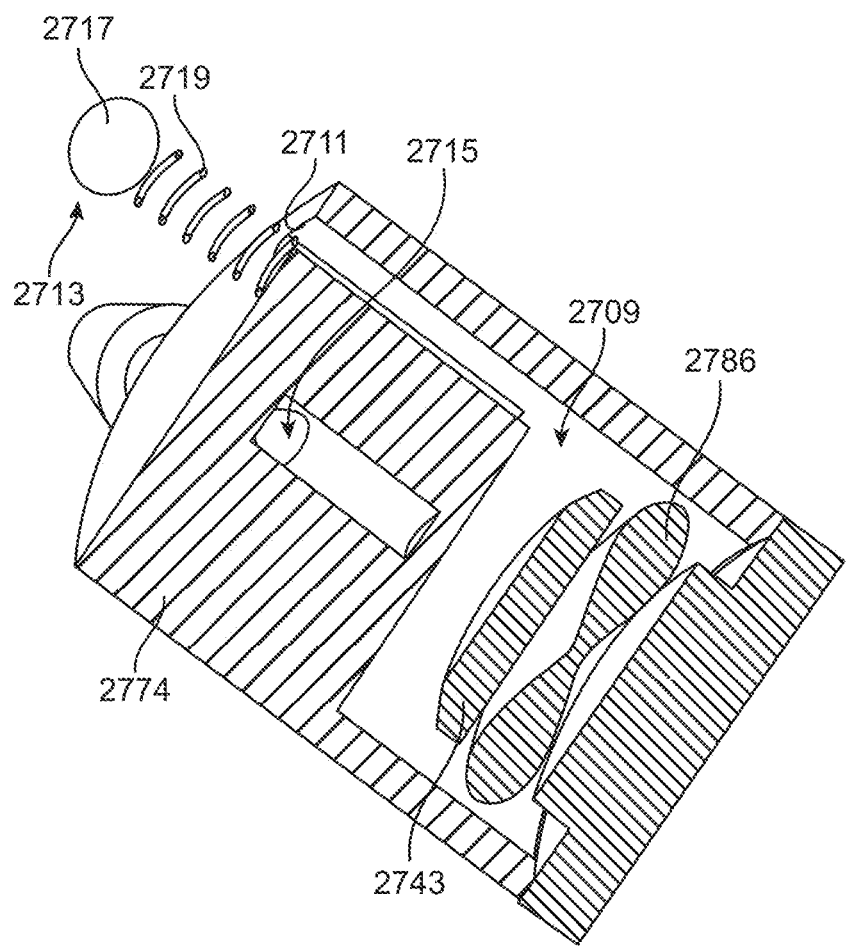
Figure 4N:
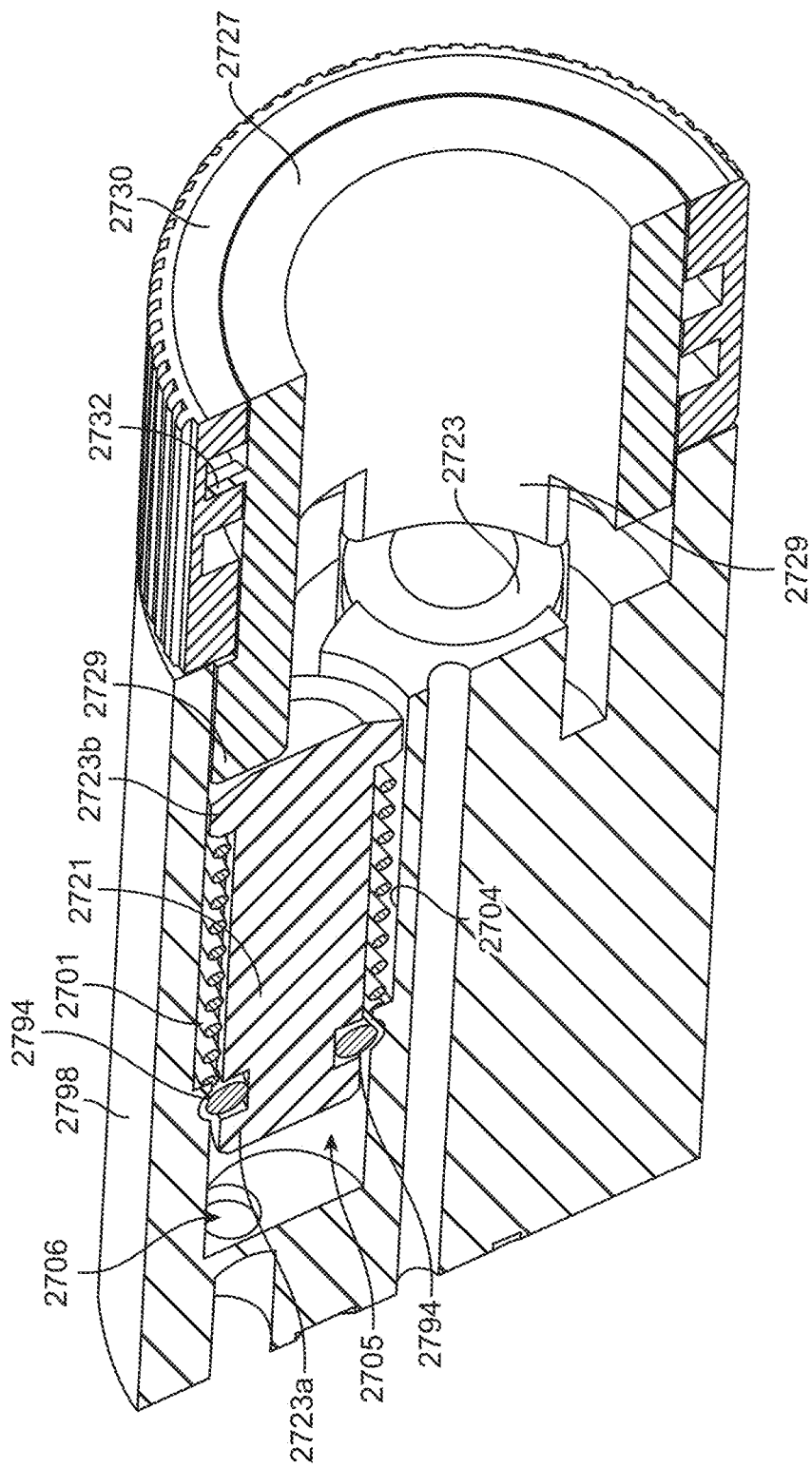
Figure 4O:
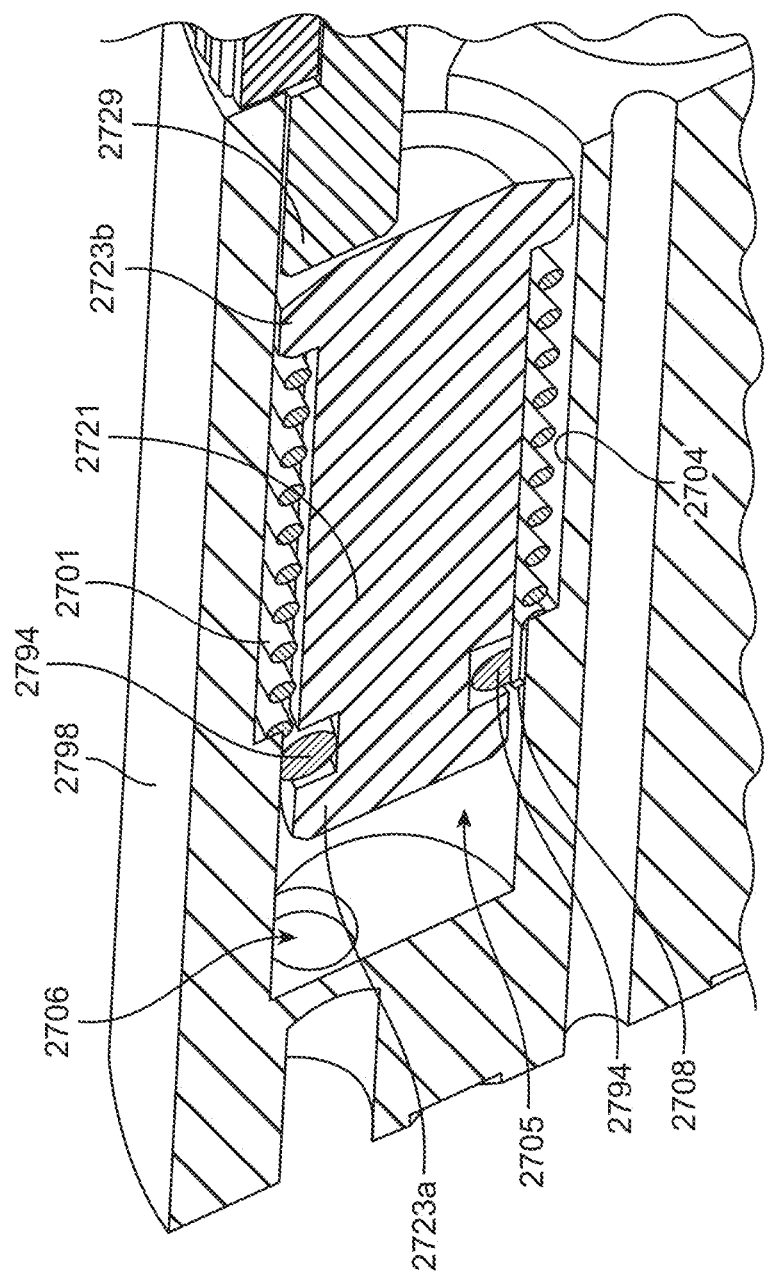
Figure 4P:
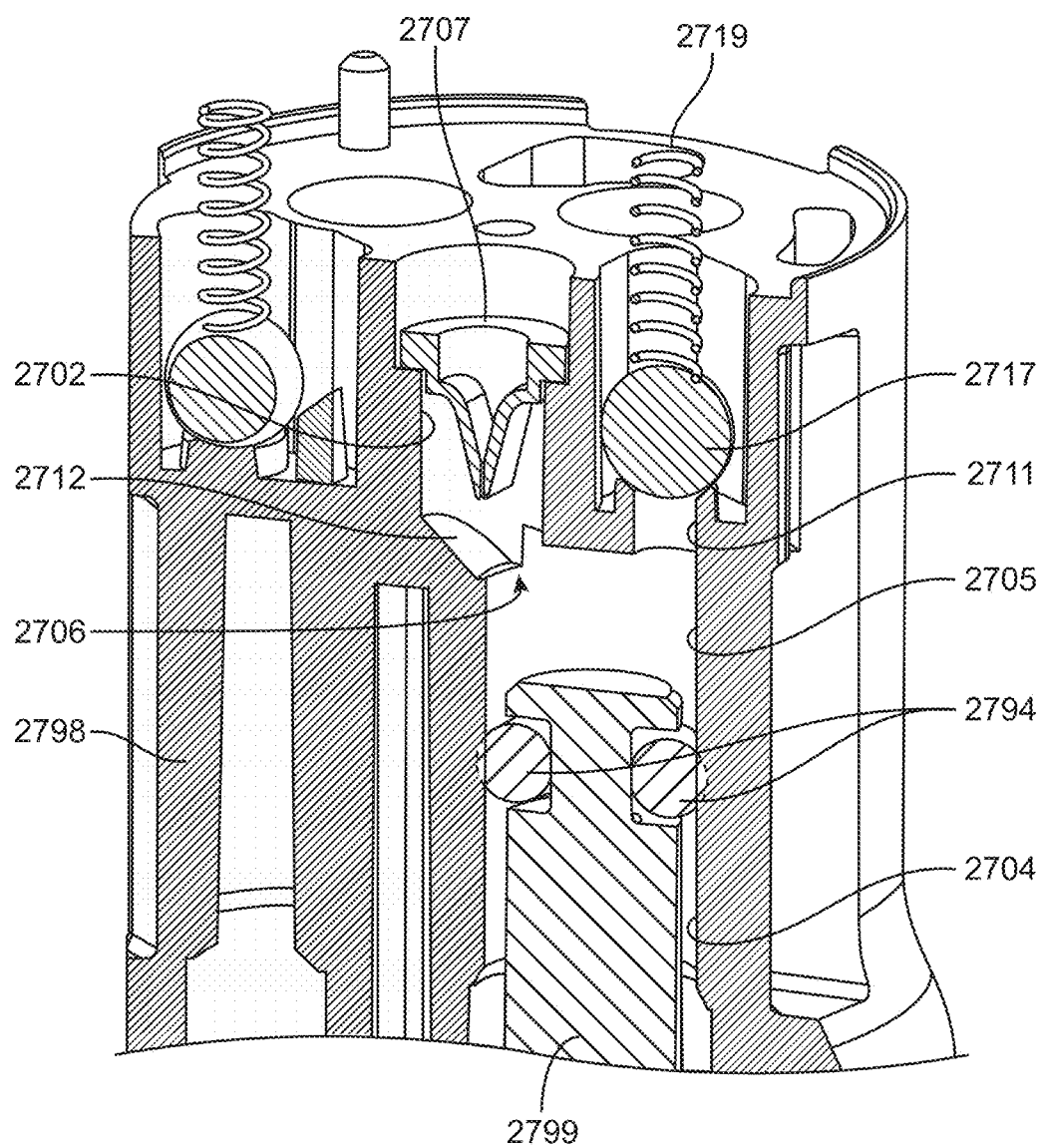
FIG. 4P is another view of the one-way valves controlling flow of material to and from the pumping chamber.

FIGS. 4A-4P illustrate an implementation of a microsurgical instrument. The device 2700 includes a hand piece 2760 having a distal, elongate member or shaft 2761 coupled to and extending longitudinally from the housing 2762 of the hand piece 2760. At least a distal end region of the shaft 2761 is configured to be inserted into the eye in a minimally-invasive manner to cut, aspirate, and/or inject material in the eye, such as during a cataract procedure. At least a portion of the shaft 2761 can be configured to oscillate or slide reciprocally relative to the hand piece 2760 in order to remove lens or other tissues of the eye. The drive mechanism is configured to oscillate the elongate member shaft.

As used herein, "oscillate" or "oscillating movements" can include any periodic, repetitive movement that occurs according to a pattern and need not be sinusoidal. The oscillating movement can include reciprocating sliding movements that occur in a back and forth manner relative to the hand piece. The oscillating movement can include repeatedly advancing and retracting the elongate member along its longitudinal axis. The repeated advancing and retracting may occur along the longitudinal axis, but the path the oscillating movements take need not be linear. The path of movement can occur non-linearly (i.e. away from the longitudinal axis during at least a portion of the movement) along an elliptical pathway or a curvilinear pathway or a slight side-to-side motion in combination with a back-and-forth motion. The path of movement can be rotational, orbital, or torsional around the longitudinal axis of the device or other type of movement relative to the longitudinal axis of the device including three-dimensional movements in which the elongate member moves back and forth as well as from side-to-side. The oscillating movements include profiles of repetitive patterns that may change depending on where in the cycle of oscillation the movement occurs. The oscillating movements can be asymmetric in profile, as will be described in more detail below.

The shaft 2761, which may be referred to herein as "cutter" or "cutter tube" or "elongate member" can be configured for different techniques, including phacoemulsification, vitrectomy, bag polishing, or other technique. At least a portion of the shaft 2761 can include a tubular, oscillating elongate member having an internal lumen extending through it such that fluids can be delivered and/or aspirated through the oscillating elongate member. The distal end of the shaft 2761 can define an opening into the lumen. The shaft can be configured to oscillate in order to jackhammer lens tissue and aspirate it out of the eye similar to conventional phacoemulsification cutting tips. The shaft 2761 can be configured to perform vitrectomy and incorporate inner and outer tubes having side openings into the lumen. The inner and outer tubes can slide reciprocally with one another to chop and remove hard lens material. Any of a variety of configurations of the elongate member are considered herein. The shaft 2761 may have inner and outer members or the shaft 2761 may include only a single tubular element configured to oscillate relative to the hand piece to cut and aspirate material. Where the shaft is described as having an inner elongate member coaxially arranged within an outer tubular member, the inner elongate member can be a solid rod and need not include an inner lumen. The oscillating elongate member need not be tubular, but instead can be formed as a solid element. In some implementations, the elongate member has a sharpened cutting tip or bevel, which can include a needle tip. The elongate member can include a cutting element having a sharpened needle tip and can be a solid element extending through an outer tubular member and aspiration forces applied through the lumen of the outer tubular member such that fluids and tissues are drawn into an annular gap extending between the inner and outer members. The elongate member can have an inner lumen and distal edge configured to cut tissue. The distal edge can be sharpened while the opening into the tube can be cut at an angle to the elongate axis of the elongate member or perpendicular to the elongate axis of the elongate member. The inner lumen of the elongate member can be configured to aspirate material therethrough, such as ocular lens material, lens fragments, vitreous, and/or fluids from the eye. Thus, aspiration forces can be applied through the inner lumen of the elongate member. However, aspiration forces can also be applied through a lumen of a tubular outer member extending over the elongate member such that aspiration occurs through the annular space between the two in order to receive and/or deliver fluids to the treatment site. In such a configuration, the gap between the tubular outer member and the inner member can vary, for example, between about 0.001" to about 0.100". In some implementations, the aspiration forces can be applied through both the inner elongate member having a lumen and the lumen through the outer tubular member.

Again with respect to FIGS. 4A-4D, the hand piece 2760 of the device 2700 can include a disposable portion 3205 configured to be releasably coupled to a durable, reusable portion 3210. The disposable portion 3205 generally includes components of the hand piece 2760 configured to come into direct contact with fluids and materials from the eye, for example the elongate member including the distal cutting tip, the irrigation line, waste line, connection sites for the irrigation line and waste line, etc. The disposable portion 3205 can include an aspiration pump such as a piston pump having a plurality of pistons housed within corresponding piston cylinders. The rotational cam assembly capable of being rotated by the motor via a motor coupler can be positioned within the disposable portion 3205 or the reusable portion 3210. The reusable portion 3210 generally includes the components of the hand piece 2760 that are configured to remain outside the fluid path, for example the components configured to drive the aspiration pump and/or the cutting elements. The reusable portion 3210 may include the motor, the actuator for actuating the motor, a motor coupler. The reusable portion 3210 may be re-sterilized and reused. It should be appreciated that the reusable portion 3210 may also be disposable and manufactured by lower cost materials such that it is financially feasible for the portion 3210 to also be disposed of after use.

The devices described herein can incorporate a protective drape or sterility sheath configured to protect against inadvertent contamination of the sterile components of the device by the non-sterile components of the device. FIGS. 20A-20B show view of an instrument 2700 incorporating the sterility sheath 3505. The sterility sheath 3505 can include a flexible, tubular cover 3510 having a first end attached to the instrument via a coupler 3515 and a second end attached to a pull tab 3520. The coupler 3515 can be an annular element configured to couple the first end of the tubular cover 3510 to the proximal end region of the disposable portion 3205. The cover 3510 can have a furled configuration prior to deployment of the sheath 3505 (see FIG. 20A) and an unfurled configuration after deployment of the sheath 3505 (see FIG. 20B). The cover 3510 in the furled configuration can be a folded such as in an accordion pattern, rolled, or otherwise compactly encased relative to the instrument to minimize its footprint prior to use. The cover 3510 in the unfurled configuration unfolds or unrolls such that the durable portion 3210 of the instrument may be contained within the cover 3510 between the coupler 3515 and the pull tab 3520. The cover 3510 can be a flexible, tubular element configured to receive at least the durable portion 3210 of the instrument including the housing of the durable portion 3210 as well as at least a length of attachments to the durable portion 3210 such as power cable 2757 and fluid tubes extending from the proximal region of the instrument. In some implementations, the length of the cover 3510 is from about 5 inches up to about 30 inches long. The cover 3510 can be any of a variety of materials, particularly cheap disposable materials such as plastic, fabric, or paper. The material of the cover 3510 is designed to go from a furled to an unfurled configuration without tearing or ripping and is sufficiently flexible enough to avoid impacting a user's grip on the instrument. In some implementations, the cover 3510 is a transparent or translucent plastic material such that a user may still view the housing of the instrument through the cover 3510 when in the unfurled configuration over the housing of the reusable portion 3210. The coupler 3515 can be less flexible than a material of the cover 3510. In some implementations, the coupler 3515 can be formed of a material such as cardboard, plastic, metal, or other material. The pull tab 3520 attached to the second end of the tubular cover 3510 can have an annular portion 3522 configured to surround the furled cover 3510 and capture it between an inner surface of the annular portion 3522 and an outer surface of the coupler 3515. The pull tab 3520 can also incorporate gripper portion 3524 configured to be grasped and pulled by a user to withdraw the pull tab 3520 proximally thereby causing the cover 3510 to unfurl over the durable portion 3210 of the instrument. The gripper portion 3524 of the pull tab 3520 can incorporate one or more surface features 3526 configured to improve a user's grip on the tab 3520.

The housing of the device 2700 can be formed of a relatively rigid, lightweight material(s). The two housing portions 3205, 3210 can couple together using a variety of mechanisms such as threads, snap-lock, bayonet, and the like. The coupling mechanism can include a release button configured to uncouple the two housing portions. The coupling between the disposable portion 3205 and the reusable portion 3210 may be purely mechanical or may involve both mechanical and electronic couplings. For example, the disposable portion 3205 may have an electronic input configured to electronically couple with a portion of the reusable portion 3210. Alternatively, the disposable portion 3205 may have an input configured to mechanically couple and interact with the reusable portion 3210. Coupling between the portions 3205, 3210 will be described in more detail below.

The disposable portion 3205 or the durable portion 3210 of the hand piece 2760 can include one or more inputs or actuators. The hand piece 2760 may also be actuated remotely, for example, by the computing unit 115 of the system 100. Use of the term "hand piece" herein can include a hand piece coupled to a robotic arm or robotic system or other computer-assisted surgical system in which the user uses a computer console to manipulate the controls of the instrument. The computer can translate the user's movements and actuation of the controls to be then carried out on the patient by the robotic arm.

Each of these components as well as the coupling between the disposable and durable, reusable portions 3205, 3210 of the hand piece 2760 will be described in more detail below.

The microsurgical instrument device 2700 can include a suction or vacuum source that is found within an interior of the hand piece 2760. Thus, the device 2700 can be a fully hand-held device capable of being used without the system 100 and/or without the external suction source (i.e. aspiration pump 145 of the fluid system 110). The vacuum source can be a pump having any of a variety of configurations, including but not limited to bellows mechanism, diaphragm pump, venturi pump, entrapment pump, positive displacement pump, regenerative pump, momentum transfer pump, micro pumps, or the like. The vacuum source can, but need not be, a piston pump and can incorporate any of a variety of mechanisms configured to generate a negative pressure within the lumen of the elongate member.

When the device 2700 is operatively coupled to the fluid system 110 of the system 100, for example, the external vacuum source (i.e. aspiration pump 145 via aspiration line 165) of the fluid system 110 may provide aspiration support to the vacuum applied from within the hand-piece of the device 2700. The aspiration pump 145 of the fluid system 110 can be configured to provide a continuous vacuum through the shaft 2761 of the device 2700 and can be activated during certain phases of a procedure. For example, during a first portion of use aspiration through the device 2700 may be provided by aspiration pump 145 and during a second portion of use aspiration through the device 2700 may be provided by the aspiration pump within the hand piece 2760 of the device 2700. The pulsatile vacuum can be applied within the hand piece 2760 of the device 2700 whereas the continuous vacuum can be applied via the system 100 that is remote from the device 2700. In still further implementations, the same pump can be selectively actuated between a continuous vacuum and vacuum with pulses of increased negative pressure. The pulses of negative pressure can be applied by actuation of one or more valves, such as due to movement of one or more pistons or actuation of the valves by a computing unit. In some implementations, the computing unit 115 of microsurgical system 100 can coordinate activation of the different functions of the system 100 and device 2700 during use. For example, the computing unit 115 can control initiation of irrigation flow by opening valves 150, onset of continuation aspiration via aspiration pump 145, initiation of pulsed vacuum within the hand piece 2760 alone or in combination with cutting, as well as maintain balance of fluids and pressure within the eye as described throughout. It should be appreciated the control of fluid balance within the eye can also be maintained by a mechanical pumping system as will be described in more detail below (see FIGS. 10A-10C, 11A-11B, and 12).

Incorporating a vacuum source within the hand-held portion of the device (e.g. near the distal cutting tip) minimizes the volume of the aspiration flow path improving control and responsiveness while decreasing latency or hysteresis. Conventional phaco devices and other devices using a vacuum source remote from the hand-piece suffer from slow responsiveness and lower effective vacuum applied at the treatment site. Conventional systems have long, compliant suction lines connecting the vacuum source to the hand-piece. Compliance within a fluidic system can increase the time for suction to be transmitted from the suction source to the treatment site when the suction source is activated (and deactivated). Compliance within a fluidic system can also contribute to frictional losses in vacuum transmitted to the treatment site resulting in the effective vacuum amount being different from the theoretical vacuum setting at the source. For example, a remote vacuum source set at 600 mmHg may effectively transmit to the treatment site only 200 mmHg. The latency and hysteresis in conventional phaco devices having a remote vacuum source suffer from the risk of large surge volume following a clog, particularly when the vacuum source is set at the higher flow rates. Surge volume in conventional systems includes the compliant suction line extending between the remote vacuum source and the hand-piece, which can be quite large (e.g. greater than 20 mL in some instances). Users tend to set the vacuum source a lower levels to mitigate this lack of control and increased risk in surge volume at the higher flow rates.

The devices described herein can apply a greater effective vacuum at the treatment site and more rapidly respond to pressure changes, and by avoiding the line losses associated with conventional systems. The devices described herein have improved responsiveness and control even when used with the higher vacuum settings. If an occlusion occurs due to a piece of lens blocking the distal opening, the vacuum will build (e.g. up to about 500 to 600 mmHg or more). When the blockage passes breaking the seal, the surge associated with the devices described herein is significantly improved as compared to conventional devices having only remote vacuum sources. For example, the surge volume of the devices described herein can be as low as about 100 cubic mm, 200 cubic mm, or no more than about 300 cubic mm, whereas conventional phacoemulsification systems can have surge volumes that can be 10×, 20×, 50×, or 100× greater than this volume. The surge volume is smaller because the devices described herein have a comparatively shorter aspiration flow path between vacuum source and target treatment site. The short aspiration flow path may also be substantially rigid or non-compliant. For example, greater than 50%, 55%, 60%, 65%, 70%, 75%, 80%, 85%, 90% of the aspiration flow path of the devices described herein can be rigid resulting in no more than 10%, 15%, 20%, 25%, 30%, 35%, 40%, 45%, or 50% compliance in the aspiration flow path. The substantially non-compliant and short aspiration flow path of the devices described herein reduces the potential surge volume and also reduces the dead space that can contribute to the latency effect and lack of responsiveness.

In some implementation, the aspiration pump in the hand piece can be a piston pump incorporating a plurality of reciprocating pistons. As best shown in FIGS. 4H-4K, The vacuum source can be positioned in fluid communication with a vacuum manifold 2774 located within the interior of the housing. The shaft 2761 can include an oscillating elongate member 2755 sized and configured to extend through an anterior chamber of the eye and to the capsular bag. The elongate member 2755 can extend through an outer protective sleeve 2759. The outer protective sleeve 2759 can be stationary and thereby protect the corneal incision or other tissues through which the shaft 2761 extends from being impacted by oscillating movements of the elongate member 2755. The shaft 2761 can also include a single tubular elongate member 2755 that oscillates without any outer sleeve 2759. However, it is preferable the shaft 2761 include a protective sleeve surrounding at least a portion of the oscillating elongate member 2755, for example, to protect the cornea from tissue damage due to being exposed to the oscillating movements of the elongate member 275.

The elongate member 2755 can include a port or opening near a distal end 2765 of the shaft 2761 that communicates with an inner lumen through the elongate member 2755 fluidly coupled to the aspiration pump and defining at least a portion of an aspiration waste line or suction path leading from the distal opening towards a proximal opening of the elongate member 2755. The elongate member can include an open distal end having a distal cutting tip. The shaft 2761 can extend through the vacuum manifold 2774 such that the proximal opening of the elongate member 2755 communicates with a vacuum chamber 2703 of the vacuum manifold 2774 (see FIGS. 4J-4K). The proximal opening of the elongate member 2755 is maintained within this vacuum chamber 2703 during oscillating movements of the elongate member 2755. A vacuum may be applied within the vacuum manifold 2774 to aspirate the dissected tissue from the eye through the lumen. The dissected tissue enters the lumen of the elongate member 2755 at the distal opening and exits the lumen of the elongate member 2755 through the proximal opening. In other implementations, the aspiration lumen can be formed between the outer protective sleeve 2759 and the outer surface of the elongate member 2755 to a proximal opening from the lumen 2763.

A plurality of seals 2786, such as O-rings that provide low resistance to movement, can prevent and/or substantially reduce the passage of fluid around the shaft 2761 (see FIG. 4I). The vacuum manifold 2774 can be coupled to a piston manifold 2798 such that the vacuum chamber 2703 of the vacuum manifold 2774 is in fluid communication with one or more pumping chambers 2705 in the piston manifold 2798. The piston manifold 2798 houses the pistons 2799 movable within the respective pumping chambers 2705 that are powered by a drive mechanism within the durable portion 3210 such as the motor 2756 upon coupling the disposable portion 3205 with the durable portion 3210. The one or more pistons 2799 generate a vacuum within the pumping chambers 2705 as well as the vacuum chamber 2703 for aspiration of material through the shaft 2761.

The pistons 2799 of the aspiration pump are driven by a cam system driven by a drive mechanism having the motor 2756. The cam system will be described in more detail below. The motor 2756 for the aspiration pump can be a brushless DC motor or any type of motor or driver suitable for rotating a shaft. In an implementation, the pump motor 2756 can be an electric motor that incorporates gear reduction via a gear box or other mechanism. In an implementation, the durable portion 3210 incorporates a HarmonicDrive gear reduction configured to achieve at least a 30:1 reduction.

The device is shown having three reciprocating pistons 2799, but it should be appreciated the device 2700 can include one, two, three, or more pistons 2799 movably positioned within their respective pumping chambers 2705. Multiple pistons 2799 bouncing back and forth within their pumping chambers 2705 may create a pulsatile vacuum or full vacuum delivered to a distal portion of the lumen of the elongate member in pulses of negative pressure. The pulsatile vacuum allows for application of full vacuum through the distal shaft 2761 without risk for collapse of the anterior chamber. While at the peak of the pulse, the system can generate a high vacuum. However, since it is pulsed, the average aspiration flow rate can be low enough for the irrigation inflow to maintain proper anterior chamber support even under these high vacuums at the pulse peak.

Still with respect to FIGS. 4H-4K, the vacuum chamber 2703 is configured to be in fluid communication with the one or more pumping chambers 2705 via a respective opening 2706 regulated by a one-way valve 2707. The configuration of the one-way valve 2707 can vary including a duckbill valve (as shown in FIG. 4L), ball check valve, lift-check valve, stop-check valve and other types of valves that allow flow of fluid in a single direction and cut-off flow of fluid in the opposite direction. Movement of the pistons 2799 in a first direction within the pumping chambers 2705 creates a vacuum such that material from the eye is drawn into the lumen 2763 of the elongate member 2755, emptied into the vacuum chamber 2703, and pulled through the one-way valve 2707 into the pumping chamber 2705. Movement of the pistons 2799 in a second, opposite direction within the pumping chambers 2705 expels material from the pumping chamber 2705 and out of the system. The material can be expelled from the system into a disposal enclosure coupled to an exit port 2715 as described elsewhere herein.

Figure 7A:
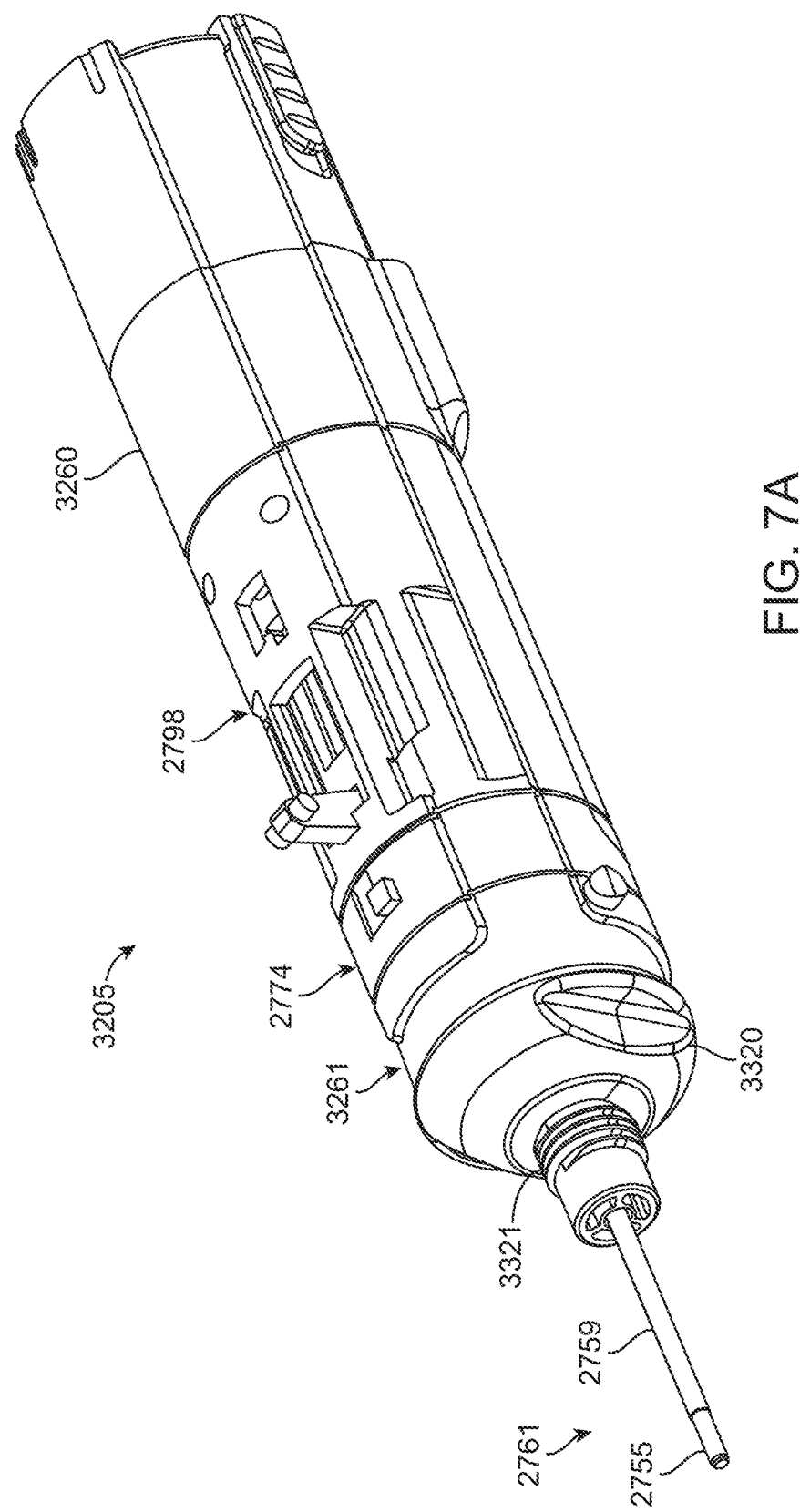
FIGS. 7A-7H illustrate various views of a microsurgical instrument.
Figure 7B:
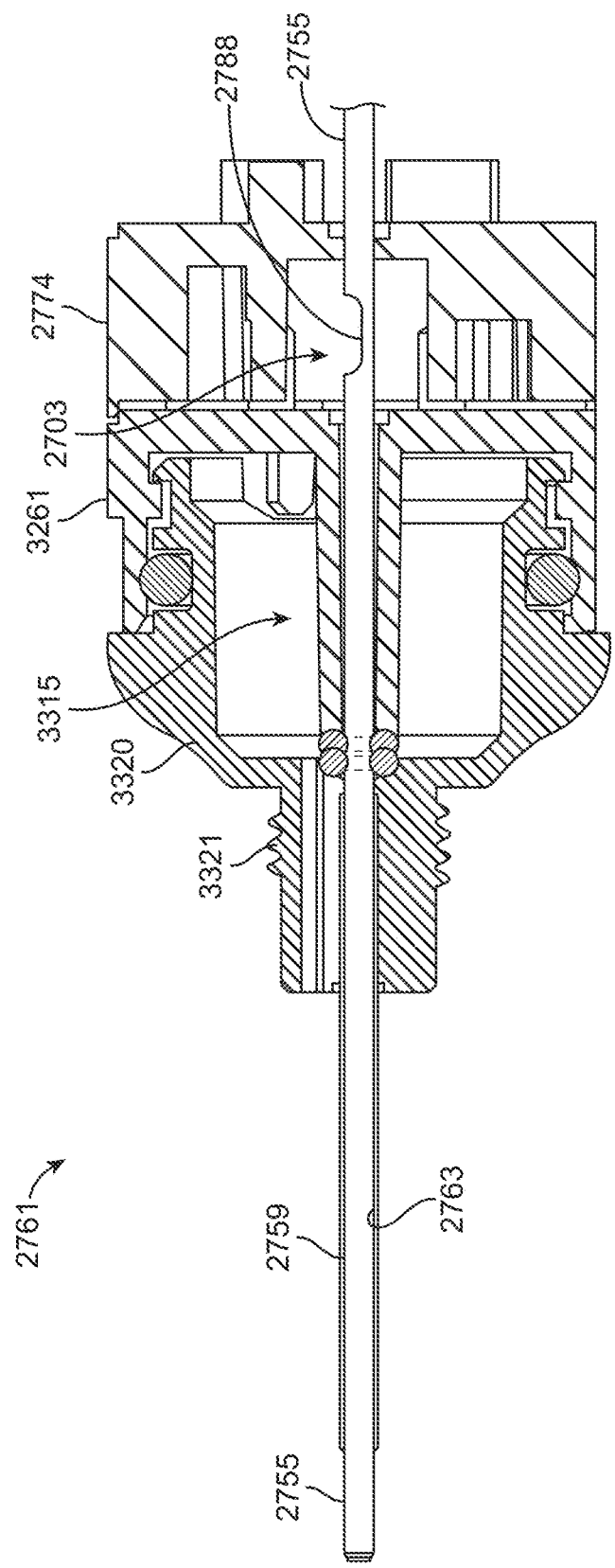

FIGS. 4L-4M show the vacuum manifold 2774 can additionally include an evacuation chamber 2709. The evacuation chamber 2709 is sealed off from the vacuum chamber 2703 such that material drawn into the system can be purged from the system without being pushed back out through the shaft 2761. The seal between the chambers 2703 and 2709 can be provided by one or more O-rings 2786. As mentioned, the vacuum chamber 2703 is configured to be in fluid communication with the one or more pumping chambers 2705 through respective one-way valves 2707 positioned within openings 2706. In some implementations, a recess 2702 between the valve opening 2706 and the pumping chamber 2705 can have a floor 2712 that is angled to encourage movement and clearing of material through the valve 2707 into the pumping chamber 2705 (see FIG. 4P). The angle of the floor 2712 relative to the axis of the valve 2707 can vary from about from about 1 degrees up to about 90 degrees. In some implementations, the angle can be about 20 degrees up to about 45 degrees. The angle of the floor 2712 can be selected to guide lens fragments and material aspirated from the eye towards the pumping chamber 2705. The floor 2712 can also be flat (see, e.g., FIG. 7D showing the floor of the recess below the valve 2707 that is at 90 degree angle relative to the axis of the valve opening). The evacuation chamber 2709 is in fluid communication with each of the one or more pumping chambers 2705 through other openings or waste channels 2711 regulated by respective valves 2713. The configuration of the valves 2713 can vary including a ball type check valve or a duckbill valve. As described above, movement of the pistons 2799 in a first direction within their respective pumping chambers 2705 (e.g. towards a proximal end of the device 2700) draws material from the vacuum chamber 2703 into the pumping chamber 2705 through the valves 2707. Movement of the pistons 2799 in a second, opposite direction within their respective pumping chambers 2705 (e.g. towards the distal end of the device 2700) causes pressure to build within the piston manifold 2798. The pressure opens the valves 2713 in the piston manifold 2798. The waste material may enter the vacuum manifold 2774 through the waste channels 2711 (e.g. see three openings shown in FIG. 7C). The waste may combine in the vacuum manifold 2774 and exit the device through the evacuation chamber 2709. The evacuation chamber 2709 shown in FIG. 7C may be an oval-shaped channel that runs through the vacuum and piston manifolds 2774, 2798 although it should be appreciated that other shapes are considered herein. During this purge of material, the one-way valves 2707 between the one or more pumping chambers 2705 and the vacuum chamber 2703 prevents the backflow of material into the vacuum chamber 2703, the lumen 2763, and out the cutting tip. However, the openings or waste channels 2711 between the one or more pumping chambers 2705 and the evacuation chamber 2709 allows for the material to freely enter the evacuation chamber 2709 and ultimately out the exit port 2715 of the evacuation chamber 2709 at least until flow is cut off by the valves 2713.

As described above, movement of the pistons 2799 in a proximal direction creates a vacuum within the pumping chamber 2705. In some implementations, the valve 2713 is a ball check valve. The ball 2717 of the valve 2713 is pushed proximally by the spring 2719 away from opening or waste channel 2711 between the pumping chamber 2705 and the evacuation chamber 2709 thereby opening the valve 2713. Upon movement of the pistons 2799 in a distal direction, fluid pressure builds within the pumping chamber 2705 increasing fluid pressure within the chamber and urging the material towards the opening into the waste channel 2711 of the valve 2713. The ball 2717 of the valve 2713 is pushed distally against the spring 2719 such that the spring 2719 compresses and the ball 2717 is urged against the valve opening into the waste channel 2711 thereby closing the valve (see FIG. 4M). The pumping chambers 2705 are substantially devoid of material upon closure of the valve 2713.

The instrument can incorporate a plurality of one-way valves that are positioned to allow for fluid flow in and also out of the pumping chamber 2705. The configuration of the valves can vary. In some implementations, the valves are non-compliant, one-way valves like ball valves incorporating a relatively rigid ball as discussed above. In other implementations, the valves are compliant. For example, the valves 2707 described herein can be slightly compliant silicone valves such as duckbill valves. The valves 2713 can also be slightly compliant valves. The ball 2717 of the valve 2713 need not be rigid, but can be formed of a material that is compliant under a given amount of pressure. The valve 2713 also need not be a ball valve. The valve 2713 can also be a silicone valve like a duckbill valve similar to valves 2707, except positioned to allow flow in a direction opposite of valve 2707. Thus, valves 2707 can be duckbill valves that allow for flow through the valve in a first direction (i.e. from the eye towards the pumping chamber 2705) and valves 2713 can also be duckbill valves that allow for flow through the valves 2713 in a second, opposite direction (i.e. from the pumping chamber 2705 through the opening 2711 towards the waste channel). Compliant valves such as duckbill valves provide for fluid flow under a certain degree of pressure with very little motion of the valve components.

In other implementations, valve 2713 is a ball check valve. The ball 2717 can be rigid and substantially non-compliant such as a hard plastic or metal material. The compliant valves may deform as a reverse positive pressure is imparted on them whereas the non-compliant valves do not deform. If the valve between the vacuum chamber 2703 and the pumping chamber 2705 is a compliant valve and the ball 2717 is substantially non-compliant, then as the piston is travelling distally and generating positive pressure to evacuate the material from the pumping chamber 2705, the positive pressure can cause a deformation of the compliant valve and a small purge or regurgitation of an amount of fluid out the distal opening of the shaft 2761. This regurgitation may occur on every back and forth cycle of the piston 2799. In some embodiments, the regurgitation may be optimized further by the design of the pumping chamber 2705. In the pumping chamber 2705, the outlet opening connecting the pumping chamber 2705 to the evacuation chamber 2709 may be located, for example, on the side of the chamber and configured such that the piston 2799 may travel beyond the outlet opening. In this embodiment, after the piston 2799 has moved distally beyond the outlet opening there is no other route for fluid evacuation. Therefore, as the pistons 2799 continue to travel distally creating a moment of positive pressure within the pumping chamber 2705 after closure of the valves 2713 that causes a short regurgitation of material at the distal end of the shaft 2761.

Again with respect to FIGS. 4H-4J and also FIG. 4N-4P, each of the pistons 2799 can include an elongate central piston rod 2721 surrounded by a spring 2701 extending between piston heads 2723a, 2723b. The spring 2701 is biased to urge the piston 2799 proximally towards a proximal end of the pumping chamber 2705. A distal piston head 2723a and sliding O-ring seal 2794 are positioned within the pumping chamber 2705. The piston rod 2721, spring 2701, and proximal piston head 2723b are positioned within a piston chamber 2704 within the piston manifold 2798 located proximal to the pumping chamber 2705. The distal piston head 2723a, sliding seal 2794, and piston rod 2721 are capable of sliding within the pumping chamber 2705. The pumping chamber 2705 has an inner dimension that is smaller than the piston chamber 2704 and the outer dimension of the spring 2701. Thus, as the piston 2799 move towards the distal end region of the pumping chamber 2705, the spring 2701 gets compressed within the piston chamber 2704 between the proximal piston head 2723b and the lower end of the pumping chamber 2705.

The pistons 2799 are moved towards the distal end region of the pumping chamber 2705 by the drive mechanism. In some implementations, the drive mechanism incorporates a rotating cam 2769 (see FIGS. 4I-4K). The rotating cam 2769 positioned proximal to the pistons 2799 is configured to urge the pistons 2799 distally towards the distal end of their respective pumping chambers 2705. As the cam 2769 rotates, it applies a distally-directed force sequentially against the proximal piston heads 2723b of the pistons 2799. The springs 2701 of the pistons 2799 are, in turn, sequentially compressed. Upon further rotation of the cam 2769, the distally-directed force against the proximal piston heads 2723 is sequentially removed and the springs 2701 sequentially urge the pistons 2799 backwards creating a vacuum within the respective pumping chambers 2705 through the one-way valves 2707.

As best shown in FIGS. 4C-4D, a gear head 2752 of the motor 2756 can be coupled to the rotating cam 2769 via a motor coupler 2795. FIG. 4F shows the motor coupler 2795 can have a bore 2789 in a proximal end configured to receive the gear head 2752. FIG. 4E shows the motor coupler 2795 can have one or more projections 2796 on a distal end configured to abut and engage with corresponding wedged-shaped projections 2797 on the proximal end of the cam 2769. The cam 2769 rotates as the gear head 2752 rotates. A distal end of the cam 2769 is configured to insert within a proximal opening into a bore 2791 of the piston manifold 2798 (see FIG. 4F). At least a portion of the cam 2769 can be positioned within the bore 2791 such that a cam surface 2725 on the distal end of the cam 2769 can engage with proximal piston heads 2723b of the pistons 2799 within the piston manifold 2798. The cam surface 2725 is configured to provide reciprocal linear motion of the pistons 2799 within the piston manifold 2798. The geometry of the cam surface 2725 can be designed to provide different motion profiles of the pistons 2799 in their respective piston chambers 2704 and thereby create different vacuum profiles (i.e. smooth continuous, continuous with spikes in negative pressure, or discontinuous pulsed negative pressure). The cam surface 2725 can be elliptical, eccentric, egg, or snail-shaped. During a first fraction of rotation of the cam 2769, the proximal piston heads 2723b slide along the ramped portion of the cam surface 2725 and the piston 2799 is moved distally along the longitudinal axis of the device. During a second fraction of rotation of the cam 2769, the proximal piston heads 2723b slide past the cam surface 2725 that terminates at ledge 2726 (see FIG. 4E). When the piston heads 2723b drop off ledge 2726 the distally-directed force against the pistons 2799 by the cam 2769 is released. The spring 2701 surrounding the piston rod 2721 urges the proximal piston head 2723b in a proximal direction towards the proximal end region of the piston chamber 2704. A complete revolution of the cam 2769 therefore allows for axial movement of each piston 2799 in succession. The piston heads 2723b slide along the cam surface 2725 and extend in the distal direction at a first rate and the piston heads 2723b drop off the cam surface 2725 and retract in the proximal direction at a second rate that is much faster than the first rate.

The timing of this piston movement can vary based on the geometry of the cam surface 2725 and the location of the ledge 2726 relative to the cam surface 2725. For example, the timing of when one piston retracts to create a negative pressure within the chamber relative to when the next piston retracts to create a negative pressure can be a function of the cam surface 2725 geometry. The cam surface 2725 can incorporate a ledge 2726 such that each piston retracts quickly upon reaching the ledge 2726. The piston 2799 extends at a first rate in a distal direction as it moves along the cam surface 2725 and then at a second, faster rate in the proximal direction as it drops off the ledge 2726. In other implementations, the cam surface 2725 has a first ramp connected to the ledge 2726 by a second ramp. The first ramp of the cam surface 2725 allows for gradual extension of each piston 2799 and the second ramp allows for gradual retraction of each piston 2799. Thus, each piston 2799 will gradually retract a distance before the piston 2799 drops off the ledge 2726 to quickly retract the rest of the rearward travel. Movement of the pistons 2799 involved in creating aspiration forces and movement of the elongate member 2755 involved in cutting can be linked due to the rotating cam mechanism, as will be described in more detail below and with respect to FIGS. 10A-10C, 11A-11B, and 12.

In some implementations, the cycles of negative pressure can be interspersed with short regurgitation via application of positive pressure between pulses of negative pressure. The short periods of vacuum can be interspersed by short periods of decreasing vacuum or no vacuum. In some implementations, the cycles of negative pressure include short periods of vacuum interspersed by short periods of positive pressure thereby resulting in a short regurgitation of fluid through the distal shaft during each cycle of piston movement. Whether or not positive pressure is applied between the pulses of vacuum, the pulsatile vacuum creates pulses of discontinuous negative pressure through the elongate shaft that can be between about 10 inHg up to about 30 inHg, preferably as close to full vacuum as possible. In some implementations, the device can create pulses of discontinuous negative pressure through the internal lumen of the elongate member at a cycling frequency. The device can also create pulses of discontinuous positive pressure having the same cycling frequency. Thus, the pulses of discontinuous negative pressure are interspersed by the pulses of discontinuous positive pressure. The cycling of the negative pressure pulses and positive pressure pulses can be very fast (e.g. up to about 5000 Hz-10,000 Hz) and very small volumes (e.g. 10 uL up to about 1 mL). The cycling frequency of the pulses can be, for example, at least about 0.5 Hz up to about 5000 Hz, or between 1 Hz and 4000 Hz, or between about 10 Hz up to about 2000 Hz. In still further implementations, the cycling of the negative pressure pulses provided by the pump can overlap with one another such that the effective aspiration pressure provided is substantially smooth and continuous.

The pulses of discontinuous negative pressure aspirate a first amount of material into the internal lumen through the opening at the cycling frequency. The pulses of discontinuous positive pressure expel a second amount of material at the cycling frequency from the internal lumen through the opening. The volume of material being moved per cycle can vary, but is generally relatively small, for example, between about 0.1 mL up to about 1.0 mL, or approximately 0.5 mL. Each piston bore or pumping chamber 2705 can have a diameter of about 0.05" to about 0.50". The stroke length of each piston can be between about 0.10" to about 0.50". The pistons can create a stroke volume of about 50 cubic mm to about 200 cubic mm. In an implementation, the piston bore diameter is about 0.20" and has a stroke length of about 0.20" and a stroke volume of about 100 cubic mm. In some implementations, the nominal amount of fluid removed per pulse is about 100 microliters, or between 10 microliters up to about 1000 microliters. The second amount of material can be substantially less than the first amount of material within this general range of fluid amounts. The pulses of discontinuous negative pressure can be interspersed by discontinuous periods of lessening vacuum, no vacuum, or positive pressure at the same frequency.

FIGS. 4N-4P show a piston stop 2727 coupled to a proximal end region of the piston manifold 2798. As discussed elsewhere herein, the aspiration pump of the device can include a plurality of pistons, each of the plurality of pistons being housed within a respective cylinder. Each of the cylinders are fluidly coupled to the inner lumen of the elongate member. The drive mechanism can include a rotational cam assembly capable of being rotated by the motor via a rotatable coupler. Rotation of the rotational cam assembly causes the plurality of pistons to generate pulses of discontinuous negative pressure within the inner lumen. The piston hard stop 2727 is configured to limit proximal travel of the plurality of pistons within their respective cylinders. The piston hard stop is configured to toggle between a high vacuum position and a low vacuum position. When in the high vacuum position, the piston hard stop 2727 is retracted proximally relative to the cylinders allowing for maximum proximal travel of each piston within its respective cylinder. When in the low vacuum position, the piston hard stop 2727 is advanced distally relative to the cylinders limiting proximal travel of each piston within its respective cylinder to less than a maximum proximal travel. Toggling the piston hard stop 2727 also allows for switching between a continuous aspiration position and a pulsatile aspiration position. When in the pulsatile aspiration position, the piston hard stop 2727 is retracted proximally relative to the cylinders allowing for maximum proximal travel of each piston within its respective cylinder. When in the continuous aspiration position, the piston hard stop 2727 is advanced distally relative to the cylinders limiting proximal travel of each piston within its respective cylinder to less than a maximum proximal travel. The selective modification of the aspiration provided by the aspiration pump is described in more detail below.

The piston stop 2727 can be a generally cylindrical element configured to surround the rotating cam 2769. A distal end region of the piston stop 2727 can define one or more projections 2729 configured to project into a proximal end region of each of the piston chambers 2704 in the piston manifold 2798. The projections 2729 can abut against the proximal piston heads 2723b of respective pistons 2799 when positioned at a proximal-most end region of their respective piston chambers 2704. For example, if the device 2700 includes three pistons 2799 positioned in three piston chambers 2704, the piston stop 2727 includes three projections 2729 configured to abut against the proximal piston head 2723b of each of the three pistons 2799. The piston stop 2727 provides a hard stop to the proximal linear travel of the pistons 2799 upon expansion of the springs 2701. The piston stop 2727 limits the overall volume of the pumping chamber 2705 that can be achieved. The relative position of the projections 2729 within the piston chambers 2704 can be adjustable. In some implementations, an adjustment ring 2730 can be positioned around an outer surface of the piston stop 2727. The adjustment ring 2730 can be available to a user through one or more windows 2731 in the housing 2762 of the hand-held portion 2760 (see FIGS. 4A-4B). The adjustment ring 2730 can have a threaded inner surface configured to engage with a corresponding pin 2732 on an outer surface of the piston stop 2727 (see FIG. 4K). The pin 2732 is configured to slide within the threads of the adjustment ring 2730 such that the piston stop 2727 travels axially along the longitudinal axis of the device. As the piston stop 2727 is adjusted to be positioned further distal relative to the piston manifold 2798, the projections 2729 extend further into the piston chambers 2704 and limit the linear travel of the pistons 2799 in the proximal direction upon expansion of the springs 2701. This, in turn, limits the size of the pumping chamber 2705. As the piston stop 2727 is adjusted to be positioned more proximally relative to the piston manifold 2798, the projections 2729 are withdrawn from the piston chambers 2704 and do not limit (or limit to a lesser degree) the linear travel of the pistons 2799 in a proximal direction upon expansion of the springs 2701. This, in turn, maximizes the size of the pumping chamber 2705. The piston stop 2727 also can be selectively modified or adjusted by a user to determine the type of vacuum created by the aspiration pump and applied by the pistons within their respective chambers 2704 (e.g. smooth continuous vacuum or smooth continuous with spikes in pulsatile vacuum).

In some implementations, the vacuum source can create a sudden rise in vacuum forming a vacuum profile that causes the cornea and the eye to effectively "bounce" up and down during application of pulsed vacuum. For example, when the pistons 2799 are sprung backwards they can create the sudden rise in vacuum forming a vacuum profile that resembles a "saw tooth" (i.e. suction-pause-suction). Limiting the backwards travel of the pistons 2799 inside their respective pumping chambers 2705 can reduce the amount of suction impact or shock that is created each time the pistons are sprung backwards. The piston limit thereby limits the maximum suction created with each piston travel reducing the impact this abrupt suction can have on the eye. The vacuum created with each backwards travel of the piston 2799 can be greater than 500 mmHg up to about 700 mmHg.

The amount of pulsatile vacuum can be adjusted by limiting the travel of the pistons in a rearward direction such as with a piston hard stop 2727. In some implementations, the relative relationship of the disposable to reusable portions 3205, 3210 is adjustable and, in turn, can limit the distance the pistons can travel backwards. For example, the further the reusable portion 3210 is positioned onto the disposable portion 3205, the more limited the piston travel is due to the piston hard stop. The position of the piston stop can be adjustable to provide a plurality of selectable vacuum settings. In some procedures or certain steps of a procedure, higher pressures may be more desirable than in other procedures or steps of the procedure. The higher pressure can be selected, for example, by actuating the piston stop to a wider setting such that the piston can travel a longer distance per cycle and maximum vacuum achieved. In some implementations, the piston stop position can be toggled between a "high vacuum" position and a "low vacuum" position by clicking an adjustor. In other implementations, the piston stop positioned can be "dialed in" to any of a plurality of vacuum settings that are conveniently selected during use. In still further implementations, the piston stop position can be selectively adjusted to achieve a smooth, continuous vacuum or a pulsed vacuum, which will be described in more detail below.

In some implementations, the device is limited from achieving maximum vacuum by incorporating a feature that automatically bypasses the shaft 2761 depending on whether a threshold vacuum is reached. For example, a bleed valve or other bypass mechanism can be incorporated to prevent a threshold amount of vacuum from being applied at a distal opening of the shaft 2761 and into the eye. A bypass to turn on or off the suction can limit the maximum amount of vacuum that can be generated within the eye even if the opening into the shaft 2761 is clogged. This bypass can prevent the vacuum from building in the event of a blockage to create less surge upon removal of that blockage. The bypass mechanism can be adjustable or selective such that a user can choose whether or not they want the potential for maximum vacuum or something less than maximum vacuum applied.

Other mechanisms for preventing occlusion break surge can also be incorporated. For example, a valve such as a diaphragm valve, an umbrella valve, mushroom valve, or similar type valve can be incorporated within the aspiration line of the hand piece to prevent surge during aspiration. The valve in the hand piece may be normally open during use and temporarily close in response to reach a threshold pressure or flow rate within the waste line. The valve can be a movable member that floats above an orifice near the tip of the disposable portion of the hand piece. The valve can include a flexible mushroom head formed of a compliant material, or a flap positioned above an orifice. If the suction flow rate or pressure is below the threshold value, the gap between the orifice and the mushroom head of the valve is maintained in an open position. If the threshold value is reached, the gap between the orifice and the mushroom head of the valve narrows to a closed position. When fragments of tissue occlude the tip of the shaft and the aspiration pump 145 continues operating, a build-up of vacuum in the aspiration line can occur. There can also occur a sudden spike in flow rate once the occlusion clears. This is referred to as post-occlusion surge. However, the amount of fluid volume removed during the surge is limited by closure of the valve. The sudden spike in flow rate due exposure of the lumen to the built-up negative pressure within the aspiration line causes the mushroom head of the valve to be moved against the orifice thereby cutting off aspiration to the lumen. The valve stays closed until the aspiration pressure in the line and the flow rate returns back to the threshold value. The valve then moves to uncover the orifice thereby opening the connection between the lumen of the cutter tube and the waste line allowing material to once again move through the lumen and out towards the waste. The volume of fluid removed from the eye during the surge is limited to a very small amount of fluid in the lumen of the shaft before the valve closes off all flow thereby preventing noticeable anterior chamber shallowing.

FIG. 21 illustrates an implementation of an anti-surge valve 3530. The valve 3530 can be incorporated a variety of cutting/aspirating devices including the instruments described herein as well as in conventional phacoemulsification hand pieces configured to be coupled to a remote aspiration pump having a long, compliant fluid lines. The valve 3530, which can be located within the aspiration waste line, can be configured to limit flow rate through the elongate member 2755 to minimize post-occlusion surge. The anti-surge valve 3530 can be configured to limit flow through the aspiration waste line when a flow rate of aspiration is above a threshold value and is configured to allow flow through the aspiration waste line when the flow rate of aspiration is below the threshold value.

The shaft 2761 can include an elongate member 2755 having an opening near a distal end of the shaft 2761 into the lumen 2763 as well as a notch or proximal opening 2788 a distance away from the distal end of the shaft 2761. Material aspirated from the eye can enter the lumen 2763 of the elongate member 2755 through the distal opening and exit the lumen 2763 via the proximal opening 2788. The elongate member 2755 can extend through the vacuum chamber 2703 of the vacuum manifold 2774 such that the proximal opening 2788 communicates with the vacuum chamber 2703. The proximal opening 2788 is maintained within the vacuum chamber 2703 during oscillating movements of the elongate member 2755.

Material drawn into the vacuum chamber 2703 due to movement of the pistons 2799 within their piston chambers can be directed towards the pumping chamber 2705 (not shown in FIG. 21) through the anti-surge valve 3530. The valve 3530 can include an elastomeric silicone diaphragm 3532 that is arranged over a seat 3534. The diaphragm 3532 is configured to deflect toward the seat 3534 thereby closing the gap and preventing flow towards the pumping chamber 2705. Flow above a certain rate or upper threshold value creates a pressure differential on either side of the diaphragm 3532 causing deflection and closing of the valve 3530. As an example, the flow may be limited to about 40 mL/minute. Flow is forced through an effective orifice and thus, there is a pressure differential between one side of the diaphragm 3532 and the other. The pressure differential can be about 1.0 psi for an annular gap of about 0.015". The 1.0 psi can be sufficient to deflect the diaphragm 3532 against the valve seat 3534 thereby blocking flow and eliminating surge through the elongate member 2755. In some implementations, a small groove across the valve seat 3534 (e.g. having a depth of about 0.010") can allow the pressure between chambers on either side of the diaphragm 3532 to equalize after the surge event is over. FIG. 21 illustrates the valve 3530 in an open configuration such that flow can proceed through the gap between the diaphragm 3532 and the valve seat 3534. When pressure in chamber 2703 is greater than the pressure in chamber 3536 the diaphragm 3532 deflects against the seat 3534 to limit flow rate through the elongate member 2755. When pressure in chamber 2703 approaches the pressure in chamber 3536, the diaphragm 3532 deflects back away from the seat 3534 allowing flow through the gap and through the elongate member 2755.

Figure 22A:
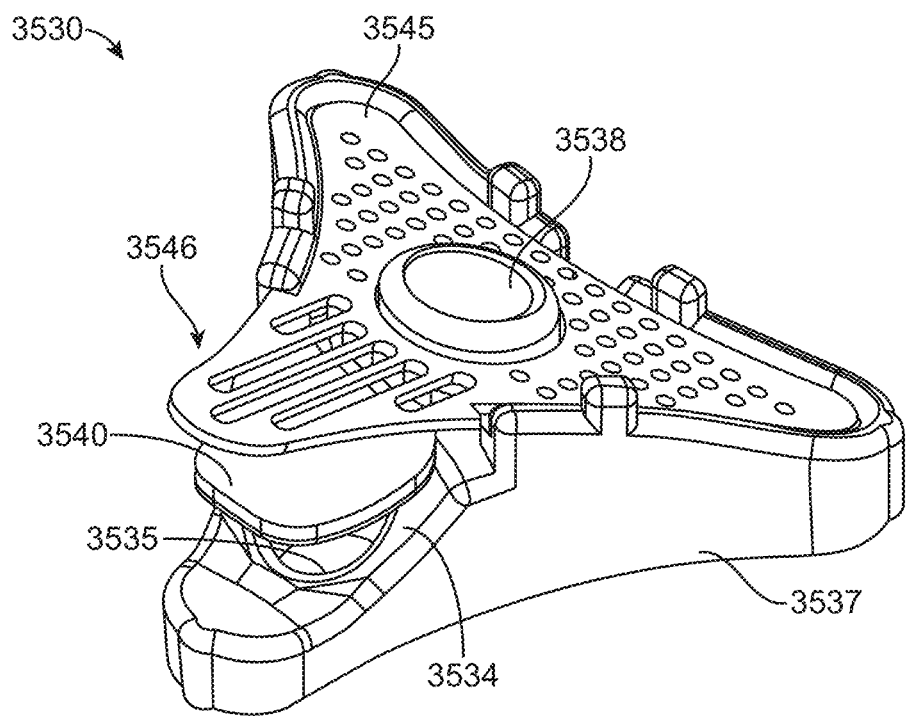
Figure 22B:
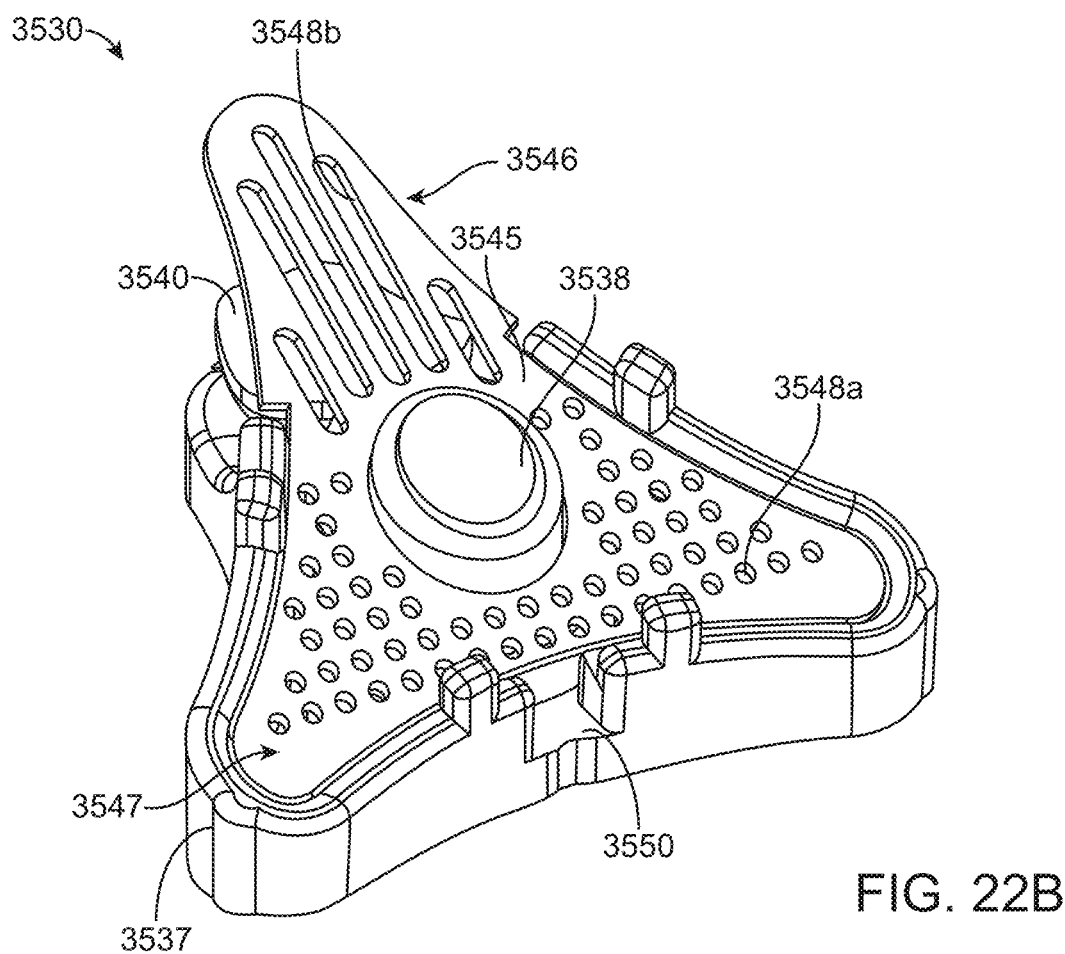
Figure 22C:
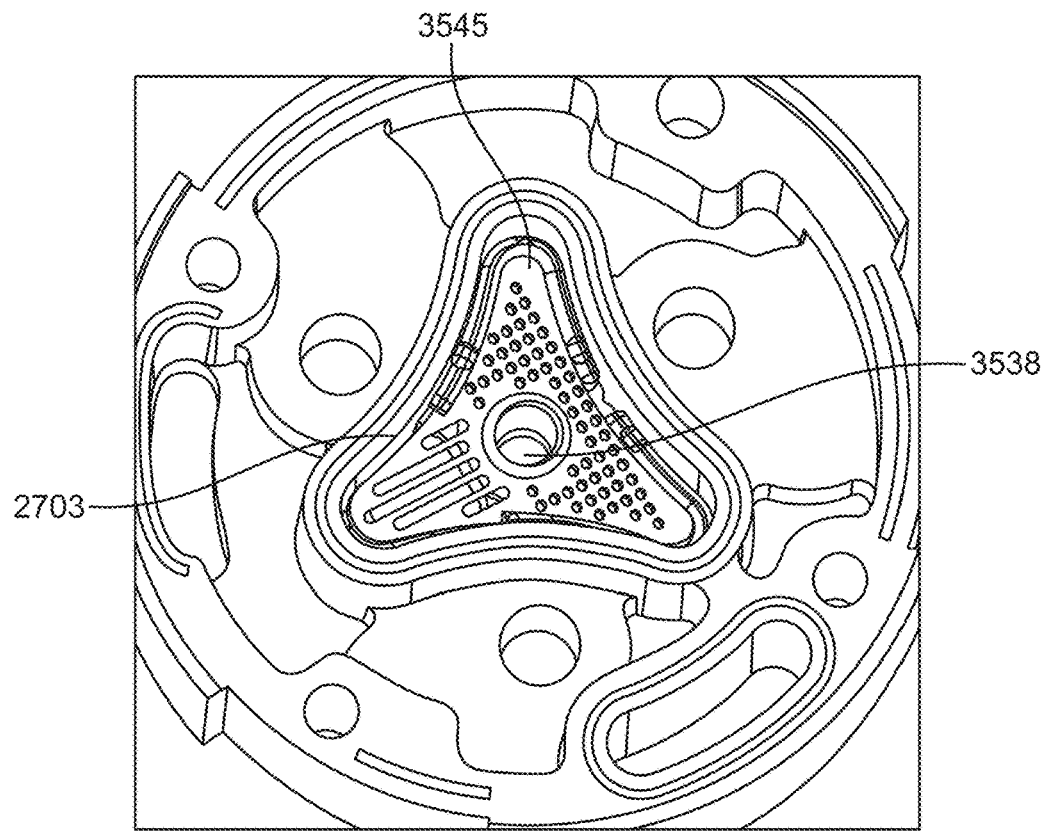
Figure 22D:
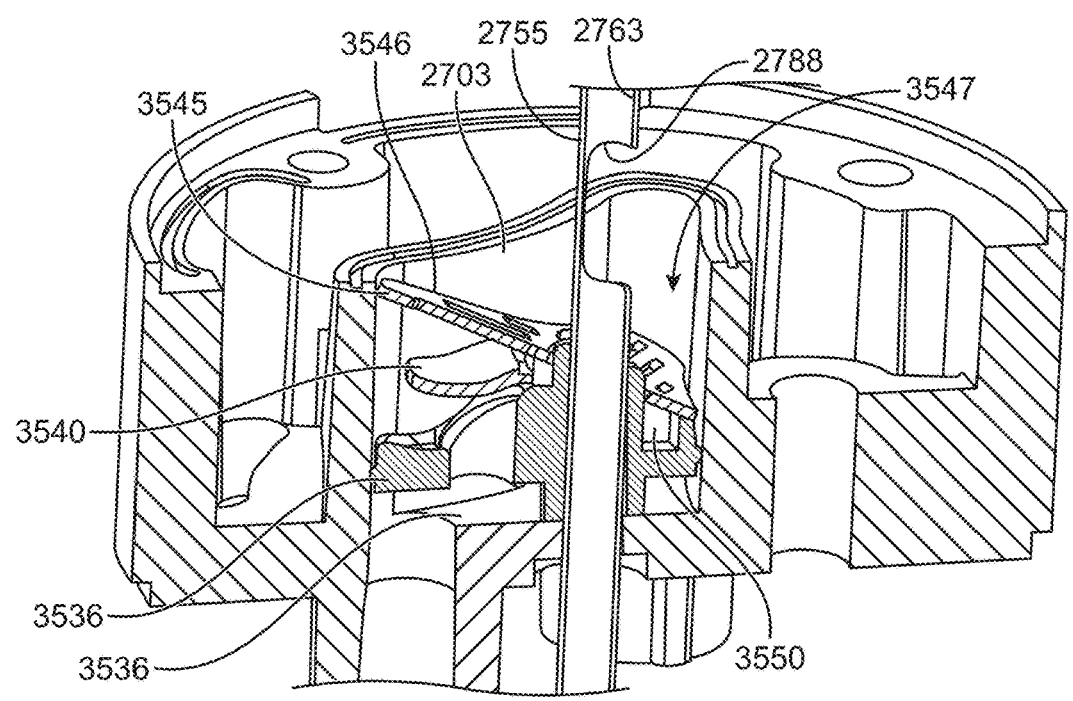

FIGS. 22A-22D show an implementation of a valve 3530 having a filter 3545. The configuration of the valve 3530 can vary including diaphragm valve as discussed above, umbrella valve, flapper valve, or other valve incorporating a deflectable feature configured to close and open the valve 3530 upon changes in flow through the vacuum chamber 2703. As discussed above, the proximal opening 2788 of the elongate member 2755 remains on a distal side of the valve 3530 within vacuum chamber 2703. Material aspirated from the eye exits the lumen 2763 of the elongate member 2755 through the proximal opening 2788 into the vacuum chamber 2703. The valve insert 3537 can incorporate a central bore 3538 through which the elongate member 2755 extends. The valve 3530 can include a deflectable petal 3540 arranged over the seat 3534. The petal 3540 is configured to deflect toward the seat 3534 during a surge event thereby closing the gap and preventing flow towards the pumping chamber 2705 as described in more detail above. The petal 3540 can have a non-planar shape. For example, FIG. 22D shows the petal 3540 can be cupped or having a concave shape.

The anti-surge valve 3530 can incorporate a filter 3545 on its upstream side (i.e. vacuum chamber 2703 side) to prevent large lens fragments aspirated through the lumen from clogging the valve area. The filter 3545 can have an outer perimeter configured to substantially engage with an inner perimeter of the vacuum chamber 2703 or the valve insert 3537 positioned in sealing engagement with the vacuum chamber 2703. The filter 3545 can be positioned over the petal 3540 such that it does not come into contact with the deflectable element while still preventing material over a threshold size from approaching the seat 3534. In some implementations, the filter 3545 can be arranged within the vacuum chamber 2703 such that it extends perpendicular to the longitudinal axis A of the shaft or is positioned so it is not perpendicular to the longitudinal axis A. For example, the filter 3545 can be angled relative to the longitudinal axis A from about 15 degrees to about 50 degrees. FIG. 22D shows the filter 3545 positioned at an angle relative to the longitudinal axis A such that there appears to be an uphill end 3546 of the filter 3545 and a downhill end 3547 of the filter 3545. The angle of the filter 3545 within the chamber 2703 results in the uphill end 3546 of the filter 3545 being located closer to the distal end of the device and the downhill end 3547 of the filter 3545 being located further away from the distal end of the device. The uphill end 3546 of the filter 3545 can be positioned a distance away from and allow for deflectable motion of the petal 3540 of the valve 3530. The plane of the filter 3545 can be generally flat and obstruction-free to encourage larger particles to roll down the surface of the filter 3545 towards the downhill end 3546 away from the valve 3530. In some implementations, the filter 3545 can incorporate a weep hole 3550 on its downhill end 3546 that can trap material away from the location of the valve 3530.

In some implementations, the filter 3545 is a mesh filter, frit, or other porous element. The filter 3545 can incorporate a plurality of openings 3548 extending through it that are configured to allow fluid flow through the filter 3545 while preventing passage of material fragments over a threshold size from passing through the filter 3545 and entering the chamber 3536. The filter 3545 prevents large fragments from clogging the area near the valve seat 3534 that would prevent closure of the valve opening 3535 through the seat 3534 by the petal 3540. The plurality of openings 3548 extending through the filter 3545 can vary in size and shape and can be uniform or non-uniform. The plurality of openings 3548 can be arranged in a pattern or can be random. FIG. 22A-22C illustrate a first plurality of opening 3548*a* in the downhill end 3547 of the filter 3545 having a first shape and a second plurality of openings 3548*b* in the uphill end 3546 of the filter 3545 having a second, different shape. For example, the first plurality of openings 3548*a* can be small, round openings whereas the second plurality of openings 3548*b* can be elongate slots that are larger in overall size compared to the first plurality of openings 3548*a*. The larger slot-shaped plurality of openings 3548*b* can be located on a region of the filter that is positioned over the petal 3540 to encourage closure of the valve 3530 upon increased flow.

The plurality of openings 3548 whether uniform or non-uniform in size and/or shape can be arranged in any of a variety of patterns through the filter 3545. The size, shape, number, and/or pattern can be designed to encourage a desired flow of material through the filter 3545 or to prevent flow of material through the filter 3545 and instead travel across a surface of the filter 3545. A first plurality of openings 3548 can be positioned in a first region of the filter 3545, a second plurality of openings 3548 can be positioned in a second region of the filter 3545, a third plurality of openings 3548 can be positioned in a third region of the filter, etc. thereby forming a pattern of openings of the filter 3545. Each of the plurality of openings 3548 can itself also form a pattern of openings. For example, the plurality of openings 3548 can be a plurality of elongate slots having different lengths. A first central elongate slot can have a first length and be bound on either side by second elongate slots having a second, shorter length. The second elongate slots can, in turn, be bounded on an outer side by third elongate slots having a third, shorter length, and so on. The first, second, and third slots can thereby form a pattern and the pattern can be repeated in more than one region of the filter 3545. Thus, the filter 3545 can have a primary pattern of openings and the primary pattern of openings can be arranged into secondary patterns of openings, and so on.

It can be desirable to limit the maximum vacuum pressure that can be achieved with each proximal travel of each piston. Limiting the maximum vacuum can provide additional safety with regard to the capsular bag and the eye as a whole. For example, the impact the system has on the integrity of the capsular bag and the anterior chamber can be directly related to the degree of suction applied at the distal tip. Limiting the overall vacuum pressure (e.g. by at least about 2%, 3%, 4%, 5%, 10%, 15%, 20%, 25%, up to about 50% of maximum vacuum otherwise achievable) can prevent issues such as tearing of the capsular bag or "trampolining" of the anterior chamber.

FIG. 4O illustrates an implementation of a vacuum bypass feature 2708 configured to limit the maximum vacuum pressure in each pumping chamber 2705. The bypass feature 2708 can have any of a variety of configurations. In an implementation, the bypass feature 2708 can be a small longitudinal indentation, divot or groove in the cylindrical wall of each pumping chamber 2705 (see FIG. 4O). As described above, the piston 2799 can include an elongate central piston rod 2721 surrounded by a spring 2701 extending between piston heads 2723*a*, 2723*b*. A sliding O-ring seal 2794 can be positioned around the distal piston head 2723*a* that maintains a vacuum within the pumping chamber 2705. The piston 2799 shown in FIG. 4O is positioned in the cylindrical pumping chamber 2705 near the end of its proximal travel path such that proximal piston head 2723*b* abuts against the piston stop 2727. When the piston head 2723*b* abuts against the piston stop 2727, the seal 2794 can be aligned with the bypass feature 2708 near the proximal end of piston travel. The bypass feature 2708 can have a length along the longitudinal axis of the cylindrical chamber such that at least a portion of the feature 2708 is located distal to the seal 2794 and at least a portion of the feature 2708 is located proximal to the seal 2794. The presence of the bypass feature 2708 on both distal and proximal sides of the seal 2794 (i.e. the higher and lower pressure sides of the chamber 2705) means an amount of ambient air can bleed momentarily from the higher pressure side into the lower pressure side of the chamber 2705 (i.e. distal to the seal 2794) at the proximal end of piston travel. The leak or bleed of ambient air can limit the extent of the vacuum pressure that would otherwise be achieved upon retraction of the piston 2799 in the proximal direction. The venting of the aspiration cavity can be to the atmospheric air or to the irrigation fluid pathway, to the waste fluid pathway, or any other cavity allowing for fluid or air to enter the aspiration cavity and the vacuum level achieved within the aspiration cavity is decreased. The venting can release the vacuum level within the aspiration cavity as well as reduce the maximum achievable vacuum level during operation. The bypass feature 2708 can be designed to achieve a desired maximum pressure value depending on a length, width, and/or depth of the groove as well as the number of grooves incorporated. The geometry of the bypass feature 2708 can also control the speed at which this vacuum pressure is created with each sequential piston retraction.

The bypass feature 2708 can vent the vacuum to atmosphere passively, as described above, or actively. For example, the bypass feature 2708 can be user-actuated as will be described in more detail below. The bypass feature 2708 can have an adjustable and/or user-selectable geometry to provide additional user control over the desired maximum pressure value that can be achieved. In an implementation, the bypass feature 2708 can be a small hole extending through the wall of the pumping chamber 2705. The diameter, length, and/or location of the hole can be variable and selectable by a user so as to achieve the desirable control of the maximum suction pressure achieved.

In some implementations, the device can incorporate a venting mechanism that can be useful in certain situations, for example, when the capsular bag is inadvertently captured in or lens material occludes the distal end of the shaft 2761. Similar to the bypass feature 2708 described above, the venting mechanism can include a small hole through the wall of the pumping chamber 2705 that can be selectively exposed or covered. The hole can be covered and/or exposed by a movable element actuatable by a button or other input on the user interface of the device allowing for a user to vent any accumulated vacuum in the pumping chambers 2705 to the atmosphere. Venting the vacuum allows, for example, material such as the capsular bag to be released from the tip of the shaft 2761. Selective activation of the venting mechanism can include pressing a button that moves a movable element normally covering the hole exposing it to atmosphere. Alternatively, selective activation of the venting mechanism can include pressing a button that moves a movable element causing it to cover a normally open hole thereby preventing venting to the atmosphere. In an implementation, the button can be coupled to the multi-stage trigger 3125 of the device described elsewhere herein. As an example, when the trigger 3125 is at its neutral state and the device is at rest, the vacuum can be vented and the suction within the system dissipates. When the trigger 3125 is depressed to activate suction, the venting can be shut off. In this example, a user having the capsular bag sucked into the tip of the device (or a piece of lens occluding the lumen) can simply let go of the trigger 3125 to vent and release the tissue.

The venting purge mechanism can additionally create a small volume of retrograde flow of fluid out the distal tip of the device in addition to venting the tip of the shaft 2761. The small fluid flow at the tip can aid in fully releasing the bag or any other materials causing a clog. In this implementation, the button to actuate the purge mechanism can be a depressible button that when depressed can force a small volume of fluid out the irrigation outlet. As such, releasing the trigger 3125 can cause venting of accumulated vacuum in the pumping chambers 2705 and pressing the purge button can urge fluid out the distal tip to further push the capsular bag away.

Figure 5A:
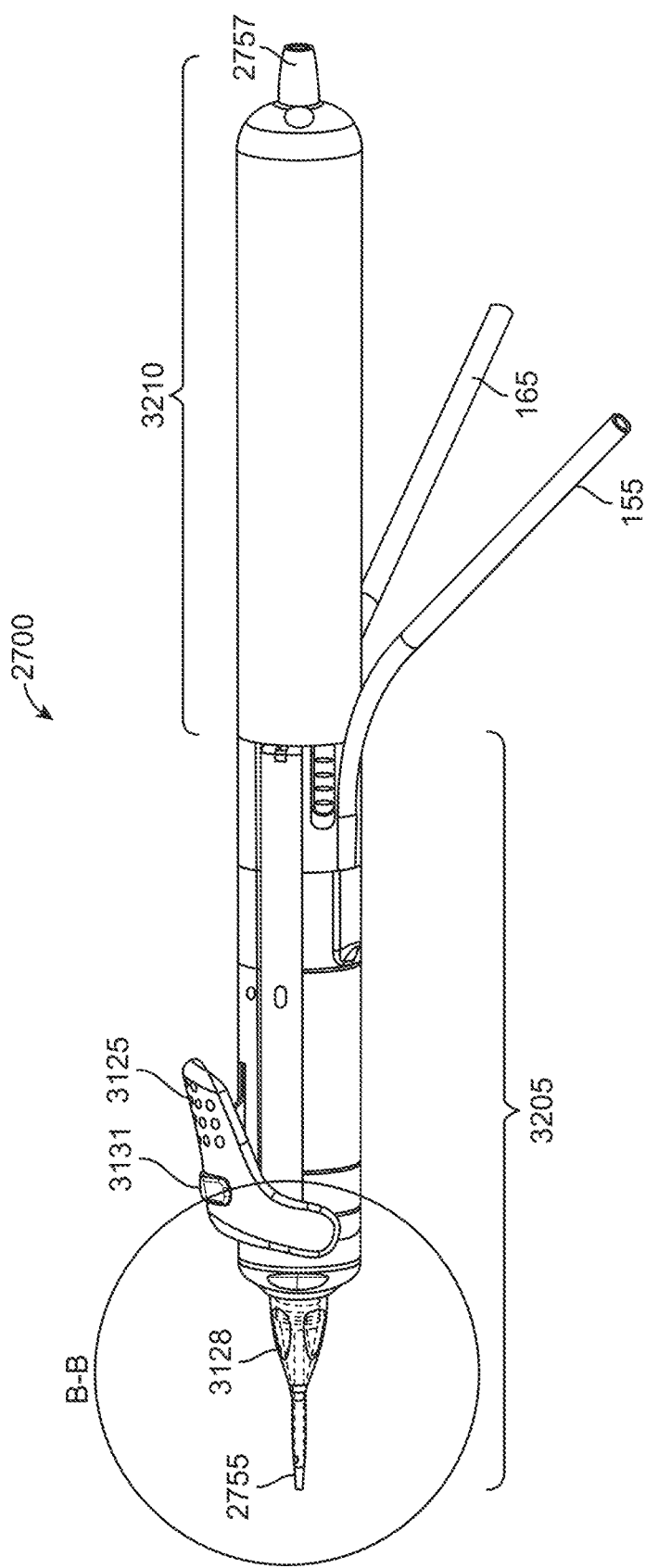
FIG. 5A shows a perspective view of a microsurgical tool having an elongate member.
Figure 5B:
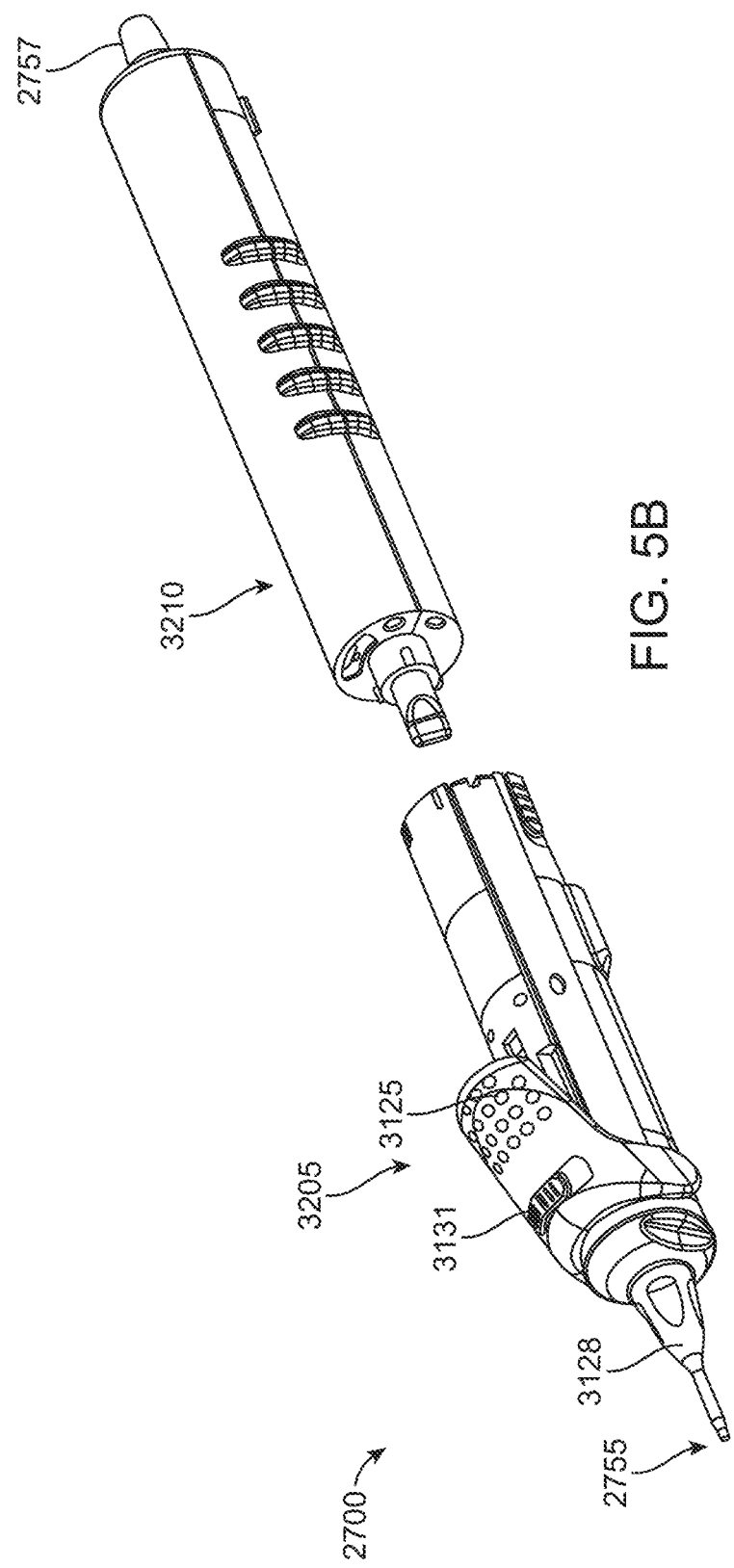
FIG. 5B shows perspective view of the durable and disposable portions of an implementation of a microsurgical instrument separated from one another.

FIGS. 5A-5H show an implementation of a microsurgical instrument. As described with respect to the implementation shown in FIGS. 4A-4O, the device 2700 of FIGS. 5A-5H can include a disposable portion 3205 configured to couple to a durable portion 3210. FIG. 5A shows the disposable and durable portions engaged with one another and FIG. 5B shows the disposable and durable portions separated from one another. As with other devices described herein, the disposable portion 3205 can include components of the hand piece 2760 configured to come into direct contact with fluids and materials from the eye whereas the durable, reusable portion 3210 generally includes the components of the hand piece 2760 that are configured to remain outside the fluid path, for example the components configured to drive the aspiration pump and/or the cutting element.

Figure 5C:
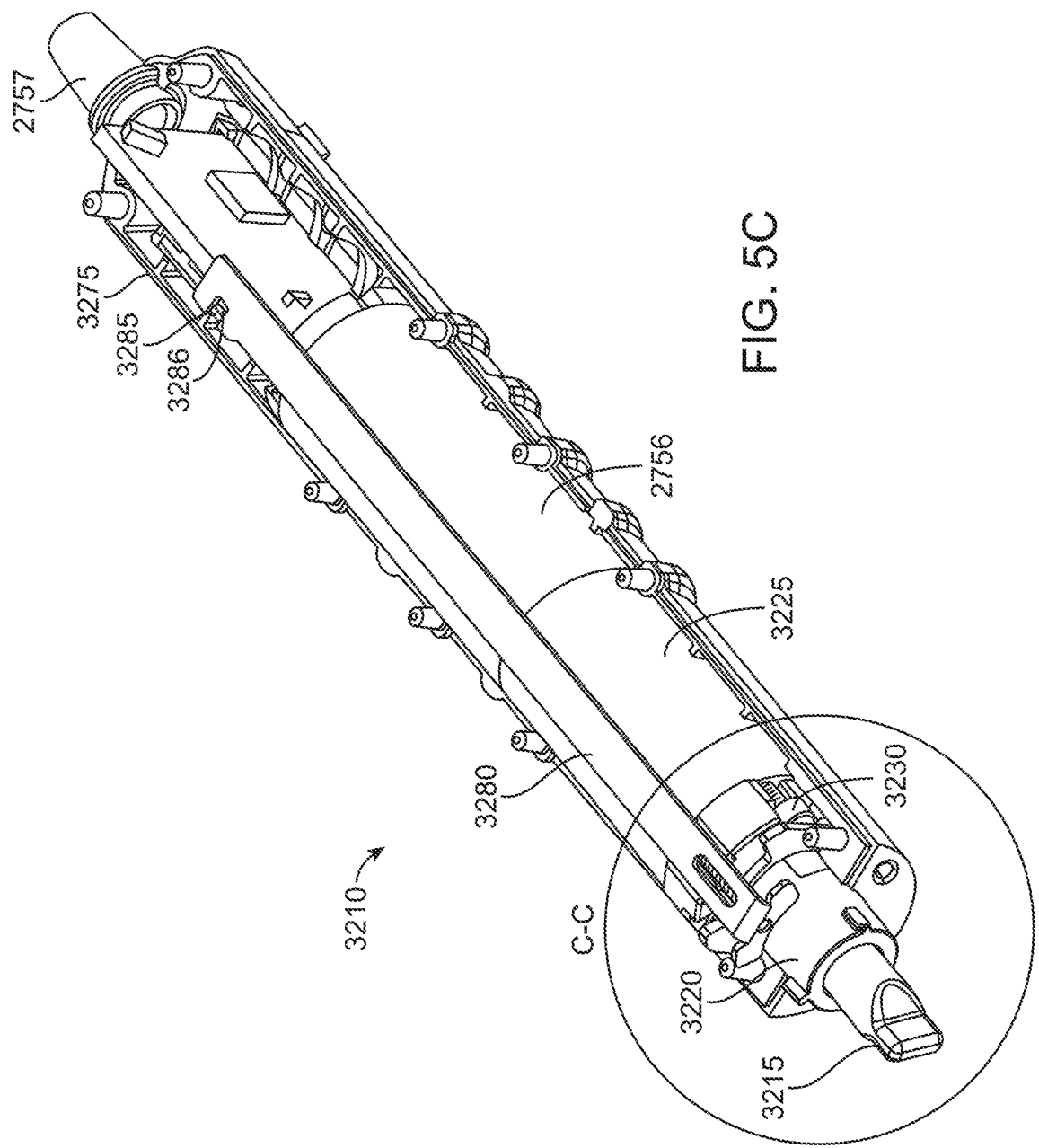
FIG. 5C shows a partial view of the durable portion of the instrument of FIG. 5B.
Figure 5D:
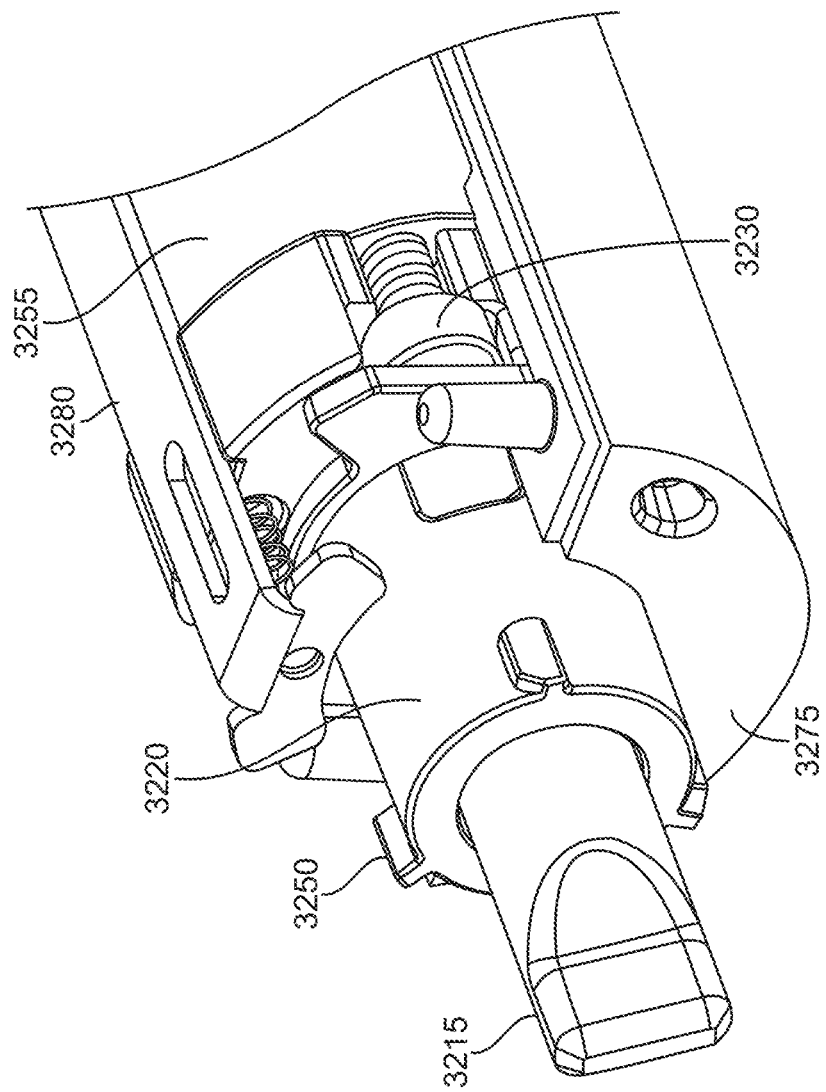
FIG. 5D shows a detailed view of the durable portion of FIG. 5C taken at circle C-C.
Figure 5E:
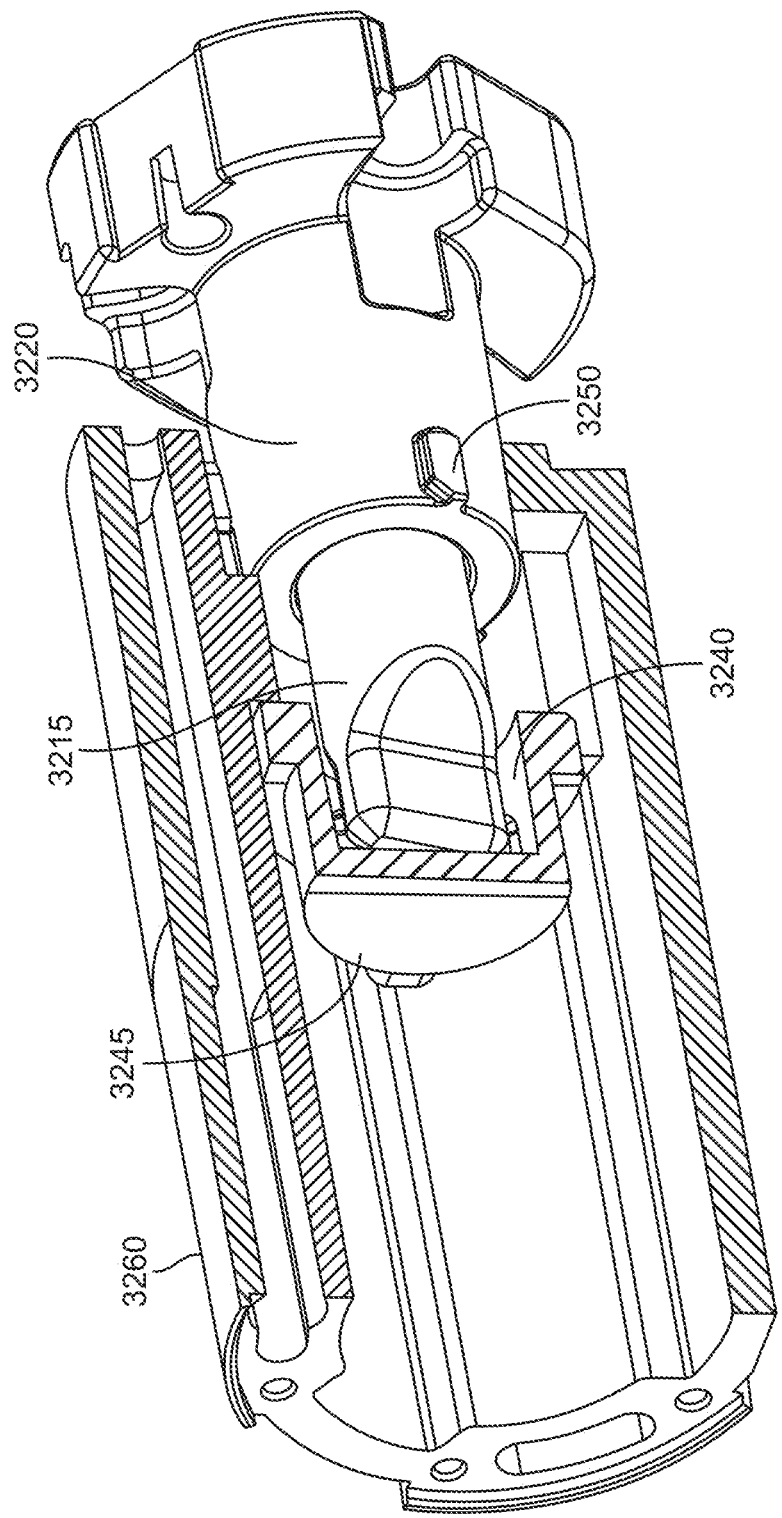
FIGS. 5E-5H are various views of the coupling between the durable and disposable portions of FIG. 5B.
Figure 5F:
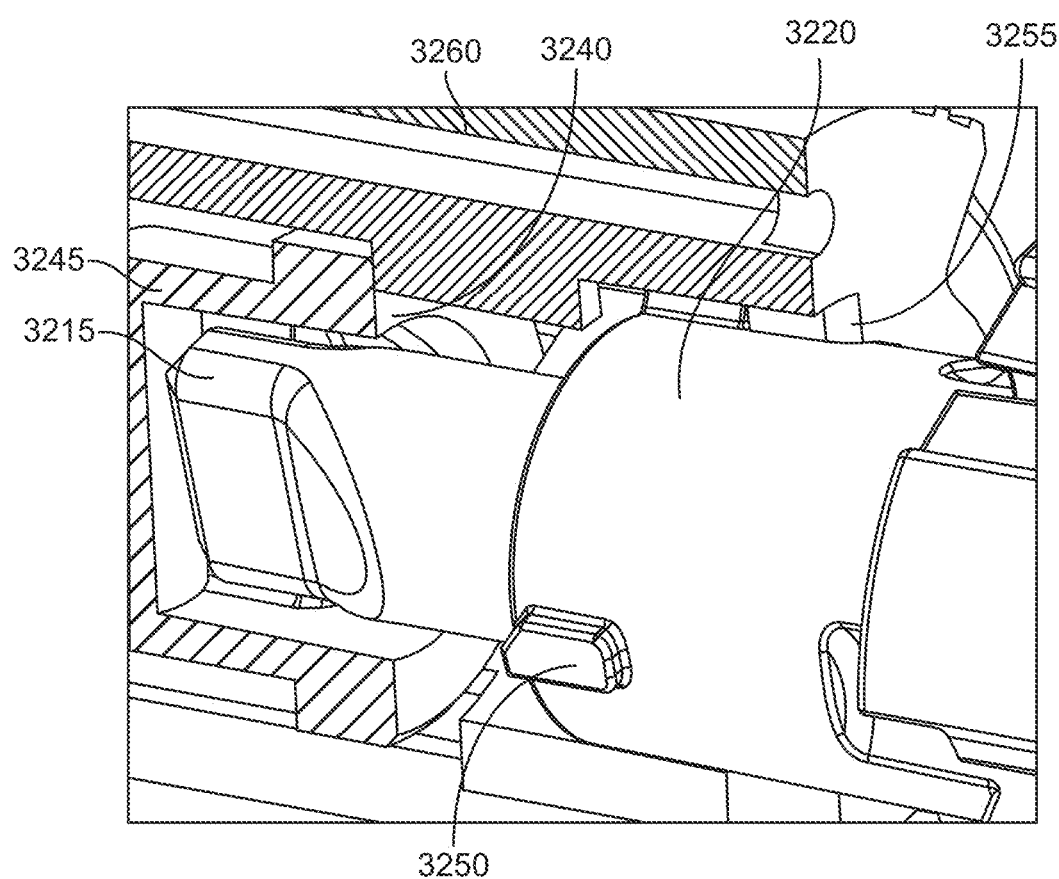
Figure 5G:
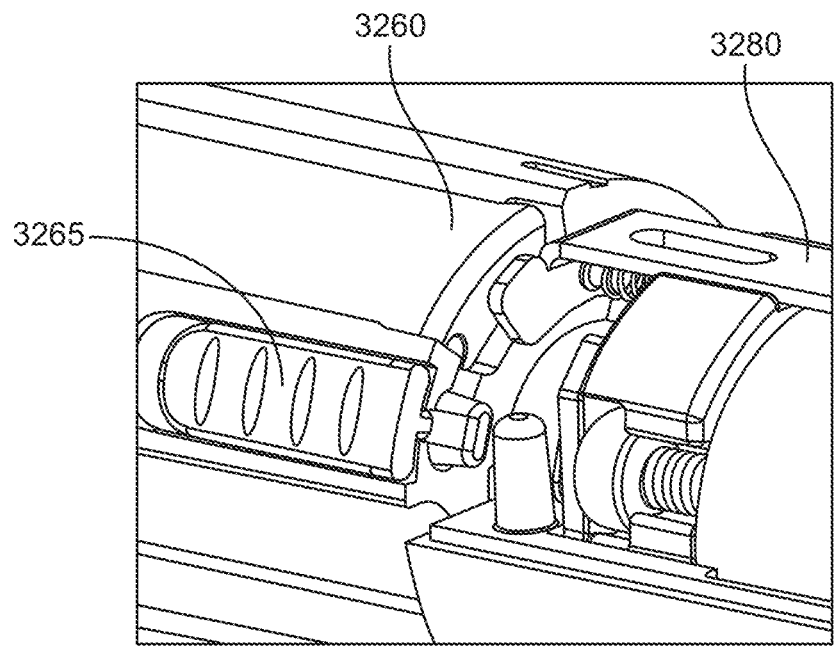
Figure 5H:
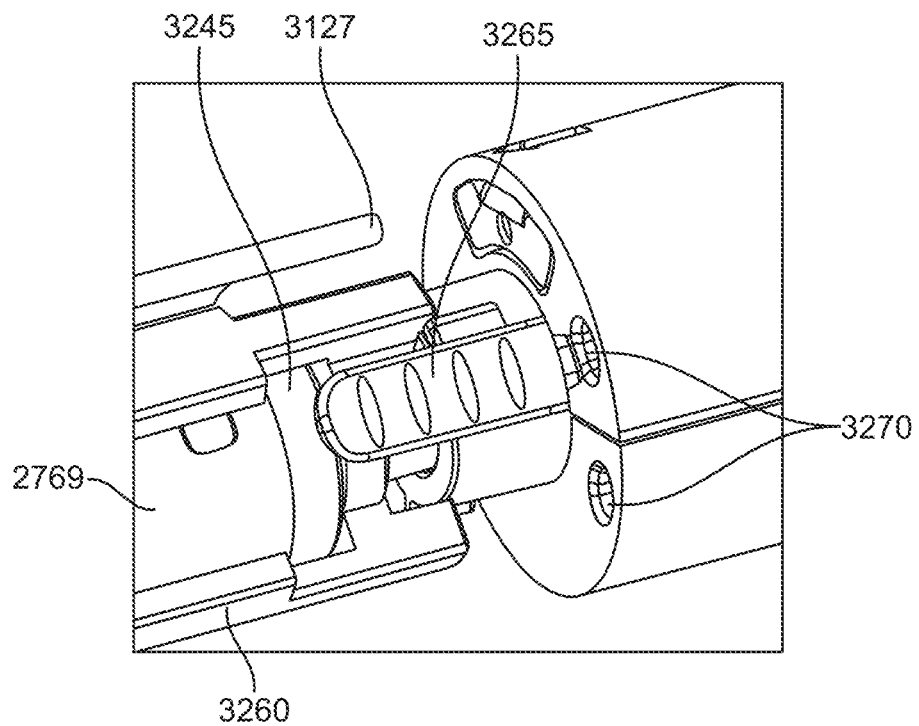

FIG. 5C shows a partial view of the reusable, durable portion 3210 of the device 2700 including a drive mechanism such as a motor 2756 with or without a gear box 3225. The motor 2756 can be a brushless DC motor or any type of motor or driver suitable for rotating a shaft as described elsewhere herein.

Power can be supplied to the drive mechanism by the power system 120 of the system 100 when the device is operatively coupled to the system 100. The device can be operatively coupled to the system 100 via a cable 2757 extending through the housing of the durable portion 3210. The cable 2757 may also be configured to connect the device 2700 to a wall socket. The drive mechanism can also be powered by one or more batteries. The battery can be incorporated within a region of the housing, either internally or coupled to a region of the housing such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein such as spring power or any other suitable internal or external power source. In some implementations, rather than the battery back mounted on or in the handle, which can increase the size of the handle, the battery pack can be mounted elsewhere such as on a user's arm or wrist of the arm holding the instrument during a procedure. A short cable connector can connect the mounted battery back to the device such that only this linkage extends from the handle of the device 2700 during use. Thus, no foot pedal or other tethering connection need be linked to the device 2700. This can provide the user with more portability, flexibility, and freedom of movement and without worrying about catching cables or other tethers during use.

FIGS. 5C-5H illustrate an implementation of how the durable and disposable portions of the device 2700 may be coupled together into operative communication. With respect to FIGS. 5C-5D, a bayonet motor adaptor 3220 can be fixed to the gear box 3225 via a plurality of motor screws 3230. A motor coupler 3215 can extend through the motor adaptor 3220 and attach to the output 3235 of the gear box 3225. The motor coupler 3215 can extend distal from the adaptor 3220 at a distal end region of the durable portion 3210. There can be clearance between the motor adaptor 3220 and motor coupler 3215 such that the motor coupler 3215 is free to rotate with the motor 2756. The durable portion 3210 can insert into the proximal end of the disposable portion 3205 such that the end of the motor coupler 3215 mates with a slot 3240 on the rotating cam coupler 3245 in the disposable portion 3205 (see FIGS. 5E-5F). Bosses 3250 on the bayonet motor adaptor 3220 can slide through L-shaped slots 3255 on the proximal end of the rear manifold 3260. The durable portion 3210 can be rotated around the longitudinal axis relative to the disposable portion 3205 (i.e. clockwise) such that the bosses 3250 lock the motor coupler 3215 into the rear manifold 3260 in the axial direction. The bosses 3250 on the bayonet motor adaptor 3220 can slide into the slot 3240 on the rear manifold 3260. Once rotated, the bosses on the bayonet motor adaptor 3220 can lock the durable and disposable portions 3210, 3205 together in the axial direction. The release button 3265 can be spring-loaded and attached to the rear manifold 3260 of the disposable portion 3205 (see FIGS. 5G-5H). After the durable portion 3210 is inserted into the disposable portion 3205, the user can rotate the durable portion 3210 until the release button 3265 extends into one of the two cavities 3270 on the housing 3275 depending on the device setting as will be described below.

Figure 6A:
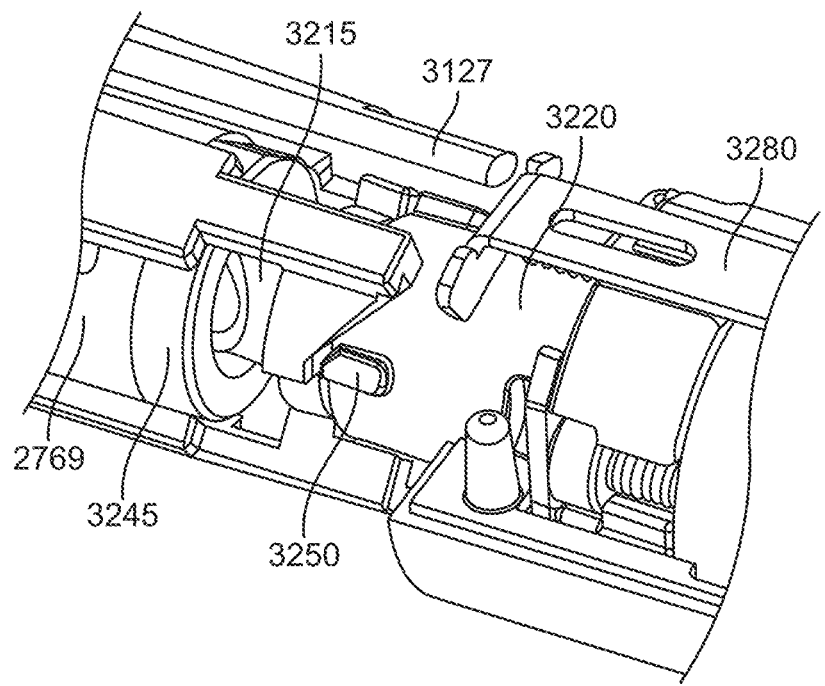
FIGS. 6A-6D show selectable vacuum settings of the instrument of FIG. 5B.
Figure 6B:
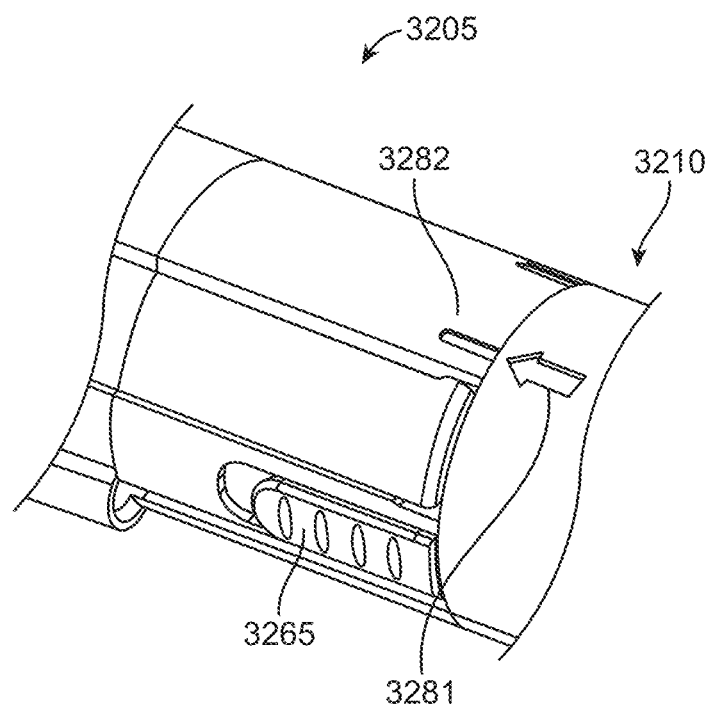
Figure 6C:
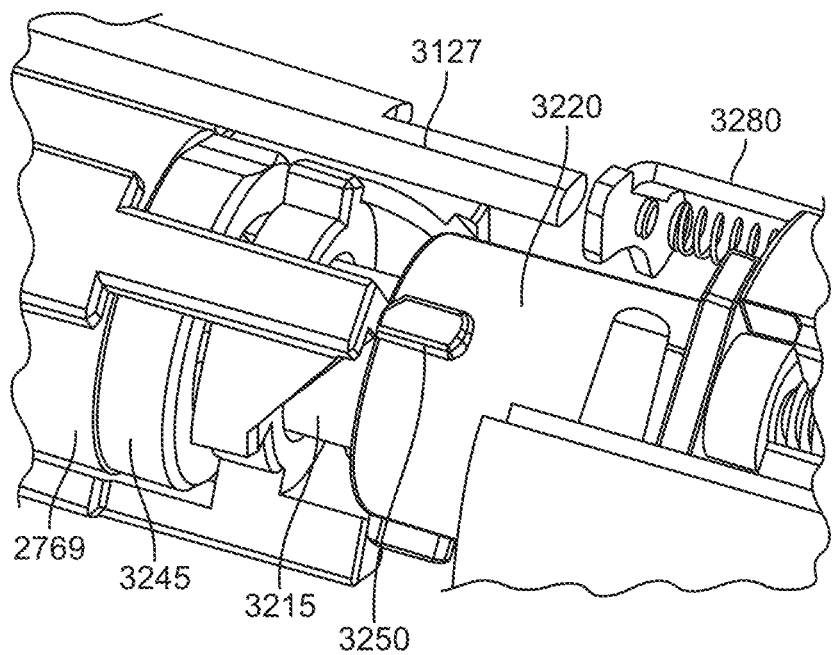
Figure 6D:
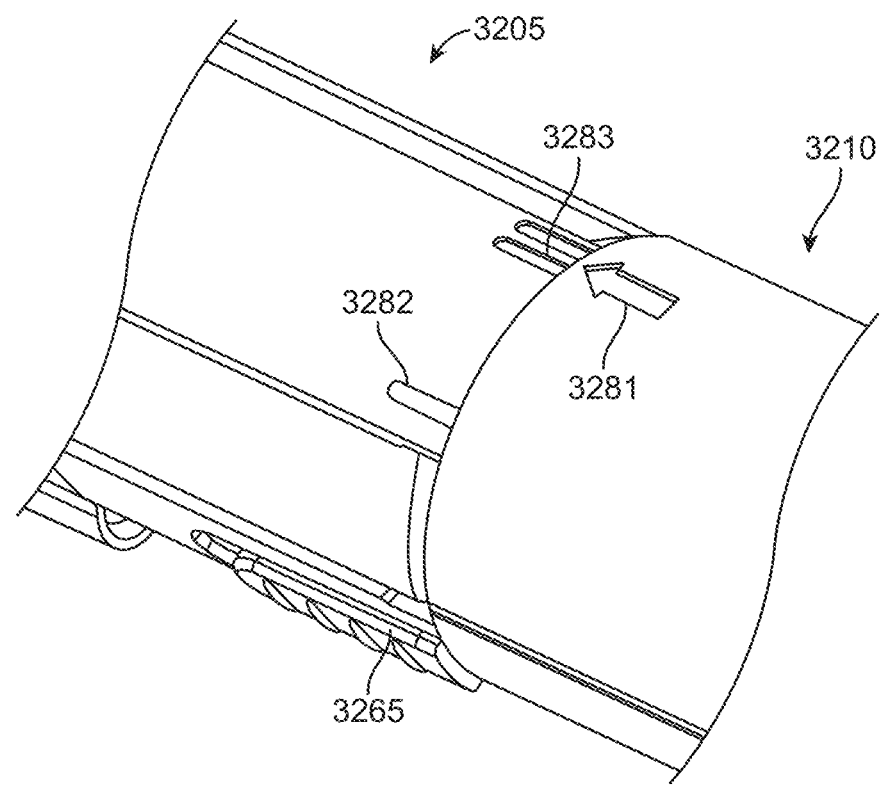

As discussed above, the amount of pulsatile vacuum can be adjusted by limiting the travel of the pistons in a rearward direction such as with a piston hard stop 2727. FIGS. 6A-6D illustrate an implementation of a device having selectable vacuum settings. After inserting the durable portion 3210 into the disposable portion 3205, the user may decide which piston hard stop setting to use. FIGS. 6A-6B show a default setting where the piston hard stop 2727 (not visible) can be in its full proximal position. This allows for a full stroke of the pistons, providing full vacuum via the hand-piece. The user can select this setting by aligning a selector 3281 on the housing of the reusable portion 3210 (e.g. an arrow) with a first indicator 3282 (e.g. a single notch) on the outer surface of the rear manifold 3260 of the disposable portion 3205. Once aligned, the release button 3265 can snap into an appropriate cavity on the housing 3275. FIGS. 6C-6D illustrate an alternate setting that can limit the piston travel and decrease maximum vacuum and flow rate and/or that can create a smooth continuous vacuum. The alternate setting can be selected by inserting the durable portion 3210 into the disposable portion 3205. While holding the release button 3265 in its distal position, the user can rotate the durable portion 3205 until the selector 3281 on the housing of the reusable portion 3210 aligns with a second indicator 3283 (e.g. a dual notch) on an outer surface of the rear manifold 3260 of the disposable portion 3205. As the durable portion 3210 is rotated past the default position (i.e. indicator 3282), the bosses 3250 on the bayonet motor adaptor 3220 slide on the ramp surface of the piston hard stop thereby driving the piston hard stop 2727 in the distal direction. The release button 3265 can then be released such that it snaps into the appropriate cavity on the housing 3275 of the disposable portion 3205. Other adjustment mechanisms for the vacuum are considered herein.

The above is provided as an example of how the different device settings can be activated. The user features that provide guidance regarding which setting is selected can vary as can the mechanism by which the settings are selected. For example, the notches and arrows can be replaced by other indicators providing user guidance regarding setting.

As described above, the microsurgical instrument 2700 can include a suction or vacuum source found within an interior of the hand piece 2760. The vacuum source can be positioned in fluid communication with the vacuum manifold 2774 located within the interior of the housing. FIG. 7A is a perspective, partial view of the disposable portion 3205 of the device 2700 showing a front manifold 3261 coupled to the vacuum manifold 2774, the piston manifold 2798, and a rear manifold 3260. The elongate member 2755 of the shaft 2761 can include an opening near a distal end of the shaft 2761 into the lumen 2763 and a notch or proximal opening 2788 a distance away from the distal end of the shaft 2761 (see FIG. 7B). The elongate member 2755 of the shaft 2761 can extend through the vacuum chamber 2703 of the vacuum manifold 2774 such that the proximal opening 2788 communicates with the vacuum chamber 2703. The proximal opening 2788 of the elongate member 2755 is maintained within the vacuum chamber 2703 during oscillating movements of the elongate member 2755. The lens material can bypass the nosecone 3320 and the front manifold 3261 to exit the lumen 2763 of the elongate member 2755 into the chamber 2703 of the vacuum manifold 2774 through the proximal opening 2788.

Figure 7C:
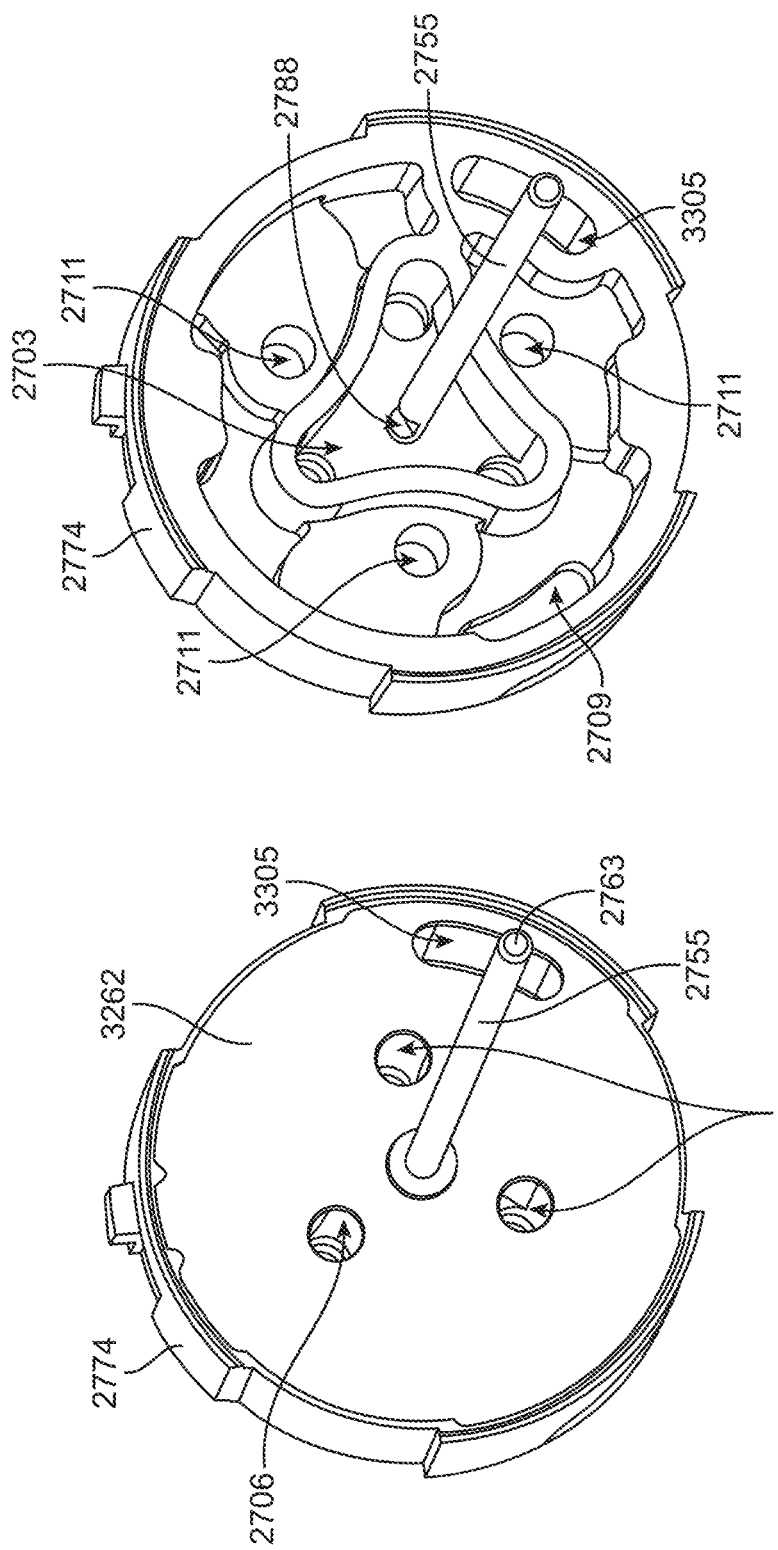
Figure 7D:
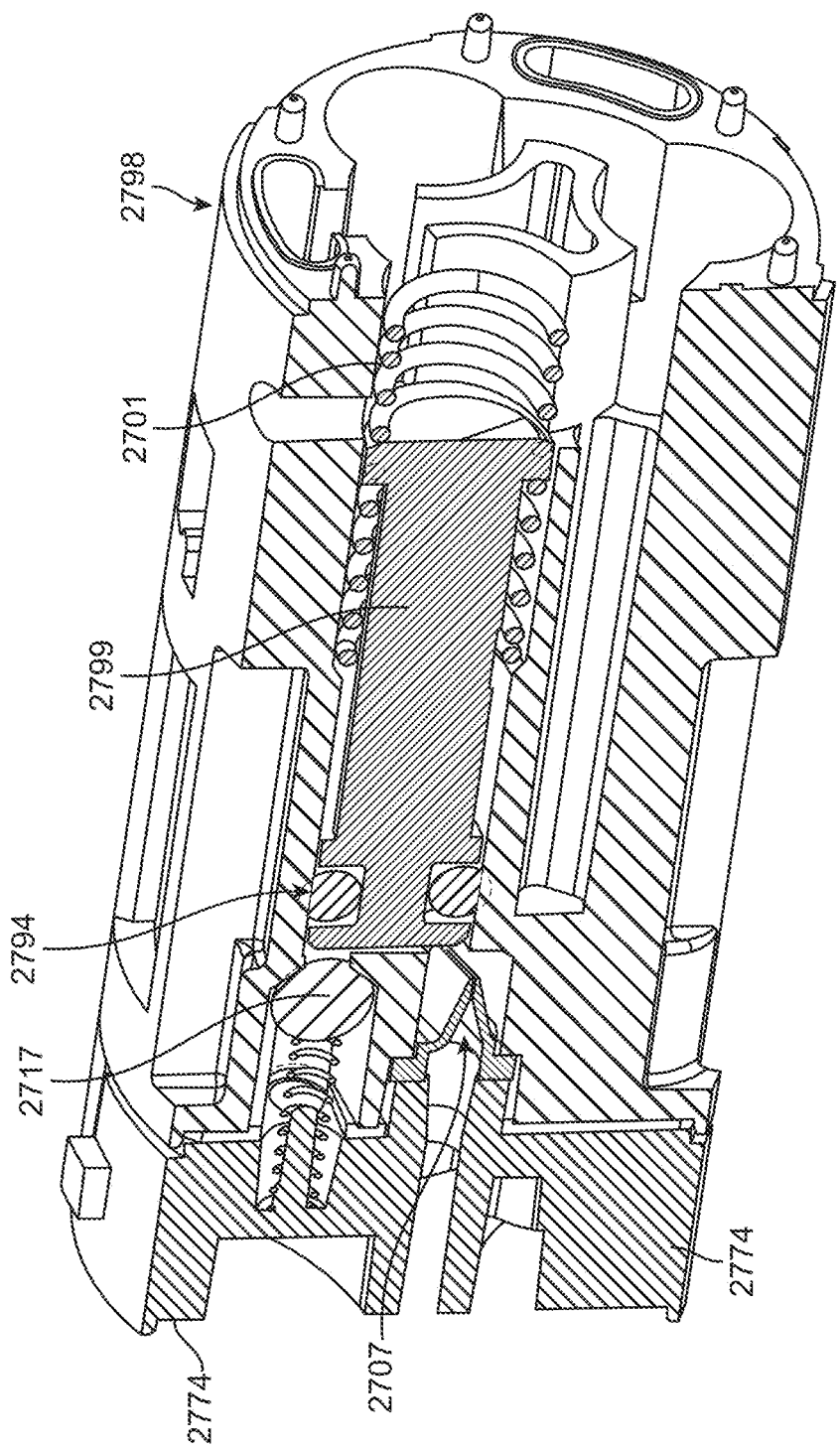

FIG. 7C shows the proximal opening 2788 in the elongate member 2755 positioned within the vacuum chamber 2703. Vacuum can pull lens material through the elongate member 2755. The lens material may exit the lumen 2763 of the elongate member 2755 through the proximal opening 2788 and enter into the vacuum chamber 2703 of the vacuum manifold 2774. Lens material is not intended to travel proximal of the proximal opening 2788 in the elongate member 2755. The vacuum chamber 2703 is configured to be in fluid communication with the one or more pumping chambers 2705 via a respective opening 2706 regulated by a one-way valve 2707 (see, e.g., FIG. 4L). The configuration of the one-way valve 2707 can vary including a duckbill valve, ball check valve, lift-check valve, stop-check valve and other types of valves that allow flow of fluid in a single direction and cut-off flow of fluid in the opposite direction. As described elsewhere herein, movement of the pistons 2799 in a first direction within the pumping chambers 2705 (i.e. proximally or towards the rear of the hand piece) creates a vacuum that can be supplied to the lumen of the elongate member 2755 through the openings 2706 on the vacuum manifold 2774 that surround the elongate member 2755. A gasket 3262 separates the vacuum chamber 2703, which can be defined by the cavity in the center, and the evacuation chamber 2709 (see FIG. 7C). Upon supplying vacuum to the lumen of the elongate member 2755, material from the eye is drawn into the lumen 2763 of the elongate member 2755, emptied into the vacuum chamber 2703, and pulled through the one-way valve 2707 into the pumping chamber 2705. Movement of the pistons 2799 in a second, opposite direction within the pumping chambers 2705 (i.e. distally or towards the front of the hand piece) causes pressure to build within the piston manifold 2798 and expels material from the pumping chamber 2705 and out of the system. The material can be expelled from the system into a disposal enclosure coupled to an exit port as described elsewhere herein.

Figure 7E:
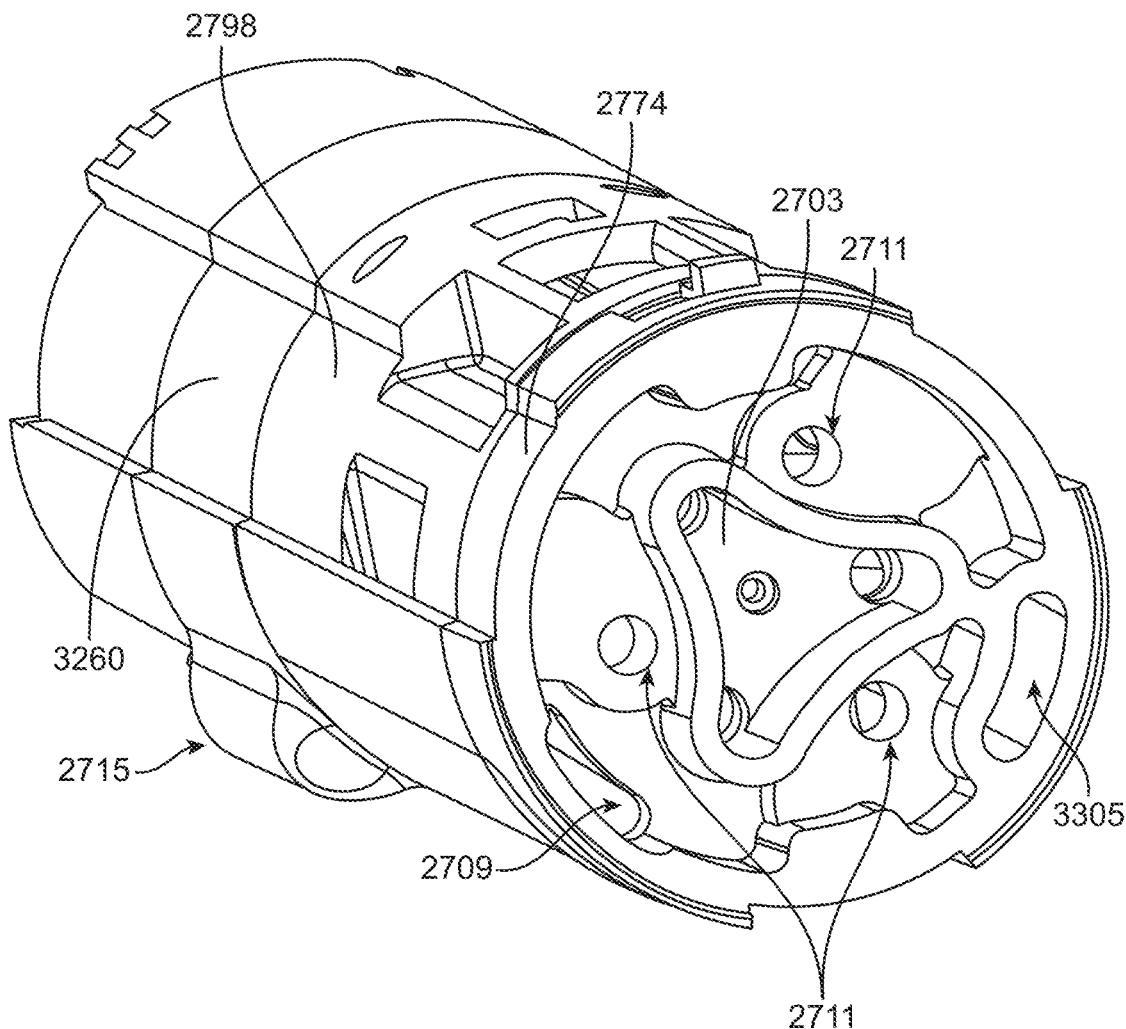

FIG. 7D illustrates the position of the piston 2799 in the pumping chamber 2705 of the piston manifold 2798. As the pistons 2799 move towards the rear of the device (i.e. proximally), a vacuum is drawn through the compliant one-way valves 2707, as described elsewhere herein. The valves 2707 can be connected to the channels in the vacuum manifold 2774. The vacuum can pull waste material from the vacuum manifold 2774, through the valves 2707 into the piston manifold 2798. As the pistons 2799 move towards the front of the device, pressure builds within the piston manifold 2798. The pressure opens the ball check valves 2713 and allows pressurized waste material to pass through the ball check valves 2713 in the piston manifold 2798. The waste material may enter the vacuum manifold 2774 through the waste channels 2711 (e.g. three round openings shown in FIG. 7E). The waste may combine in the vacuum manifold 2774 and exit the device through an evacuation chamber 2709. The evacuation chamber 2709 is shown in FIG. 7E as an oval-shaped channel that runs through the vacuum, piston, and rear manifolds 2774, 2798, and 3260 although it should be appreciated that other shapes are considered herein. Waste may exit the device via the waste port 2715 on the rear manifold 3260.

Figure 7G:
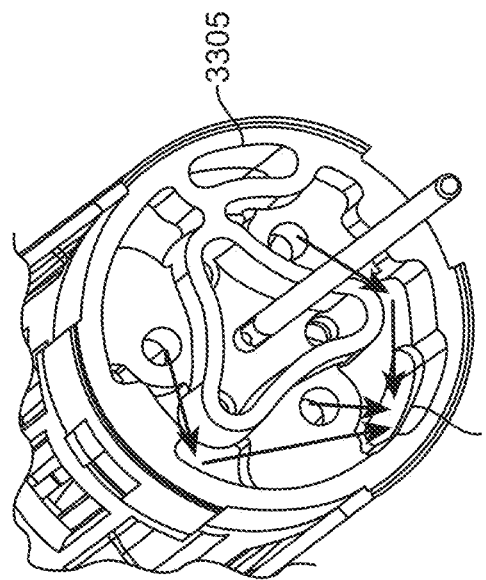
Figure 7F:
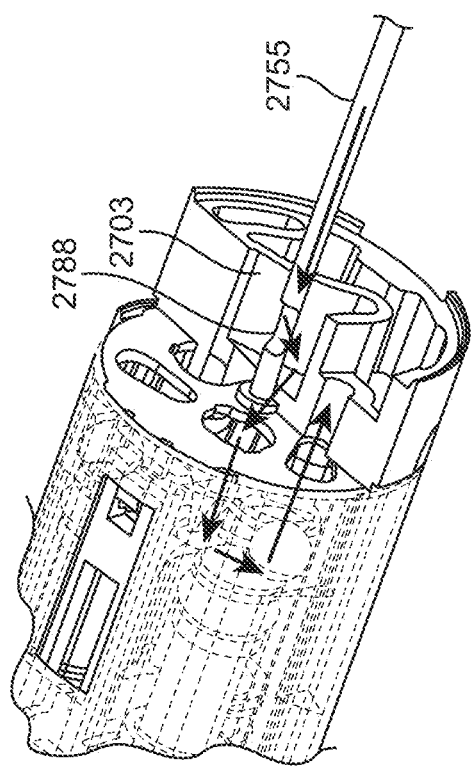
Figure 7H:
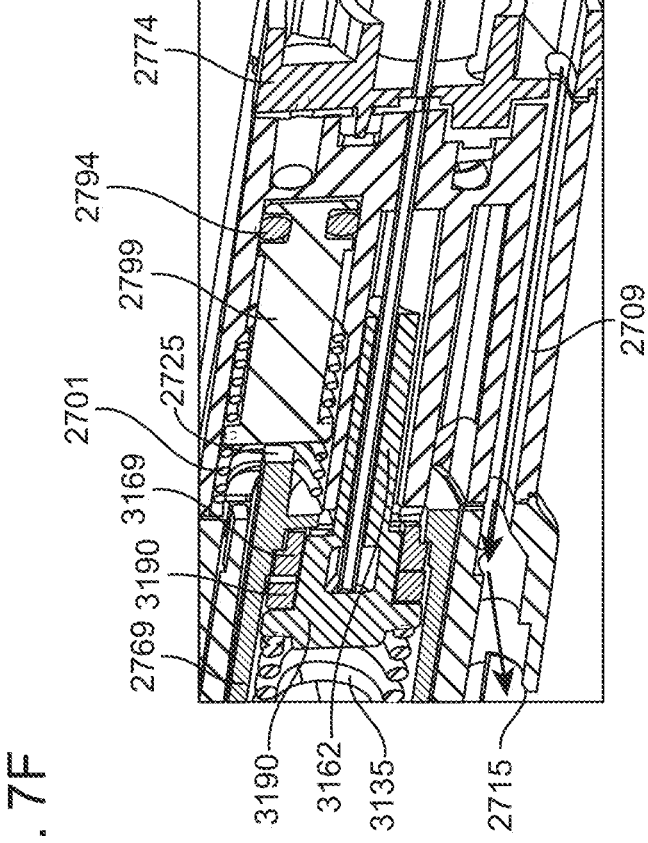

FIGS. 7F-7H show an example of the aspiration and waste fluid paths (arrows) through the instrument. Lens material and/or fluid from the eye may enter the lumen 2763 of the elongate shaft 2755 and travel into the chamber 2703 via the proximal opening 2788 into the pumping chamber via the one-way valve and back out the pumping chamber via the ball valve (see FIG. 7F). The lens material/fluid is drawn toward the evacuation chamber 2709 (see FIG. 7G). The lens material/fluid travels through the evacuation chamber 2709 extending through the vacuum manifold 2774, the piston manifold 2798, and the rear manifold 3260 towards the waste port 2715 (see FIG. 7H).

The vacuum pulses can be designed to occur suddenly, for example, by a piston 2799 falling off the ledge 2726 of the cam surface 2725 and being pushed proximally towards the proximal end of the pumping chamber 2705 by the piston spring 2701 as described above and as shown in FIGS. 8A-8B. The timing of this retraction due to the ledge 2726 can be leveraged to achieve a more pulsatile vacuum profile. Pulsatile vacuum can be beneficial for breaking up the lens and removing the lens material from the eye in that the peak vacuum level can be higher for these short bursts of time than can be achieved if steady vacuum is applied because the flow rate is kept below a nominal amount (e.g. 50 mL/minute). High peaks of vacuum are created, but a low overall flow rate can be maintained.

Figure 8A:
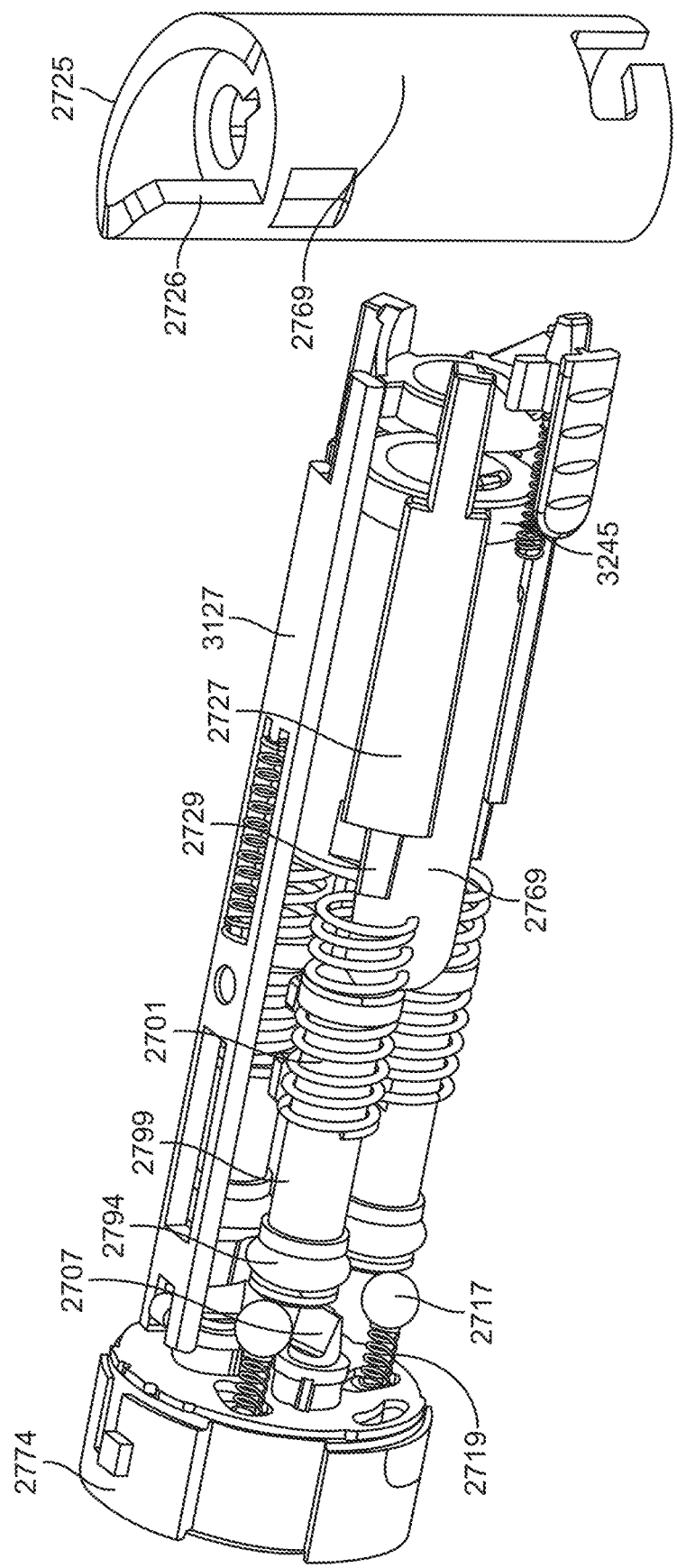
Figure 8B:
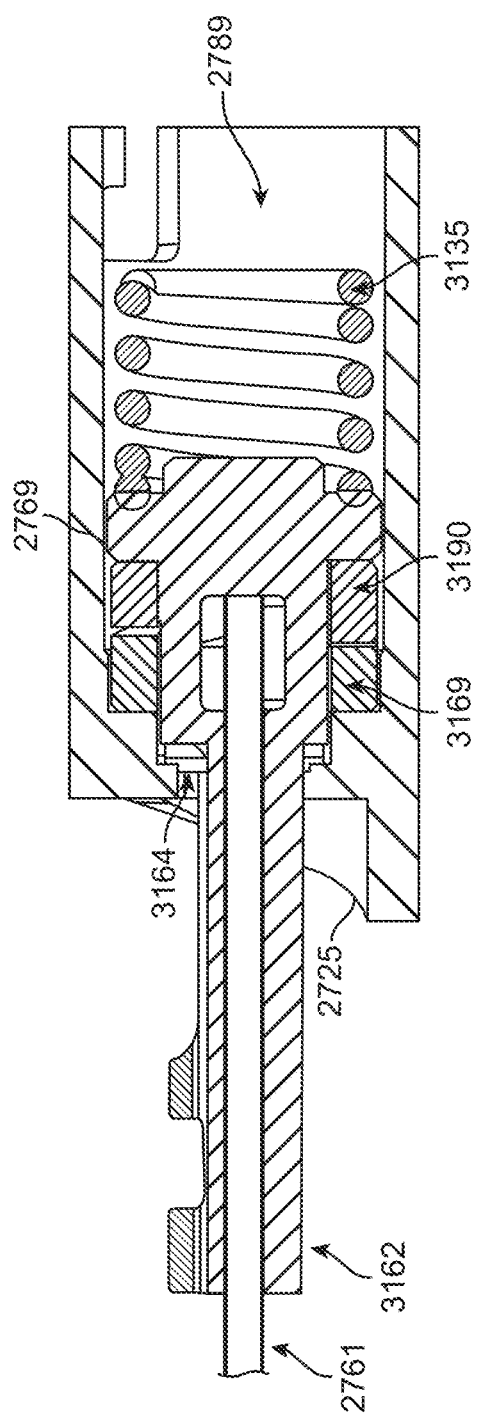
Figure 8E:
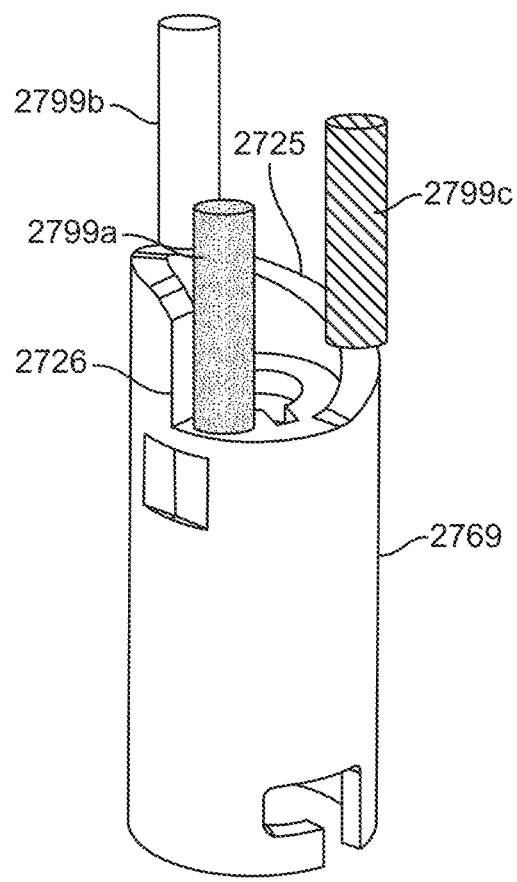
FIG. 8E schematically illustrates piston movements on a cam surface.

The timing of when a first piston is retracting and the next piston retracts can be a function of the geometry of the cam surface 2725 and the relative movements of the pistons within the piston chamber. The vacuum pulses can be designed to occur more smoothly such that the vacuum provided is substantially continuous, rather than discontinuous with momentary pauses between vacuum pulses. In some implementations, a first piston may retract and the second piston not start retracting until after a dwell period of the first piston retraction (see FIG. 8E) thereby creating a pulsatile vacuum profile. As described above, the device can include a cam 2769 having a cam surface 2725 configured to provide reciprocal linear motion of the pistons 2799. FIG. 8E illustrates in schematic movement of the pistons 2799a, 2799b, 2799c along the cam surface 2725 of the cam 2769. The cam surface 2725 terminates at a sharp drop-off or ledge 2726. During rotation of the cam 2769, the pistons 2799a, 2799b, 2799c slide along the cam surface 2725 and thereby extend in a distal direction. Upon reaching the ledge 2726, a first piston 2799a drops off the ledge 2726 retracting quickly in a proximal direction creating a spike in negative pressure. The geometry of the cam surface 2725 creates a dwell time of no negative pressure before the next piston 2799b reaches the ledge 2726 and retracts creating a second spike in negative pressure. The result is a series of discontinuous pulses of negative pressure.

In other implementations, the second piston may start retracting during a phase of the first piston retraction such that the vacuum profile is smoother and more continuous. FIGS. 8F-8H illustrate in schematic an implementation of the cam 2769 where the geometry of the cam surface 2725 is designed to having a more gradual slope for piston retraction prior to terminating at the ledge 2726. The geometry of the cam surface 2725 can be designed such that one of the plurality of pistons 2799 is retracting (i.e. creating a negative pressure within the pumping chamber 2705) at a constant rate. FIG. 8F shows the first piston 2799a near the end of its proximal travel within the piston chamber just prior to the ledge 2726. The second piston 2799b is poised to begun its retraction along the gradual slope prior to the first piston 2799a dropping off the ledge 2726. FIG. 8G and FIG. 8H illustrate further rotation of the cam 2769 and movement of the pistons along the cam surface 2725. Before the second piston 2799b drops off ledge 2726, the third piston 2799c will begin its retraction along the gradual slope of the cam surface 2725. This timing of piston retractions creates a flow rate of fluid out of the eye that is substantially continuous compared to the geometry of the cam surface 2725 shown in FIG. 8E that is discontinuous with moments of no vacuum being drawn. However, the presence of the ledge 2726 can create small spikes in negative pressure on top of the continuous negative pressure being applied by the retracting pistons. The first piston 2799a retract a first distance along the cam surface 2725 at a first rate thereby creating a first negative pressure. The second piston 2799b can start retracting at the first rate along the cam surface 2725 prior to the first piston 2799a dropping off the ledge 2726 maintaining that negative pressure. The first piston 2799a then drops off the ledge 2726 retracting the remaining distance at a second, faster rate thereby creating a spike in negative pressure.

In some implementations, the device can be switched between two vacuum modes. The first mode can be a substantially continuous vacuum mode without the spike in negative pressure due to the pistons 2799 dropping off the ledge 2726. The second mode can be a substantially continuous vacuum mode with the spikes in negative pressure. When in the first mode, the piston retraction can be limited to a fraction of the maximum piston travel within the chamber. For example, the piston stop 2727 can be selectively used to limit the piston travel within its chamber to a distance less than the maximum distance. As described elsewhere herein, the device can include a piston stop 2727 coupled to a proximal end region of the piston manifold 2798. The piston stop 2727 can be a generally cylindrical element surrounding the cam 2769 such that the cam 2769 extends through the cylindrical piston stop 2727 to contact the proximal ends of the pistons 2799. The piston stop 2727 can include a projection 2729 configured to project into a proximal end region of its respective piston chamber 2704 to make contact with the proximal ends of the pistons 2799. Thus, both the cam 2769 and the projections 2729 of the piston stop 2727 are configured to contact the proximal ends of the pistons 2799, the cam 2769 on an inner region and the projections 2729 on an outer region. The projections 2729 of the piston stop 2727 can provide a hard stop to the linear travel of the pistons 2799 in a proximal direction. For example, maximum piston travel within its piston chamber can be a distance of 5 mm. The projection 2729 of the piston stop 2727 can be advanced into the piston chamber by 2 mm to thereby limit proximal retraction of the piston 2799 to a distance of 3 mm rather than the maximum 5 mm. As the cam 2769 turns and the pistons 2799 extend and retract along the cam surface 2725, the projections 2729 of the piston stop 2727 can effectively prevent the pistons 2799 from dropping off the ledge 2726 creating a smooth, continuous negative pressure without the spike in negative pressure. When the projections 2729 of the piston stop 2727 are withdrawn from the piston chamber, the pistons 2799 can once again travel the maximum distance and can drop off the ledge 2726 creating a spike in negative pressure.

The irrigation source can provide a constant pressure of irrigating fluid that does not change with the vacuum level. The suction flow rate out of the eye during the peak vacuum can be higher than the irrigation flow rate into the eye resulting in a momentarily lower pressure in the eye. The pressure source of the irrigating fluid can be raised so that its nominal flow rate is higher than the maximum suction flow rate at the peak vacuum pulse to avoid this low pressure situation. It is preferable, however, to keep the pressure of the irrigating fluid source lower so that the pressure within the eye remains lower than a set amount during a procedure when the vacuum is not being applied. Alternatively, the device can incorporate a mechanism that is capable of delivering quick rushes or discontinuous pulses of irrigating fluid into the eye. Each pulse of irrigation fluid can be timed to occur during each pulse of negative pressure when the suction flow rate is at its maximum. The balance of fluid within the eye can remain more consistent and the drop in pressure within the eye during the peak vacuum point is minimized.

FIGS. 9A-9C shows the device having an irrigation sleeve 3128 coupled to over a region of the shaft 2761. The irrigation sleeve 3128 can include one or more irrigation openings 3124 configured to deliver fluid from the irrigation line 155 to the eye during use. The irrigation can be supplied from the fluid system 110 of microsurgical system 100 as described above and as shown in FIGS. 1A-1B and FIG. 2.

In some implementations, the device can incorporate an irrigation reservoir in communication with the irrigation flow path, for example, a reservoir located near the distal tip of the device that is configured to store an amount of irrigation fluid from the irrigation source 130. Locating an irrigation fluid reservoir very close to the tip of the device allows virtually immediate replenishing of the aspirated fluid volume. The irrigation reservoir can be configured to store an amount of fluid from the irrigation line 155 near where the irrigation fluid is being delivered. The irrigation reservoir can fill with irrigation fluid such that in the event of a blockage and a sudden rush of vacuum through the distal opening of the shaft 2761, the irrigation fluid stored up in the irrigation reservoir can be available to fill in the volume removed by the increased vacuum. The fluid from the irrigation reservoir in the hand piece can be pulled into the eye almost instantaneously upon the increase in negative pressure to maintain a balance in pressure within the eye to avoid damage or collapse of the anterior chamber. The system 100 can also provide a balance in fluid pressure within the eye to avoid damage or collapse of the anterior chamber as described above. The irrigation reservoir in the hand piece can be a compliant chamber such as balloon or incorporate another compliant element configured to urge fluid out of the reservoir as will be described in more detail below.

FIG. 9A shows an irrigation reservoir as a central cavity 3315 in the disposable portion 3205 of the hand piece. The central cavity 3315 provides for irrigation fluid that is very close to the tip of the device within the disposable portion 3205. An irrigation channel 3305 extending from a port 3310 on an exterior of the rear manifold 3260 can be in fluid communication with the central cavity 3315 of the nosecone 3320 at the distal end of the instrument. The irrigation channel(s) 3305 can run through a plurality of manifolds of the instrument. For example, the irrigation channel 3305 can run from the rear manifold 3260 through the piston manifold 2798, the vacuum manifold 2774, to the front manifold 3261. One or more openings 3124 or ports in the irrigation sleeve 3128 can allow irrigation fluid to exit the central cavity 3315 and flow into the irrigation sleeve 3128 that surrounds the cutter tube or shaft 2761. The irrigation fluid can flow out of the irrigation sleeve 3128 via the openings 3124 near the distal end of the irrigation sleeve 3128.

Figure 10A:
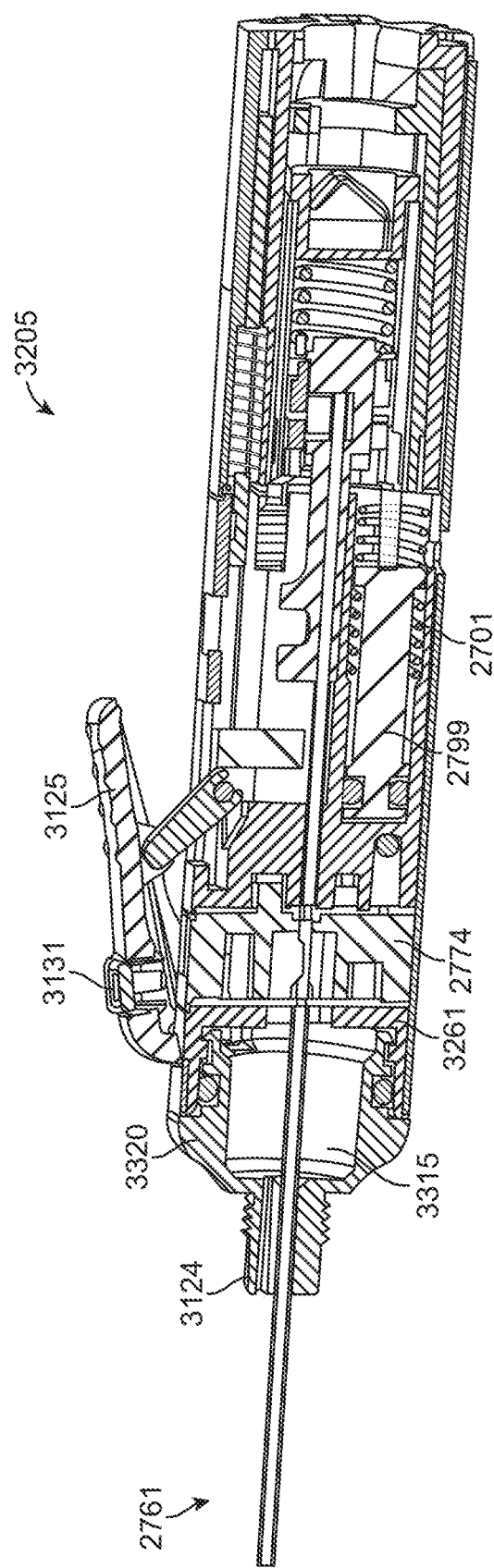
FIGS. 10A-10C show various views of an implementation of the microsurgical instrument of FIGS. 9A-9C.
Figure 10B:
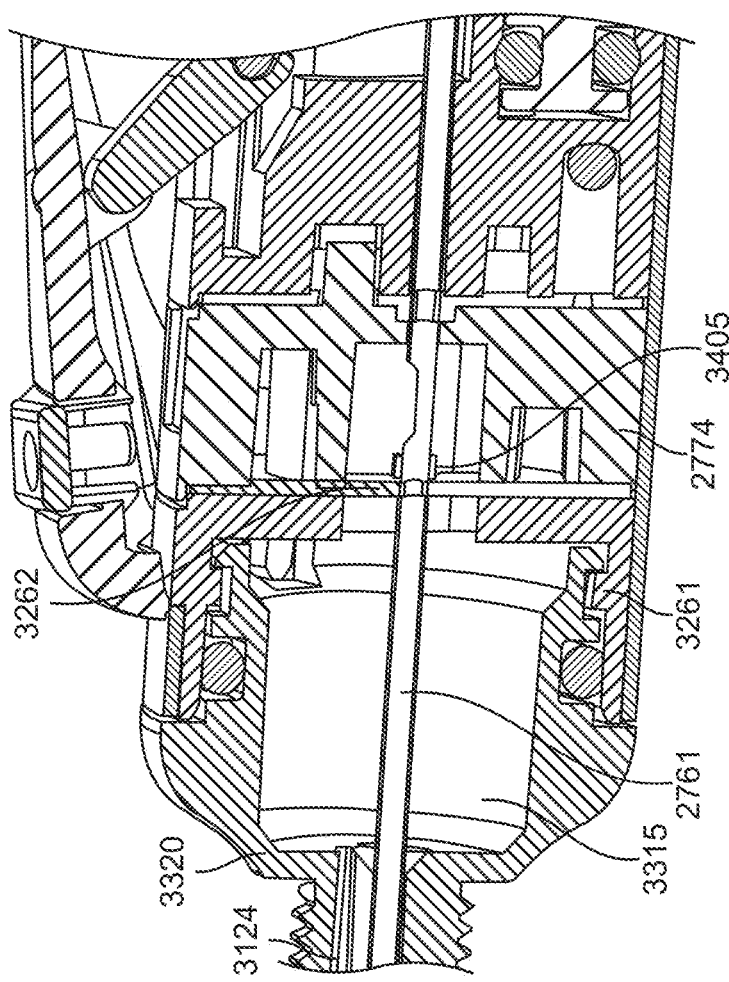
Figure 10C:
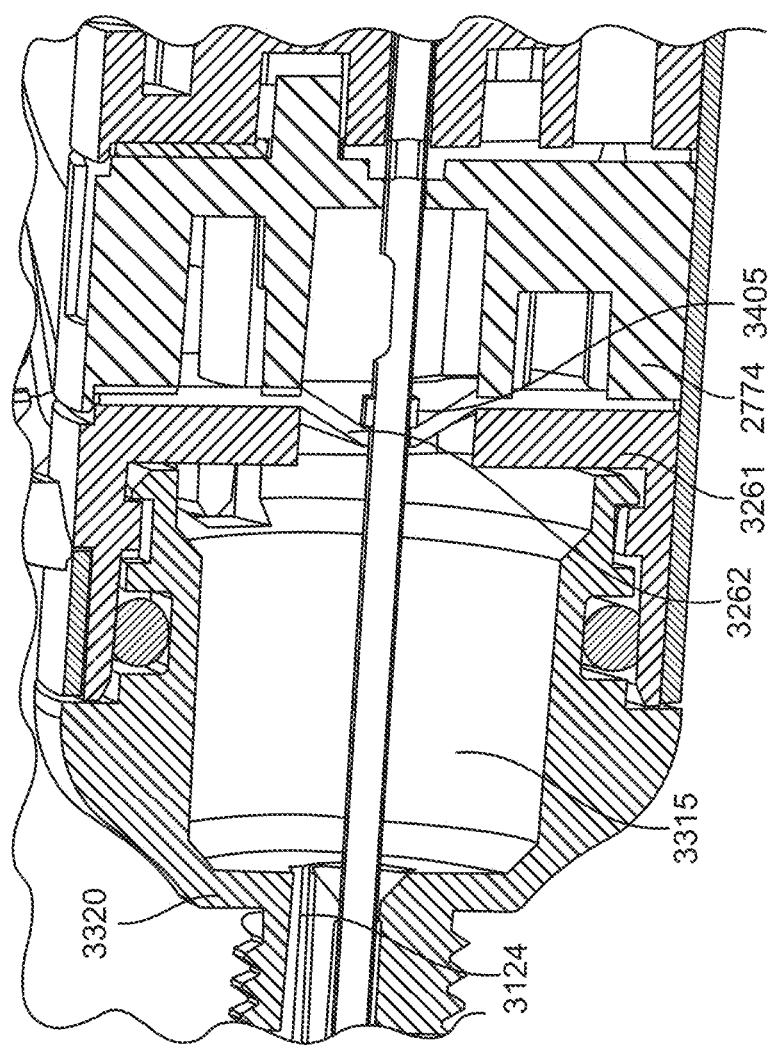

Again with respect to FIG. 9A, the irrigation channel 3305 can extend from the port 3310 on the exterior of the rear manifold 3260 into a central cavity 3315 of the nosecone 3320 at the distal end region of the instrument. The irrigation channel 3305 can run from the rear manifold 3260 through the piston manifold 2798, the vacuum manifold 2774, to the front manifold 3261 such that irrigation fluid is retained within the central cavity 3315 of the nosecone. The cutter tube or shaft 2761 can expel irrigation fluid quickly from the central cavity 3315. As best shown in FIGS. 10A-10C, a front gasket 3262 can be positioned between the vacuum manifold 2774 and the front manifold 3261. The shaft 2761 can include a hub 3405 positioned near where the shaft 2761 extends through the front gasket 3262. The front gasket 3262 can act like a diaphragm in that it can move back and forth to cause fluid flow from the central cavity 3315. In its resting state (FIGS. 10A-10B), the gasket 3262 remains flat. During operation of the device, the movement of the shaft 2761 in a distal, forward direction is timed to occur immediately after one of the pistons 2799 has moved in a proximal direction (e.g. pushed proximally by a spring 2701). Thus, forward movement of the shaft 2761 is timed to occur at the peak in suction flow rate through the shaft 2761. The hub 3405 of the shaft 2761 pushes against the front gasket 3262 when the shaft 2761 moves distally thereby urging the gasket 3262 outward into the central cavity 3315 containing the irrigating fluid causing a burst of irrigation fluid to exit the central cavity 3315 through irrigation opening 3124 (see FIG. 9B). When the shaft 2761 is retracted proximally and the hub 3405 is pulled away from the gasket 3262, the gasket 3262 returns to its flat, resting position. The gasket 3262 thereby acts as a positive displacement diaphragm causing delivery of irrigation fluid during forward movement of the shaft 2761 and peak vacuum conditions. The front gasket area that flexes outward can vary in size. For example, a larger front gasket area can expel more fluid from the device when the shaft 2761 moves distally.

Figure 11A:
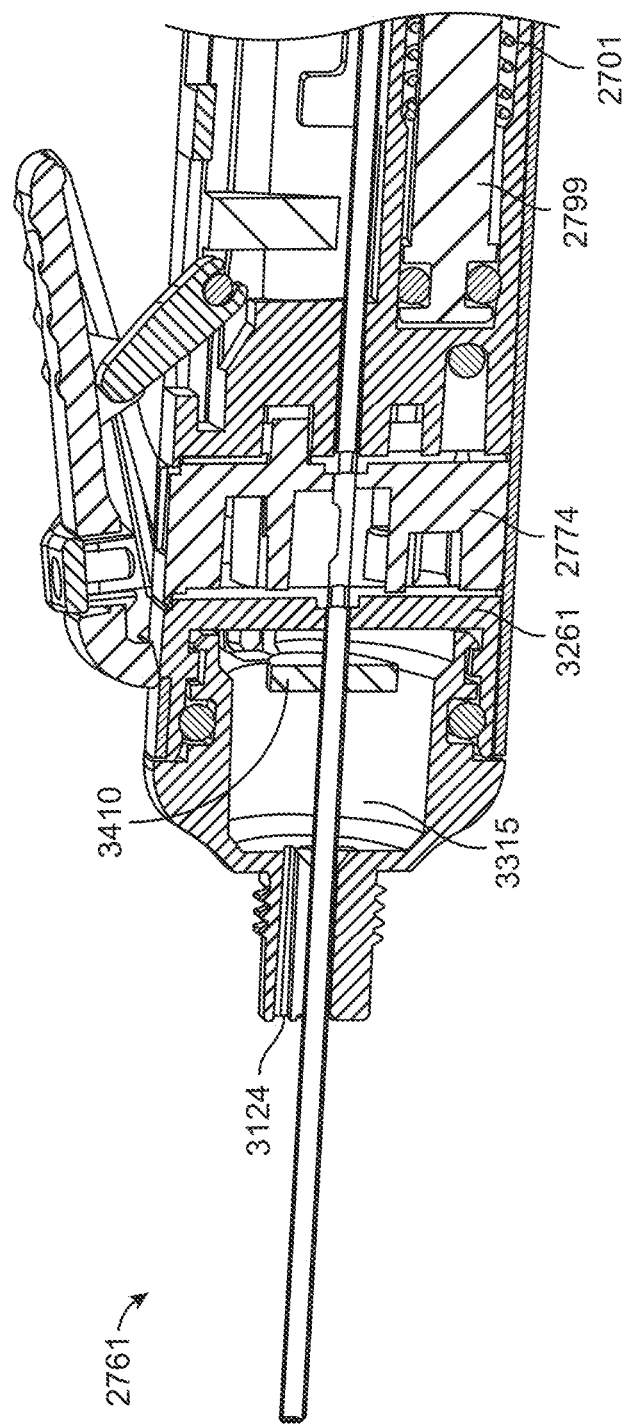
FIGS. 11A-11B show partial, cross-sectional views of further implementations of the microsurgical instrument of FIGS. 10A-10C.
Figure 11B:
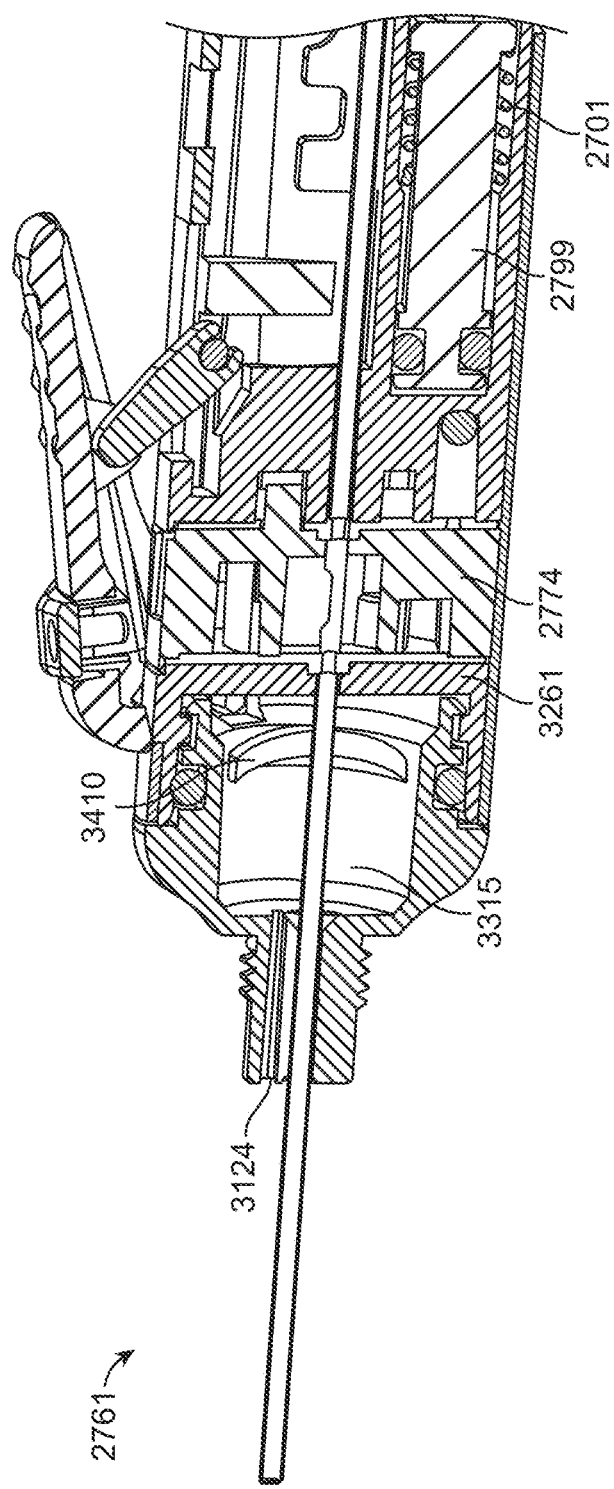

Alternatively or additionally, the device can incorporate a disc 3410 positioned within the central cavity 3315 that is coupled to the hub 3405 on the shaft 2761 such that the disc 3410 moves along with the shaft 2761. The disc 3410 can create an impulse within the central cavity 3315 containing the irrigating fluid to compel the irrigating fluid to move from the cavity 3315, through the irrigation opening 3124 and into the eye. The disc 3410 can be circular as shown in FIGS. 11A-11B or another shape. In some implementations, the disc 3410 has a concave shape such that the concave surface is facing distally and the convex surface is facing proximally (see FIG. 11B). The concavity aids in moving fluid forward out of the central cavity 3315. In some implementations, the disc 3410 forms a tight seal with the internal bore of the central cavity 3315. As the shaft 2761 moves, the disc 3410 acts like a piston of a positive displacement pump to move fluid out of the central cavity 3315. When the disc 3410 moves forward it reduces the volume of the central cavity 3315, increases the pressure thereby expelling the fluid from the device.

Figure 12:
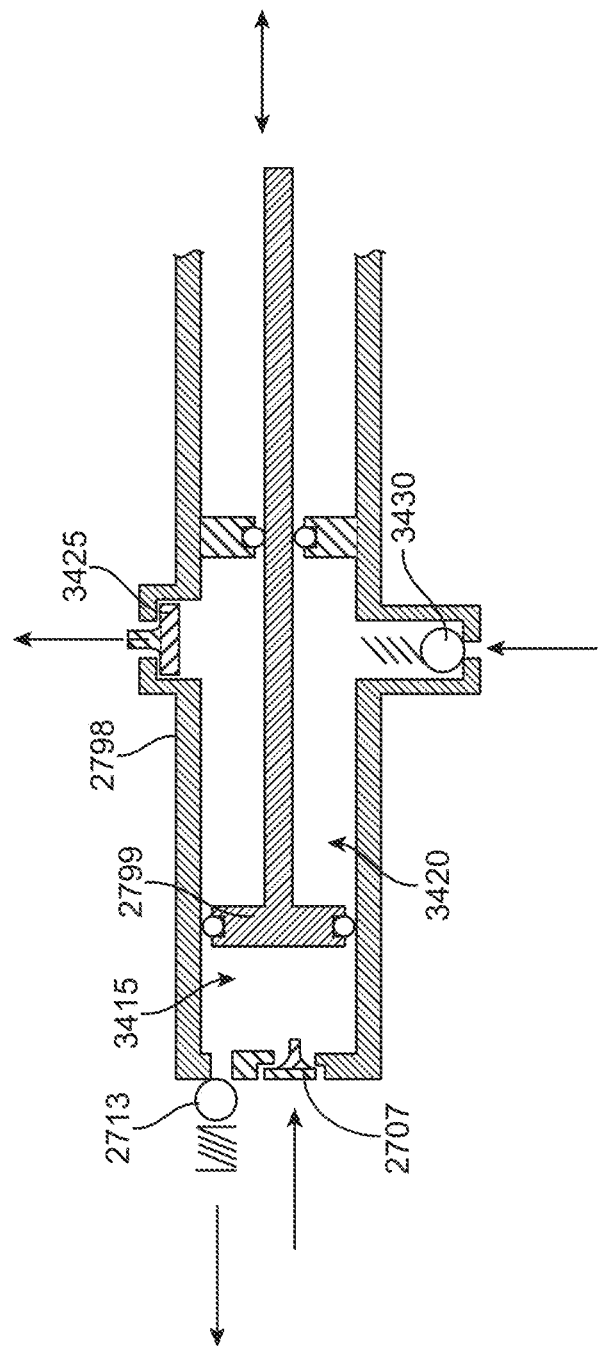
FIG. 12 is a schematic representation of a pumping manifold incorporating a combined irrigation pulse and vacuum pulse system.

The volumetric displacement of the piston or gasket can be sized such that it approximates the fluid removed from the eye by the suction. For example, FIG. 12 illustrates an implementation of a positive displacement mechanism for injection of irrigation fluid from the device that is coordinated with the vacuum pulses. The positive displacement of irrigation fluid can occur at the same time and of equal volume and equal flow rate as that of the fluid being removed from the eye. Similar to implementations described above, fluid from the eye can be drawn into a piston manifold 2798 through a first one-way valve 2707 as a piston 2799 retracts proximally. The fluid from the eye can then be evacuated from the piston manifold 2798 via another valve 2713. During this purge of material, the one-way valves 2707 (i.e. positioned between the one or more pumping chambers and the vacuum chamber) prevents the backflow of material out the cutting tip whereas the valve 2713 (i.e. positioned between the one or more pumping chamber and the evacuation chamber) allows for the material to freely exit the piston manifold 2798 at least until flow is cut off by the valves 2713 as described elsewhere herein. Upon closure of the valve 2713, the piston manifold 2798 is substantially devoid of material.

Still with respect to FIG. 12, the movement of each of the pistons 2799 back and forth to draw fluid from the eye in and evacuate the fluid out of the device can be coordinated with irrigation fluid delivery to the eye. Each piston 2799 can divide the pumping chamber of the piston manifold 2798 into two pumping chambers. The distal pumping chamber 3415 can control movement of eye material into and out of the device as described above. The proximal pumping chamber 3420 can control movement of irrigation fluid into and out of the device. The size of the pumping chambers 3415, 3420 have an inverse relationship with one another. As the piston 2799 is withdrawn, the size of the distal pumping chamber 3415 increases to draw fluid from the eye into the device through valve 2707. Simultaneously, the size of the proximal pumping chamber 3420 decreases urging the irrigation fluid through irrigation outlet valve 3425 and into the eye. As the piston 2799 is extended distally, the size of the distal pumping chamber 3415 decreases to evacuate the eye fluid into the evacuation chamber through valve 2713. Simultaneously, the size of the proximal pumping chamber 3420 gets larger to draw more irrigation fluid into the proximal pumping chamber 3420 via irrigation inlet valve 3430. Thus, with each pulse of vacuum applied to the eye, a pulse of irrigation fluid is delivered to the eye. With each evacuation of fluid from the device, the irrigation fluid volume is primed again in preparation for the next pulse of vacuum.

In some implementations, the irrigation pulses can originate from outside the device. For example, a device can be connected to the irrigation source 130 container and provide an irrigation pulse by momentarily increasing the pressure within the irrigation source 130 container. In the case of a flexible bag of BSS, a device can be incorporated to compress the bag at regular pulses. In the case of a rigid bottle of BSS, air pressure can be increased in pulses to achieve pulses of irrigation fluid to flow from the container. The pulses can be timed relative to the vacuum pulses as described above. In some implementations, the control processor 180 of the computing unit 115 of the system 100 can sense when the motor 2756 in the instrument is at a given state of rotating and thereby calculate when the vacuum pulses are occurring. This data can be used to time the irrigation pulses with the vacuum pulses.

FIGS. 9A-9B illustrate a distal end region of the disposable portion 3205 showing the elongate member 2755 extending beyond a distal end of an irrigation sleeve 3128. The irrigation sleeve 3128 may include one or more openings 3124 near its distal end through which irrigation fluid may be delivered into the eye near the terminus of the elongate member 2755. The irrigation sleeve 3128 can extend proximally over the elongate member 2755 and couple with a distal end region of the disposable portion 3205. The distal end region of the disposable portion 3205 can include a nose cone or tip 3320 configured to receive the irrigation sleeve 3128. The tip 3320 and the irrigation sleeve 3128 can each be removably attached to the hand piece. The irrigation sleeve 3128 can be a standard irrigation sleeve (e.g. irrigation tips by MST, Redmond, Wash.) having a substantially flexible, distal tubular portion 3133 and a less compliant, proximal coupling portion 3134. The tip 3320 can include external threads 3321 (see FIG. 7A) or other coupling features on a front end region configured to engage with corresponding threads or features on the proximal coupling portion 3134 of the irrigation sleeve 3128.

The tip 3320 can be configured for any of a variety of techniques a user desires to perform with the hand piece during a procedure. Any of a variety of accessory tips may be reversibly coupled to the distal end region of the disposable portion 3205 depending on the procedure in the eye a user desired to perform. The tips may be configured for phacoemulsification, bag polishing, vitrectomy, and other procedures. The proximal end region of the exchangeable tip 3320 can incorporate a reversible coupling feature 3323 and a sealing element 3325 such as an O-ring (see FIG. 9A). The configuration of the coupling feature 3323 can vary including, but not limited to threads, snap lock, interference fit, bayonet, or other feature configured to allow the tip 3320 to affix to and seal with the disposable portion 3205.

The exchangeable tip 3320 can include a lens removal protective sleeve 2759 as described elsewhere herein. The protective sleeve 2759 can be fixedly coupled and extend from the distal end region of the tip 3320 (see FIG. 7A). The sleeve 2759 can be sized and shaped to be positioned concentrically over the elongate member 2755 along at least a portion of the proximal length of the elongate member 2755. The sleeve 2759 is configured to protect corneal tissues from damage where the elongate member 2755 extends through the corneal incision during motion of the elongate member 1755. The protective sleeve 2759 may be formed of substantially flexible or elastic material such as silicone or a substantially rigid material such as a rigid plastic extrusion or metal hypotube. In some implementations, the sleeve 2759 can be a rigid tube having an inner diameter that is closely matched to an outer diameter of the elongate member 2755 resulting in a low clearance between the two. The low clearance between the elongate member 2755 and the sleeve 2759 means the sleeve 2759 maintains a small outer diameter such that the incision size through the cornea is minimized while still allowing for relative sliding between the inner and outer shafts. The elongate member 2755 can have a maximum outer dimension of between 0.5 mm and 1.4 mm.

Generally, the shaft 2761 (including the protective sheath and irrigation sleeve, if present) has a maximum cross-sectional diameter that is suitable for minimally-invasive procedures in the eye to minimize the corneal incision size. In some implementations, the maximum cross-sectional diameter of the distal shaft 2761 is about 1.25 mm. The maximum cross-sectional diameter can be smaller than this or can be larger than this diameter, for example, no more than about 2 mm in diameter, no more than about 3 mm in diameter, up to about 4 mm in diameter, or up to about 5 mm in diameter. As described elsewhere herein, a distal opening from the shaft 2761 can have a smaller inner diameter in relation to the inner diameter of the lumen extending through the shaft 2761 to mitigate problems with clogging. In some implementations, the difference between the nominal inner diameter of the shaft 2761 and the inner diameter of the distal opening can be between about 0.003" to about 0.006". In some implementations, the shaft 2761 can have a nominal inner diameter of about 0.0375" that narrows at the distal opening to about 0.033". Thus, eye tissue pieces that are less than the tip diameter can be aspirated into the lumen of the shaft 2761 and once inside the lumen are less likely to get stuck or cause a clog because the inner diameter of the remainder of the lumen is larger than the inner diameter of the distal opening.

The sleeve 2759 may be rigidly coupled to the tip 3320, exchangeable, or may be retractable. The length of the sleeve 2759 can vary, but is generally at least as long as necessary to cover the region of the elongate member 2755 that extends through the incision. A user can cover the oscillating elongate member 2755 and use a different sort of tip during a procedure, for example for capsular bag polishing and cortical tissue removal following lens extraction. Longer length of the sleeve 2759 can cover half the stroke length of the oscillating elongate member 2755, thereby reducing exposed stroke length of the oscillating elongate member 2755. The protective sleeve 2759 can be longitudinally positionable such that the effective stroke length of the oscillating elongate member 2755 can be adjusted from zero to 100% of its uncovered stroke length. The protective sleeve 2759 can also be positioned so that the oscillating elongate member 2755 remains recessed a certain depth within the protective sleeve 2759. This can prevent ocular tissue from coming into contact with the oscillating elongate member 2755, and effectively resulting in a suction-only mode of operation. The protective sleeve 2759 when positioned to reduce the effective cutting tube stroke length can prevent tissues from 'lollipopping' on the end of the elongate member 2755 by pushing stuck tissue off the elongate member 2755 as the elongate member 2755 tip retracts within the protective sleeve 2759.

The color of the exchangeable tip 3320 and/or the sleeve of the tip 3320 can provide information regarding the length of the sleeve and for what purpose it is useful. The lens cutting protective sleeve 2759 can be shorter than, for example, a sleeve configured to be used with a bag polishing tip. As such, a tip 3320 configured for lens removal may be a first distinguishable color such as blue and a tip configured for bag polishing may be a second distinguishable color such as white. Other markers, indicators, colors, are considered as well for easily distinguishing between the tips.

The microsurgical instruments described herein can be packaged in a kit that is part of a single, sterile package together one or more other components used in a cataract procedure. FIG. 23 shows an implementation of a kit 3600 that can include the instrument 225 with or without a sterility sheath 3505 attached, a lens removal tip 3320a, and a bag polishing tip 3320b. The lens removal tip 3320a and the bag polishing tip 3320b can be interchanged for one another depending on the stage of the procedure. The kit 3600 can also include a drip chamber 3625 having a spike 3630 configured to insert within an irrigation source such as a bottle of balanced saline solution. The drip chamber 3625 can be coupled to irrigation tubing 3655, which in turn can couple with an irrigation coupling on the instrument 225. The irrigation tubing 3655 can be provided with a pinch valve 3658 that is finger-actuated in order to open and close the irrigation tubing 3655. The kit 3600 can also include a waste container 3660 having waste tubing 3665 configured to couple an outlet from the instrument 225 to the waste container 3660. All the components in the kit 3600 can be sterile packaged within a container 3605.

In some implementations, a vitrectomy style cutting sleeve having a side opening for cutting in a guillotine style fashion. The sleeve can be inserted over the elongate member 2755 such that the elongate member 2755 extends through and is coaxially arranged within an outer tube such that the elongate member 2755 slides reciprocally within the outer tube. This style cutting element can be particularly useful for chopping and removing harder lens material. The outer tube can be a stationary tubular element coupled to a distal end region of the hand held portion and the elongate member 2755 can be movable such that it can oscillate within the lumen of the outer tube. The distal tip of the elongate member 2755 can be formed into a cutting edge, such as a short, sharpened bevel. In operation, tissue may enter into the outer tube through the side opening and be dissected by the cutting edge as the elongate member 2755 is reciprocated within the outer tube. This vitrectomy style cutting tip can further include a removable or retractable outer sheath for sliding over the side openings, for example, during insertion of the shaft into the anterior chamber. During insertion, the cutting area of the shaft can remain covered within the outer protective sheath to prevent snagging on the incision or other eye tissues prior to cutting. After insertion, the sheath can be retracted or otherwise removed when the operator is ready to start cutting and/or aspirating. The retraction can be manually activated by a user or can be automatically retracted by the device upon actuation of cutting and/or aspiration. After cutting/aspiration is complete and the instrument is ready to be removed from the eye, the sheath can be advanced distally to once again cover the openings.

The exchangeable tips 3320 can be used with elongate members 2755 that are substantially straight, particularly where the sleeves of the tips 3320 are rigid. In some implementations where the elongate member 2755 is curved away from the longitudinal axis or incorporates a feature angled relative to the longitudinal axis, the sleeve of the exchangeable tips 3320 may be flexible to allow for the sleeve to insert over the elongate member 2755.

Again with respect to FIGS. 9A-9C, the irrigation fluid line can connect to the disposable portion 3205 of the hand piece via an irrigation port 3310. The location of the irrigation port 3310 can vary, but generally the irrigation port 3310 is arranged relative to the irrigation fluid line such that the irrigation fluid line is not integrated or embedded within or extending through a significant length of the hand piece as is the case with conventional hand pieces. In an implementation, the irrigation port 3310 can be located near a distal end region of the disposable portion 3205 near where the irrigation sleeve 3128 couples with the tip 3320. The irrigation port 3310 provides a substantially rigid connection to the otherwise flexible irrigation line such that fluid from the irrigation source may be delivered through the irrigation sleeve 3128 to the eye. The location of the aspiration port can also vary.

The irrigation fluid line (and also the waste fluid line) can extend along at least a portion of the housing in a proximal direction away from the distal end of the instrument. In some implementations, a proximal end region of the housing (e.g. a lower surface of the durable reusable portion 3210 housing) can include one or more surface features configured to capture the tubing of the irrigation fluid line and/or the tubing of the waste line. In an implementation, the feature is a molded slot shaped to receive the convex shape of the tubing. The irrigation tubing can be captured within a first slot and the waste tubing can be captured within a second slot. The slots can capture the tubing such as by a snap fit or by interference fit. The fit can be effective with or without the sleeve 3128 in place between the tubing and the slots.

The irrigation source 130 can couple to the irrigation sleeve 3128 via the irrigation fluid line 155. The irrigation sleeve 3128 can extend over at least a portion of the protective sleeve 2759 as shown in FIG. 9B. The irrigation sleeve 3128 (and optionally the sleeve 2759) can be removed from the hand piece, for example, as part of a removable tip 3320 or removed individually from the tip 3320 via threads or other coupling feature. FIG. 9B shows the irrigation sleeve 3128 threaded onto a forward end of the tip 3320 having external threads 3321 and extending over a proximal region of the elongate member 2755.

The device can include a multi-way input or trigger 3125. The trigger 3125 can be positioned on the reusable, durable portion 3210 of the device or the disposable portion 3205. FIGS. 13A-13C illustrate different configurations of an implementation of the multi-way trigger 3125 on the device configured to control various functions of the device. The trigger 3125 can have a plurality of positions configured to turn on or off (or increase or decrease) one or more functions of the device. In some embodiments, the trigger 3125 can include a toggle switch 3131. The toggle switch 3131 can limit the movement of the trigger 3125 in certain positions. For example, if the toggle switch 3131 is positioned in a first position (e.g. to the right), the trigger 3125 may be limited in its amount of rotation to perhaps 75% of its normal range of motion. If the toggle switch 3131 is positioned in a second position (e.g. to the left), the trigger 3125 may move its full 100% range of motion. This may provide a hard stop for the trigger 3125 that the user can select. For example, in some embodiments, the speed of device increases linearly as the trigger 3125 is actuated. The surgeon may position the toggle switch 3131 to the first position such that when trigger 3125 is depressed (or otherwise actuated) to its 75% of range of motion a predetermined or preprogrammed motor speed is achieved. This may allow the user to easily switch between different motor speeds when they have fully depressed the trigger 3125 depending on what position the toggle switch 3131 is set.

The instrument can also incorporate a selector ring 3136 such as an annular structure coupled to an outer surface of the housing, such as the disposable portion 3205 of the housing (see FIGS. 20A-20B). The selector ring 3136 can be twisted manually by a user to switch off cutting function of the instrument by preventing oscillation of the distal shaft 2761. For example, in order to place the instrument in an irrigation/aspiration-only mode the selector ring 3136 can be moved into a first position that blocks the cutting function of the tip. The instrument may then be placed into an irrigation/aspiration/cutting mode by twisting the selector ring 3136 into a second position that allows for cutting function of the tip. Preferably, the instrument may also be placed into irrigation-only, irrigation/aspiration-only, and irrigation/aspiration/cutting modes without needing to twist the selector ring 3136. For example, the degree of depression of the trigger 3125 can turn on and/or off different functions of the instrument, which will be described in more detail below.

The trigger 3125 can have a resting position as shown in FIG. 13A. The user can actuate the trigger 3125 to move into a first actuated position (e.g. a partially depressed position) configured to start or increase at least one or more functions of the device (see FIG. 13B). In some implementations, the first actuated position can turn on both pulsed vacuum and oscillation of the distal shaft 2761 thereby providing vacuum-plus-cutting function. In other implementations, the first actuated position can turn on irrigation of the fluid system 110 of system 100 thereby providing irrigation-only function prior to initiation of aspiration (i.e. due to activation of aspiration pump 145). The trigger 3125 can have at least second actuated position (e.g. fully depressed position) configured to pause or decrease one or more functions of the device (see FIG. 13C). For example, the trigger 3125 in the second actuated position can suspend oscillation of the shaft 2761 while the vacuum through the shaft 2761 continues thereby providing a vacuum-only function. A spring can be incorporated that allows the trigger 3125 to return to a default (i.e. upward) position upon release.

The first actuated position can provide irrigation and/or vacuum without any oscillation of the shaft 2761 until a further amount of "throw" is achieved by the trigger 3125. The device can be programmed in any of a variety of ways such that a user may selectively activate certain functions of the device with the trigger 3125. For example, in the case of a depressible trigger as shown in FIGS. 13A-13C that can cause the motor 2756 to spin up to 100% speed, a first amount of throw in the trigger 3125 can activate a first function of the device, such as vacuum and/or irrigation while keeping the oscillation of the shaft 2761 shut off. A further amount of throw in the trigger 3125 can then initiate oscillation of the shaft 2761. This can allow for irrigation fluid to be delivered without any cutting action in the early stage of trigger actuation, for example, the first 10% of throw after which changing the position of the trigger 3125 can change the rate of oscillation, pulsed vacuum, and/or aspiration.

Various configurations of the input are considered herein. As an example configuration, the input can be mechanical like the trigger 3125 described above such that it couples to a button rod 3127 that is movable along a longitudinal axis of the device as the trigger 3125 is actuated into one of a plurality of positions (shown in FIGS. 13A-13C). For example, when the trigger 3125 is moved from the resting position into the first actuated position, the trigger 3125 can move the button rod 3127 a distance proximal such that a proximal end of the button rod 3127 extends a first distance into a proximal portion of the hand-held portion of the device (e.g., the durable portion 3210). When the trigger 3125 is moved from the first actuated position into the second actuated position, the trigger 3125 can move the button rod 3127 such that the proximal end of the button rod 3127 extends a second distance into the proximal portion of the handheld portion of the device (FIG. 13C). The button rod 3127 in addition to changing the speed of oscillation can prevent movement of the shaft 2761 altogether. Movement of the button rod 3127 in a proximal direction P can also move the shaft 2761 in a proximal direction thereby preventing the proximal end of the shaft 2761 from interacting with the drive mechanism configured to cause the shaft 2761 to oscillate (e.g. camming teeth).

The extension of the button rod 3127 into the proximal portion (e.g. the reusable, durable portion 3210) can impact the speed of the motor 2756. For example, speed of rotation of the motor 2756 can be controlled by a potentiometer 3285 linked to the trigger 3125 or a non-contact sensor configured to sense motion of the trigger. A potentiometer ribbon 3280 can extend between a distal end region of the durable portion 3210 and configured to activate the potentiometer 3285. For example, the proximal end of the potentiometer ribbon 3280 can include a cut-out 3286 or other feature configured to engage with the potentiometer 3285 such that movement of the ribbon 3280 impacts the activation of the potentiometer 3285. As best shown in FIGS. 5B, 5C, 5H, 6A, and 6C, the proximal end of the button rod 3127 can interact with the distal end of the potentiometer ribbon 3280 extending within the durable portion 3210 of the handheld portion of the device. Movement of the potentiometer ribbon 3280 can, in turn, activate the potentiometer 3285 engaged with the cut-out 3286 of the ribbon 3280. The potentiometer 3285 can, in turn, change the speed of the motor rotation.

Figure 14A:
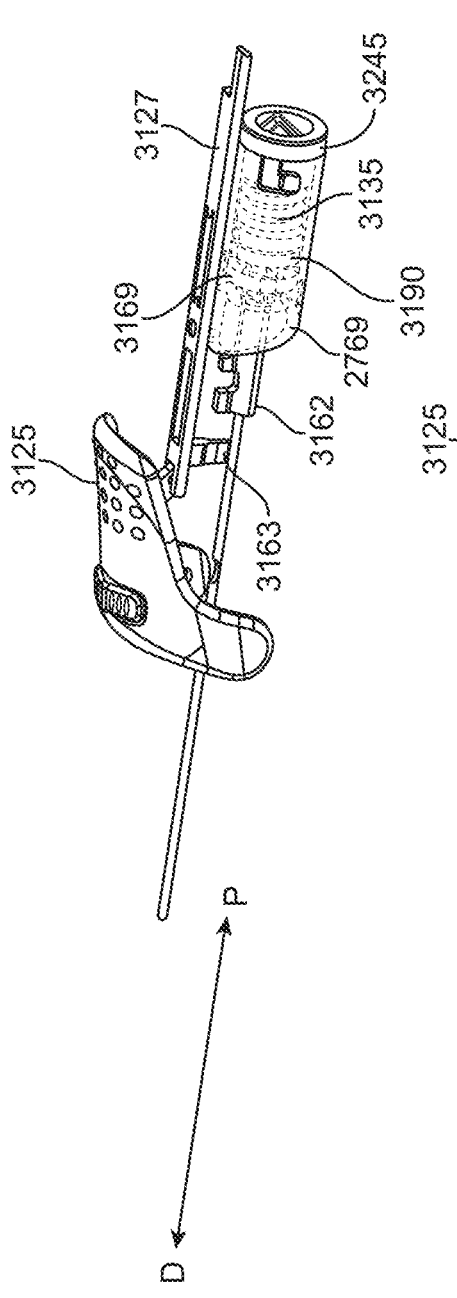
FIGS. 14A-14C illustrate partial views of the tool of FIGS. 13A-13C in the various stages of actuation.
Figure 14B:
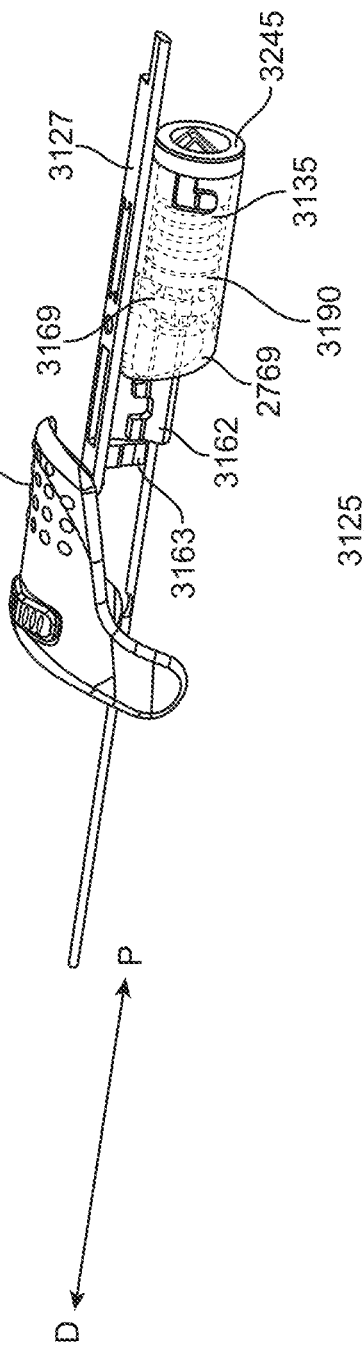
Figure 14C:
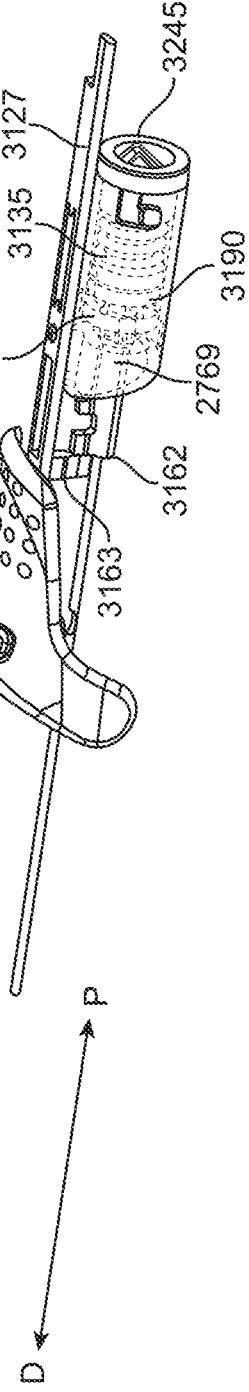

The rotation of the motor 2756 can be converted into linear motion of the elongate shaft 2761. FIGS. 14A-14C correspond to FIGS. 13A-13C and FIGS. 15A-15C. Each of the figures illustrate how movement of the trigger 3125 and the button rod 3127 affect movement of the shaft 2761 relative to a camming mechanism. The camming mechanism can include rotating cam 2769 and cutter cams 3169, 3190. In the resting state of the actuator 3125 shown in FIG. 14A, the rod 3127 is in a distal-most position and moved away from a proximal spline 3162 of the shaft 2761. As mentioned elsewhere herein, the movement of the pistons 2799 in creating aspiration forces can be linked to and coordinated with the movement of the shaft 2761 to cut material via the rotating cam mechanism. The rotating cam 2769 can spin to move pistons 2799 within the hand held portion. Rotating cam 2769 can be affixed to distal cutter cam 3169 such that the rotating cam 2769 and distal, cutter cam 3169 spin together (see FIGS. 8A-8D). For example, distal, cutter cam 3169 can be positioned within bore of rotating cam 2769. An outer surface of distal, cutter cam 3169 can include one or more projections 3168 (see FIG. 8C) sized and shaped to insert within one or more corresponding indents on an inner surface of rotating cam 2769. It should be appreciated that any number of coupling arrangements between the cams 2769, 3169 are considered herein such that they are linked and spin together. Distal, cutter cam 3169 can include teeth 3132 on its proximal-facing surface configured to engage corresponding teeth on the distal-facing surface of proximal cam follower 3190. As cutter cam 3169 rotates, the teeth 3132 slide along teeth 3132 of the proximal cam follower 3190. The cam follower 3190, cutter spline 3162, and shaft 2761 are pushed backward until the teeth 3132 of the distal cutter cam 3169 reach step 3933 on the cam follower 3190 (see FIG. 15C) At this point, the force of the spring 3135 urges the shaft 2761, the cutter spline 3162, and the cam follower 3190 forward or in a distal direction D. A cutter cushion 3164 can be incorporated to provide dampening as the cutter spline 3162 springs back toward the distal position the cutter cushion 3164 may reduce the noise that the device makes during operation by dampening the cutter spline as it is sprung forward. The shaft 2761 oscillates back and forth as the cams 2769, 3169 spin. Upon full actuation of the actuator 3125, the rod 3127 is moved further in a proximal direction P until a feature 3163 of the rod 3127 engages with the spline 3162 of the shaft 2761 (see FIG. 14C). The rod 3127 pulls the spline proximally. The movement disengages the distal cutter cam 3169 from the cam follower 3190 preventing the teeth 3132 from engaging such that no motion of the shaft 2761 occurs.

Figure 16A:
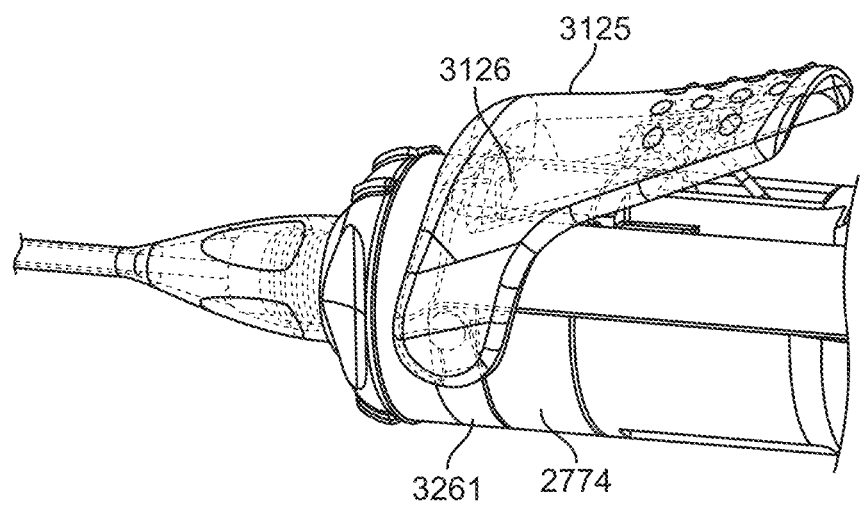
FIGS. 16A-16B illustrate an implementation of a venting mechanism coupled to a multi-stage trigger.
Figure 16B:
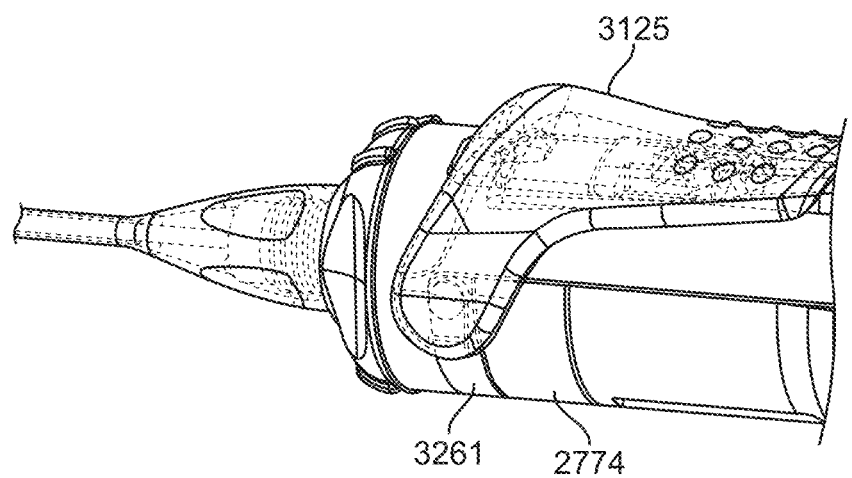

As mentioned above, the devices described herein can incorporate a venting mechanism to allow suction within the system to dissipate, for example, when a user desires to release an inadvertently captured capsular bag or when the device is idle. The venting mechanism can be coupled functionally to the multi-stage trigger 3125 such that when the trigger 3125 is idle, the venting mechanism can actively vent the device and when the trigger 3125 is activated to aspirate, the venting mechanism can be shut off. FIGS. 16A-16B illustrate an implementation of the venting mechanism coupled to actuation of the multi-stage trigger 3125. As described elsewhere herein, the trigger 3125 in its first, idle configuration can be biased upwards such that upon release of manual pressure on the trigger 3125 aspiration shuts off. Downward motion of the trigger 3125 can trigger aspiration (as well as irrigation and/or oscillation as described elsewhere herein). Downward motion of the trigger 3125 can also cause motion of a shutter 3126 coupled to an underside of the trigger 3125. The shutter 3126 can insert between the front manifold 3261 and the vacuum manifold 2774 thereby affecting aspiration drawn through the device. Thus, when the trigger 3125 is in the idle configuration and biased upwards, the shutter 3126 is in a configuration suitable for venting the system. When the trigger 3125 is urged downwards to activate aspiration, the shutter 3126 is in a configuration suitable for creating suction and venting is turned off.

Figure 16D:
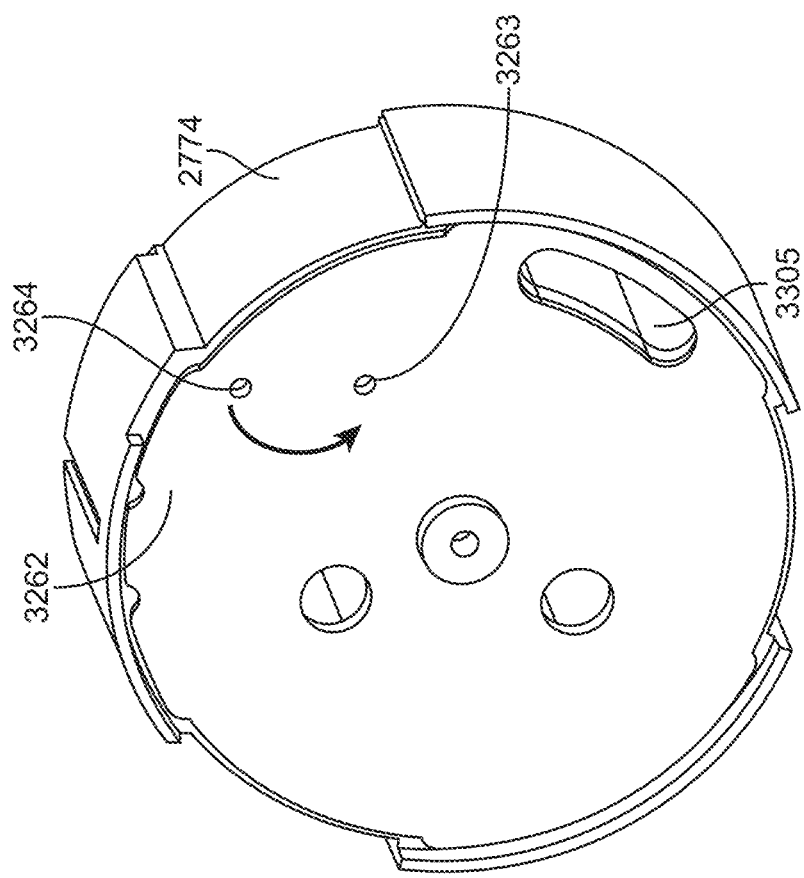
FIGS. 16C-16D illustrate a vacuum manifold covered by a gasket incorporating the venting mechanism of FIGS. 16A-16B from a distal end perspective.
Figure 16C:
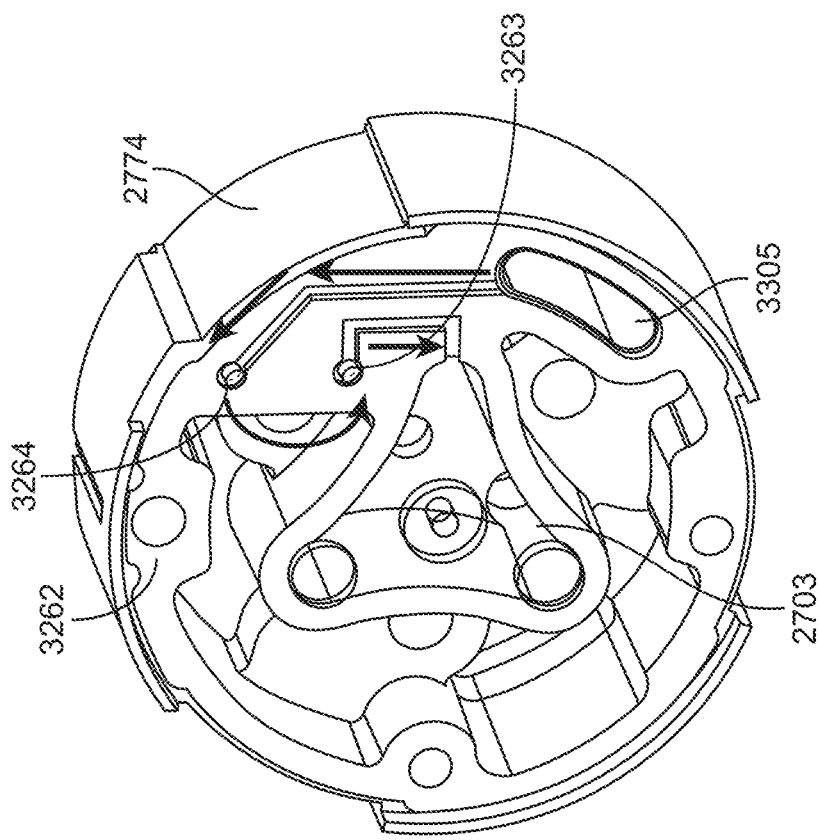
Figure 16H:
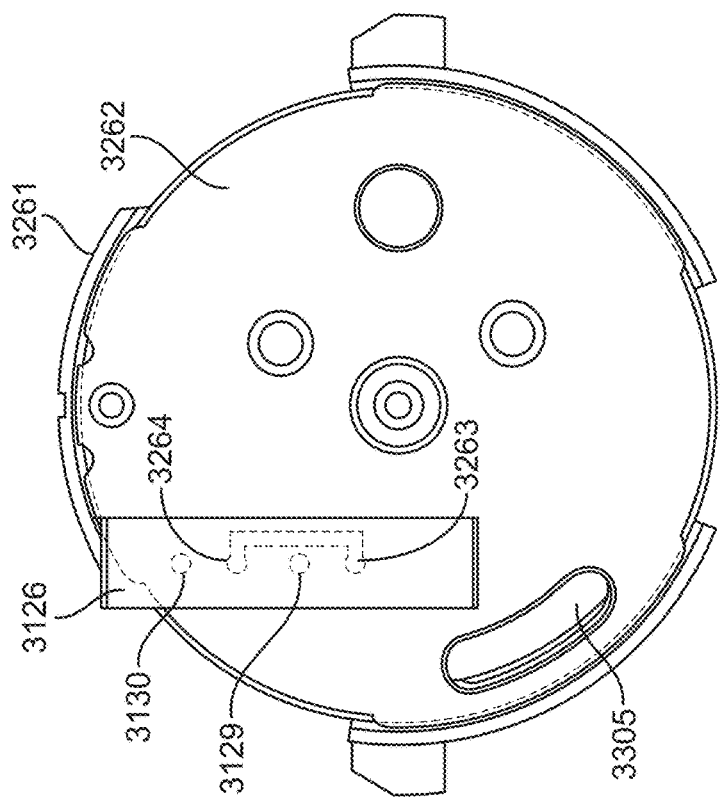
FIGS. 16G-16H illustrate the venting mechanism of FIGS. 16C-16D from a proximal end perspective without the vacuum manifold shown.
Figure 16G:
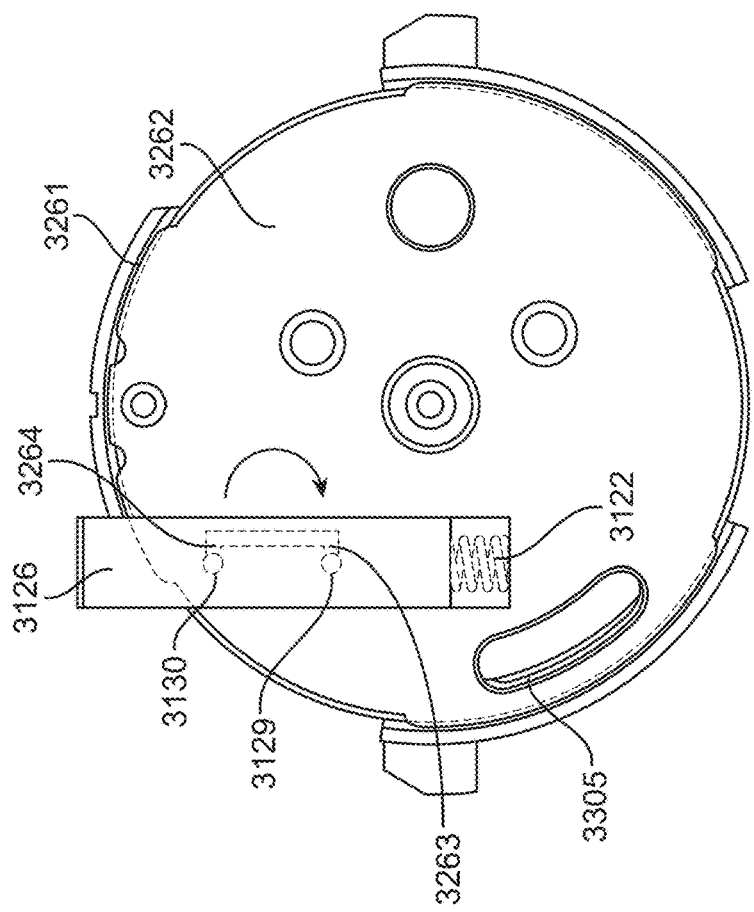

FIGS. 16C-16D show the vacuum manifold 2774 covered by a gasket 3262. The gasket 3262 is shown positioned on a distal end of the vacuum manifold 2774 such that the gasket 3262 separates the vacuum manifold 2774 from the front manifold 3261. As described elsewhere herein the vacuum manifold 2774 and the gasket 3262 can define a vacuum chamber 2703. An irrigation fluid channel 3305 can extend through the vacuum manifold 2774 and the gasket 3262. The gasket 3262 can include a first vent opening 3263 and a second vent opening 3264 through its thickness. The first vent opening 3263 may fluidly connect with the vacuum chamber 2703 and the second vent opening 3264 may fluidly connect with the irrigation fluid channel 3305. FIGS. 16E-16F show the shutter 3126 positioned between the front manifold 3261 and the gasket 3262 covering the vacuum manifold 2774 and FIGS. 16G-16H show the relative alignment of the shutter 3126 and the gasket 3262. The shutter 3126 can likewise include a first vent opening 3129 and a second vent opening 3130 through its thickness. The shutter 3126 can be urged upward such as with a shutter spring 3122 when the device is idle. The shutter 3126 in the upward position results in the first and second vent openings 3129, 3130 of the shutter 3126 to align with the first and second vent openings 3263, 3264 of the gasket 3262. Alignment of the openings completes a fluid channel between the vacuum chamber 2703 and the irrigation fluid channel 3305 causing any negative pressure within the system to dissipate. FIGS. 16C-16D and also FIG. 16G illustrate the venting of negative pressure between the vacuum chamber 2703 and the irrigation fluid channel 3305. The arrows illustrate the venting path from the higher pressure irrigation fluid channel 3305 and the lower pressure vacuum chamber 2703 when the vent openings 3129, 3130 of the shutter 3126 align with the vent openings 3263, 3264 of the gasket 3262. Urging the trigger 3125 downward may also move the shutter 3126 downward between the manifolds 2774, 3261. The vent openings 3129, 3130 of the shutter 3126 may thereby be urged out of alignment with the vent openings 3263, 3264 of the gasket 3262 to shut off the fluid channel between the vacuum chamber 2703 and the irrigation fluid channel 3305 (see FIG. 16H). This allows for the generation of aspiration pressure within the vacuum chamber 2703 as described elsewhere herein.

Movement of the user-activated shutter 3126 can determine whether the vacuum that is generated within the vacuum chamber 2703 of the device is vented or maintained. The vacuum chamber 2703 may be connected to atmospheric air, to the irrigation fluid pathway 3305, to the waste fluid pathway 2709, or any other cavity. By doing so, any maintained vacuum within the vacuum chamber 2703 is vented through this connection. Fluid or air may enter the vacuum chamber 2703 and the vacuum level within the cavity will decrease. It should be appreciated that the shutter 3126 need not be coupled to the trigger 3125 and can have a separate actuator that can be activated when a user desires to release the vacuum from the device. It should also be appreciated that any of a variety of methods to vent the vacuum are considered herein.

Asymmetric Motion and Aspiration Profiles

As mentioned above, the devices described herein can include a shaft configured to be inserted into the eye in a minimally-invasive manner to cut, aspirate, and/or inject material in the eye. The shaft can be a vitrectomy-style cutting element having a hollow, elongate member extending through an outer member with a side opening configured to capture and cut pieces of tissue. The shaft can also include a phacoemulsification ("phaco") style tip, which also includes a movable elongate member with or without an outer member. Oscillating movements of the elongate member can occur using any of a variety of mechanisms, such as a rotating cam element as described elsewhere herein. The oscillating movements can be created in a manner that avoids the deleterious effects typical of phacoemulsification on the delicate eye tissues such as corneal endothelial cells.

Phacoemulsification can incorporate two main methods of action: 1) mechanical jack hammering, and 2) cavitation. In the case of jackhammering, the oscillating movements of the tip mechanically impacts the tissue at a high speed to break up the tissue into ever smaller fragments. Cavitation involves the creation of gas bubbles as a consequence of high velocity oscillation of the phaco tip. Phaco tip retraction speeds are sufficient to create zones of pressure low enough to cause the formation of gas bubbles as dissolved gases are drawn out of the fluid. As the phaco tip transitions from retraction to forward motion, these bubbles then collapse and implode, which results in very high temperatures (e.g. 3000° C.) and pressures (e.g. 10,000 atm). It is generally thought that the combination of high temperatures and high pressures helps to emulsify the tissue fragments. While the role cavitation plays in breaking up eye tissue is debatable, the role cavitation plays as the primary driver behind the deleterious effects of phacoemulsification on the surrounding eye tissue during cataract surgery is not. High temperatures, shock waves, and the creation of free-radicals in the eye are of concern to the health of the corneal endothelial cells.

In an implementation, one or more of the devices described herein can include an oscillating tip configured to move in a manner that reduces, attenuates, or prevents problems of cavitation during phacoemulsification. The oscillating tip can be incorporated in an "all-in-one" sort of device having a vacuum source within the handle to apply pulsatile vacuum. Alternatively, the oscillating tip can be incorporated in a device used in connection with another device configured to apply pulsatile vacuum remotely. As described above, the various features and functions of the devices described herein can be applied to conventional devices and systems known in the art to be useful for cutting, fragmenting, emulsifying, or otherwise impacting tissues at or near a surgical site. For example, the pulsatile vacuum and/or asymmetric motion profiles described herein can be incorporated into phacoemulsification systems and vitrectomy systems known in the art. For example, the features described herein can be incorporated as an additional hardware or software feature of the phacoemulsification systems that are conventionally used to cause oscillation of an elongate shaft in the ultrasonic range of frequencies (e.g. above 20,000 Hz).

Again with respect to FIGS. 7A-7B, the device 2700 can include a hand-held portion coupled to a distal shaft 2761. At least a portion of the distal shaft 2761 is configured to oscillate relative to the hand-held portion. As described above, the distal shaft 2761 can include an elongate member 2755 extending through and coaxially arranged within an outer tube or protective sleeve 2759 (see FIG. 7A). The sleeve 2759 can be fixed relative to the hand piece 2760 and the elongate member 2755 can slide in a reciprocating, oscillating fashion.

The reusable, durable portion 3210 of the hand piece 2760 can include a drive mechanism operatively coupled to the elongate member 2755 of the distal shaft 2761 configured to drive movement or oscillation of the elongate member 2755 of the distal shaft 2761 relative to the hand piece 2760 and/or power the aspiration pump in the hand piece.

The device can include a camming mechanism configured to move the shaft 2761. The camming mechanism can include a rotating cam 2769 and cutter cams 3169, 3190 (see FIGS. 8A-8D, 17A-17D, 14A-14C and 15A-15C). The rotating cam 2769 can be affixed to distal cutter cam 3169 such that the rotating cam 2769 and distal, cutter cam 3169 spin together. For example, distal cutter cam 3169 can be positioned within bore of rotating cam 2769. An outer surface of distal, cutter cam 3169 can include one or more projections 3168 (see FIG. 8C) sized and shaped to insert within one or more corresponding indents on an inner surface of rotating cam 2769. It should be appreciated that any number of coupling arrangements between the cams 2769, 3169 are considered herein such that they are linked and spin together. Distal, cutter cam 3169 can include teeth 3132 on its proximal-facing surface configured to engage corresponding teeth on the distal-facing surface of proximal cam follower 3190. As cutter cam 3169 rotates, the teeth 3132 slide along teeth 3132 of the proximal cam follower 3190. The cam follower 3190, cutter spline 3162, and shaft 2761 are pushed backward until the teeth 3132 of the distal cutter cam 3169 reach step 3933 on the cam follower 3190 (see FIG. 15C) At this point, the force of the spring 3135 urges the shaft 2761, the cutter spline 3162, and the cam follower 3190 forward or in a distal direction D. A cutter cushion 3164 can be incorporated to provide dampening as the cutter spline 3162 springs back toward the distal position the cutter cushion 3164 may reduce the noise that the device makes during operation by dampening the cutter spline as it is sprung forward. The shaft 2761 oscillates back and forth as the cams 2769, 3169 spin.

Figure 17A:
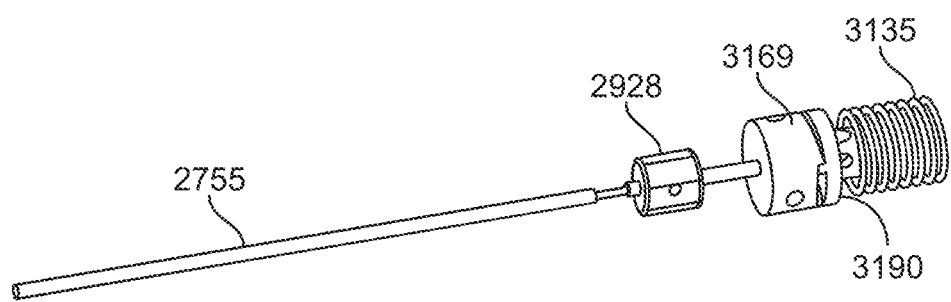
FIG. 17A is a perspective view of an elongate member coupled to an implementation of an oscillating drive mechanism.

FIG. 17A illustrates the elongate member 2755 connected to a hub or cam follower 3190. The cam follower 3190 can have camming surfaces on its distal end that engages with a cutter cam 3169. The proximal end of the cam follower 3190 can be connected to a spring 3135 that pushes the cam follower 3190 distally. The elongate member 2755 can also be connected to an orientation locking feature 2928 such as a rectangular block that prevents the elongate member 2755 and the cam follower 3190 from rotating. FIG. 17B shows as the cutter cam 3169 rotates, the camming surfaces cause the cam follower 3190 to move proximally, compressing the spring 3135 further. The camming surfaces have a step 3933 that allows the cam follower 3190 to drop forward (i.e. distally) again at a certain point in the rotation. At this point, the spring 3135 pushes the cam follower 3190 quickly forward until the camming surfaces engage again. Through such a mechanism, the tip 2765 of the elongate member can retract with a retraction speed profile that is at least in part a function of the rotational speed of the cutter cam 3169. The rotational speed of the cutter cam 3169 can be controlled so that the maximum tip retraction speed remains below the critical 'cavitation threshold speed' that would otherwise result in cavitation in the eye. The tip 2765 of the elongate member 2755 can then extend with an extension speed profile that is at least in part a function of the force of the spring 3135 and mass of the tip assembly. In this way, the average retraction speed can be slow, i.e. below the cavitation threshold speed, but the average extension speed can be fast, i.e. close to or higher than the average retraction speed of a typical phacoemulsification tip. Thus, the benefits of mechanical jackhammering can be achieved while the deleterious effects of cavitation are entirely avoided.

The repeated advancing and retracting may occur along the longitudinal axis, but the path the oscillating movements take need not be purely linear. In an implementation, the shaft 2761 can incorporate a feature configured to impart a moment to the shaft 2761 upon reaching maximum distal extension causing motion in a side-to-side manner along with the axial oscillation. Side-to-side motion can shear lens tissue to reduce the size of fragments for aspiration through the lumen thereby reducing the propensity for clogging. For example, FIG. 17G shows the shaft 2761 extending from the front manifold 3261 and through central cavity 3315 of the tip 3320. The shaft 2761 can incorporate a hammer 3172 extending outward from the longitudinal axis A of the shaft 2761. The hammer 3172 can include a first end 3174 fixedly coupled to a region of the shaft 2761 that remains within the central cavity 3315 during forward and backward motion of the shaft 2761. The hammer 3172 can include a second end 3176 extending laterally outward from the first end 3174. The second end 3176 can extend a distance away from the longitudinal axis A of the shaft 2761 sufficient to make contact with a surface of the instrument upon maximum distal extension of the shaft 2761. The shaft 2761 is configured to enter a bore 3180 of the forward end region 3182 of the tip 3320. Rather than a region of the shaft 2761 bottoming out in a symmetrical manner, the second end 3176 of the hammer 3172 can abut against a region of the tip 3320 in an asymmetrical manner. For example, the second end 3176 can abut against a region of the tip 3320 defining an opening 3184 into the bore 3180 through which the shaft 2761 extends. In some implementations, at least one washer 3186 can be positioned within the central cavity 3315 surrounding the opening 3184 into the bore 3180. The second end 3176 of the hammer 3172 can abut against the washer 3186 upon distal extension of the shaft 2761 relative to the tip 3320. The hammer 3172 can make contact with the washer 3186 in an off-center or asymmetrical manner relative to the longitudinal axis A of the shaft 2761 upon maximum distal extension. The off-center contact between the hammer 3172 and the washer 3186 imparts a moment to the shaft 2761 causing it to sway side-to-side relative to the longitudinal axis A. The sway at the tip of the shaft 2761 can be between 0.001" up to about 0.010" from center upon bottoming-out occurs between the washer 3186 and the hammer 3172. In some implementations, the sway is approximately 0.006" side-to-side "wag" upon bottoming-out. The washer 3186 can be a thin, shim washer. The shim washer can be in 0.001" increments.

When in use, the drive mechanism is capable of retracting the shaft in a proximal direction with a retraction speed profile and advancing the shaft in a distal direction with an extension speed profile. The retraction speed profile can be different from the extension speed profile. Additionally, the movement profile of the elongate member can be coordinated with a vacuum profile. For example, while a pulse of vacuum is being applied through the elongate member (i.e. through the distal opening from the elongate member), the elongate member can be simultaneously fired in the distal direction. The pulsed vacuum can be internally generated within the handle portion 2760 of the device 2700 or externally generated and valved within the handle, as described elsewhere herein. Where the elongate member is described as moving in forward and distal directions relative to the treatment site vibrations of the elongate member are considered as well. The elongate member can be vibrated in a similar fashion to conventional phacoemulsification systems. Thus, the elongate member can be vibrated while a pulse of vacuum is applied and at some phase in the vacuum pulse or thereafter, the vibration and the vacuum can be turned off such that the system comes to rest before initiating a vibration-vacuum sequence again. The coordination between the movement and/or vibration of the elongate member and the vacuum applied through the elongate member is described in more detail below.

Figure 18A:
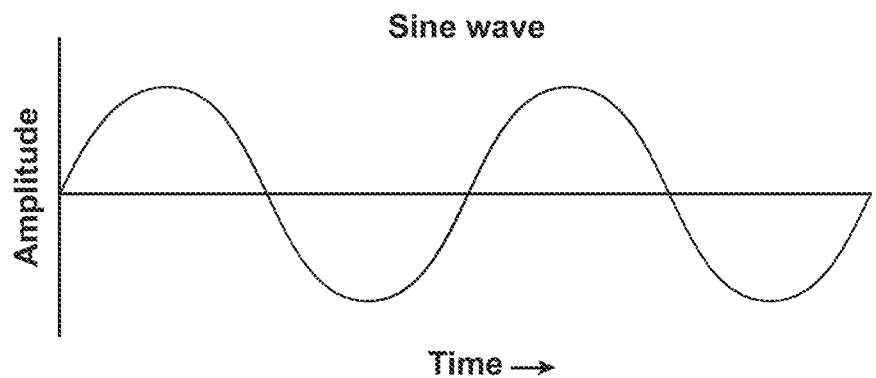
FIG. 18A shows a symmetric, sinusoidal motion profile of an elongate member of conventional phacoemulsification systems.
Figure 18B:
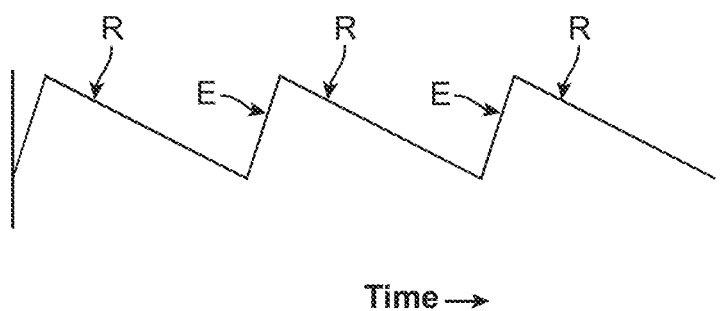
FIG. 18B shows an asymmetric, non-sinusoidal motion profile of an elongate member.
Figure 18C:
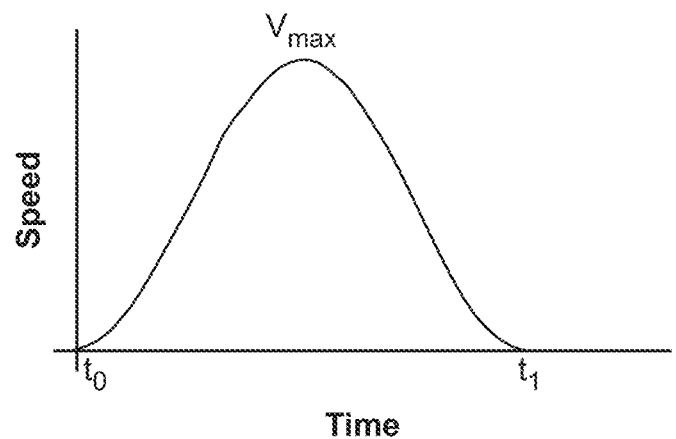
FIG. 18C shows a symmetric motion profile for an elongate member where an extension speed profile is the same as a retraction speed profile of the elongate member.

FIGS. 18A and 18C illustrate typical motion profiles of conventional phacoemulsification tips. Conventional phacoemulsification tips have a substantially sinusoidal motion profile in which the average speed of the tip is substantially the same during proximal retraction as during distal extension (see FIG. 18A). In contrast, the oscillating elongate member of the devices described herein have a generally non-sinusoidal motion profile in which the average tip speed of the retraction speed profile and the average tip speed of the extension speed profile can be substantially different providing an overall asymmetric movement profile for the oscillating elongate member (see FIG. 18B). Additionally, conventional phacoemulsification tips have maximum tip speed ($V_{maxR}$) of the retraction speed profile R that is substantially the same as the maximum tip speed ($V_{maxE}$) of the extension speed profile E and thus, their motion profiles substantially overlap (see FIG. 18C). The oscillating elongate member of the devices described herein have maximum tip speed ($V_{maxR}$) of the retraction speed profile R that is substantially lower than the maximum tip speed ($V_{maxE}$) of the extension speed profile E and thus, their motion profiles do not substantially overlap (see FIG. 18D).

Figure 18D:
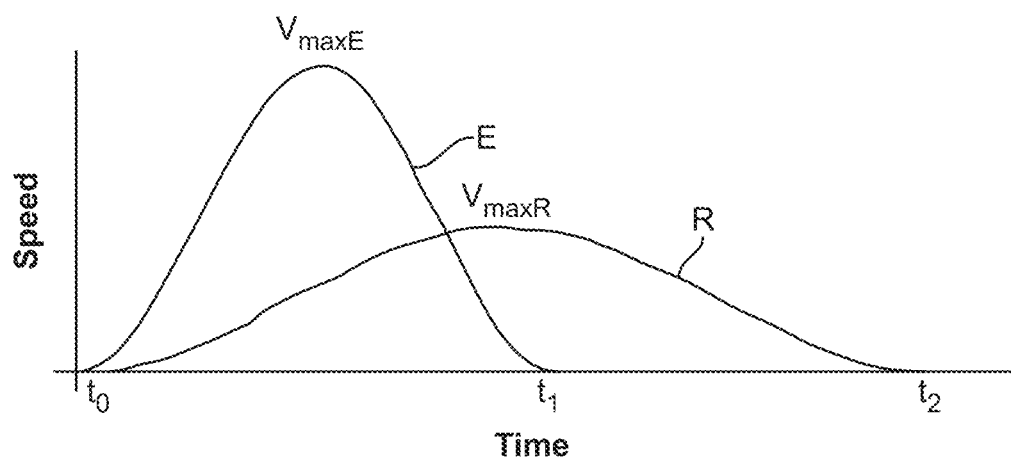
FIG. 18D shows an asymmetric motion profile for an elongate member where an extension speed profile differs from a retraction speed profile of the elongate member.

FIG. 18C illustrates a motion profile provided by a conventional phacoemulsification system in which the extension and retraction speed profiles are substantially the same. For example, a 40,000 Hz phaco system having a 0.1 mm amplitude speed may have a $V_{max}$ of approximately 12.6 meters/second where the time $T_1$ is approximately 0.0125 ms. FIG. 18D illustrates a motion profile provided by the devices described herein. The $V_{maxE}$ may be substantially the same as $V_{maxE}$ of a conventional phacoemulsification system, but the $V_{maxR}$ may be substantially lower such that full retraction is complete at time $T_2$. Thus, the device may have a lower $V_{avg}$.

Figure 18E:
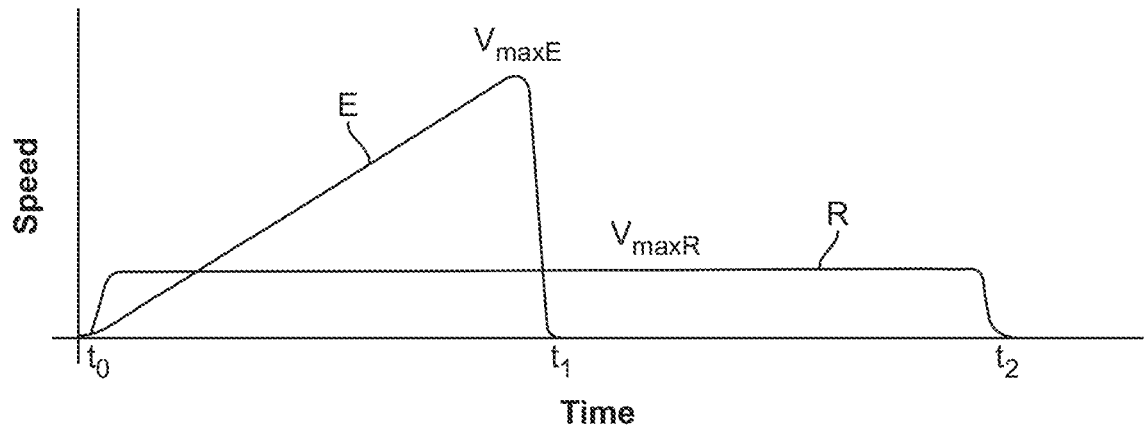
FIGS. 18E-18F show additional examples of extension speed profiles and retraction speed profiles of an elongate member where the profiles are different.
Figure 18F:
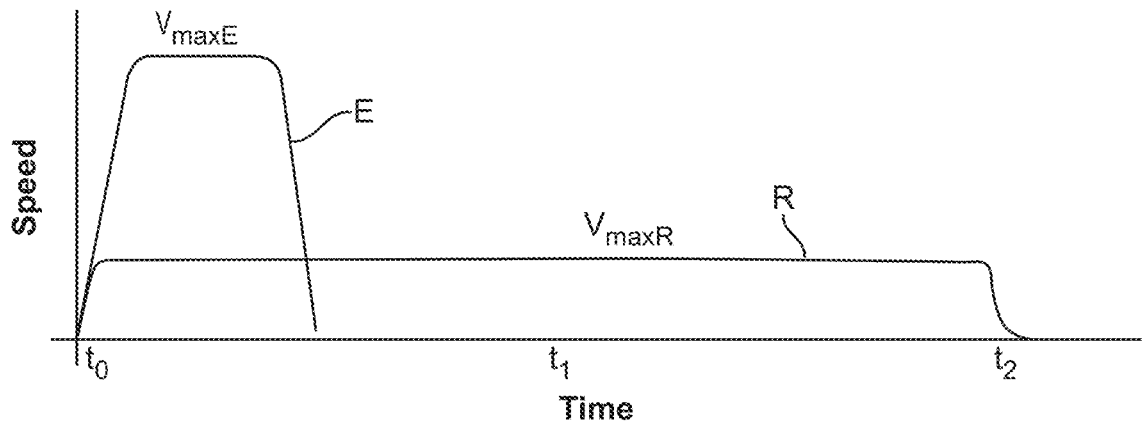

FIGS. 18E-18F illustrate additional asymmetric motion profiles considered herein. The extension speed E can increase linearly to $V_{maxE}$ as the spring force compels the elongate member forward until it reaches its stroke limit and drops to zero before being retracted. As the elongate member is retracted (e.g. as the cam rotates it pulling the elongate member back at a roughly constant speed), the retraction speed R increases to $V_{maxR}$ before slowing to a stop. The retraction speed profile R can form a plateau during which time the retraction speed is roughly constant. Retraction phase is complete at time $T_2$, which is longer than the time $T_1$ it took to complete the extension phase. There can include period of dwell or a pause between extension and retraction phases. The $V_{maxE}$ can be roughly the same as conventional phaco systems (e.g. between about 8 to 12 meters/second). The $V_{maxR}$ can be much lower than conventional phaco systems (e.g. less than about 0.02 meters/second). It should be appreciated that speeds of extension and retraction can vary and that any of a number of non-sinusoidal tip motion profiles are considered herein. In some implementations the $V_{maxE}$ can be between about 2 meters/second and 50 meters/second and the $V_{maxR}$ can be between about 0.001 meters/second and 2 meters/second.

In conventional phacoemulsification, the speed profile and movement profile of the movable elongate member are generally sinusoidal. Meaning, the movement of the distal tip of the elongate member oscillates in a sinusoidal wave pattern, for example, corresponding to a supplied voltage to the piezoelectric crystal. The speed of the distal tip therefore also oscillates in a sinusoidal manner as the derivative of the movement profile. FIG. 18G shows an implementation of non-sinusoidal movement of the distal tip of an elongate member (bottom panel) relative to its extension and retraction speed profiles (top panel). Both the speed profiles and the corresponding movement profiles are shown as being non-sinusoidal. The distal tip can have a dwell time between the extension and retraction cycles. Between $t_0$ and $t_1$, the distal tip can extend forward with a speed profile that may be a sine wave or any other profile. At $t_1$, the distal tip can pause for a dwell period between $t_1$ and $t_2$. The dwell period can be about 0.050 milliseconds, or between about 0.001 and 0.025 milliseconds. At $t_2$, the distal tip can retract with a speed profile that may also follow a sine curve. The movement of the distal tip resembles a sine wave having a dwell at its most extended position.

The non-sinusoidal patterns, for example as shown in FIG. 18G, can reduce the likelihood of cavitation because the dwell time allows for the fluid in the eye that is displaced by movement of the elongate member during extension to return to a zero momentum state before retraction of the elongate member begins. During conventional sinusoidal patterns, the elongate member pushes the fluid away from the distal tip and then retracts immediately while the fluid may still be traveling away from the distal tip thereby increasing the likelihood of cavitation due to the relative velocity of the fluid to the distal tip. The relative velocity of the fluid to the distal tip is higher if the fluid of the eye is being carried away from the tip by momentum while the distal tip itself begins retracting. The dwell period can allow the fluid being displaced to return towards a zero momentum or zero velocity state before the distal tip begins to retract. In this implementation, the extension speed profile and the retraction speed profile may be similar or identical, but the overall speed profile and movement of the distal tip is non-sinusoidal. Other implementations are contemplated herein. For example, the elongate member can slow down more gradually as it approaches its fully extended position than a typically sine wave pattern would. As the elongate member retracts, the profile would follow a more symmetric path. Any number of other non-sinusoidal patterns are considered.

It should be appreciated that the term "non-sinusoidal" as used herein can be defined as a movement or speed profile that does not follow a simple sine wave pattern of oscillating movement. A simple sine wave may be defined by a single frequency, a single phase shift, and a single amplitude. Certain complex profiles may be generated by adding or subtracting sine waves. However, these complex profiles may also be considered non-sinusoidal because their addition or subtraction does not follow a simple, single sine wave pattern.

The drive mechanism is capable of retracting the elongate member in a proximal direction with a retraction speed profile and advancing the elongate member in a distal direction with an extension speed profile such that the retraction speed profile is different from the extension speed profile. The average retraction speed of the elongate member from the retraction speed profile can be lower than the average extension speed of the elongate member from the extension speed profile. Thus, the drive mechanism operatively coupled to the elongate member is configured to asymmetrically oscillate the elongate member. The extension speed profile E can include a $V_{maxE}$ and the retraction speed profile R can include a $V_{maxR}$ where the $V_{maxR}$ is less than the $V_{maxE}$. The $V_{maxR}$ of the elongate member is generally kept below a threshold speed at which cavitation bubbles would be generated in the eye. Without limiting this disclosure to any particular threshold speed, one of skill in the art would understand the theoretical speed of retraction at which cavitation occurs is generally about 5 meters/second. As such, the $V_{maxR}$ of the elongate member may be maintained below about 5 meters/second.

The oscillating movements of elongate members driven by conventional phacoemulsification systems may have a degree of variability due to normal losses during movement (e.g. due to friction or other environmental factors). This variability may impact the average speeds achieved during retraction and extension such that the retraction speed profile and extension speed profile are not identical or perfectly sinusoidal. However, this normal variability during movements of component parts is not intentionally engineered or designed to occur (i.e. a control processor operating according to program instructions stored in a memory; or hardware in operable communication with the control processor designed to achieve different speeds depending on phase of cycling). Thus, normal variability in speed during movement is not considered to be contributing to or resulting in an asymmetric motion profile. The asymmetric motion profiles described herein are consciously engineered or designed motion profiles intended to be substantially reproducible during each cycling and not merely due to chance variability.

As described elsewhere herein, the vacuum source of the device can be configured to provide pulses of discontinuous negative pressure. Movement of the pistons creating vacuum pulses can be coordinated or linked to phases of movement of the elongate cutter member.

Figure 19A:
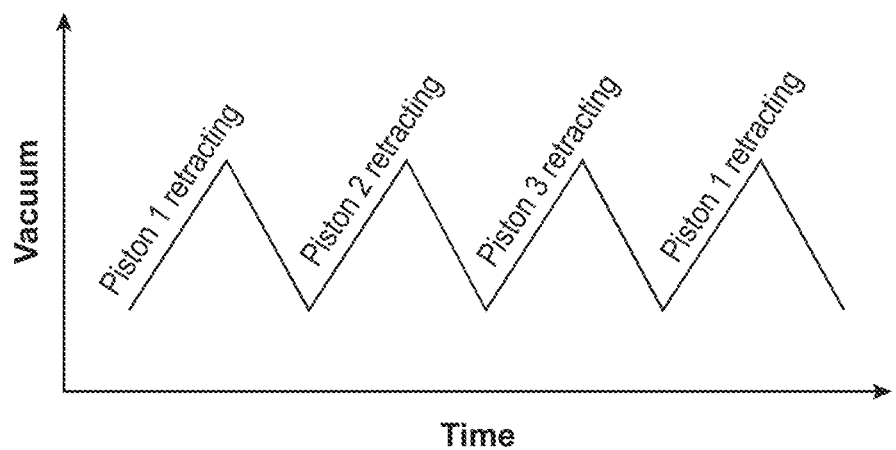
FIG. 19A shows an implementation of a vacuum profile.
Figure 19B:
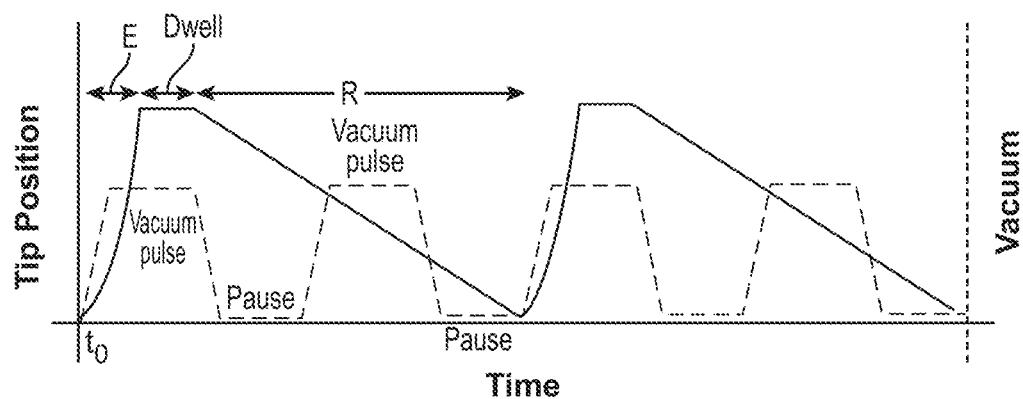
FIGS. 19B-19D show overlap between an asymmetric, non-sinusoidal motion profile for an elongate member (solid line) and a vacuum profile for aspiration through the elongate member (hatched line).
Figure 19C:
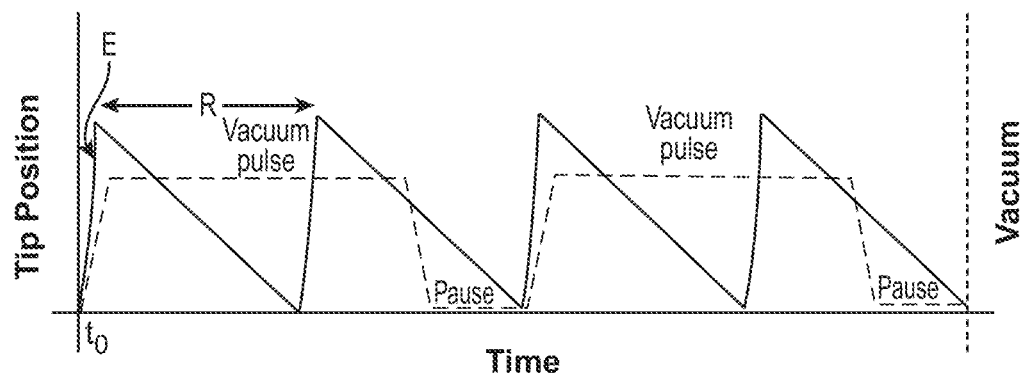
Figure 19D:
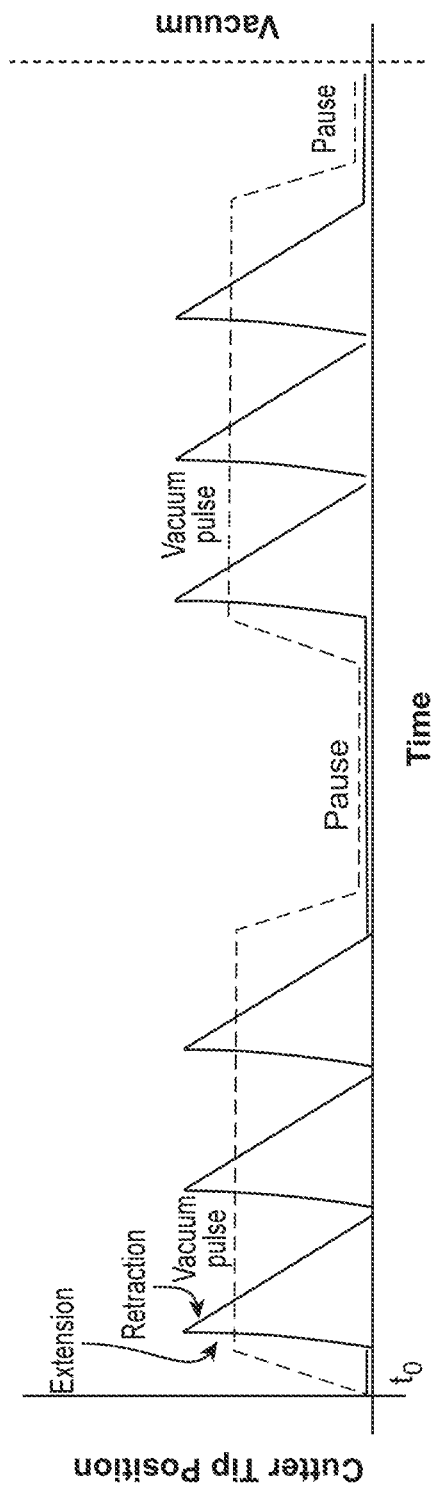

For example, a pulse of aspiration can be drawn through the lumen of the elongate member during at least a portion of the extension as the elongate member moves in a distal direction and/or during at least a portion of the retraction as the elongate member moves in a proximal direction. FIG. 19A illustrates an implementation of a vacuum profile over time for the pulsatile vacuum applied through the distal end region of the lumen of the elongate member. As described elsewhere herein, the vacuum source can include a pump having a plurality of pistons configured to move sequentially within their respective pumping chambers creating periods of increasing vacuum interspersed by periods of decreasing vacuum. In some implementations, the increase in vacuum can occur faster than the decrease in the vacuum providing a vacuum profile. The pulsatile vacuum profile applied through the lumen of the distal shaft can be synchronized with the motion profile of the elongate member performing the cutting such that at least a part of the period of negative pressure is applied during a certain phase of movement. FIGS. 19B-19D show the movement of the elongate member (solid lines) relative to the periods of negative pressure (hatched lines) applied through the elongate member. The period of negative pressure (i.e. vacuum pulse) can occur during at least part of the forward stroke or distal extension E of the elongate member, dwell time after distal extension E and before proximal retraction R, and/or during at least part of the proximal retraction R of the elongate member. For example, FIG. 19B shows a first pulse of vacuum pressure occurs during the extension E of the elongate member as well as the dwell time after extension E and before retraction R. The first pulse of vacuum pressure ends during the retraction R phase and a second pulse of vacuum begins and ends before the same retraction phase ends. FIG. 19C shows another implementation where a first pulse of vacuum pressure begins during extension E of the elongate member and is maintained during retraction R phase of the elongate member as well as during a second extension E of the elongate member. FIG. 19B shows the vacuum pulse having about 2× the frequency of tip movement and FIG. 19C shows the tip movement having about 2× the frequency of the vacuum pulse. Both FIG. 19B and FIG. 19C show vacuum pulse occurring during a portion of the extension E and retraction R. FIG. 19D shows another implementation of the coordination between elongate member movement and application of negative pressure. The motion profile of the elongate member (solid lines) need not correspond with a single trapezoidal vacuum pulse (hatched lines). Rather, the motion of the elongate member can allow for multiple extensions E and retractions R (or oscillations) during a single pulse of vacuum. FIG. 19D illustrates the movement of the elongate member or tip oscillation can begin after the vacuum pulse is initiated. Once the pulse of vacuum returns back to zero, the movement of the elongate member or tip oscillation can cease. The system can then enter a rest period for both motion and vacuum for a period of time before the next sequence begins.

Figure 19E:
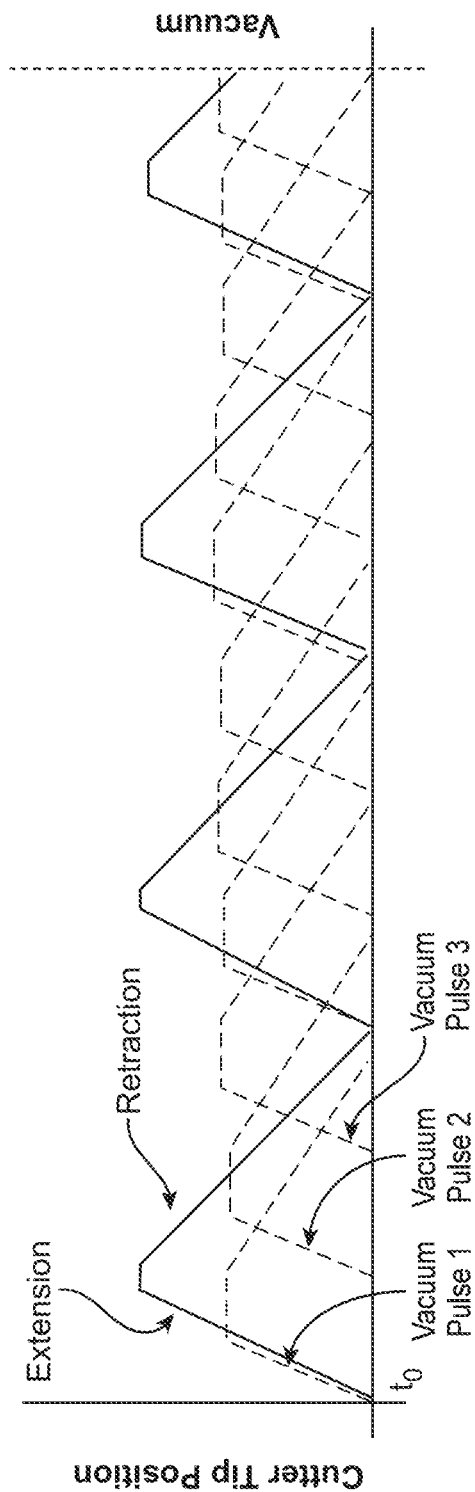
FIG. 19E shows overlap between an asymmetric, non-sinusoidal motion profile for an elongate member (solid line) and a vacuum profile for aspiration through the elongate member (hatched line).
Figure 19F:
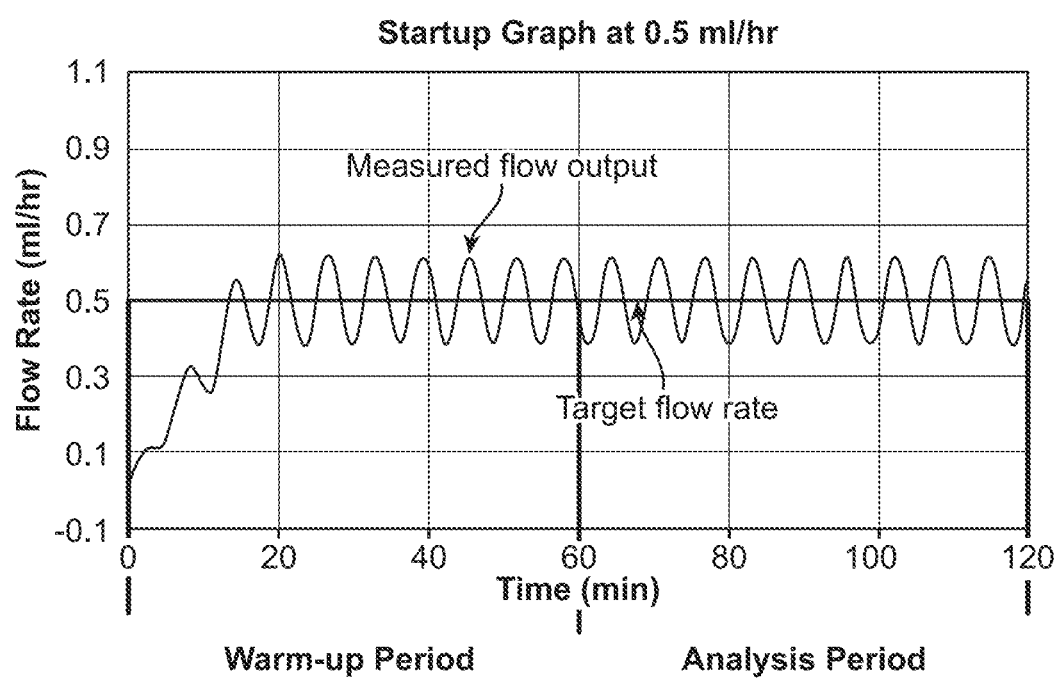
FIG. 19F shows overlap between an asymmetric, non-sinusoidal motion profile for an elongate member (solid line)

As discussed above, the geometry of the cam surface 2725 can be designed to have a more gradual slope on the retraction side such that the retraction periods of the pistons 2799 overlap in a manner that provides a substantially continuous vacuum (with or without a spike in negative pressure as described above). FIG. 19E shows the movement of the elongate member (solid lines) relative to the periods of negative pressure (hatched lines) applied through the elongate member. Retraction of a first piston 2799a can create a first pulse of vacuum and retraction of a second piston 2799b can create a second pulse of vacuum that overlaps with the first pulse. Retraction of a third piston 2799c can create a third pulse of vacuum that overlaps with the second pulse of vacuum and so on. The result is a substantially continuous vacuum pressure that occurs during both extension and retraction of the elongate member.

The vacuum applied during the period of overlapping pulses can, but need not, have a reduced maximum vacuum compared to the implementation of pulsed vacuum where the pulses do not significantly overlap.

It should be appreciated that any number of various relative frequencies are considered herein and that these are illustrations of some examples of the relative speed profiles and vacuum profiles.

The displacement or travel distance of the tip 2765 can vary, but is generally greater than phacoemulsification tips known in the art. Typical phacoemulsification tips have a tip displacement of on the order of about 0.1 mm and move at a frequency of between about 20-40 kHz. The tips 2765 described herein can have a greater displacement distance and a lower frequency. For example, the displacement achieved by the tip 2765 can be between about 0.05 mm-1.0 mm at a frequency of about 2-2,000 Hz. In this way, the devices described herein may not be ultrasonic and may not generate the heat associated with harmful effects in the eye during cataract surgery. In some implementations, the tip 2765 is pushed forward by a spring 3135. A longer stroke distance can allow for the tip to achieve a higher final speed $V_{maxE}$ at the time of impact with eye tissue.

Figure 17E:
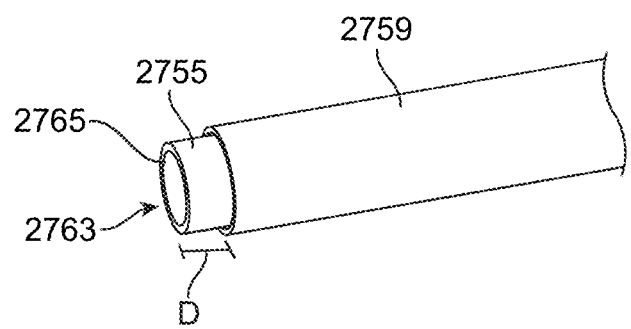
FIGS. 17E and 17F are partial views of an elongate member having inner and outer tubes in an extended and a retracted state, respectively.
Figure 17F:
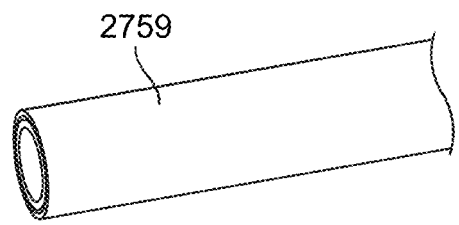
Figure 17G:
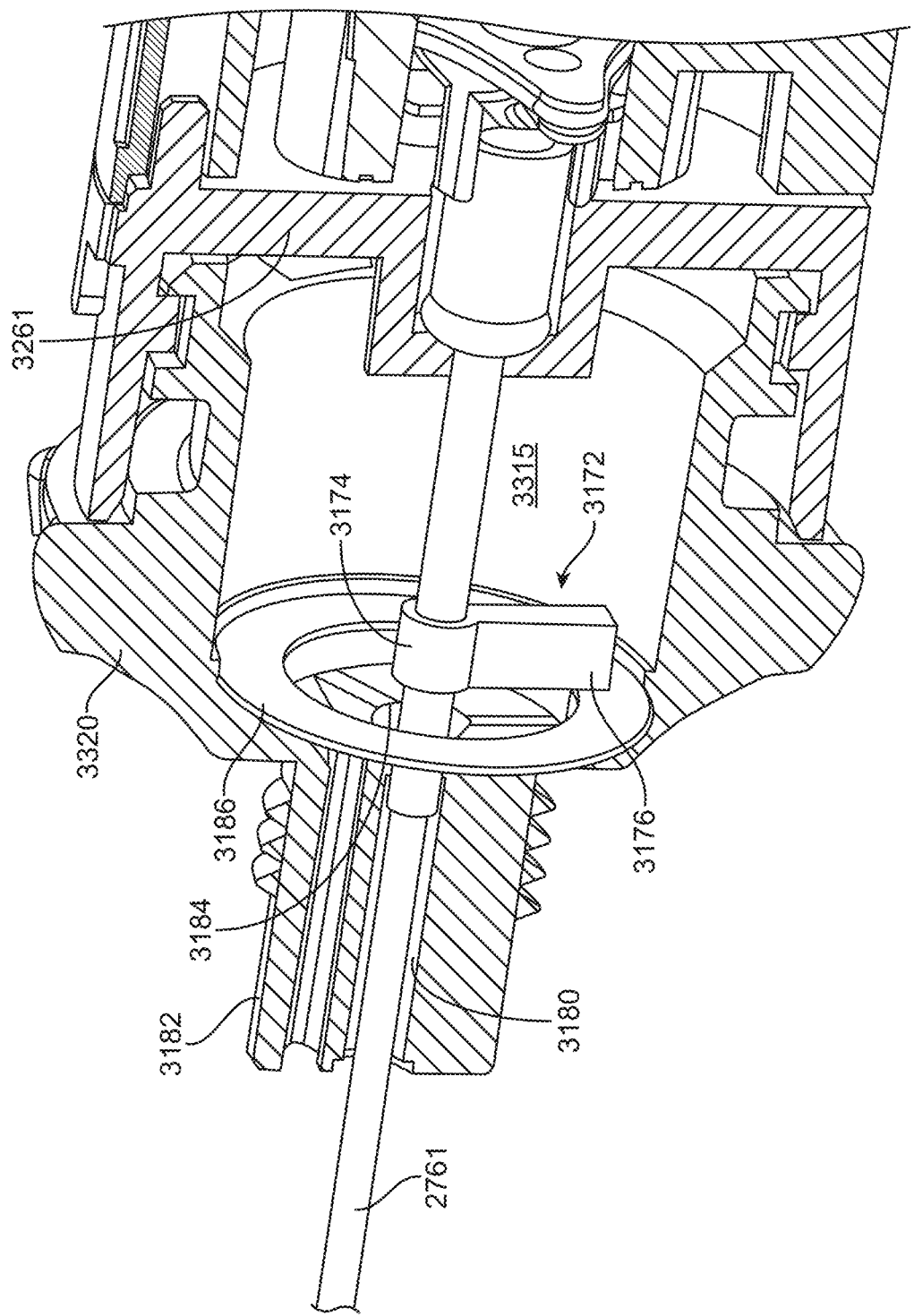
FIG. 17G is a partial, cross-sectional view of an elongate member in full distal extension.

As described herein, the device 2700 can have an outer tube or protective sleeve 2759 that extends over the elongate member 2755 (see FIGS. 17E-17F). Relative lengths of the inner and outer members 2755, 2759 can be such that a distal tip 2765 of the elongate member 2755 extends beyond a distal end of the protective sleeve 2759 when it is fully extended in a distal direction forming a fully extended configuration. The distal tip of the elongate member 2755 in the fully extended configuration is positioned distal of a distal opening of the protective sleeve 2759. A distance between the distal opening of the protective sleeve 2759 and the distal tip of the elongate member 2755 in the fully extended configuration defines an extension distance D. The elongate member 2755 fully retracts into the protective sleeve 2759 when it is in a fully retracted position. The distance the distal tip of the elongate member 2755 moves relative to the protective sleeve 2759 from the fully retracted configuration to the fully extended configuration defines a travel distance. The extension distance can be less than the travel distance, for example, half the travel distance. In some configurations the travel distance is between about 0.05 mm to about 1.0 mm and the extension distance is between about 0.1 mm to about 0.5 mm. Therefore, the distal tip 2765 of the elongate member 2755 can be only exposed to the eye tissue for a portion of its motion profile. For example, the elongate member 2755 may extend forward about 0.5 mm from its fully retracted position and approximately half of this stroke may be within the protective sleeve 2759 such that only the last 0.25 mm of the stroke the elongate member 2755 extends beyond the protective sleeve 2759. In this way, the elongate member 2755 can accelerate to a high speed before it impacts the eye tissue. Retraction of the elongate member 2755 fully into the protective sleeve 2759 provides a further benefit in that it may help separate eye tissue from the distal tip 2765 of the elongate member 2755 as it retracts into the protective sleeve 2759 preventing the eye tissue from 'lollipopping' onto the distal tip 2765 of the elongate member 2755.

The drive mechanism operatively coupled to the elongate member 2755 configured to cause oscillating movements of the elongate member 2755 can vary including electric, piezoelectric, magnetostrictive, electromagnetic, hydraulic, pneumatic, mechanic, or other type of drive mechanism known in the art. In some implementations, the elongate member 2755 can be driven by a drive mechanism incorporating camming mechanism and a spring element 3135 as described above. However, other energy modalities are considered herein for driving the elongate member 2755, which can include asymmetric or non-sinusoidal motion discussed herein. The elongate member 2755 can be reciprocated by a drive mechanism including a motor contained within an interior of the housing (e.g. the durable reusable portion of the housing). The motor can be any type of motor or driver suitable for rotating a shaft. The motor can drive both the oscillation of the elongate member and the aspiration pump within the hand piece. The configuration of the motor can vary including, any of a variety of rotation motors, stepper motor, AC motor, DC motor, a piezoelectric motor, a voice coil motor, or other motor. The motor may be coupled to a gear reduction system such as a harmonic drive to produce the desired output speed as described elsewhere herein.

In some implementations, the drive mechanism of the device can incorporate a piezoelectric element configured to drive the elongate member, such as by driving the cam follower 3190 forward and backward. The piezoelectric element can respond to changes in voltage by decreasing or increasing in size. A high frequency voltage connected to the piezoelectric element can generate a motion profile of the tip 2765 that matches the frequency of the supplied voltage. The voltage signals sent to the piezoelectric element can be generally non-sinusoidal in shape and therefore the tip 2765 moves in a generally non-sinusoidal pattern as described elsewhere herein. The voltage may have a waveform that contracts the piezoelectric elements slower than it allows them to expand. This moves the tip 2765 slower on the retraction stroke than on the extension stroke. Any number of motion profiles may be commanded based on the voltage waveform supplied to the piezoelectric element. For example, two or more overlapping voltage sinusoidal waveforms can be supplied to the piezoelectric element that creates an interference effect such that a non-sinusoidal wave form is created.

In still further implementations, a combination of mechanisms and modalities are incorporated in the device to drive the elongate member with a non-sinusoidal motion profile. For example, an electromagnetic coil can be configured to move a ferritic core forward with the application of a current through the coil. The core can be configured to be driven forward by the electromagnetic coil, but then retract backwards (i.e. proximally) through the force of a compressed spring. Therefore, with an increase in current through the coil, the core is driven forward. With the current is reduced, the core retracts backward. In this manner, the core may be connected to a cutter member so that the extension forward can be executed quickly by the sudden increase in current in the coil, but the retraction may be slower by the force of the compressed spring.

One or more aspects of the devices described herein (i.e. instrument 225 and the system 100) can be programmed by a user. A user can program one or more aspects of the drive mechanism, for example, the speed profile of the motor of the instrument on the external computing device 200 or system 100. The control processor can be programmed by an input on the device itself or programmed remotely such as by an external computing device 200 having an input. The control processor can operate according to program instructions stored in a memory. Any of a variety of adjustable functions of the instrument may be programmed this way including, but not limited to travel distance of the elongate member, frequency of oscillation of the elongate member, extension speed profile, retraction speed profile, maximum extension speed (VmaxE), minimum extension speed (VminE), maximum retraction speed (VmaxR), minimum retraction speed (VminR), average extension speed (VavgE), average retraction speed (VavgR), vacuum level, or any other aspect of the motion profile. In some implementations, the distance the elongate member moves with each cycle can be adjustably programmed such that the amplitude of its oscillation is selectable within a range of about 0.5 Hz to about 5000 Hz, or frequency in a range of about 2 Hz to about 2000 Hz. The oscillation frequency can be less than ultrasonic, for example, less than about 20,000 Hz or within the ultrasonic range (e.g. about 20,000 Hz, to about 120,000 Hz, up to the gigahertz range).

One of more aspects of the aspiration pumps (e.g. aspiration pump 145 of the system 100 as well as aspiration pump 245 of the instrument 225) can also be programmed by a user to control the vacuum applied at the distal end region of the elongate member including, but not limited to flow rate of aspiration, minimum vacuum pressure, maximum vacuum pressure, frequency of vacuum pulses, or any other aspect of the vacuum profile. In some implementations, the flow rate of aspiration can be adjustably programmed within a range of between about 5-100 ml/min.

It should be appreciated that the asymmetric motion profile with or without the vacuum pulse described herein can be applied to known phacoemulsification systems typically used for cataract surgery and vitrectomy. Conventional phacoemulsification systems configured to move an elongate member at ultrasonic frequency to remove eye tissue can implement the one or more motion profiles and/or vacuum profiles as described herein via software or hardware, for example by circuits providing a certain voltage causing the asymmetric movements. Thus, the asymmetric motion profiles and pulsed vacuum profiles described herein can be applied to a machine configured to oscillate at ultrasonic frequencies.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the device to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A system for extracting lens material from an eye, the system comprising:
   a surgical instrument comprising:
      a drive mechanism having a motor;
      a first aspiration pump driven by the drive mechanism, wherein the first aspiration pump is a piston pump;
      an elongate member sized and configured to extend through an anterior chamber of the eye and to a capsular bag of the eye, the elongate member comprising:
         an inner lumen fluidly coupled to the first aspiration pump and defining at least a portion of an aspiration waste line of the surgical instrument; and an open distal end having a distal cutting tip; and
an anti-surge valve located within the aspiration waste line that is configured to passively close when flow upstream of the anti-surge valve is above a threshold value and is configured to passively open when flow upstream of the anti-surge valve is below the threshold value,
wherein the elongate member is configured to be oscillated by the drive mechanism; and
a fluid system remote from the surgical instrument.

2. The system of claim 1, wherein the first aspiration pump is configured to create discontinuous, pulsatile aspiration through the inner lumen to aspirate the lens material from the eye into the inner lumen.

3. The system of claim 1, wherein the fluid system further comprises an irrigation line fluidly coupling a source of irrigation fluid of the fluid system to the surgical instrument.

4. The system of claim 3, wherein the irrigation line of the fluid system comprises a valve configured to control irrigation fluid flow through the irrigation line of the fluid system.

5. The system of claim 4, further comprising an input on a housing of the surgical instrument.

6. The system of claim 5, wherein the input is a multi-way trigger configured to activate different functions of the surgical instrument depending on degree of trigger depression.

7. The system of claim 6, wherein a first degree of trigger depression opens the valve of the irrigation line of the fluid system placing the surgical instrument into an irrigation-only mode.

8. The system of claim 7, wherein a second degree of trigger depression places the surgical instrument in an irrigation-continuous aspiration mode.

9. The system of claim 8, wherein a third degree of trigger depression activates the first aspiration pump and oscillation of the elongate member placing the surgical instrument in an irrigation-pulsed aspiration-cutting mode.

10. The system of claim 9, wherein trigger depression beyond the third degree of trigger depression increases at least one of oscillation frequency and aspiration flow rate.

11. The system of claim 5, wherein the input incorporates a sensing mechanism selected from the group consisting of capacitive sensor, optical sensor, magnetic sensor, electromagnetic sensor, and Hall-Effect sensor.

12. The system of claim 1, wherein the surgical instrument comprises a hand-held portion comprising a proximal, reusable portion releasably coupleable to a distal, disposable portion.

13. The system of claim 12, wherein a rotatable coupler is configured for releasably operatively coupling rotation of the motor to the distal, disposable portion.

14. The system of claim 12, wherein the proximal, reusable portion is configured to remain outside of the eye.

15. The system of claim 1, wherein the first aspiration pump comprises a plurality of pistons, each of the plurality of pistons being housed within a respective cylinder, each of the cylinders fluidly coupled to the inner lumen of the elongate member.

16. The system of claim 15, wherein the drive mechanism further comprises a rotational cam assembly capable of being rotated by the motor via a rotatable coupler, wherein rotation of said rotational cam assembly causes the plurality of pistons to generate pulses of discontinuous negative pressure within the inner lumen.

17. The system of claim 16, wherein aspiration created by the first aspiration pump is selectively modifiable by a user.

18. The system of claim 17, wherein the surgical instrument further comprises a piston hard stop configured to limit proximal travel of the plurality of pistons within their respective cylinders.

19. The system of claim 18, wherein the piston hard stop is configured to toggle between a high vacuum position and a low vacuum position.

20. The system of claim 19, wherein when in the high vacuum position, the piston hard stop is retracted proximally relative to the cylinders allowing for maximum proximal travel of each piston within its respective cylinder.

21. The system of claim 19, wherein when in the low vacuum position, the piston hard stop is advanced distally relative to the cylinders limiting proximal travel of the each piston within its respective cylinder to less than a maximum proximal travel.

22. The system of claim 18, wherein the piston hard stop is configured to toggle between a continuous aspiration position and a pulsatile aspiration position.

23. The system of claim 22, wherein when in the continuous aspiration position, the piston hard stop is advanced distally relative to the cylinders limiting proximal travel of each piston within its respective cylinder and relative to the rotational cam assembly of the drive mechanism.

24. The system of claim 22, wherein when in the pulsatile aspiration position, the piston hard stop is retracted proximally relative to the cylinders allowing full proximal travel of each piston within its respective cylinder and relative to the rotational cam assembly of the drive mechanism.

25. The system of claim 1, wherein when the anti-surge valve is closed fluid flow through the aspiration waste line is limited when the anti-surge valve is open fluid flow through the aspiration waste line is allowed.

26. The system of claim 25, wherein the threshold value is 40 milliliter (ml)/minute.

27. The system of claim 1, wherein the anti-surge valve is a diaphragm valve, an umbrella valve, or a mushroom valve.

28. The system of claim 1, wherein the anti-surge valve further comprises a filter.

29. A device for extracting lens material from an eye, the device comprising:
a drive mechanism having a motor;
an aspiration pump driven by the drive mechanism that is selectively modifiable by a user, the aspiration pump being a piston pump comprising a plurality of pistons housed within respective cylinders;
an elongate member configured to be oscillated by the drive mechanism, the elongate member sized and configured to extend through an anterior chamber of the eye and to a lens within a capsular bag of the eye, the elongate member comprising:
an inner lumen fluidly coupled to the aspiration pump and defining at least a portion of an aspiration waste line; and
an open distal end having a distal cutting tip,
wherein aspiration created by the aspiration pump and delivered through the inner lumen to aspirate the lens material from the eye into the inner lumen is selectively modifiable between continuous aspiration and discontinuous, pulsatile aspiration, wherein proximal travel of the plurality of pistons within their respective cylinders determines whether the aspiration created is continuous aspiration or discontinuous, pulsatile aspiration.

30. The device of claim 29, wherein the drive mechanism further comprises a rotational cam assembly capable of being rotated by the motor via a rotatable coupler, wherein rotation of the rotational cam assembly causes the plurality of pistons to generate pulses of discontinuous negative pressure within the inner lumen.

31. The device of claim 30, further comprising a piston hard stop configured to limit a distance of the proximal travel of the plurality of pistons within their respective cylinders.

32. The device of claim 31, wherein when in the continuous aspiration position, the piston hard stop is advanced distally relative to the cylinders limiting the distance of proximal travel of each piston within its respective cylinder and relative to the rotational cam assembly of the drive mechanism such that a rate of the proximal travel of each piston is defined by a slope of a cam surface.

33. The device of claim 31, wherein when in the pulsatile aspiration position, the piston hard stop is retracted proximally relative to the cylinders allowing full proximal travel distance of each piston within its respective cylinder and relative to the rotational cam assembly of the drive mechanism such that a rate of the proximal travel of each piston is influenced by a spring force.

34. The device of claim 29, further comprising an anti-surge valve assembly incorporating a deflectable feature arranged over a valve seat.

35. The device of claim 34, wherein the anti-surge valve assembly is configured to limit aspiration through the elongate member when a flow rate is above a threshold value and is configured to allow aspiration through the elongate member when the flow rate is below the threshold value.

36. The device of claim 34, wherein the anti-surge valve assembly further comprises a filter on an upstream side of the valve assembly.

37. The device of claim 29, further comprising a multi-stage trigger configured to activate different functions of the device depending on a degree of trigger depression.

38. The device of claim 37, wherein downward motion of the multi-stage trigger initiates aspiration.

39. The device of claim 37, wherein the multi-stage trigger is functionally coupled to a venting mechanism.

40. The device of claim 37, wherein a first degree of trigger depression activates the motor to drive the aspiration pump and wherein a second degree of trigger depression additionally activates oscillation of the elongate member.

41. The device of claim 29, wherein the discontinuous, pulsatile aspiration is characterized by the elongate member undergoing a plurality of oscillations during a single pulse of vacuum.

42. The device of claim 41, wherein motion of the elongate member begins after the single pulse of vacuum is initiated.

43. The device of claim 42, wherein the single pulse of vacuum returns back to zero and motion of the elongate member ceases prior to another pulse of vacuum being initiated.

* * * * *